US011257569B1

(12) United States Patent
Dite et al.

(10) Patent No.: US 11,257,569 B1
(45) Date of Patent: Feb. 22, 2022

(54) METHODS OF ASSESSING RISK OF DEVELOPING A SEVERE RESPONSE TO CORONAVIRUS INFECTION

(71) Applicant: GENETIC TECHNOLOGIES LIMITED, Fitzroy (AU)

(72) Inventors: Gillian Sue Dite, Thornbury (AU); Nicholas Mark Murphy, Point Cook (AU); Richard Allman, Manor Lakes (AU)

(73) Assignee: GENETIC TECHNOLOGIES LIMITED, Fitzroy (AU)

( * ) Notice: Subject to any disclaimer, the term of this patent is extended or adjusted under 35 U.S.C. 154(b) by 0 days.

(21) Appl. No.: 17/368,471

(22) Filed: Jul. 6, 2021

Related U.S. Application Data

(63) Continuation of application No. PCT/AU2021/050507, filed on May 26, 2021.

(30) Foreign Application Priority Data

| May 27, 2020 | (AU) | 2020901739 |
| Jun. 19, 2020 | (AU) | 2020902052 |
| Sep. 30, 2020 | (AU) | 2020903536 |
| Feb. 17, 2021 | (AU) | 2021900392 |

(51) Int. Cl.
| G16B 40/00 | (2019.01) |
| G16H 50/70 | (2018.01) |
| C12Q 1/6876 | (2018.01) |
| G16H 50/30 | (2018.01) |
| G16H 10/40 | (2018.01) |
| G16H 10/60 | (2018.01) |

(52) U.S. Cl.
CPC ........... *G16B 40/00* (2019.02); *C12Q 1/6876* (2013.01); *G16H 10/40* (2018.01); *G16H 10/60* (2018.01); *G16H 50/30* (2018.01); *G16H 50/70* (2018.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 5,695,934 A | 12/1997 | Brenner |
| 5,714,330 A | 2/1998 | Brenner |
| 5,750,341 A | 5/1998 | Macevicz |
| 6,174,670 B1 | 1/2001 | Wittwer |
| 6,306,597 B1 | 10/2001 | Macevicz |
| 6,485,944 B1 | 11/2002 | Church |
| 6,511,803 B1 | 1/2003 | Church |
| 6,787,308 B2 | 9/2004 | Balasubramanian |
| 6,833,246 B2 | 12/2004 | Balasubramanian |
| 6,898,531 B2 | 5/2005 | Sheehan |
| 2003/0108919 A1 | 6/2003 | Kautzer |
| 2005/0130173 A1 | 6/2005 | Leamon |
| 2019/0019760 A1 | 1/2019 | Peng |
| 2021/0050116 A1* | 2/2021 | Sabeti ..................... G06Q 50/01 |
| 2021/0340636 A1* | 11/2021 | Brambati ............... C12Q 1/701 |

FOREIGN PATENT DOCUMENTS

| WO | WO 92/02638 | 2/1992 |
| WO | WO 2005/086770 A2 | 9/2005 |

OTHER PUBLICATIONS

International Search Report dated Aug. 9, 2021 in connection with PCT International Application No. PCT/AU2021/050507.
Written Opinion of the International Searching Authority dated Aug. 9, 2021 in connection with PCT International Application No. PCT/AU2021/050507.
Olesen, M. S. et al., "A novel KCND3 gain-of-function mutation associated with early-onset of persistent lone atrial fibrillation", Cardiovascular Research, 2013, vol. 98, pp. 488-495.
Bloch, E. M. et al., "Deployment of convalescent plasma for the prevention and treatment of COVID-19", The Journal of Clinical Investigation, 2020, vol. 130, No. 6, pp. 2757-2765, first published Apr. 7, 2020.
Dite, G. S. et al., "Development and validation of a clinical and genetic model for predicting risk of severe COVID-19", medRxiv, doi: https://doi.org/10.1101/2021.03.09.21253237, published Mar. 12, 2021.
Dite, G. S. et al., "An integrated clinical and genetic model for predicting risk of severe COVID-19: A population-based case-control study", PLoS One, 2021, vol. 16, No. 2, e0247205, first published Feb. 16, 2021.
Adessi et al. (2000) Nucl. Acids Res. 28, E87.
Bennett et al. (2005) Pharmacogenomics 6: 373-382.
Brenner et al. (2000) Nat. Biotechnol. 18:630-634.
Centres for Disease Control and Prevention. (2020) COVIDView: a weekly surveillance summary of U.S. COVID-19 activity. Available from https://www.cdc.gov/coronavirus/2019-ncov/covid-data/pdf/covidview-08-07-2020.pdf (accessed Aug. 14, 2020).
Chee et al. (1996) Science 274:610-614.
COVID-19 Host Genetics Initiative. (2020) Eur J Hum Genet 28:715-718.
Dayem et al. (2018) Nucl. Acids Res. 46:W109-W113.
Devlin and Risch (1995) Genomics. 29: 311-322.
Ellinghaus et al. (2020) N. Engl. J. Med. doi: 10.1056/NEJMoa2020283.
Fodor (1997b) Science 277: 393-395.
Hartl et al. (1981) A Primer of Population Genetics Washington University, Saint Louis.

(Continued)

*Primary Examiner* — Channing S Mahatan
(74) *Attorney, Agent, or Firm* — Gary J. Gershik

(57) ABSTRACT

The present disclosure relates to methods and systems for assessing the risk of a human subject developing a severe response to a Coronavirus infection, such as a severe acute respiratory syndrome coronavirus 2 (SARS-CoV-2) virus infection.

Figure 1:
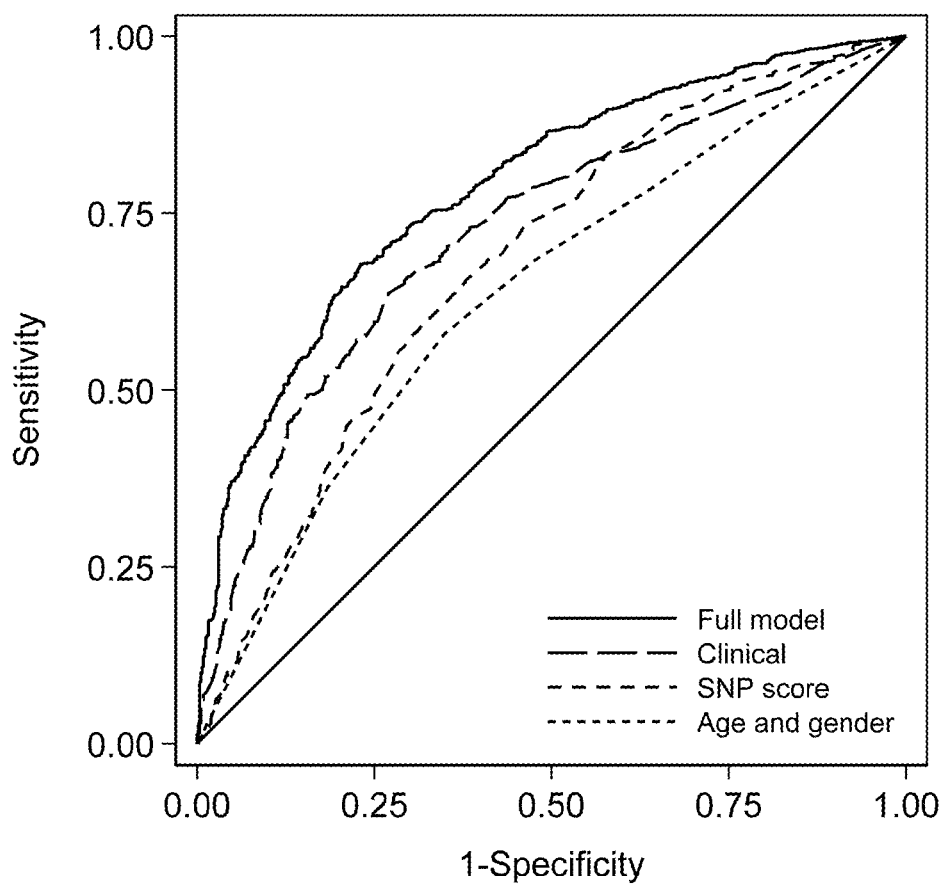

6 Claims, 6 Drawing Sheets
Specification includes a Sequence Listing.

(56) References Cited

OTHER PUBLICATIONS

Hopper (2015) J. Epidemiol. 182:863-867.
Katella (2021) Yale Medicine, May 13, 2021 (www.yalemedicine.org/news/covid-19-vaccine-comparison).
Kuo et al. (2020) J Gerontol A Biol Sci Med Sci, 2020, vol. 75, No. 11, 2231-2232.
Lockhart (1998) Nature Medicine 4:1235-1236.
Lynch and Walsh (1998) Genetics and Analysis of Quantitative Traits, Sinauer Associates, Inc. Sunderland Mass. ISBN 0-87893-481-2.
Machiela et al. (2015) Bioinformatics 31:3555-3557.
MacLean et al. (2009) Nature Rev. Microbiol, 7:287-296.
Margulies et al. (2005) Nature 437: 376-380.
Mealiffe et al. (2010) J. Natl. Cancer Inst. 102:1618-1627.
Melzer et al. (2008) PLoS Genect. 4:el000072.
Mitra et al. (2003) Analytical Biochemistry 320:55-65.
Morozova & Marra (2008) Genomics 92:255.
Pairo-Castineira et al. (2020) Nature https://doi.org/10.1038/s41586-020-03065-y.
Petrilli et al. (2020) BMJ 369:ml966. doi: 10.1136/bmj.ml966.
Sapolsky et al. (1999) Genet Anal: Biomolec Engin 14:187-192.
Shendure et al. (2005) Science 309:1728-1732.
Slatkin and Excoffier (1996) Heredity 76: 377-383.
Thomas (1998) Heredity 81 (1998) 703-705.
Van Moorsel et al. (2020) medRxiv preprint doi: https://doi.org/10.1101/2020.05.12.20099333.
Voelkerding et al. (2009) Clinical Chem. 55: 641-658.
Williamson et al. (2020) Nature 584:430436.
Wolpin et al. (2010) Cancer Res. 70:1015-1023.

\* cited by examiner

SEQUENCE LISTING

<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: Primer for rs11549298

<400> SEQUENCE: 1
acctggtatc agtgaagagg atcag                    25

<210> SEQ ID NO 2
<211> LENGTH: 25
<212> TYPE: DNA
<213> ORGANISM: Artificial Sequence
<220> FEATURE:
<223> OTHER INFORMATION: Primer for rs11549298

<400> SEQUENCE: 2
tcttgataca actgtaagaa gtggt                    25

<210> SEQ ID NO 3
<211> LENGTH: 25
<212> TYPE: DNA
<213> ORGANISM: Artificial Sequence
<220> FEATURE:
<223> OTHER INFORMATION: Primer for rs112317747

<400> SEQUENCE: 3
tatttctttg ttgccctcta tctct                    25

<210> SEQ ID NO 4
<211> LENGTH: 25
<212> TYPE: DNA
<213> ORGANISM: Artificial Sequence
<220> FEATURE:
<223> OTHER INFORMATION: Primer for rs112317747

<400> SEQUENCE: 4
gaaagagatg ggttggcatt attat                    25

<210> SEQ ID NO 5
<211> LENGTH: 25
<212> TYPE: DNA
<213> ORGANISM: Artificial Sequence
<220> FEATURE:
<223> OTHER INFORMATION: Primer for rs2034831

<400> SEQUENCE: 5
taaaattaga actggagggc tgggt                    25

<210> SEQ ID NO 6
<211> LENGTH: 25
<212> TYPE: DNA
<213> ORGANISM: Artificial Sequence
<220> FEATURE:
<223> OTHER INFORMATION: Primer for rs2034831

<400> SEQUENCE: 6
tggcattata aacactcact gaagt                    25

<210> SEQ ID NO 7
<211> LENGTH: 25
<212> TYPE: DNA
<213> ORGANISM: Artificial Sequence -continued

```
<220> FEATURE:
<223> OTHER INFORMATION: Primer for rs112641600

<400> SEQUENCE: 7
aatgccatct gatgagagaa gtttt                                           25

<210> SEQ ID NO 8
<211> LENGTH: 25
<212> TYPE: DNA
<213> ORGANISM: Artificial Sequence
<220> FEATURE:
<223> OTHER INFORMATION: Primer for rs112641600

<400> SEQUENCE: 8
tacagtttta aaaatgggcg tttct                                           25

<210> SEQ ID NO 9
<211> LENGTH: 25
<212> TYPE: DNA
<213> ORGANISM: Artificial Sequence
<220> FEATURE:
<223> OTHER INFORMATION: Primer rs10755709

<400> SEQUENCE: 9
tataataaca cgtggaagtg aaaat                                           25

<210> SEQ ID NO 10
<211> LENGTH: 25
<212> TYPE: DNA
<213> ORGANISM: Artificial Sequence
<220> FEATURE:
<223> OTHER INFORMATION: Primer for rs10755709

<400> SEQUENCE: 10
ttgtttgtat gtgtgaaatg attct                                           25

<210> SEQ ID NO 11
<211> LENGTH: 25
<212> TYPE: DNA
<213> ORGANISM: Artificial Sequence
<220> FEATURE:
<223> OTHER INFORMATION: Primer for rs118072448

<400> SEQUENCE: 11
aagcaaacta ttcttcagga atcca                                           25

<210> SEQ ID NO 12
<211> LENGTH: 25
<212> TYPE: DNA
<213> ORGANISM: Artificial Sequence
<220> FEATURE:
<223> OTHER INFORMATION: Primer for rs118072448

<400> SEQUENCE: 12
atttctgcat ttcactttgt gtggt                                           25

<210> SEQ ID NO 13
<211> LENGTH: 25
<212> TYPE: DNA
<213> ORGANISM: Artificial Sequence
<220> FEATURE:
<223> OTHER INFORMATION: Primer for rs7027911

<400> SEQUENCE: 13
gtaaatgctg ctaacagagc tcttt                                           25
```

```
<210> SEQ ID NO 14
<211> LENGTH: 25
<212> TYPE: DNA
<213> ORGANISM: Artificial Sequence
<220> FEATURE:
<223> OTHER INFORMATION: Primer for rs7027911

<400> SEQUENCE: 14
gaagagagtt tattagcaag gcctc                                      25

<210> SEQ ID NO 15
<211> LENGTH: 25
<212> TYPE: DNA
<213> ORGANISM: Artificial Sequence
<220> FEATURE:
<223> OTHER INFORMATION: Primer for rs71481792

<400> SEQUENCE: 15
catttgggaa aagccactga atgga                                      25

<210> SEQ ID NO 16
<211> LENGTH: 25
<212> TYPE: DNA
<213> ORGANISM: Artificial Sequence
<220> FEATURE:
<223> OTHER INFORMATION: Primer for rs71481792

<400> SEQUENCE: 16
agattgacta gccgttgaga gtaga                                      25

<210> SEQ ID NO 17
<211> LENGTH: 25
<212> TYPE: DNA
<213> ORGANISM: Artificial Sequence
<220> FEATURE:
<223> OTHER INFORMATION: Primer for rs1984162

<400> SEQUENCE: 17
actgactcct gacactcttg aagcg                                      25

<210> SEQ ID NO 18
<211> LENGTH: 25
<212> TYPE: DNA
<213> ORGANISM: Artificial Sequence
<220> FEATURE:
<223> OTHER INFORMATION: Primer for rs1984162

<400> SEQUENCE: 18
gactcttctc tggcatcttc tcatg                                      25
```

METHODS OF ASSESSING RISK OF DEVELOPING A SEVERE RESPONSE TO CORONAVIRUS INFECTION

CROSS-REFERENCE TO RELATED APPLICATIONS

This application is a continuation of PCT International Application No. PCT/AU2021/050507, filed May 26, 2021, which claims the priority of each of Australian Application No. 2020901739, filed May 27, 2020, Australian Application No. 2020902052, filed Jun. 19, 2020, Australian Application No. 2020903536, filed Sep. 30, 2020, and Australian Application No. 2021900392, filed Feb. 17, 2021 the contents of each of which are hereby incorporated by reference in their entirety into this application.

REFERENCE TO SEQUENCE LISTING

This application incorporates-by-reference nucleotide and/or amino acid sequences which are present in the file named "210706_91753_SequenceListing_DH.txt", which is 4 kilobytes in size, and which was created Jul. 5, 2021 in the IBM-PC machine format, having an operating system compatibility with MS-Windows, which is contained in the text file filed Jul. 6, 2021 as part of this application.

FIELD OF THE INVENTION

The present disclosure relates to methods and systems for assessing the risk of a human subject developing a severe response to a coronavirus infection such as a severe acute respiratory syndrome coronavirus 2 (SARS-CoV-2) viral infection.

BACKGROUND OF THE INVENTION

In December 2019, there were a series of unexplained cases of pneumonia reported in Wuhan, China. On 12 Jan. 2020, the World Health Organization (WHO) tentatively named this new virus as the 2019 novel coronavirus (2019-nCoV). On 11 Feb. 2020, the WHO formally named the disease triggered by 2019-nCoV as coronavirus disease 2019 (COVID-19). The coronavirus study group of the International Committee on Taxonomy of Viruses named 2019-nCoV as severe acute respiratory syndrome coronavirus 2 (SARS-CoV-2). The WHO declared the virus a Public Health Emergency of International Concern on 30 Jan. 2020. The WHO eventually declared a pandemic on 11 Mar. 2020.

Like many complex diseases, there are a multitude of host factors that influence the severity of disease once infected with a virus. This means viral infections are complex multifactorial diseases like many cancers, cardiovascular disease and diabetes.

As global health systems try to manage resources and governments attempt to manage their respective economies there is a need to identify which people are at most risk of developing severe symptoms in response to the viral infection. Such a tool would enable earlier hospitalization and targeted treatments which may lead to the saving of lives. Of great importance to the economy, there is potential that lower risk individuals could be recommended to continue their normal employment given the lower risk of developing a life threatening disease should they contract a Coronavirus infection such as a SARS-Cov-2 viral infection.

SUMMARY OF THE INVENTION

The present inventors have found that a severe response to a Coronavirus infection risk model provides useful risk discrimination for assessing a subject's risk of developing a severe response to a Coronavirus infection such as a SARS-CoV-2 infection.

In an aspect, the present invention provides a method for assessing the risk of a human subject developing a severe response to a Coronavirus infection, the method comprising performing a genetic risk assessment of the human subject, wherein the genetic risk assessment involves detecting, in a biological sample derived from the human subject, the presence at least two polymorphisms associated with a severe response to a Coronavirus infection.

In an embodiment, the Coronavirus is an Alphacoronavirus, Betacoronavirus, Gammacoronavirus or an Deltacoronavirus.

In an embodiment, the Coronavirus is Alphacoronavirus 1, Human coronavirus 229E, Human coronavirus NL63, *Miniopterus* bat coronavirus 1, *Miniopterus* bat coronavirus HKU8, Porcine epidemic diarrhea virus, *Rhinolophus* bat coronavirus HKU2, *Scotophilus* bat coronavirus 512, Betacoronavirus 1 (Bovine Coronavirus, Human coronavirus OC43), Hedgehog coronavirus 1, Human coronavirus HKU1, Middle East respiratory syndrome-related coronavirus (MERS), Murine coronavirus, *Pipistrellus* bat coronavirus HKU5, *Rousettus* bat coronavirus HKU9, Severe acute respiratory syndrome-related coronavirus (SARS-CoV or SARS-CoV-2), *Tylonycteris* bat coronavirus HKU4, Avian coronavirus, Beluga whale coronavirus SW1, Bulbul coronavirus HKU11 or Porcine coronavirus HKU15.

In an embodiment, the Coronavirus is Severe acute respiratory syndrome-related coronavirus (SARS-CoV or SARS-CoV-2), Middle East respiratory syndrome-related coronavirus (MERS), Human coronavirus OC43, Human coronavirus HKU1, Human coronavirus 229E or Human coronavirus NL63.

In an embodiment, the Coronavirus is a Betacoronavirus.

In an embodiment, the Betacoronavirus is Severe acute respiratory syndrome-related coronavirus (SARS-CoV or SARS-CoV-2), Middle East respiratory syndrome-related coronavirus (MERS), Human coronavirus OC43 or Human coronavirus HKU1.

In an embodiment, the Coronavirus (Betacoronavirus) is Severe acute respiratory syndrome-related coronavirus (SARS-CoV or SARS-CoV-2), Middle East respiratory syndrome-related coronavirus (MERS), Human coronavirus OC43 or Human coronavirus HKU1.

In an embodiment, the Coronavirus (Betacoronavirus) is Severe acute respiratory syndrome-related coronavirus (SARS-CoV or SARS-CoV-2) or Middle East respiratory syndrome-related coronavirus (MERS).

In a preferred embodiment, the Coronavirus (Betacoronavirus) is Severe acute respiratory syndrome coronavirus 2 (SARS-CoV-2).

In an embodiment, the method comprises detecting the presence of at least three, at least four, at least five, at least six, at least seven, at least eight, at least nine, at least ten, at least 20, at least 30, at least 40, at least 50, at least 60, at least 70, at least 80, at least 100, at least 120, at least 140, at least 160, at least 180, at least 200, at least 250, at least 300 or at least 306 polymorphisms associated with a severe response to a Coronavirus infection.

In an embodiment, the polymorphisms are selected from Tables 1 to 6, 8, 19 or 22 or a polymorphism in linkage disequilibrium with one or more thereof.

In an embodiment, the method at least comprises detecting polymorphisms at one or more or all of rs10755709, rs112317747, rs112641600, rs118072448, rs2034831, rs7027911 and rs71481792, or a polymorphism in linkage disequilibrium with one or more thereof.

In an embodiment, the method at least comprises detecting polymorphisms at one or more or all of rs10755709, rs112317747, rs112641600, rs115492982, rs118072448, rs1984162, rs2034831, rs7027911 and rs71481792, or a polymorphism in linkage disequilibrium with one or more thereof.

In an embodiment, the polymorphisms are selected from Table 1, Table 6a, Table 6b or a polymorphism in linkage disequilibrium with one or more thereof.

In an embodiment, the polymorphisms are selected from any one of Tables 1 to 6, 8, 19 or 22, or a polymorphism in linkage disequilibrium with one or more thereof.

In an embodiment, the polymorphisms are selected from Table 3 or a polymorphism in linkage disequilibrium with one or more thereof. In an embodiment, at least three polymorphisms are analysed.

In an embodiment, the method comprises, or consists of, detecting the presence of at least 60, or each, of the polymorphisms provided in Table 4 or a polymorphism in linkage disequilibrium with one or more thereof.

In another embodiment, the polymorphisms are selected from Table 2 or a polymorphism in linkage disequilibrium with one or more thereof.

In a further embodiment, the polymorphisms are selected from Table 3 and/or Table 8 or a polymorphism in linkage disequilibrium with one or more thereof.

In an embodiment, the polymorphisms are selected from Table 3 or a polymorphism in linkage disequilibrium with one or more thereof.

In an embodiment, the method comprises, or consists of, detecting the presence of each of the polymorphisms provided in Table 3 or a polymorphism in linkage disequilibrium with one or more thereof.

The genetic risk assessment may be combined with clinical risk factors to further improve the risk analysis. Thus, in an embodiment, the method further comprises
performing a clinical risk assessment of the human subject; and
combining the clinical risk assessment and the genetic risk assessment to obtain the risk of a human subject developing a severe response to a Coronavirus infection.

In an embodiment, the clinical risk assessment includes obtaining information from the subject on, but not necessarily limited to, one or more of the following: age, family history of a severe response to a Coronavirus infection, race/ethnicity, gender, body mass index, total cholesterol level, systolic and/or diastolic blood pressure, smoking status, does the human have diabetes, does the human have a cardiovascular disease, is the subject on hypertension medication, loss of taste, loss of smell and white blood cell count.

In another embodiment, the clinical risk assessment is based only on one or more or all of age, body mass index, loss of taste, loss of smell and smoking status.

In a further embodiment, the clinical risk assessment is based only on one or more or all of age, loss of taste, loss of smell and smoking status.

In an embodiment, the clinical risk assessment includes obtaining information from the subject on one or more or all of: age, gender, race/ethnicity, blood type, does the human have or has had an autoimmune disease, does the human have or has had an haematological cancer, does the human have or has had an non-haematological cancer, does the human have or has had diabetes, does the human have or has had hypertension and does the human have or has had a respiratory disease (other than asthma). In an embodiment, the autoimmune disease is rheumatoid arthritis, lupus or psoriasis.

In an embodiment, the clinical risk assessment includes obtaining information from the subject on one or more or all of: age, gender, race/ethnicity, blood type, height, weight, does the human have or has had an cerebrovascular disease, does the human have or has had a chronic kidney disease, does the human have or has had diabetes, does the human have or has had an haematological cancer, does the human have or has had hypertension, does the human have or has had an immunocompromised disease, does the human have or has had an haematological cancer, does the human have or has had liver disease, does the human have or has had an non-haematological cancer, and does the human have or has had a respiratory disease (other than asthma).

The skilled person would appreciate that numerous different procedures can be followed to combine the clinical and genetic risk assessments. In an embodiment, combining the clinical risk assessment and the genetic risk assessment comprises multiplying the risk assessments. In an embodiment, combining the clinical risk assessment and the genetic risk assessment comprises adding the risk assessments.

The inventors, for the first time, have identified numerous polymorphisms associated with a subject's risk of developing a severe response to a Coronavirus infection. Thus, in another aspect, the present invention provides a method for assessing the risk of a human subject developing a severe response to a Coronavirus, the method comprising detecting, in a biological sample derived from the human subject, the presence of a polymorphism provided in any one of Tables 1 to 6, 8, 19 or 22, or a polymorphism in linkage disequilibrium therewith.

In an embodiment, the polymorphism is provided in Table 19 and/or 22 or is a polymorphism in linkage disequilibrium therewith.

In an embodiment, the polymorphism is provided in Table 1 or Table 6a or is a polymorphism in linkage disequilibrium therewith.

In an embodiment, the polymorphism is provided in Table 3 or Table 6a or is a polymorphism in linkage disequilibrium therewith.

In an embodiment, the polymorphism is provided in Table 3, Table 6, is rs2274122, is rs1868132, is rs11729561, is rs1984162, is rs8105499 or is a polymorphism in linkage disequilibrium therewith.

In an embodiment, the polymorphism is provided in Table 3, is rs2274122, is rs1868132, is rs11729561, is rs1984162, is rs8105499 or is a polymorphism in linkage disequilibrium therewith.

In another aspect, the present invention provides a method of determining the identity of the alleles of fewer than 100,000 polymorphisms in a human subject selected from the group of subjects consisting of humans in need of assessment for the risk of developing a severe response to a Coronavirus infection to produce a polymorphic profile of the subject, comprising (i) selecting for allelic identity analysis at least two polymorphisms provided in any one of Tables 1 to 6, 8, 19 or 22, or a polymorphism in linkage disequilibrium with one or more thereof, (ii) detecting, in a biological sample derived from the human subject, the polymorphisms, and (iii) producing the polymorphic profile of the subject screening based on the identity of the alleles analysed in step (ii), wherein fewer than 100,000 polymorphisms are selected for allelic identity analysis in step (i) and the same fewer than 100,000 polymorphisms are analysed in step (ii).

In an embodiment of the above aspect, fewer than 100,000 polymorphisms, fewer than 50,000 polymorphisms, fewer than 40,000 polymorphisms, fewer than 30,000 polymorphisms, fewer than 20,000 polymorphisms, fewer than 10,000 polymorphisms, fewer than 7,500 polymorphisms, fewer than 5,000 polymorphisms, fewer than 4,000 polymorphisms, fewer than 3,000 polymorphisms, fewer than 2,000 polymorphisms, fewer than 1,000 polymorphisms, fewer than 900 polymorphisms, fewer than 800 polymorphisms, fewer than 700 polymorphisms, fewer than 600 polymorphisms, fewer than 500 polymorphisms, fewer than 400 polymorphisms, fewer than 300 polymorphisms, fewer than 200 polymorphisms, or fewer than 100 polymorphisms, are selected for allelic identity.

In an embodiment of each of the above aspects, the human subject can be Caucasian, African American, Hispanic, Asian, Indian, or Latino. In a preferred embodiment, the human subject is Caucasian.

In an embodiment of each of the above aspects, the method further comprises obtaining the biological sample.

In an embodiment, the polymorphism(s) in linkage disequilibrium has linkage disequilibrium above 0.9. In another embodiment, the polymorphism(s) in linkage disequilibrium has linkage disequilibrium of 1.

The present inventors have also found that a severe response to a Coronavirus infection risk model that relies solely on clinical factors provides useful risk discrimination for assessing a subject's risk of developing a severe response to a Coronavirus infection such as a SARS-CoV-2 infection. Such a test may be particularly useful in circumstances where a rapid decision needs to be made and/or when genetic testing is not readily available. Thus, in another aspect the present invention provides a method for assessing the risk of a human subject developing a severe response to a Coronavirus infection, the method comprising performing a clinical risk assessment of the human subject, wherein the clinical risk assessment comprises obtaining information from the subject on two, three, four, five or more or all of age, gender, race/ethnicity, height, weight, blood type, does the human have or has had an cerebrovascular disease, does the human have or has had a chronic kidney disease, does the human have or has had an autoimmune disease, does the human have or has had an haematological cancer, does the human have or has had an immunocompromised disease, does the human have or has had an non-haematological cancer, does the human have or has had diabetes, does the human have or has had liver disease, does the human have or has had hypertension and does the human have or has had a respiratory disease (other than asthma).

In an embodiment, the method comprises obtaining information from the subject on age and gender.

In an embodiment, the method comprises obtaining information from the subject on age, gender, race/ethnicity, height, weight, does the human have or has had an cerebrovascular disease, does the human have or has had a chronic kidney disease, does the human have or has had diabetes, does the human have or has had an haematological cancer, does the human have or has had hypertension, does the human have or has had an non-haematological cancer, and does the human have or has had a respiratory disease (other than asthma).

In an embodiment, the method comprises obtaining information from the subject on age, gender, race/ethnicity, blood type, height, weight, does the human have or has had an cerebrovascular disease, does the human have or has had a chronic kidney disease, does the human have or has had diabetes, does the human have or has had an haematological cancer, does the human have or has had hypertension, does the human have or has had an immunocompromised disease, does the human have or has had an haematological cancer, does the human have or has had liver disease, does the human have or has had an non-haematological cancer, and does the human have or has had a respiratory disease (other than asthma).

In an embodiment, the method comprises obtaining information from the subject on one or more of all of age, gender, race/ethnicity, blood type, does the human have or has had an autoimmune disease, does the human have or has had an haematological cancer, does the human have or has had an non-haematological cancer, does the human have or has had diabetes, does the human have or has had hypertension and does the human have or has had a respiratory disease (other than asthma).

In another aspect, the present invention provides a method for assessing the risk of a human subject developing a severe response to a Coronavirus infection, the method comprising
i) performing a genetic risk assessment of the human subject, wherein the genetic risk assessment involves detecting, in a biological sample derived from the human subject, polymorphisms at rs10755709, rs112317747, rs112641600, rs118072448, rs2034831, rs7027911 and rs71481792,
ii) performing a clinical risk assessment of the human subject, wherein the clinical risk assessment comprises obtaining information from the subject on age, gender, race/ethnicity, height, weight, does the human have or has had an cerebrovascular disease, does the human have or has had a chronic kidney disease, does the human have or has had diabetes, does the human have or has had an haematological cancer, does the human have or has had hypertension, does the human have or has had an non-haematological cancer, and does the human have or has had a respiratory disease (other than asthma), and
iii) combining the genetic risk assessment with the clinical risk assessment to determine the risk of a human subject developing a severe response to a Coronavirus infection.

In an embodiment,
a) a β coefficient of 0.124239 is assigned for each G allele at rs10755709;
b) a β coefficient of 0.2737487 is assigned for each C allele at rs112317747;
c) a β coefficient of −0.2362513 is assigned for each T allele at rs112641600;
d) a β coefficient of −0.1995879 is assigned for each C allele at rs118072448;
e) a β coefficient of 0.2371955 is assigned for each C allele at rs2034831;
f) a β coefficient of 0.1019074 is assigned for each A allele at rs7027911; and
g) a β coefficient of −0.1058025 is assigned for each T allele at rs71481792.

In an embodiment, the subject is between 50 and 84 years of age and
a) a β coefficient of 0.5747727 is assigned if the subject is between 70 and 74 years of age;
b) a β coefficient of 0.8243711 is assigned if the subject is between 75 and 79 years of age;
c) a β coefficient of 1.013973 is assigned if the subject is between 80 and 84 years of age;
d) a β coefficient of 0.2444891 is assigned if the subject is male;
e) a β coefficient of 0.29311 is assigned if the subject is an ethnicity other than Caucasian;

f) the subjects height (in metres (m)) and weight (in kilograms (kg)) is applied to the formula: (10 times $m^2$) divided by kg, which is multiplied by −1.602056 to provide the β coefficient to be assigned;

g) a β coefficient of 0.4041337 is assigned if the subject has ever been diagnosed as having a cerebrovascular disease;

h) a β coefficient of 0.6938494 is assigned if the subject has ever been diagnosed as having a chronic kidney disease;

i) a β coefficient of 0.4297612 is assigned if the subject has ever been diagnosed as having diabetes;

j) a β coefficient of 1.003877 is assigned if the subject has ever been diagnosed as having haematological cancer;

k) a β coefficient of 0.2922307 is assigned if the subject has ever been diagnosed as having hypertension;

l) a β coefficient of 0.2558464 is assigned if the subject has ever been diagnosed as having a non-haematological cancer; and m) a β coefficient of 1.173753 is assigned if the subject has ever been diagnosed as having a respiratory disease (other than asthma).

In an embodiment, the subject is between 18 and 49 years of age and a) a β coefficient of −1.3111 is assigned if the subject is between 18 and 29 years of age;

b) a β coefficient of −0.8348 is assigned if the subject is between 30 and 39 years of age;

c) a β coefficient of −0.4038 is assigned if the subject is between 40 and 49 years of age;

d) a β coefficient of 0.2444891 is assigned if the subject is male; e) a β coefficient of 0.29311 is assigned if the subject is an ethnicity other than Caucasian;

f) the subjects height (in metres (m)) and weight (in kilograms (kg)) is applied to the formula: (10 times $m^2$) divided by kg, which is multiplied by −1.602056 to provide the β coefficient to be assigned;

g) a β coefficient of 0.4041337 is assigned if the subject has ever been diagnosed as having a cerebrovascular disease;

h) a β coefficient of 0.6938494 is assigned if the subject has ever been diagnosed as having a chronic kidney disease;

i) a β coefficient of 0.4297612 is assigned if the subject has ever been diagnosed as having diabetes;

j) a β coefficient of 1.003877 is assigned if the subject has ever been diagnosed as having haematological cancer;

k) a β coefficient of 0.2922307 is assigned if the subject has ever been diagnosed as having hypertension;

l) a β coefficient of 0.2558464 is assigned if the subject has ever been diagnosed as having a non-haematological cancer; and m) a β coefficient of 1.173753 is assigned if the subject has ever been diagnosed as having a respiratory disease (other than asthma).

In an embodiment, the subject is between 18 and 84 years of age and a) a β coefficient of −1.3111 is assigned if the subject is between 18 and 29 years of age;

b) a β coefficient of −0.8348 is assigned if the subject is between 30 and 39 years of age;

c) a β coefficient of −0.4038 is assigned if the subject is between 40 and 49 years of age;

d) a β coefficient of 0.5747727 is assigned if the subject is between 70 and 74 years of age;

e) a β coefficient of 0.8243711 is assigned if the subject is between 75 and 79 years of age;

f) a β coefficient of 1.013973 is assigned if the subject is between 80 and 84 years of age;

g) a β coefficient of 0.2444891 is assigned if the subject is male;

h) a β coefficient of 0.29311 is assigned if the subject is an ethnicity other than Caucasian;

i) the subjects height (in metres (m)) and weight (in kilograms (kg)) is applied to the formula: (10 times $m^2$) divided by kg, which is multiplied by −1.602056 to provide the β coefficient to be assigned;

j) a β coefficient of 0.4041337 is assigned if the subject has ever been diagnosed as having a cerebrovascular disease;

k) a β coefficient of 0.6938494 is assigned if the subject has ever been diagnosed as having a chronic kidney disease;

l) a β coefficient of 0.4297612 is assigned if the subject has ever been diagnosed as having diabetes;

m) a β coefficient of 1.003877 is assigned if the subject has ever been diagnosed as having haematological cancer;

n) a β coefficient of 0.2922307 is assigned if the subject has ever been diagnosed as having hypertension;

o) a β coefficient of 0.2558464 is assigned if the subject has ever been diagnosed as having a non-haematological cancer; and p) a β coefficient of 1.173753 is assigned if the subject has ever been diagnosed as having a respiratory disease (other than asthma).

In an embodiment, in step iii) the genetic risk assessment is combined with the clinical risk assessment using the following formula:

$$\text{Log Odds (LO)} = -1.36523 + \text{SRF} + \Sigma \text{ Clinical } \beta \text{ coefficients},$$

and wherein SRF is the SNP Risk Factor which is determined using the following formula:

$$\Sigma(\text{No of Risk Alleles} \times \text{SNP } \beta \text{ coefficient}).$$

In another aspect, the present invention provides a method for assessing the risk of a human subject developing a severe response to a Coronavirus infection, the method comprising i) performing a genetic risk assessment of the human subject, wherein the genetic risk assessment involves detecting, in a biological sample derived from the human subject, polymorphisms at rs10755709, rs112317747, rs112641600, rs115492982, rs118072448, rs1984162, rs2034831, rs7027911 and rs71481792, ii) performing a clinical risk assessment of the human subject, wherein the clinical risk assessment comprises obtaining information from the subject of age, gender, race/ethnicity, blood type, height, weight, does the human have or has had an cerebrovascular disease, does the human have or has had a chronic kidney disease, does the human have or has had diabetes, does the human have or has had an haematological cancer, does the human have or has had hypertension, does the human have or has had an immunocompromised disease, does the human have or has had an haematological cancer, does the human have or has had liver disease, does the human have or has had an non-haematological cancer, and does the human have or has had a respiratory disease (other than asthma), and iii) combining the genetic risk assessment with the clinical risk assessment to determine the risk of a human subject developing a severe response to a Coronavirus infection.

In an embodiment, a) a β coefficient of 0.1231766 is assigned for each G allele at rs10755709;

b) a β coefficient of 0.2576692 is assigned for each C allele at rs112317747;

c) a β coefficient of −0.2384001 is assigned for each T allele at rs112641600;

d) a β coefficient of −0.1965609 is assigned for each C allele at rs118072448;

e) a β coefficient of 0.2414792 is assigned for each C allele at rs2034831;

f) a β coefficient of 0.0998459 is assigned for each A allele at rs7027911;

g) a β coefficient of −0.1032044 is assigned for each T allele at rs71481792;

h) a β coefficient of 0.4163575 is assigned for each A allele at rs115492982; and i) a β coefficient of 0.1034362 is assigned for each A allele at rs1984162.

In a further embodiment, the subject is between 50 and 84 years of age and a) a β coefficient of 0.1677566 is assigned if the subject is between 65 and 69 years of age;

b) a β coefficient of 0.6352682 is assigned if the subject is between 70 and 74 years of age;

c) a β coefficient of 0.8940548 is assigned if the subject is between 75 and 79 years of age;

d) a β coefficient of 1.082477 is assigned if the subject is between 80 and 84 years of age;

e) a β coefficient of 0.2418454 is assigned if the subject is male;

f) a β coefficient of 0.2967777 is assigned if the subject is an ethnicity other than Caucasian;

g) the subjects height (in metres (m)) and weight (in kilograms (kg)) is applied to the formula: (10 times $m^2$) divided by kg, which is multiplied by −1.560943 to provide the β coefficient to be assigned;

h) a β coefficient of 0.3950113 is assigned if the subject has ever been diagnosed as having a cerebrovascular disease;

i) a β coefficient of 0.6650257 is assigned if the subject has ever been diagnosed as having a chronic kidney disease;

j) a β coefficient of 0.4126633 is assigned if the subject has ever been diagnosed as having diabetes;

k) a β coefficient of 1.001079 is assigned if the subject has ever been diagnosed as having haematological cancer;

l) a β coefficient of 0.2640989 is assigned if the subject has ever been diagnosed as having hypertension;

m) a β coefficient of 0.2381579 is assigned if the subject has ever been diagnosed as having a non-haematological cancer;

n) a β coefficient of 1.148496 is assigned if the subject has ever been diagnosed as having a respiratory disease (other than asthma);

o) a β coefficient of −0.229737 is assigned if the subject has an ABO blood type;

p) a β coefficient of 0.6033541 is assigned if the subject has ever been diagnosed as having a immunocompromised disease;

q) a β coefficient of 0.2301902 is assigned if the subject has ever been diagnosed as having liver disease.

In an embodiment, in step iii) the genetic risk assessment is combined with the clinical risk assessment using the following formula:

Log Odds (LO)=1.469939+SRF+Σ Clinical β coefficients, and wherein SRF is the SNP Risk Factor which is determined using the following formula:

Σ(No of Risk Alleles×SNP β coefficient).

In an embodiment, a method of the invention further comprises determining the probability the subject would require hospitalisation if infected with a Coronavirus using the following formula:

$e^{LO}/(1+e^{LO})$, which is then multiplied by 100 to obtain a percent chance of hospitalisation being required.

In an embodiment of each of the above aspects, the risk assessment produces a score and the method further comprises comparing the score to a predetermined threshold, wherein if the score is at, or above, the threshold the subject is assessed at being at risk of developing a severe response to a Coronavirus infection.

In an embodiment, if it is determined the subject has a risk of developing a severe response to a Coronavirus infection, the subject is more likely than someone assessed as low risk, or when compared to the average risk in the population, to be admitted to hospital for intensive care.

In a further aspect, the present invention provides a method for determining the need for routine diagnostic testing of a human subject for a Coronavirus infection comprising assessing the risk of the subject for developing a severe response to a Coronavirus infection using a method of the invention.

In another aspect, the present invention provides a method of screening for a severe response to a Coronavirus infection in a human subject, the method comprising assessing the risk of the subject for developing a severe response to a Coronavirus infection using a method of the invention, and routinely screening for a Coronavirus infection in the subject if they are assessed as having a risk for developing a severe response to a Coronavirus infection.

In an embodiment of the above two aspects, the screening involves analysing the subject for the virus or a symptom thereof.

In a further aspect, the present invention provides a method for determining the need of a human subject for prophylactic anti-Coronavirus therapy comprising assessing the risk of the subject for developing a severe response to a Coronavirus infection using a method of the invention.

In yet another aspect, the present invention provides a method for preventing or reducing the risk of a severe response to a Coronavirus infection in a human subject, the method comprising assessing the risk of the subject for developing a severe response to a Coronavirus infection using a method of the invention, and if they are assessed as having a risk for developing a severe response to a Coronavirus infection 1) administering an anti-Coronavirus therapy and/or 2) isolating the subject.

In an aspect, the present invention provides an anti-Coronavirus infection therapy for use in preventing a severe response to a Coronavirus infection in a human subject at risk thereof, wherein the subject is assessed as having a risk for developing a severe response to a Coronavirus infection using a method of the invention.

Many anti-Coronavirus therapies, such as anti-SARS-CoV-2 virus therapies, are in development. The skilled person would appreciate that any therapy shown to be successful can be used in the above methods. Possible examples include, but are not limited to, intubation to assist breathing, an anti-Coronavirus—such as anti-SARS-CoV-2 virus—vaccine, convalescent plasma (plasma from people who have been infected, developed antibodies to the virus, and have then recovered), chloroquine, hydroxychloroquine (with or without zinc), Favipiravir, Remdesivir, Ivermectin, Quercetin, Kaletra (lopinavir/ritonavir), Arbidol, Baricitinib, CM4620-IE, an IL-6 inhibitor, Tocilizumab and stem cells such as mesenchymal stem cells. In another embodiment, the therapy is Vitamin D. Other examples of therapy include, Dexamethasone (or other corticosteroids such as prednisone, methylprednisolone, or hydrocortisone), Baricitinib in combination with remdesivir, anticoagulation drugs ("blood thinners"), bamlanivimab and etesevimab, convalescent plasma, tocilizumab with corticosteroids, Casirivimab and Imdevimab, Atorvastatin, GRP78 and siRNA-nanoparticle formulations.

Once a vaccine (or indeed possibly many different anti-Coronavirus therapies) is developed it is highly likely there will be supply issues and decisions will need to be made about why one person will receive the vaccine first when compared to another person. The present invention can thus be used to determine who is at most risk, and the anti-Coronavirus therapy (such as a vaccine) first administered to people assessed as likely to develop a severe response to a Coronavirus infection.

In an embodiment, the vaccine is an mRNA vaccine. In an embodiment, the vaccine is a protein vaccine. Examples of vaccines that can be administered include, but are not limited to, the Pfizer-BioNTech vaccine, the Moderna vaccine, the Johnson & Johnson vaccine, the Oxford-AstraZeneca vaccine and the Novavax vaccine (see, for example, Katella, 2021).

In another embodiment, the present invention provides a method for stratifying a group of human subjects for a clinical trial of a candidate therapy, the method comprising assessing the individual risk of the subjects for developing a severe response to a Coronavirus infection using a method of the invention, and using the results of the assessment to select subjects more likely to be responsive to the therapy.

Also provided is a kit comprising at least two sets of primers for amplifying two or more nucleic acids, wherein the two or more nucleic acids comprise a polymorphism selected from any one of Tables 1 to 6, 8, 19 or 22, or a single nucleotide polymorphism in linkage disequilibrium with one or more thereof.

In an embodiment, the kit comprises sets of primers for amplifying nucleic acids comprising each of the polymorphisms provided in Table 4, or a single nucleotide polymorphism in linkage disequilibrium with one or more thereof.

In another aspect, the present invention provides a genetic array comprising at least two sets of probes for hybridising to two or more nucleic acids, wherein the two or more nucleic acids comprise a polymorphism selected from any one of Tables 1 to 6, 8, 19 or 22, or a single nucleotide polymorphism in linkage disequilibrium with one or more thereof.

In an embodiment, the array comprises probes hybridising to nucleic acids comprising each of the polymorphisms provided in Table 4, or a single nucleotide polymorphism in linkage disequilibrium with one or more thereof.

In an aspect, the present invention provides a computer implemented method for assessing the risk of a human subject developing a severe response to a Coronavirus infection, the method operable in a computing system comprising a processor and a memory, the method comprising:
receiving genetic risk data for the human subject, wherein the genetic risk data was obtained by a method of the invention;
processing the data to obtain the risk of a human subject developing a severe response to a Coronavirus infection; and
outputting the risk of a human subject developing a severe response to a Coronavirus infection.

In an aspect, the present invention provides a computer implemented method for assessing the risk of a human subject developing a severe response to a Coronavirus infection, the method operable in a computing system comprising a processor and a memory, the method comprising:
receiving clinical risk data and genetic risk data for the human subject, wherein the clinical risk data and genetic risk data were obtained by a method of the invention;
processing the data to combine the clinical risk data with the genetic risk data to obtain the risk of a human subject developing a severe response to a Coronavirus infection; and
outputting the risk of a human subject developing a severe response to a Coronavirus infection.

In a further aspect, the present invention provides a computer-implemented method for assessing the risk of a human subject developing a severe response to a Coronavirus infection, the method operable in a computing system comprising a processor and a memory, the method comprising:
receiving at least one clinical variable associated with the human subject, wherein at least one clinical variable was obtained by a method of the invention;
processing the data to obtain the risk of a human subject developing a severe response to a Coronavirus infection; and
outputting the risk of a human subject developing a severe response to a Coronavirus infection.

In an embodiment of the three above aspects, processing the data is performed using a risk assessment model, where the risk assessment model has been trained using a training dataset comprising data relating to Coronavirus infection response severity and the genetic data and/or clinical data. In another embodiment, the method further comprises displaying or communicating the risk to a user.

In an aspect, the present invention provides a system for assessing the risk of a human subject developing a severe response to a Coronavirus infection comprising:
system instructions for performing a genetic risk assessment of the human subject according to a method of the invention; and
system instructions to obtain the risk of a human subject developing a severe response to a Coronavirus infection.

In an aspect, the present invention provides a system for assessing the risk of a human subject developing a severe response to a Coronavirus infection comprising:
system instructions for performing a clinical risk assessment and a genetic risk assessment of the human subject according to a method of the invention; and
system instructions for combining the clinical risk assessment and the genetic risk assessment to obtain the risk of a human subject developing a severe response to a Coronavirus infection.

In an aspect, the present invention provides a system for assessing the risk of a human subject developing a severe response to a Coronavirus infection comprising:
system instructions for performing a clinical risk assessment of the human subject using the method according to any one of claims 20 to 26 or 36 to 39; and
system instructions to obtain the risk of a human subject developing a severe response to a Coronavirus infection.

In an embodiment, the risk data for the subject is received from a user interface coupled to the computing system. In another embodiment, the risk data for the subject is received from a remote device across a wireless communications network. In another embodiment, the user interface or remote device is a SNP array platform. In another embodiment, outputting comprises outputting information to a user interface coupled to the computing system. In another embodiment, outputting comprises transmitting information to a remote device across a wireless communications network.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Receiver operating characteristic curves for models with different amounts of information. The area under the receiver operating characteristic curve was 0.786 for the combined model, 0.723 for the clinical model, 0.680 for the SNP score, and 0.635 for the age and sex model.

Figure 2:
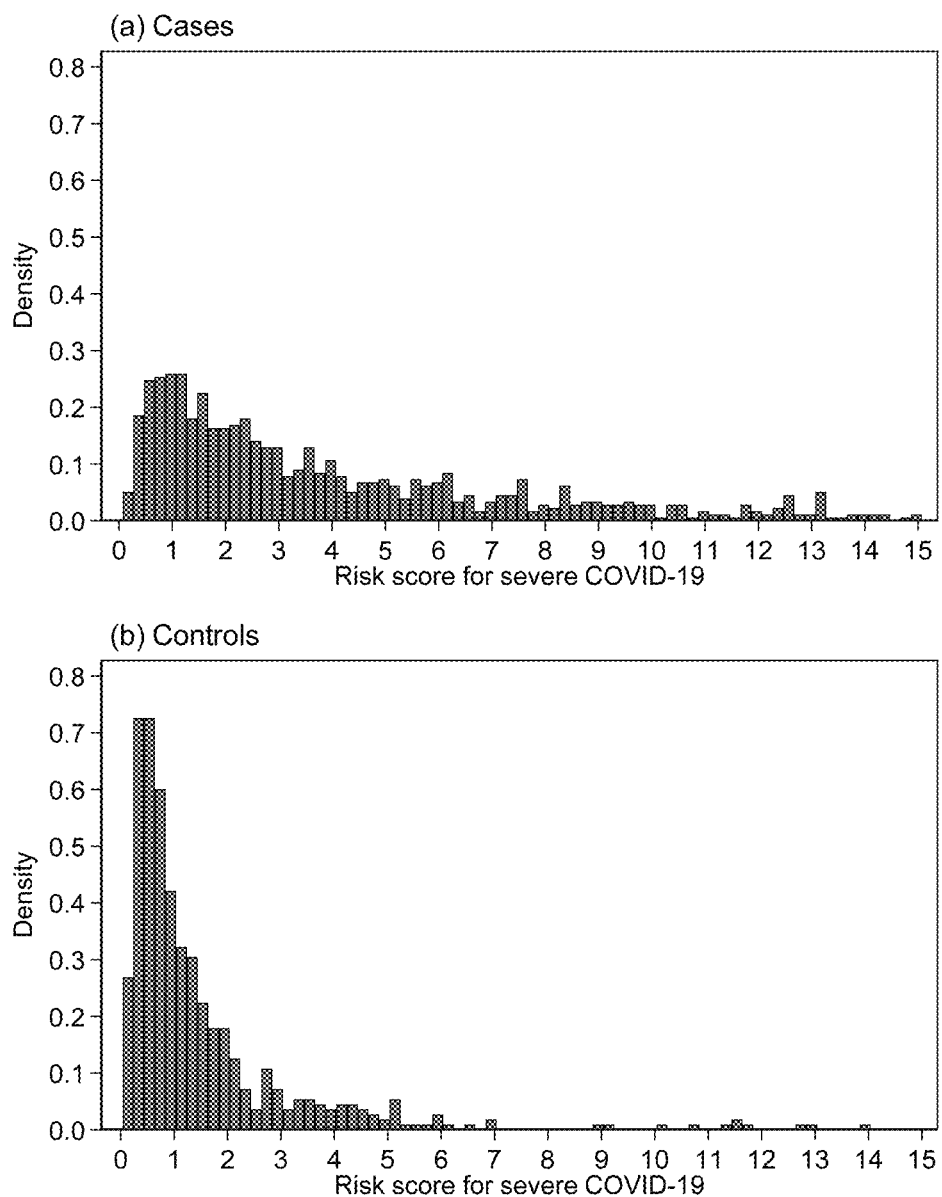

FIG. 2. Distribution of COVID risk score for (a) cases and (b) controls. Note that 130 (13%) cases and 6 (1%) controls with scores over 15 have been omitted to facilitate the display of the distribution.

Figure 3:
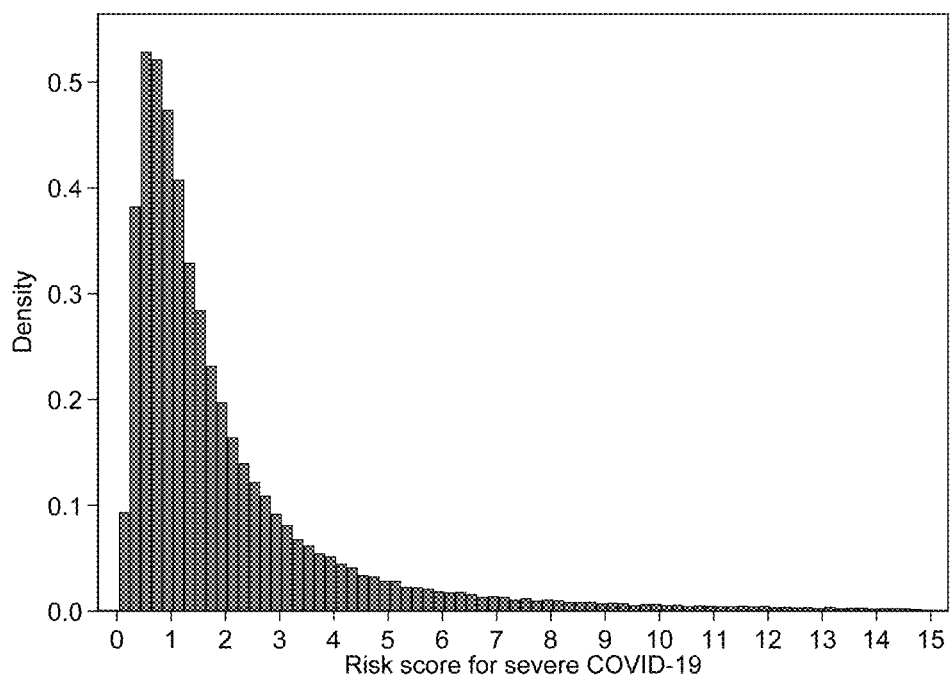

FIG. 3. Distribution of COVID-19 risk score in UK Biobank. Note that 7,769 (1.8%) scores over 15 have been omitted to facilitate the display of the distribution.

Figure 4:
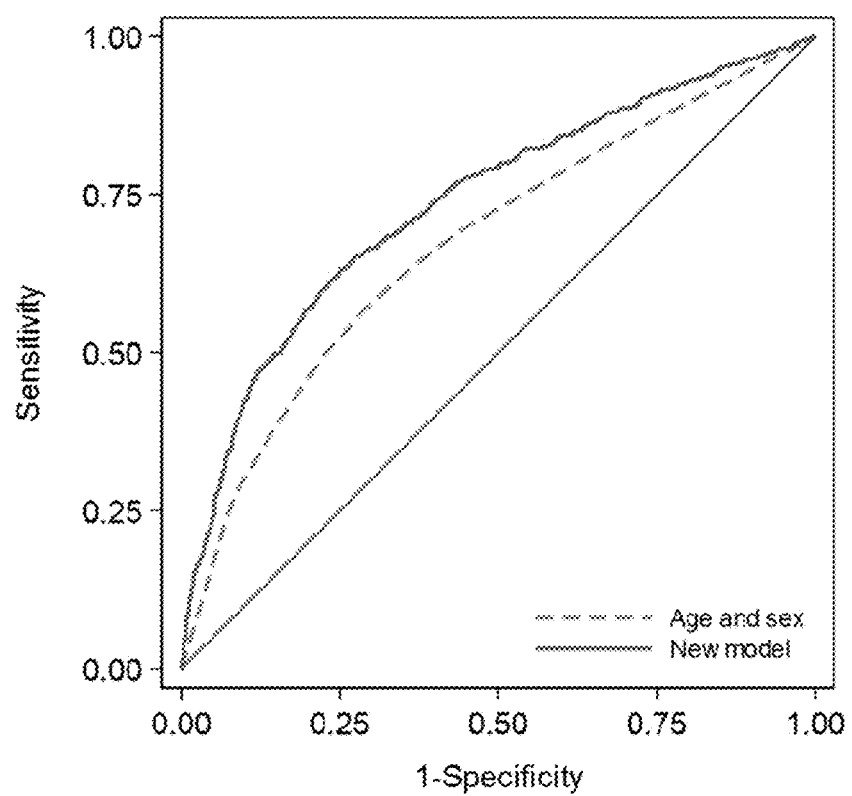

FIG. 4. Receiver operating characteristic curves for the age and sex model and the "full model" in the 30% validation dataset. The new model has an area under the curve (AUC) of 0.732 (95% CI=0.708, 0.756) and the age and sex model has an AUC of 0.671 (95% 0=0.646, 0.696).

Figure 5:
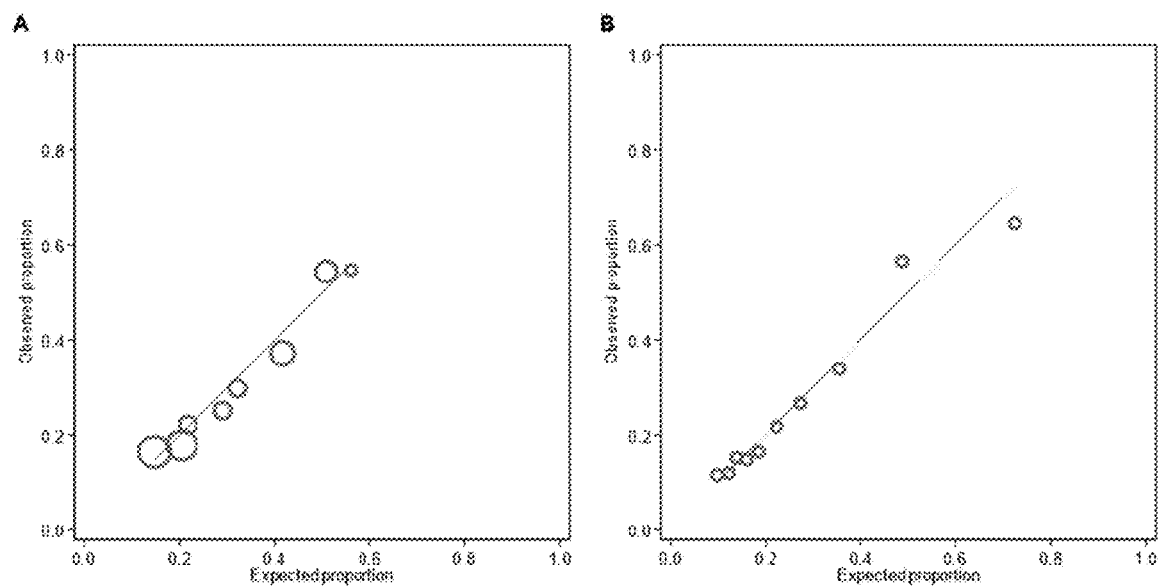

FIG. 5. Calibration plots for the (A) age and sex model and (B) "full model" in the validation dataset.

Figure 6:
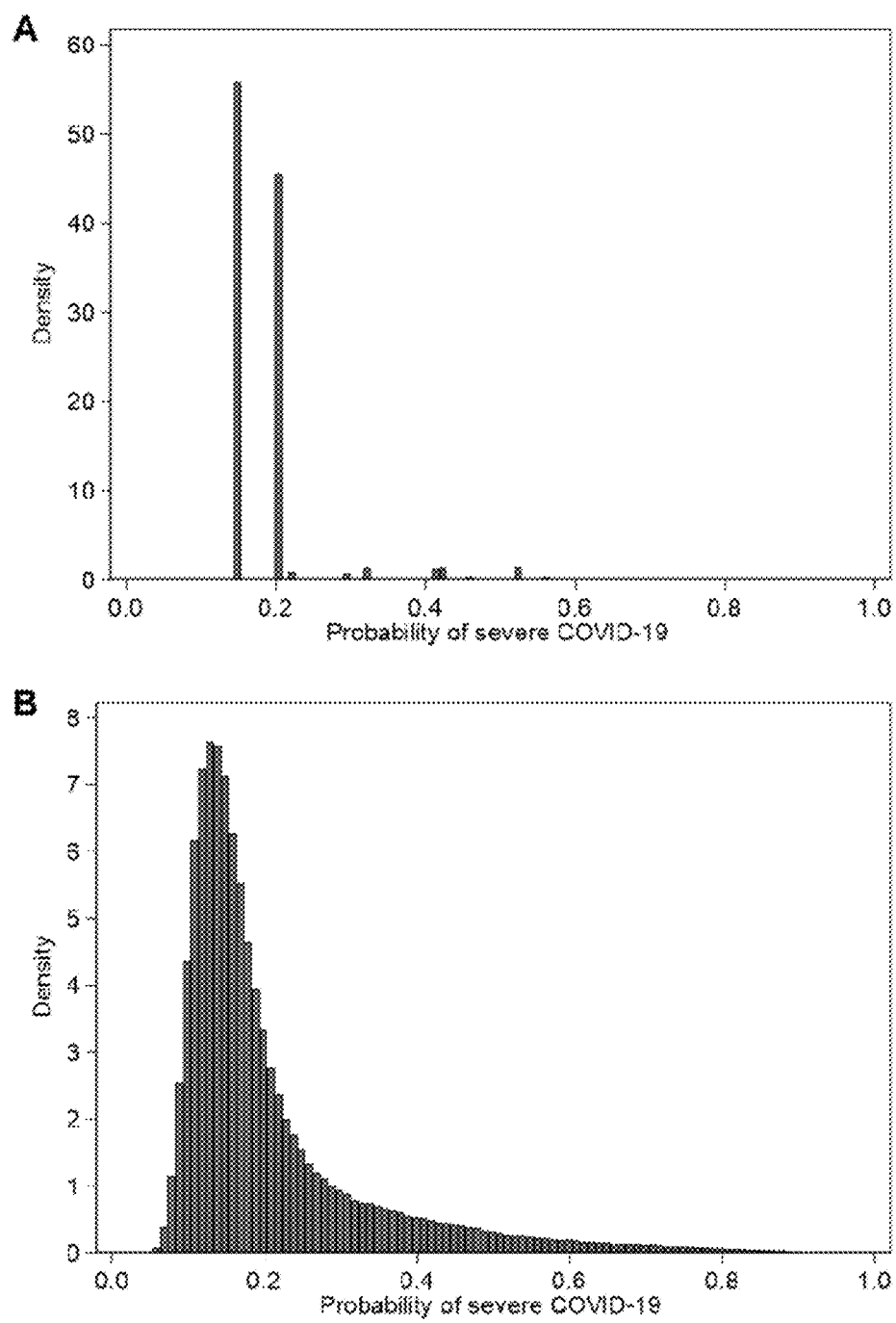

FIG. 6. Distribution of probability of severe COVID-19 in all of UK Biobank for (A) age and sex model and (B) the full model.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., epidemiological analysis, molecular genetics, risk assessment and clinical studies).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

It is to be understood that this disclosure is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, optionally include plural referents unless the content clearly dictates otherwise. Thus, for example, reference to "a probe" optionally includes a plurality of probe molecules; similarly, depending on the context, use of the term "a nucleic acid" optionally includes, as a practical matter, many copies of that nucleic acid molecule.

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−10%, more preferably +/−5%, more preferably +/−1%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

"Coronavirus" is a group of related RNA viruses that typically cause diseases in mammals and birds, such as respiratory tract infections in humans. Coronaviruses constitute the subfamily Orthocoronavirinae in the family Coronaviridae. Coronaviruses are enveloped viruses with a positive-sense single-stranded RNA genome and a nucleocapsid of helical symmetry. Coronaviruses have characteristic club-shaped spikes that project from their surface. Examples of Coronaviruses which cause disease in humans include, but are not necessarily limited to, Severe acute respiratory syndrome-related coronavirus (SARS-CoV or SARS-CoV-2), Middle East respiratory syndrome-related coronavirus (MERS), Human coronavirus OC43, Human coronavirus HKU1, Human coronavirus 229E and Human coronavirus NL63. In some embodiments, the SARS-CoV-2 the strain is selected from, but not limited to, the L strain, the S strain, the V strain, the G strain, the GR strain, the GH strain, hCoV-19/Australia/VIC01/2020, BetaCoV/Wuhan/WIV04/2019, B.1.1.7 variant, B.1.351 variant, B.1.427 variant, B.1.429 variant and P.1 variant.

As used herein, "risk assessment" refers to a process by which a subject's risk of developing a severe response to a Coronavirus infection can be assessed. A risk assessment will typically involve obtaining information relevant to the subject's risk of developing a severe response to a Coronavirus infection, assessing that information, and quantifying the subject's risk of developing a severe response to a Coronavirus infection, for example, by producing a risk score.

As used herein, the term "a severe response to a Coronavirus infection" encompasses any factor, or a symptom thereof, considered by a medical practitioner that would warrant the subject being hospitalised, the subject's life being at risk, or the subject requiring assistance to breath.

Examples of symptoms of a severe response to a Coronavirus infection include, but are not limited to, difficulty breathing or shortness of breath, chest pain or pressure, loss of speech or loss of movement. A phenotype that displays a predisposition for a severe response to a Coronavirus infection, can, for example, show a higher likelihood that a severe response to a Coronavirus infection will develop in an individual with the phenotype than in members of a relevant general population under a given set of environmental conditions (diet, physical activity regime, geographic location, etc.).

As used herein, "biological sample" refers to any sample comprising nucleic acids, especially DNA, from or derived from a human patient, e.g., bodily fluids (blood, saliva, urine etc.), biopsy, tissue, and/or waste from the patient. Thus, tissue biopsies, stool, sputum, saliva, blood, lymph, or the like can easily be screened for polymorphisms, as can essentially any tissue of interest that contains the appropriate nucleic acids. In one embodiment, the biological sample is a cheek cell sample. These samples are typically taken, following informed consent, from a patient by standard medical laboratory methods. The sample may be in a form taken directly from the patient, or may be at least partially processed (purified) to remove at least some non-nucleic acid material.

As used herein, "gender" and "sex" are used interchangeably and refer to an individual's biological reproductive anatomy. In an embodiment, an individual's gender/sex is self-identified.

As used herein, "human subject", "human" and subject" are used interchangeably and refer to the individual being assessed for risk of developing a severe response to a coronavirus infection.

A "polymorphism" is a locus that is variable; that is, within a population, the nucleotide sequence at a polymorphism has more than one version or allele. One example of a polymorphism is a "single nucleotide polymorphism" (SNP), which is a polymorphism at a single nucleotide position in a genome (the nucleotide at the specified position varies between individuals or populations). Other examples include a deletion or insertion of one or more base pairs at the polymorphism locus.

As used herein, the term "SNP" or "single nucleotide polymorphism" refers to a genetic variation between individuals; e.g., a single nitrogenous base position in the DNA of organisms that is variable. As used herein, "SNPs" is the plural of SNP. Of course, when one refers to DNA herein, such reference may include derivatives of the DNA such as amplicons, RNA transcripts thereof, etc.

The term "allele" refers to one of two or more different nucleotide sequences that occur or are encoded at a specific locus, or two or more different polypeptide sequences encoded by such a locus. For example, a first allele can occur on one chromosome, while a second allele occurs on a second homologous chromosome, e.g., as occurs for different chromosomes of a heterozygous individual, or between different homozygous or heterozygous individuals in a population. An allele "positively" correlates with a trait when it is linked to it and when presence of the allele is an indicator that the trait or trait form will occur in an individual comprising the allele. An allele "negatively" correlates with a trait when it is linked to it and when presence of the allele is an indicator that a trait or trait form will not occur in an individual comprising the allele.

A marker polymorphism or allele is "correlated" or "associated" with a specified phenotype (a severe response to a Coronavirus infection susceptibility, etc.) when it can be statistically linked (positively or negatively) to the phenotype. Methods for determining whether a polymorphism or allele is statistically linked are known to those in the art. That is, the specified polymorphism occurs more commonly in a case population (e.g., a severe response to a Coronavirus infection patients) than in a control population (e.g., individuals that do not have a severe response to a Coronavirus infection). This correlation is often inferred as being causal in nature, but it need not be, simple genetic linkage to (association with) a locus for a trait that underlies the phenotype is sufficient for correlation/association to occur.

The phrase "linkage disequilibrium" (LD) is used to describe the statistical correlation between two neighbouring polymorphic genotypes. Typically, LD refers to the correlation between the alleles of a random gamete at the two loci, assuming Hardy-Weinberg equilibrium (statistical independence) between gametes. LD is quantified with either Lewontin's parameter of association (D') or with Pearson correlation coefficient (r) (Devlin and Risch, 1995). Two loci with a LD value of 1 are said to be in complete LD. At the other extreme, two loci with a LD value of 0 are termed to be in linkage equilibrium. Linkage disequilibrium is calculated following the application of the expectation maximization algorithm (EM) for the estimation of haplotype frequencies (Slatkin and Excoffier, 1996). LD ($r^2$) values according to the present disclosure for neighbouring genotypes/loci are selected above 0.1, preferably, above 0.2, more preferable above 0.5, more preferably, above 0.6, still more preferably, above 0.7, preferably, above 0.8, more preferably above 0.9, ideally about 1.0.

Another way one of skill in the art can readily identify polymorphisms in linkage disequilibrium with the polymorphisms of the present disclosure is determining the LOD score for two loci. LOD stands for "logarithm of the odds", a statistical estimate of whether two genes, or a gene and a disease gene, are likely to be located near each other on a chromosome and are therefore likely to be inherited. A LOD score of between about 2-3 or higher is generally understood to mean that two genes are located close to each other on the chromosome. Various examples of polymorphisms in linkage disequilibrium with the polymorphisms of the present disclosure are shown in Tables 1 to 6, 8, 19 or 22. The present inventors have found that many of the polymorphisms in linkage disequilibrium with the polymorphisms of the present disclosure have a LOD score of between about 2-50. Accordingly, in an embodiment, LOD values according to the present disclosure for neighbouring genotypes/loci are selected at least above 2, at least above 3, at least above 4, at least above 5, at least above 6, at least above 7, at least above 8, at least above 9, at least above 10, at least above 20 at least above 30, at least above 40, at least above 50.

In another embodiment, polymorphisms in linkage disequilibrium with the polymorphisms of the present disclosure can have a specified genetic recombination distance of less than or equal to about 20 centimorgan (cM) or less. For example, 15 cM or less, 10 cM or less, 9 cM or less, 8 cM or less, 7 cM or less, 6 cM or less, 5 cM or less, 4 cM or less, 3 cM or less, 2 cM or less, 1 cM or less, 0.75 cM or less, 0.5 cM or less, 0.25 cM or less, or 0.1 cM or less. For example, two linked loci within a single chromosome segment can undergo recombination during meiosis with each other at a frequency of less than or equal to about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.75%, about 0.5%, about 0.25%, or about 0.1% or less.

In another embodiment, polymorphisms in linkage disequilibrium with the polymorphisms of the present disclosure are within at least 100 kb (which correlates in humans to about 0.1 cM, depending on local recombination rate), at least 50 kb, at least 20 kb or less of each other.

For example, one approach for the identification of surrogate markers for a particular polymorphism involves a simple strategy that presumes that polymorphisms surrounding the target polymorphism are in linkage disequilibrium and can therefore provide information about disease susceptibility. Thus, as described herein, surrogate markers can therefore be identified from publicly available databases, such as HAPMAP, by searching for polymorphisms fulfilling certain criteria which have been found in the scientific community to be suitable for the selection of surrogate marker candidates (see, for example, Table 6a which provides surrogates of the polymorphisms in Table 3, and Table 6b which provides surrogates of the polymorphisms in Table 4).

"Allele frequency" refers to the frequency (proportion or percentage) at which an allele is present at a locus within an individual, within a line or within a population of lines. For example, for an allele "A," diploid individuals of genotype "AA," "Aa," or "aa" have allele frequencies of 1.0, 0.5, or 0.0, respectively. One can estimate the allele frequency within a line or population (e.g., cases or controls) by averaging the allele frequencies of a sample of individuals from that line or population. Similarly, one can calculate the allele frequency within a population of lines by averaging the allele frequencies of lines that make up the population. In an embodiment, the term "allele frequency" is used to define the minor allele frequency (MAF). MAF refers to the frequency at which the least common allele occurs in a given population.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "locus" is a chromosomal position or region. For example, a polymorphic locus is a position or region where a polymorphic nucleic acid, trait determinant, gene or marker is located. In a further example, a "gene locus" is a specific chromosome location (region) in the genome of a species where a specific gene can be found.

A "marker," "molecular marker" or "marker nucleic acid" refers to a nucleotide sequence or encoded product thereof (e.g., a protein) used as a point of reference when identifying a locus or a linked locus. A marker can be derived from genomic nucleotide sequence or from expressed nucleotide sequences (e.g., from an RNA, nRNA, mRNA, a cDNA, etc.), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Nucleic acids are "complementary" when they specifically hybridize in solution, e.g., according to Watson-Crick base pairing rules. A "marker locus" is a locus that can be used to track the presence of a second linked locus, e.g., a linked or correlated locus that encodes or contributes to the population variation of a phenotypic trait. For example, a marker locus can be used to monitor segregation of alleles at a locus, such as a quantitative trait locus (QTL), that are genetically or physically linked to the marker locus. Thus, a "marker allele," alternatively an "allele of a marker locus" is one of a plurality of polymorphic nucleotide sequences found at a marker locus in a population that is polymorphic for the marker locus. Each of the identified markers is expected to be in close physical and genetic proximity (resulting in physical and/or genetic linkage) to a genetic element, e.g., a QTL, that contributes to the relevant phenotype. Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of allele specific hybridization (ASH), detection of single nucleotide extension, detection of amplified variable sequences of the genome, detection of self-sustained sequence replication, detection of simple sequence repeats (SSRs), detection of single nucleotide polymorphisms (SNPs), or detection of amplified fragment length polymorphisms (AFLPs).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

An "amplicon" is an amplified nucleic acid, e.g., a nucleic acid that is produced by amplifying a template nucleic acid by any available amplification method (e.g., PCR, LCR, transcription, or the like).

A "gene" is one or more sequence(s) of nucleotides in a genome that together encode one or more expressed molecules, e.g., an RNA, or polypeptide. The gene can include coding sequences that are transcribed into RNA which may then be translated into a polypeptide sequence, and can include associated structural or regulatory sequences that aid in replication or expression of the gene.

A "genotype" is the genetic constitution of an individual (or group of individuals) at one or more genetic loci. Genotype is defined by the allele(s) of one or more known loci of the individual, typically the compilation of alleles inherited from its parents.

A "haplotype" is the genotype of an individual at a plurality of genetic loci on a single DNA strand. Typically, the genetic loci described by a haplotype are physically and genetically linked, i.e., on the same chromosome strand.

A "set" of markers (polymorphisms), probes or primers refers to a collection or group of markers probes, primers, or the data derived therefrom, used for a common purpose, e.g., identifying an individual with a specified genotype (e.g., risk of developing a severe response to a Coronavirus infection). Frequently, data corresponding to the markers, probes or primers, or derived from their use, is stored in an electronic medium. While each of the members of a set possess utility with respect to the specified purpose, individual markers selected from the set as well as subsets including some, but not all of the markers, are also effective in achieving the specified purpose.

The polymorphisms and genes, and corresponding marker probes, amplicons or primers described above can be embodied in any system herein, either in the form of physical nucleic acids, or in the form of system instructions that include sequence information for the nucleic acids. For example, the system can include primers or amplicons corresponding to (or that amplify a portion of) a gene or polymorphism described herein. As in the methods above, the set of marker probes or primers optionally detects a plurality of polymorphisms in a plurality of said genes or genetic loci. Thus, for example, the set of marker probes or primers detects at least one polymorphism in each of these polymorphisms or genes, or any other polymorphism, gene or locus defined herein. Any such probe or primer can include a nucleotide sequence of any such polymorphism or gene, or a complementary nucleic acid thereof, or a transcribed product thereof (e.g., a nRNA or mRNA form produced from a genomic sequence, e.g., by transcription or splicing).

As used herein, "Receiver operating characteristic curves" (ROC) refer to a graphical plot of the sensitivity vs. (1−specificity) for a binary classifier system as its discrimination threshold is varied. The ROC can also be represented equivalently by plotting the fraction of true positives (TPR=true positive rate) vs. the fraction of false positives (FPR=false positive rate). Also known as a Relative Operating Characteristic curve, because it is a comparison of two operating characteristics (TPR & FPR) as the criterion changes. ROC analysis provides tools to select possibly optimal models and to discard suboptimal ones independently from (and prior to specifying) the cost context or the class distribution. Methods of using in the context of the disclosure will be clear to those skilled in the art.

As used herein, the phrase "combining the first clinical risk assessment and the genetic risk assessment" refers to any suitable mathematical analysis relying on the results of the assessments. For example, the results of the first clinical risk assessment and the genetic risk assessment may be added, more preferably multiplied.

As used herein, the terms "routinely screening for a severe response to a Coronavirus infection" and "more frequent screening" are relative terms, and are based on a comparison to the level of screening recommended to a subject who has no identified risk of developing a severe response to a Coronavirus infection.

Genetic Risk Assessment

In an aspect, a method for assessing the risk of a human subject developing a severe response to a Coronavirus infection of the invention involves detecting the presence of a polymorphism provided in any one of Tables 1 to 3, 5a or 6, or Tables 1 to 6, 8, 19 or 22, or a polymorphism in linkage disequilibrium therewith. In another aspect, a method of the invention involves a genetic risk assessment performed by analysing the genotype of the subject at two or more loci for polymorphisms associated with a severe response to a Coronavirus infection. Various exemplary polymorphisms associated with a severe response to a Coronavirus infection are discussed in the present disclosure. These polymorphisms vary in terms of penetrance and many would be understood by those of skill in the art to be low penetrance polymorphisms.

The term "penetrance" is used in the context of the present disclosure to refer to the frequency at which a particular polymorphism manifests itself within human subjects with a severe response to a Coronavirus infection. "High penetrance" polymorphisms will almost always be apparent in a human subject with a severe response to a Coronavirus infection while "low penetrance" polymorphisms will only sometimes be apparent. In an embodiment polymorphisms assessed as part of a genetic risk assessment according to the present disclosure are low penetrance polymorphisms.

As the skilled addressee will appreciate, each polymorphism which increases the risk of developing a severe response to a Coronavirus infection has an odds ratio of association with a severe response to a Coronavirus infection of greater than 1.0. In an embodiment, the odds ratio is greater than 1.02. Each polymorphism which decreases the risk of developing a severe response to a Coronavirus infection has an odds ratio of association with a severe response to a Coronavirus infection of less than 1.0. In an embodiment, the odds ratio is less than 0.98. Examples of such polymorphisms include, but are not limited to, those provided in Tables 1 to 3, 5a or 6, or Tables 1 to 6, 8, 19 or 22, or a polymorphism in linkage disequilibrium with one or more thereof. In an embodiment, the genetic risk assessment involves assessing polymorphisms associated with increased risk of developing a severe response to a Coronavirus infection. In another embodiment, the genetic risk assessment involves assessing polymorphisms associated with decreased risk of developing a severe response to a Coronavirus infection. In another embodiment, the genetic risk assessment involves assessing polymorphisms associated with an increased risk of developing a severe response to a Coronavirus infection and polymorphisms associated with a decreased risk of developing a severe response to a Coronavirus infection.

In an embodiment, at least three, at least four, at least five, at least six, at least seven, at least eight, at least nine, at least ten, at least 20, at least 30, at least 40, at least 50, at least 60, at least 70, at least 80, at least 100, at least 120, at least 140, at least 160, at least 180, at least 200, at least 250, at least 300 or at least 306 polymorphisms associated with a severe response to a Coronavirus infection are analysed.

In an embodiment, the at least three, at least four, at least five, at least six, at least seven, at least eight, at least nine, at least ten, at least 20, at least 30, at least 40, at least 50, at least 60, at least 70, at least 80, at least 100, at least 120, at least 140, at least 160, at least 180, at least 200, at least 250, at least 300 or at least 306 polymorphisms associated with a severe response to a Coronavirus infection are selected from the polymorphisms provided in Tables 1 to 3, 5a or 6, Tables 1 to 6, 8, 19 or 22, or a polymorphism in linkage disequilibrium with one or more thereof.

TABLE 1

Informative polymorphisms of the invention.

| Chromosome | Position | SNP ID | Alleles | p-value for association |
|---|---|---|---|---|
| 1 | 31624029 | rs12083278 | G,C | 0.00000243 |
| 1 | 87628173 | rs10873821 | C,T | 0.0000228 |
| 1 | 63766718 | rs112728381 | C,T | 0.0000252 |
| 1 | 2998313 | rs12745140 | G,A | 0.0000317 |
| 1 | 36374101 | rs2765013 | C,T | 0.000039 |
| 1 | 36549664 | rs2274122 | G,A | 0.000107 |
| 1 | 186287454 | rs1830344 | T,C | 0.000127 |
| 1 | 187364290 | rs7517532 | G,C | 0.000136 |
| 1 | 114893146 | rs574339 | T,C | 0.000169 |
| 1 | 222722631 | rs61825527 | A,C | 0.000194 |
| 1 | 31380174 | rs4303117 | A,C | 0.000199 |
| 1 | 88237749 | rs72714531 | T,C | 0.000223 |
| 1 | 101661978 | rs11166552 | C,T | 0.000257 |
| 1 | 37147203 | rs219007 | C,T | 0.000271 |
| 1 | 184803508 | rs630030 | A,G | 0.000271 |
| 1 | 60210649 | rs1004772 | T,C | 0.000289 |

TABLE 1-continued

Informative polymorphisms of the invention.

| Chromosome | Position | SNP ID | Alleles | p-value for association |
|---|---|---|---|---|
| 1 | 83665753 | rs9432945 | C,T | 0.000293 |
| 1 | 36172029 | rs6664663 | C,G | 0.000304 |
| 1 | 161229986 | rs5778200 | A,AC | 0.000326 |
| 1 | 107941708 | rs17018870 | G,A | 0.000328 |
| 1 | 14216150 | rs17350970 | C,T | 0.000346 |
| 1 | 55046392 | rs300269 | G,A | 0.000355 |
| 1 | 230906775 | rs3790971 | A,G | 0.000357 |
| 1 | 60214250 | rs3990361 | A,G | 0.000386 |
| 1 | 208388679 | rs78771609 | A,G | 0.000395 |
| 1 | 3680362 | rs146866117 | T,C | 3.21516E-05 |
| 1 | 10993680 | rs75721992 | C,T | 8.03153E-09 |
| 1 | 15698556 | rs12562412 | G,C | 7.34872E-05 |
| 1 | 15758944 | rs117338853 | A,G | 9.31685E-05 |
| 1 | 16109212 | rs72647169 | G,C | 1.72286E-05 |
| 1 | 17295659 | rs199765517 | T,C | 6.47434E-05 |
| 1 | 20072025 | rs199727655 | A,G | 3.41489E-05 |
| 1 | 22538788 | rs78360109 | A,G | 1.32276E-06 |
| 1 | 34829829 | rs79955780 | G,A | 8.74145E-05 |
| 1 | 38661814 | rs61778695 | C,A | 4.43093E-05 |
| 1 | 67804320 | rs578200723 | GTTA,G | 0.000000482 |
| 1 | 72488455 | rs116544454 | T,G | 1.85829E-05 |
| 1 | 109823418 | rs144022094 | T,C | 3.57493E-05 |
| 1 | 109933450 | rs56072034 | A,G | 4.12342E-05 |
| 1 | 168696733 | rs76129265 | T,G | 7.51539E-05 |
| 1 | 204092087 | rs201772428 | A,G | 4.3011E-06 |
| 1 | 206776460 | rs35252702 | A,G | 1.56671E-07 |
| 1 | 207610967 | rs61821114 | T,C | 3.00757E-05 |
| 1 | 210901242 | rs1934624 | A,T | 5.48665E-05 |
| 1 | 218938774 | rs76354174 | A,G | 7.54499E-05 |
| 1 | 230907829 | rs143186556 | A,G | 5.46536E-05 |
| 1 | 231133014 | rs200114138 | A,G | 3.96515E-06 |
| 1 | 46618634 | rs17102023 | G,A | 0.5 |
| 1 | 150271556 | rs115492982 | A,G | 0.01 |
| 1 | 152684866 | rs2224986 | T,C | 0.8 |
| 1 | 192526317 | rs74508649 | T,C | 0.9 |
| 1 | 239197542 | rs112317747 | C,T | 0.05 |
| 2 | 36905013 | rs6714112 | C,A | 0.00000781 |
| 2 | 217524986 | rs2270360 | A,C | 0.0000245 |
| 2 | 11239618 | rs62120103 | C,T | 0.000116 |
| 2 | 42181679 | rs6740960 | A,T | 0.00012 |
| 2 | 137073048 | rs6430625 | A,G | 0.000144 |
| 2 | 75788396 | rs759255 | C,A | 0.000181 |
| 2 | 11694251 | rs4313952 | A,G | 0.000194 |
| 2 | 140976470 | rs9941558 | A,G | 0.000196 |
| 2 | 13900135 | rs61101702 | TAATA,T | 0.0002 |
| 2 | 182396974 | rs6760007 | T,C | 0.0002 |
| 2 | 46584059 | rs34136947 | T,G | 0.000222 |
| 2 | 6948980 | rs55900661 | G,A | 0.000235 |
| 2 | 175367762 | rs4972443 | T,C | 0.000237 |
| 2 | 217553774 | rs3755137 | T,A | 0.000263 |
| 2 | 2965401 | rs1729903 | C,T | 0.000271 |
| 2 | 182359592 | rs16867434 | T,C | 0.000275 |
| 2 | 50825372 | rs116302817 | C,T | 0.000322 |
| 2 | 217701606 | rs111437052 | A,G | 0.000343 |
| 2 | 52551249 | rs115352379 | T,C | 0.000344 |
| 2 | 45503541 | rs6749256 | G,C | 0.000397 |
| 2 | 11662023 | rs62120186 | C,T | 0.000403 |
| 2 | 52998723 | rs62127009 | A,G | 0.000408 |
| 2 | 22958939 | rs59447738 | G,T | 8.21388E-05 |
| 2 | 23005876 | rs73918088 | A,C | 7.50922E-05 |
| 2 | 25861939 | rs189303418 | T,C | 0.000040202 |
| 2 | 34108876 | rs1718746 | C,G | 8.52475E-05 |
| 2 | 34119632 | rs1705143 | A,G | 8.08594E-05 |
| 2 | 64630299 | rs872241 | G,A | 7.17367E-05 |
| 2 | 64641736 | rs11676644 | C,T | 0.000032141 |
| 2 | 115258481 | rs56735442 | A,G | 3.59163E-05 |
| 2 | 122952399 | rs75945051 | G,A | 4.38486E-05 |
| 2 | 126726522 | rs76187206 | C,G | 5.74668E-05 |
| 2 | 160721407 | chr2_160721407 | A,AC | 4.45501E-05 |
| 2 | 179428061 | rs11896637 | T,C | 1.81846E-06 |
| 2 | 179441917 | rs72646881 | C,T | 1.59099E-05 |
| 2 | 179612315 | rs145581345 | C,T | 8.45307E-05 |
| 2 | 181910717 | rs78593095 | A,G | 2.26398E-05 |
| 2 | 191278341 | rs6725814 | G,A | 1.88302E-05 |
| 2 | 79895332 | rs183569214 | G,T | 0.7 |
| 2 | 80029580 | rs77764981 | T,G | 0.6 |
| 2 | 182353446 | rs2034831 | A,G | 0.02 |
| 3 | 141408691 | rs6440031 | A,G | 0.0000714 |
| 3 | 1093795 | rs1504061 | C,G | 0.0000716 |
| 3 | 125837737 | rs1868132 | C,T | 0.000102 |
| 3 | 125649876 | rs6438947 | T,C | 0.000126 |
| 3 | 38759465 | rs9990137 | A,G | 0.000148 |
| 3 | 155736888 | rs4680228 | C,T | 0.000157 |
| 3 | 24759067 | rs71328493 | C,G | 0.000213 |
| 3 | 46628726 | rs1829538 | G,T | 0.000257 |
| 3 | 71238088 | rs111323182 | T,A | 0.00027 |
| 3 | 143909347 | rs13089585 | T,C | 0.000302 |
| 3 | 2357581 | rs56035150 | A,G | 0.000318 |
| 3 | 5893097 | rs74827709 | G,T | 0.000342 |
| 3 | 21751839 | rs1080021 | A,G | 0.000366 |
| 3 | 25519583 | rs1864903 | A,G | 0.000366 |
| 3 | 173319456 | rs6800283 | T,C | 0.000366 |
| 3 | 195949310 | rs35516030 | AG,A | 0.000375 |
| 3 | 170214459 | rs2008829 | G,T | 0.000376 |
| 3 | 38736230 | rs12639182 | C,T | 0.000395 |
| 3 | 18486173 | rs62240975 | G,A | 0.000405 |
| 3 | 170266664 | rs139670481 | AAATT,A | 0.000406 |
| 3 | 170961913 | rs115037737 | G,A | 0.000407 |
| 3 | 2748191 | rs80225140 | G,A | 8.74289E-06 |
| 3 | 34944013 | rs17032477 | G,A | 3.63638E-05 |
| 3 | 65100060 | rs2128405 | C,A | 1.71219E-05 |
| 3 | 70783491 | rs6766000 | T,C | 2.00031E-05 |
| 3 | 81810551 | rs35196441 | T,G | 3.53506E-05 |
| 3 | 154812638 | rs2196521 | G,A | 3.73634E-05 |
| 3 | 160379672 | rs4679910 | G,A | 1.90222E-05 |
| 3 | 171853417 | rs73167212 | G,A | 0.00002702 |
| 3 | 27188298 | rs17317135 | A,G | 0.0000641 |
| 3 | 177796194 | rs74911757 | T,C | 1.43291E-05 |
| 3 | 3184653 | rs1705826 | G,C | 0.5 |
| 3 | 45841938 | rs35896106 | T,C | 0.04 |
| 3 | 45900634 | rs76374459 | C,G | 0.03 |
| 3 | 45908514 | rs35652899 | G,C | 0.04 |
| 3 | 45916222 | rs12639224 | T,C | 0.7 |
| 3 | 45916786 | rs34901975 | A,G | 0.09 |
| 3 | 46018781 | rs71615437 | G,A | 0.1 |
| 3 | 46049765 | rs13433997 | C,T | 0.1 |
| 3 | 46180416 | rs10510749 | T,C | 0.9 |
| 3 | 46222037 | rs115102354 | G,A | 0.7 |
| 3 | 62936766 | rs13062942 | G,A | 0.09 |
| 3 | 148718087 | rs76488148 | T,G | 0.03 |
| 4 | 69705994 | rs115162070 | G,A | 0.00000356 |
| 4 | 44418592 | rs35540967 | T,C | 0.0000289 |
| 4 | 5821922 | rs3774882 | C,G | 0.0000349 |
| 4 | 5821921 | rs3774881 | T,C | 0.0000459 |
| 4 | 112613026 | rs112641600 | C,T | 0.000058 |
| 4 | 106943200 | rs11729561 | T,C | 0.000104 |
| 4 | 163076494 | rs62331317 | G,A | 0.000113 |
| 4 | 5820342 | rs28426993 | C,T | 0.000114 |
| 4 | 35945837 | rs111866232 | G,C | 0.000157 |
| 4 | 106909473 | rs78699658 | A,G | 0.000213 |
| 4 | 99439788 | rs7668981 | C,T | 0.000273 |
| 4 | 187239747 | rs7687352 | A,G | 0.000288 |
| 4 | 60236874 | rs12498396 | G,A | 0.000292 |
| 4 | 60147523 | rs13126577 | T,C | 0.000293 |
| 4 | 24316054 | rs28735003 | T,C | 0.000295 |
| 4 | 96348686 | rs4277782 | T,C | 0.000314 |
| 4 | 162009814 | rs35850287 | C,T | 0.00033 |
| 4 | 39943691 | rs115509062 | G,C | 6.54964E-05 |
| 4 | 45117625 | rs75072424 | A,G | 2.80438E-05 |
| 4 | 69795670 | rs144454074 | A,G | 4.19779E-05 |
| 4 | 73555556 | rs28616128 | G,A | 3.02015E-06 |
| 4 | 75191300 | rs115044024 | C,T | 4.15557E-05 |
| 4 | 84216649 | rs144185023 | A,G | 3.72469E-05 |
| 4 | 87939942 | rs76456240 | C,T | 9.48747E-05 |
| 4 | 121958473 | rs202221151 | C,T | 1.61977E-06 |
| 4 | 142326546 | rs76589765 | G,A | 4.20983E-06 |
| 4 | 151724769 | rs116015734 | T,C | 9.26679E-05 |
| 4 | 153821201 | rs62319956 | C,A | 2.01266E-06 |
| 4 | 170238293 | rs76519323 | A,C | 2.30315E-05 |
| 4 | 170498270 | rs74557505 | C,T | 6.57926E-05 |

TABLE 1-continued

Informative polymorphisms of the invention.

| Chromosome | Position | SNP ID | Alleles | p-value for association |
|---|---|---|---|---|
| 4 | 181162752 | rs17069033 | T,G | 1.35337E−05 |
| 4 | 185567903 | rs4647611 | C,G | 2.72675E−05 |
| 4 | 27383278 | rs6810404 | A,C | 0.0000988 |
| 5 | 173989338 | rs2220543 | T,A | 0.0000187 |
| 5 | 180216905 | rs10577599 | CAT,C | 0.000025 |
| 5 | 142252549 | rs10039856 | C,T | 0.0000585 |
| 5 | 123950404 | rs4240376 | G,T | 0.000065 |
| 5 | 122832716 | rs62377777 | T,C | 0.0000653 |
| 5 | 59077872 | rs62370540 | T,C | 0.000116 |
| 5 | 122559297 | rs72787582 | C,T | 0.000117 |
| 5 | 124143238 | rs71594388 | C,T | 0.000136 |
| 5 | 159258092 | rs78045322 | G,C | 0.000172 |
| 5 | 135351183 | rs72794907 | G,A | 0.000174 |
| 5 | 135435801 | rs7720483 | C,T | 0.000174 |
| 5 | 122958050 | rs70988587 | ATTC,A | 0.000215 |
| 5 | 176737309 | rs7732626 | A,G | 0.000256 |
| 5 | 59191612 | rs159616 | C,T | 0.000259 |
| 5 | 135360738 | rs35901765 | C,T | 0.000275 |
| 5 | 106396918 | rs6864971 | C,T | 0.000373 |
| 5 | 6471344 | rs507971 | C,T | 0.00038 |
| 5 | 161475413 | rs17548653 | C,T | 0.00041 |
| 5 | 6826973 | rs275444 | C,G | 3.53004E−05 |
| 5 | 19993490 | rs4466171 | A,T | 3.08251E−06 |
| 5 | 43280480 | rs55770078 | A,G | 1.16965E−05 |
| 5 | 99815379 | rs115319054 | A,C | 8.88589E−05 |
| 5 | 133519273 | rs79601653 | G,A | 9.89897E−05 |
| 5 | 155405405 | rs958444 | T,C | 2.01272E−05 |
| 5 | 160448591 | rs11749317 | C,T | 0.000000983 |
| 5 | 180237828 | rs113791144 | T,C | 0.000144 |
| 5 | 169590905 | rs4478338 | G,T | 0.3 |
| 5 | 171480160 | rs111265173 | T,C | 1 |
| 6 | 106326754 | rs9386484 | T,A | 0.00000617 |
| 6 | 45704813 | rs16873740 | T,A | 0.0000296 |
| 6 | 12216966 | rs10755709 | A,G | 0.00003 |
| 6 | 18015447 | rs140247774 | C,T | 0.000047 |
| 6 | 6925195 | rs6933436 | A,C | 0.0000983 |
| 6 | 151433520 | rs6928557 | A,C | 0.000121 |
| 6 | 170445103 | rs9366129 | C,T | 0.000133 |
| 6 | 148557644 | rs9390548 | G,A | 0.000149 |
| 6 | 137545805 | rs11759276 | A,T | 0.000183 |
| 6 | 54128003 | rs12193921 | T,C | 0.000184 |
| 6 | 54353221 | rs76378690 | G,A | 0.000206 |
| 6 | 20013937 | rs13213659 | A,G | 0.000233 |
| 6 | 148522455 | rs117687499 | G,A | 0.000262 |
| 6 | 154813083 | rs6935885 | G,C | 0.000306 |
| 6 | 18739469 | rs2328283 | A,C | 0.000333 |
| 6 | 18271083 | rs10949488 | C,T | 0.000355 |
| 6 | 20044587 | rs594259 | A,G | 0.000375 |
| 6 | 44184719 | rs2297393 | T,C | 0.000409 |
| 6 | 2885791 | rs318470 | C,A | 9.76222E−05 |
| 6 | 16217762 | rs149442766 | A,G | 3.42524E−05 |
| 6 | 26408145 | rs144114619 | A,T | 4.57681E−05 |
| 6 | 33156825 | rs41268014 | G,C | 1.61406E−05 |
| 6 | 36976747 | rs140572234 | C,G | 6.20165E−08 |
| 6 | 36999980 | rs114925152 | G,C | 0.000019845 |
| 6 | 37139030 | rs35760989 | C,G | 2.15792E−05 |
| 6 | 101279459 | rs9485415 | T,C | 2.95345E−05 |
| 6 | 147885588 | rs140643252 | A,G | 0.000080315 |
| 6 | 27604726 | rs61611950 | T,C | 0.8 |
| 7 | 114940068 | rs7800941 | G,A | 0.000199 |
| 7 | 138401542 | rs3778698 | T,C | 0.0002 |
| 7 | 99987236 | rs7798226 | T,G | 0.000222 |
| 7 | 154700565 | rs882469 | G,A | 0.000222 |
| 7 | 105125204 | rs111283303 | G,A | 0.000232 |
| 7 | 11301277 | rs7807069 | G,A | 0.000271 |
| 7 | 11362820 | rs76731008 | G,A | 0.000277 |
| 7 | 9397414 | rs13238693 | T,G | 0.000286 |
| 7 | 52994281 | rs7804465 | T,C | 0.000342 |
| 7 | 36662714 | rs58016731 | AGTCTT,A | 0.000391 |
| 7 | 6687563 | rs55944391 | C,A | 0.000395 |
| 7 | 45244259 | rs1294888 | T,C | 0.000395 |
| 7 | 14862658 | rs2109498 | A,T | 0.000419 |
| 7 | 21730647 | rs7790948 | G,T | 3.13489E−05 |
| 7 | 35720134 | rs79496619 | T,G | 3.21712E−05 |
| 7 | 38677134 | rs78966608 | A,C | 7.06676E−05 |
| 7 | 100483400 | rs200675508 | A,G | 7.25535E−05 |
| 7 | 104782689 | rs55743527 | G,T | 1.36022E−06 |
| 7 | 122122078 | rs73431600 | A,G | 5.15467E−05 |
| 7 | 122196872 | rs73433754 | A,C | 3.48011E−05 |
| 7 | 154926067 | rs117164958 | C,G | 7.61301E−06 |
| 7 | 158928541 | rs13225056 | A,G | 1.53596E−05 |
| 7 | 152960930 | rs6967210 | C,T | 0.3 |
| 8 | 16790149 | rs118072448 | T,C | 0.0000235 |
| 8 | 74268198 | rs2010843 | T,C | 0.0000556 |
| 8 | 38897470 | rs13282163 | A,C | 0.0000739 |
| 8 | 40181978 | rs11779911 | C,A | 0.0000841 |
| 8 | 38821327 | rs10808999 | A,G | 0.0000884 |
| 8 | 12850333 | rs2947375 | A,G | 0.000162 |
| 8 | 143261211 | rs72685583 | T,C | 0.000218 |
| 8 | 55488334 | rs74458553 | C,T | 0.000254 |
| 8 | 32590598 | rs4351382 | T,A | 0.000273 |
| 8 | 61303777 | rs147353244 | G,GA | 0.000327 |
| 8 | 2044114 | rs147776183 | T,C | 8.64871E−06 |
| 8 | 9478274 | rs78876374 | T,C | 8.85355E−05 |
| 8 | 19218826 | rs145746072 | A,G | 1.91735E−05 |
| 8 | 20354600 | rs13249119 | G,A | 1.33633E−05 |
| 8 | 20447019 | rs73626732 | A,G | 1.40229E−05 |
| 8 | 20460661 | rs35258926 | G,T | 9.04111E−06 |
| 8 | 39799765 | rs7845003 | T,C | 9.39614E−05 |
| 8 | 125839433 | rs118040942 | T,C | 0.000059504 |
| 8 | 130677813 | rs57557483 | A,G | 8.17573E−06 |
| 8 | 130694201 | rs75572486 | A,G | 2.53314E−05 |
| 8 | 8730488 | rs332040 | A,G | 0.9 |
| 9 | 4329170 | rs3895472 | T,C | 0.0000235 |
| 9 | 21131627 | rs12236000 | G,C | 0.0000452 |
| 9 | 75127404 | rs35460846 | A,AT | 0.0000819 |
| 9 | 81158113 | rs7027911 | A,G | 0.0000905 |
| 9 | 81158443 | rs3009696 | C,T | 0.00013 |
| 9 | 140227646 | rs11523787 | C,T | 0.000137 |
| 9 | 75061917 | rs11143296 | C,T | 0.00014 |
| 9 | 78174461 | rs13298924 | T,C | 0.00021 |
| 9 | 23650820 | rs4584238 | G,C | 0.00022 |
| 9 | 35490636 | rs10814241 | C,G | 0.00022 |
| 9 | 138202418 | rs7032559 | C,T | 0.00025 |
| 9 | 122045518 | rs487545 | T,C | 0.000269 |
| 9 | 139024232 | rs7021573 | G,A | 0.000309 |
| 9 | 75136789 | rs7022441 | G,A | 0.000343 |
| 9 | 139047766 | rs10858230 | G,A | 0.000367 |
| 9 | 138006474 | rs61018036 | G,A | 0.000373 |
| 9 | 116468053 | rs75260470 | C,T | 0.000402 |
| 9 | 10276812 | rs10959000 | A,G | 7.85152E−05 |
| 9 | 22080363 | rs16905613 | G,A | 5.78633E−06 |
| 9 | 38669062 | rs2993177 | A,G | 7.37838E−05 |
| 9 | 79453107 | rs7853955 | T,C | 5.25711E−05 |
| 9 | 83032179 | rs72744937 | G,A | 6.92799E−05 |
| 9 | 100137855 | rs200908751 | A,G | 6.57652E−05 |
| 9 | 101874496 | rs76094400 | A,G | 3.95481E−08 |
| 9 | 125704675 | rs76670825 | A,G | 5.01185E−05 |
| 9 | 125903047 | rs77089732 | A,G | 0.00005145 |
| 9 | 128794405 | rs62570501 | T,C | 7.35517E−05 |
| 9 | 131771551 | rs17455482 | A,G | 5.2118E−06 |
| 9 | 27121456 | rs71480372 | T,A | 0.7 |
| 9 | 29688719 | rs74790577 | T,A | 0.9 |
| 10 | 44015051 | rs10793436 | G,T | 0.0000302 |
| 10 | 54100345 | rs1441121 | A,T | 0.0000322 |
| 10 | 37454397 | rs1892429 | A,G | 0.0000335 |
| 10 | 37277870 | rs2091429 | A,G | 0.0000935 |
| 10 | 68576077 | rs12218365 | T,C | 0.000113 |
| 10 | 54088932 | rs75242872 | C,G | 0.000117 |
| 10 | 37370440 | rs1794410 | G,A | 0.000118 |
| 10 | 90464714 | rs303509 | T,G | 0.000118 |
| 10 | 43942080 | rs12355127 | G,A | 0.000182 |
| 10 | 6079344 | rs11256442 | T,C | 0.000183 |
| 10 | 6042472 | rs17322780 | A,G | 0.000185 |
| 10 | 63303879 | rs79589092 | GA,G | 0.000234 |
| 10 | 43563260 | rs3026716 | A,G | 0.000246 |
| 10 | 109569850 | rs12570947 | T,C | 0.000269 |
| 10 | 27204531 | rs1815323 | T,C | 0.000276 |
| 10 | 6128547 | rs7078273 | G,T | 0.000303 |
| 10 | 115225859 | rs10430681 | T,A | 0.000303 |

TABLE 1-continued

Informative polymorphisms of the invention.

| Chromo-some | Position | SNP ID | Alleles | p-value for association |
|---|---|---|---|---|
| 10 | 63420128 | rs11595927 | C,T | 0.000333 |
| 10 | 8109274 | rs520236 | C,G | 0.000349 |
| 10 | 27929163 | rs12774308 | G,A | 0.000354 |
| 10 | 31913890 | rs11008551 | G,T | 0.000366 |
| 10 | 57401482 | rs2463950 | C,T | 0.000366 |
| 10 | 72532238 | rs2253801 | T,C | 0.000387 |
| 10 | 72223789 | rs10740349 | C,G | 0.000394 |
| 10 | 3096047 | rs12241312 | C,A | 0.000403 |
| 10 | 50140588 | rs2940708 | G,A | 0.000404 |
| 10 | 67680203 | rs41313840 | G,A | 7.19977E-08 |
| 10 | 127258691 | rs7084502 | A,G | 7.81329E-05 |
| 10 | 9030308 | rs71481792 | A,T | 0.0000223 |
| 10 | 131456440 | rs79858702 | T,C | 0.000070971 |
| 10 | 123000638 | rs5016035 | G,T | 0.9 |
| 11 | 2893867 | rs10766439 | A,G | 0.0000937 |
| 11 | 2897875 | rs4929952 | C,T | 0.00011 |
| 11 | 10531548 | rs142012992 | CTTAG,C | 0.000111 |
| 11 | 69896252 | rs4980753 | A,G | 0.000199 |
| 11 | 2902105 | rs3864883 | C,T | 0.000222 |
| 11 | 126061372 | rs35747384 | G,T | 0.000237 |
| 11 | 270987 | rs7396066 | C,T | 0.000245 |
| 11 | 117755082 | rs491292 | C,T | 0.000246 |
| 11 | 130323805 | rs7109513 | C,T | 0.000256 |
| 11 | 120784855 | rs2852238 | G,C | 0.000274 |
| 11 | 119248855 | rs76560104 | T,C | 0.000279 |
| 11 | 1795214 | rs79194907 | G,A | 6.83674E-05 |
| 11 | 5146083 | rs12365149 | T,C | 3.11673E-05 |
| 11 | 44547746 | rs12275504 | G,T | 1.40655E-05 |
| 11 | 46727333 | rs149066130 | A,G | 7.98651E-05 |
| 11 | 57982229 | rs1966836 | A,G | 6.87681E-05 |
| 11 | 65414949 | rs199717374 | T,C | 1.05822E-05 |
| 11 | 78904266 | rs75970706 | T,C | 0.000040305 |
| 11 | 94665002 | rs76360689 | A,G | 1.05432E-06 |
| 11 | 133713033 | rs75786498 | A,G | 3.13102E-05 |
| 12 | 8760610 | rs11613792 | A,G | 0.00000256 |
| 12 | 106624953 | rs12823094 | T,A | 0.0000633 |
| 12 | 25427178 | rs140584644 | C,T | 0.000107 |
| 12 | 50375477 | rs7979554 | A,G | 0.000158 |
| 12 | 76404693 | rs1433362 | T,G | 0.000196 |
| 12 | 95127606 | rs6538530 | C,T | 0.000207 |
| 12 | 77114964 | rs12827237 | A,G | 0.000227 |
| 12 | 7606158 | rs11611785 | C,T | 0.000234 |
| 12 | 126551205 | rs11058488 | C,T | 0.000239 |
| 12 | 58267346 | rs112976255 | C,A | 0.000259 |
| 12 | 129567952 | rs58003804 | A,G | 0.000265 |
| 12 | 130254478 | rs73160210 | G,T | 0.000267 |
| 12 | 68010614 | rs1904551 | T,C | 0.000272 |
| 12 | 116784113 | rs1732329 | A,G | 0.000287 |
| 12 | 25159263 | rs859134 | A,G | 0.000368 |
| 12 | 129563020 | rs2002553 | G,A | 0.000387 |
| 12 | 130242016 | rs73436164 | A,G | 0.000389 |
| 12 | 125537439 | rs145578156 | AATTTTTT,A | 0.000402 |
| 12 | 67821215 | rs7955453 | C,A | 0.000403 |
| 12 | 41970164 | rs970970 | G,A | 0.000405 |
| 12 | 2144357 | rs75442877 | T,C | 0.000407 |
| 12 | 2174748 | rs117821007 | C,T | 4.86991E-05 |
| 12 | 25681286 | rs58907459 | T,C | 6.07118E-05 |
| 12 | 57589676 | rs143285614 | A,G | 2.69071E-05 |
| 12 | 125302200 | rs143093152 | G,A | 6.62377E-06 |
| 12 | 56084466 | rs7397549 | C,T | 0.9 |
| 13 | 74558505 | rs12871414 | C,T | 0.000094 |
| 13 | 23658838 | rs1984162 | A,G | 0.000103 |
| 13 | 99778655 | rs35784338 | CT,C | 0.000199 |
| 13 | 102622688 | rs7339161 | T,G | 0.000203 |
| 13 | 101425653 | rs9585503 | T,G | 0.00025 |
| 13 | 74804797 | rs2039342 | C,T | 0.000345 |
| 13 | 98753461 | rs545096 | C,G | 0.000349 |
| 13 | 71296869 | rs2249209 | A,G | 0.000385 |
| 13 | 28230642 | rs10712355 | AT,A | 0.000415 |
| 13 | 39433574 | rs138539682 | A,G | 3.32149E-05 |
| 13 | 68302925 | rs75022796 | T,C | 7.24669E-05 |
| 13 | 63178476 | rs2649134 | T,C | 0.5 |
| 14 | 72908102 | rs2238187 | A,G | 0.00000821 |
| 14 | 72934229 | rs12587980 | C,T | 0.0000933 |
| 14 | 76011690 | rs2734265 | G,A | 0.000178 |
| 14 | 72891494 | rs2238191 | C,A | 0.000196 |
| 14 | 65225452 | rs58725048 | G,C | 0.000269 |
| 14 | 41523312 | rs11157189 | A,G | 0.000314 |
| 14 | 35857405 | rs61988300 | A,G | 0.000315 |
| 14 | 97526363 | rs75607541 | T,A | 0.000337 |
| 14 | 52276643 | rs117852779 | C,T | 2.89233E-06 |
| 14 | 80405359 | rs11159425 | T,G | 4.36025E-07 |
| 14 | 80570671 | rs114463019 | G,T | 3.85403E-05 |
| 14 | 87813714 | rs28450466 | A,G | 9.45754E-05 |
| 14 | 93016441 | rs57851052 | C,T | 5.53318E-05 |
| 14 | 104863663 | rs80083325 | A,G | 0.000073746 |
| 14 | 77692036 | rs144114696 | A,G | 0.3 |
| 15 | 33908103 | rs12593288 | C,T | 0.000023 |
| 15 | 33916053 | rs2229117 | G,C | 0.0000561 |
| 15 | 27274425 | rs149380649 | CT,C | 0.000112 |
| 15 | 81412674 | rs2683240 | C,T | 0.000184 |
| 15 | 89165665 | rs73451724 | G,A | 0.000235 |
| 15 | 33407307 | rs17816808 | A,G | 0.000295 |
| 15 | 46666881 | rs1994195 | A,C | 0.000295 |
| 15 | 33914240 | rs16973753 | A,T | 0.000307 |
| 15 | 53279291 | rs719715 | G,A | 0.000321 |
| 15 | 89162709 | rs112248718 | G,A | 0.000406 |
| 15 | 22845849 | rs150408740 | G,A | 1.76793E-05 |
| 15 | 34498314 | rs75915717 | T,C | 1.0293E-06 |
| 15 | 41047777 | rs35673728 | C,T | 6.67895E-05 |
| 15 | 41254865 | rs12915860 | C,A | 1.01336E-05 |
| 15 | 41712936 | rs62001419 | A,C | 9.84979E-05 |
| 15 | 52689631 | rs1724577 | T,G | 2.42041E-05 |
| 15 | 58047086 | rs77910305 | G,C | 1.30369E-05 |
| 15 | 65851028 | rs200531541 | A,G | 3.83063E-06 |
| 15 | 78471034 | rs34921279 | T,C | 2.40367E-05 |
| 15 | 84063245 | rs12591031 | G,A | 1.16687E-05 |
| 15 | 91452594 | rs142925505 | T,C | 6.04339E-07 |
| 15 | 45858905 | rs77055952 | G,A | 0.5 |
| 15 | 48984345 | rs74750712 | G,T | 0.4 |
| 16 | 78624025 | rs72803978 | A,G | 0.0000612 |
| 16 | 4065412 | rs12448745 | A,G | 0.000148 |
| 16 | 84006469 | rs2250573 | C,A | 0.000148 |
| 16 | 6653119 | rs12934582 | T,C | 0.000264 |
| 16 | 27040235 | rs2063839 | G,A | 0.000272 |
| 16 | 6081670 | rs8053942 | C,T | 0.000304 |
| 16 | 31404502 | rs2454907 | G,A | 0.000304 |
| 16 | 85992829 | rs11117428 | T,C | 0.000318 |
| 16 | 31392047 | rs11574646 | C,T | 0.000358 |
| 16 | 78865144 | rs68020681 | T,G | 0.000404 |
| 16 | 5898969 | rs11647387 | A,C | 0.000406 |
| 16 | 49391921 | rs62029091 | A,G | 7.11949E-05 |
| 16 | 49394276 | rs8057939 | C,T | 1.12522E-05 |
| 16 | 60671279 | rs118097562 | T,A | 1.90641E-05 |
| 16 | 61851413 | rs151208133 | T,C | 6.3915E-06 |
| 16 | 81194912 | rs11642802 | C,A | 4.32104E-06 |
| 16 | 90075827 | rs201800670 | T,C | 1.60067E-05 |
| 16 | 10579876 | rs72779789 | C,G | 0.9 |
| 16 | 49311043 | rs145643452 | A,G | 0.9 |
| 17 | 9170408 | rs34761447 | C,T | 0.0000262 |
| 17 | 29737612 | rs178840 | G,A | 0.0000753 |
| 17 | 29740894 | rs35054028 | G,T | 0.00025 |
| 17 | 18671675 | rs55828488 | G,A | 0.000284 |
| 17 | 31676083 | rs59341815 | T,C | 0.000294 |
| 17 | 3110572 | rs34259120 | C,A | 0.00032 |
| 17 | 15548222 | rs55821658 | C,T | 0.000365 |
| 17 | 1462712 | rs73298816 | G,A | 5.44207E-05 |
| 17 | 3844344 | rs144535413 | T,C | 1.11488E-05 |
| 17 | 36485146 | rs147966258 | A,G | 1.64933E-05 |
| 17 | 39240563 | rs193005959 | A,C | 3.72836E-05 |
| 17 | 55803083 | rs72841559 | C,G | 2.26086E-05 |
| 17 | 56329775 | rs368901060 | ACCAT,A | 4.70507E-06 |
| 17 | 63919929 | rs7220318 | G,A | 2.39945E-05 |
| 17 | 72890474 | rs689992 | T,A | 8.97907E-05 |
| 17 | 78215658 | rs117140258 | A,G | 4.15567E-05 |
| 17 | 80443309 | rs9890316 | A,G | 0.9 |
| 18 | 67208392 | rs12958013 | T,C | 0.0000319 |
| 18 | 10016417 | rs618909 | C,A | 0.000193 |
| 18 | 649311 | rs9966612 | A,G | 0.00021 |
| 18 | 3899729 | rs2667396 | C,T | 0.000259 |

TABLE 1-continued

Informative polymorphisms of the invention.

| Chromosome | Position | SNP ID | Alleles | p-value for association |
|---|---|---|---|---|
| 18 | 59747387 | rs652473 | C,T | 0.000338 |
| 18 | 9095227 | rs16954792 | T,C | 0.000368 |
| 18 | 76506592 | rs35409638 | C,T | 0.00039 |
| 18 | 67209524 | rs34527658 | A,AT | 0.000391 |
| 18 | 4610215 | rs76902871 | G,T | 2.95635E-05 |
| 18 | 13501162 | rs2298530 | C,T | 6.48889E-05 |
| 18 | 14310187 | rs117505121 | G,A | 3.59448E-05 |
| 18 | 49288587 | rs117781678 | A,C | 4.32852E-05 |
| 18 | 76650871 | rs7240086 | G,A | 6.95487E-06 |
| 18 | 30006171 | rs142257532 | C,T | 1 |
| 19 | 44492164 | rs60744406 | A,G | 0.000019 |
| 19 | 32023957 | rs8105499 | C,A | 0.000103 |
| 19 | 3058098 | rs3217064 | C,CT | 0.000188 |
| 19 | 50693096 | rs648691 | T,C | 0.000229 |
| 19 | 6533402 | rs3097296 | T,C | 0.000306 |
| 19 | 55500034 | rs76616660 | T,C | 0.000312 |
| 19 | 15565046 | rs9646651 | G,A | 0.000323 |
| 19 | 44436733 | rs8100011 | G,A | 0.000334 |
| 19 | 57133633 | rs35011777 | C,T | 0.000365 |
| 19 | 36018109 | rs74726174 | C,T | 1.82372E-05 |
| 19 | 53333975 | rs10411226 | G,A | 0.0000923 |
| 19 | 38867031 | rs200403794 | A,G | 8.36021E-05 |
| 20 | 20344377 | rs7270923 | A,C | 0.000159 |
| 20 | 53043792 | rs6023232 | G,T | 0.000186 |
| 20 | 38792298 | rs6016275 | C,T | 0.000192 |
| 20 | 45355986 | rs2076293 | A,G | 0.000217 |
| 20 | 52985158 | rs6097944 | T,G | 0.000284 |
| 20 | 8782776 | rs138434221 | A,C | 4.80296E-06 |
| 20 | 15632993 | rs6110707 | C,T | 1.31264E-05 |
| 20 | 55021575 | rs6069749 | T,C | 2.92257E-05 |
| 20 | 55111747 | rs6014757 | A,G | 6.44584E-05 |
| 20 | 39389409 | rs56259900 | G,A | 0.6 |
| 20 | 60473717 | rs76253189 | G,C | 1 |
| 21 | 43080428 | rs2252109 | A,T | 0.0000428 |
| 21 | 43086264 | rs2849697 | T,C | 0.000144 |
| 21 | 46991937 | rs76902403 | G,A | 0.000155 |
| 21 | 41321695 | rs11701006 | G,A | 0.000196 |
| 21 | 39963301 | rs975846 | A,G | 0.000268 |
| 21 | 35423390 | rs1986076 | C,T | 0.000297 |
| 21 | 39962001 | rs9789875 | C,T | 0.000299 |
| 21 | 20402128 | rs62216866 | A,G | 0.000367 |
| 21 | 19045795 | rs73200561 | A,T | 9.40896E-05 |
| 21 | 37444937 | rs2230191 | A,G | 3.4537E-07 |
| 21 | 44424444 | rs75994231 | T,C | 0.7 |
| 22 | 22564734 | rs5757427 | A,T | 0.00000237 |
| 22 | 49677464 | rs62220604 | G,A | 0.0000355 |
| 22 | 24407483 | rs11090305 | T,C | 0.0000377 |
| 22 | 44341300 | rs17494724 | G,A | 0.000157 |
| 22 | 47986266 | rs56813510 | C,A | 0.000189 |
| 22 | 44323597 | rs139049 | C,T | 0.000306 |
| 22 | 28016883 | rs1885362 | A,C | 4.65803E-05 |
| 22 | 40056937 | rs113038998 | T,C | 1.37758E-05 |
| 22 | 44285118 | rs117421847 | A,G | 6.60782E-05 |
| 22 | 22724951 | rs7290963 | T,G | 0.0000716 |

TABLE 2

Informative polymorphisms of the invention - 306 polymorphism panel.

| Chromsome | Position | SNP ID | Allele 1 | Allele 2 | Frequency Allele 1 | Frequency Allele 2 | p-value for association | OR |
|---|---|---|---|---|---|---|---|---|
| 1 | 2998313 | rs12745140 | A | G | 0.088689 | 0.911311 | 0.000032 | 1.832076 |
| 1 | 14216150 | rs17350970 | T | C | 0.077425 | 0.922575 | 0.000346 | 0.7217155 |
| 1 | 31380174 | rs4303117 | A | C | 0.308602 | 0.691398 | 0.000199 | 0.725645 |
| 1 | 31624029 | rs12083278 | G | C | 0.295029 | 0.704971 | 0.000002 | 0.751250 |
| 1 | 36172029 | rs6664663 | G | C | 0.134612 | 0.865388 | 0.000304 | 0.816236 |
| 1 | 36374101 | rs2765013 | T | C | 0.086283 | 0.913717 | 0.000039 | 0.749941 |
| 1 | 36549664 | rs2274122 | G | A | 0.185863 | 0.814137 | 0.000107 | 0.810774 |
| 1 | 37147203 | rs219007 | T | C | 0.373057 | 0.626943 | 0.000271 | 1.161837 |
| 1 | 55046392 | rs300269 | G | A | 0.475448 | 0.524552 | 0.000355 | 1.118490 |
| 1 | 60210649 | rs1004772 | T | C | 0.156424 | 0.843576 | 0.000289 | 1.537451 |
| 1 | 60214250 | rs3990361 | G | A | 0.314799 | 0.685201 | 0.000386 | 0.880359 |
| 1 | 63766718 | rs112728381 | T | C | 0.310873 | 0.689127 | 0.000025 | 0.829006 |
| 1 | 83665753 | rs9432945 | T | C | 0.195772 | 0.804228 | 0.000293 | 1.244035 |
| 1 | 87628173 | rs10873821 | T | C | 0.247509 | 0.752491 | 0.000023 | 0.654805 |
| 1 | 88237749 | rs72714531 | C | T | 0.061964 | 0.938036 | 0.000223 | 0.615057 |
| 1 | 101661978 | rs11166552 | T | C | 0.338277 | 0.661723 | 0.000257 | 0.740338 |
| 1 | 107941708 | rs17018870 | A | G | 0.123982 | 0.876018 | 0.000328 | 1.316821 |
| 1 | 114893146 | rs574339 | C | T | 0.292471 | 0.707529 | 0.000169 | 0.838798 |
| 1 | 161229986 | rs5778200 | AC | A | 0.166927 | 0.833073 | 0.000326 | 1.100723 |
| 1 | 184803508 | rs630030 | A | G | 0.459053 | 0.540947 | 0.000271 | 0.776025 |
| 1 | 186287454 | rs1830344 | C | T | 0.099058 | 0.900942 | 0.000127 | 0.715555 |
| 1 | 187364290 | rs7517532 | C | G | 0.277242 | 0.722758 | 0.000136 | 1.274559 |
| 1 | 208388679 | rs78771609 | G | A | 0.057479 | 0.942521 | 0.000395 | 0.682444 |
| 1 | 222722631 | rs61825527 | C | A | 0.055134 | 0.944866 | 0.000194 | 0.684243 |
| 1 | 230906775 | rs3790971 | A | G | 0.296911 | 0.703089 | 0.000357 | 0.809538 |
| 2 | 2965401 | rs1729903 | T | C | 0.431488 | 0.568512 | 0.000271 | 1.363332 |
| 2 | 6948980 | rs55900661 | A | G | 0.069029 | 0.930971 | 0.000235 | 1.467029 |
| 2 | 11239618 | rs62120103 | T | C | 0.447468 | 0.552532 | 0.000116 | 0.728192 |
| 2 | 11662023 | rs62120186 | T | C | 0.141992 | 0.858008 | 0.000403 | 0.679629 |
| 2 | 11694251 | rs4313952 | G | A | 0.128053 | 0.871947 | 0.000194 | 0.692882 |
| 2 | 13900135 | rs61101702 | T | TAATA | 0.200010 | 0.799990 | 0.000200 | 0.686034 |
| 2 | 36905013 | rs6714112 | A | C | 0.138077 | 0.861923 | 0.000008 | 0.702041 |
| 2 | 42181679 | rs6740960 | A | T | 0.484269 | 0.515731 | 0.000120 | 0.838653 |
| 2 | 45503541 | rs6749256 | C | G | 0.125856 | 0.874144 | 0.000397 | 0.698683 |
| 2 | 46584059 | rs34136947 | G | T | 0.150999 | 0.849001 | 0.000222 | 0.764697 |
| 2 | 50825372 | rs116302817 | T | C | 0.055823 | 0.944177 | 0.000322 | 0.502987 |
| 2 | 52551249 | rs115352379 | C | T | 0.052932 | 0.947068 | 0.000344 | 0.802121 |

TABLE 2-continued

Informative polymorphisms of the invention - 306 polymorphism panel.

| Chromsome | Position | SNP ID | Allele 1 | Allele 2 | Frequency Allele 1 | Frequency Allele 2 | p-value for association | OR |
|---|---|---|---|---|---|---|---|---|
| 2 | 52998723 | rs62127009 | G | A | 0.146798 | 0.853202 | 0.000408 | 1.315507 |
| 2 | 75788396 | rs759255 | A | C | 0.179965 | 0.820035 | 0.000181 | 0.785823 |
| 2 | 137073048 | rs6430625 | G | A | 0.377976 | 0.622024 | 0.000144 | 0.874221 |
| 2 | 140976470 | rs9941558 | G | A | 0.215540 | 0.784460 | 0.000196 | 0.758804 |
| 2 | 175367762 | rs4972443 | C | T | 0.185607 | 0.814393 | 0.000237 | 0.755393 |
| 2 | 182359592 | rs16867434 | C | T | 0.086231 | 0.913769 | 0.000275 | 1.665760 |
| 2 | 182396974 | rs6760007 | C | T | 0.202409 | 0.797591 | 0.000200 | 1.303906 |
| 2 | 217524986 | rs2270360 | C | A | 0.265435 | 0.734565 | 0.000025 | 0.806294 |
| 2 | 217553774 | rs3755137 | A | T | 0.167060 | 0.832940 | 0.000263 | 0.869056 |
| 2 | 217701606 | rs111437052 | G | A | 0.045066 | 0.954934 | 0.000343 | 0.658309 |
| 3 | 1093795 | rs1504061 | G | C | 0.050105 | 0.949895 | 0.000072 | 1.878863 |
| 3 | 2357581 | rs56035150 | G | A | 0.051997 | 0.948003 | 0.000318 | 1.203568 |
| 3 | 5893097 | rs74827709 | T | G | 0.109834 | 0.890166 | 0.000342 | 0.744145 |
| 3 | 18486173 | rs62240975 | A | G | 0.238497 | 0.761503 | 0.000405 | 1.236323 |
| 3 | 21751839 | rs1080021 | G | A | 0.456598 | 0.543402 | 0.000366 | 1.189673 |
| 3 | 24759067 | rs71328493 | G | C | 0.121505 | 0.878495 | 0.000213 | 1.301830 |
| 3 | 25519583 | rs1864903 | G | A | 0.403176 | 0.596824 | 0.000366 | 1.057886 |
| 3 | 27188298 | rs17317135 | A | G | 0.048133 | 0.951867 | 0.000064 | 0.653752 |
| 3 | 38736230 | rs12639182 | T | C | 0.198184 | 0.801816 | 0.000395 | 0.806524 |
| 3 | 38759465 | rs9990137 | G | A | 0.341528 | 0.658472 | 0.000148 | 0.765458 |
| 3 | 46628726 | rs1829538 | G | T | 0.129451 | 0.870549 | 0.000257 | 0.757119 |
| 3 | 71238088 | rs111323182 | A | T | 0.044740 | 0.955260 | 0.000270 | 0.902081 |
| 3 | 125649876 | rs6438947 | C | T | 0.235079 | 0.764921 | 0.000126 | 1.208900 |
| 3 | 125837737 | rs1868132 | T | C | 0.111588 | 0.888412 | 0.000102 | 1.421540 |
| 3 | 141408691 | rs6440031 | A | G | 0.084557 | 0.915443 | 0.000071 | 0.730686 |
| 3 | 143909347 | rs13089585 | C | T | 0.050473 | 0.949527 | 0.000302 | 0.600404 |
| 3 | 155736888 | rs4680228 | T | C | 0.443082 | 0.556918 | 0.000157 | 1.248159 |
| 3 | 170214459 | rs2008829 | T | G | 0.285307 | 0.714693 | 0.000376 | 1.093430 |
| 3 | 170266664 | rs139670481 | A | AAATT | 0.141898 | 0.858102 | 0.000406 | 1.502990 |
| 3 | 170961913 | rs115037737 | A | G | 0.057828 | 0.942172 | 0.000407 | 0.607395 |
| 3 | 173319456 | rs6800283 | C | T | 0.089864 | 0.910136 | 0.000366 | 0.789994 |
| 3 | 195949310 | rs35516030 | A | AG | 0.263765 | 0.736235 | 0.000375 | 1.315177 |
| 4 | 5820342 | rs28426993 | T | C | 0.099661 | 0.900339 | 0.000114 | 0.575494 |
| 4 | 5821877 | rs3774881 | C | T | 0.151611 | 0.848389 | 0.000046 | 0.647570 |
| 4 | 5821922 | rs3774882 | G | C | 0.075890 | 0.924110 | 0.000035 | 0.573686 |
| 4 | 24316054 | rs28735003 | C | T | 0.144258 | 0.855742 | 0.000295 | 0.658173 |
| 4 | 27383278 | rs6810404 | A | C | 0.490985 | 0.509015 | 0.000099 | 0.776925 |
| 4 | 35945837 | rs111866232 | C | G | 0.039927 | 0.960073 | 0.000157 | 0.541922 |
| 4 | 44418592 | rs35540967 | C | T | 0.074931 | 0.925069 | 0.000029 | 1.777837 |
| 4 | 60147523 | rs13126577 | C | T | 0.497288 | 0.502712 | 0.000293 | 1.301281 |
| 4 | 60236874 | rs12498396 | A | G | 0.359748 | 0.640252 | 0.000292 | 0.875135 |
| 4 | 69705994 | rs115162070 | A | G | 0.069851 | 0.930149 | 0.000004 | 0.566347 |
| 4 | 96348686 | rs4277782 | T | C | 0.253317 | 0.746683 | 0.000314 | 1.099665 |
| 4 | 99439788 | rs7668981 | T | C | 0.434271 | 0.565729 | 0.000273 | 0.750526 |
| 4 | 106909473 | rs78699658 | G | A | 0.076853 | 0.923147 | 0.000213 | 0.769933 |
| 4 | 106943200 | rs11729561 | C | T | 0.080734 | 0.919266 | 0.000104 | 0.776444 |
| 4 | 112613026 | rs112641600 | T | C | 0.104676 | 0.895324 | 0.000058 | 0.646736 |
| 4 | 162009814 | rs35850287 | C | T | 0.469632 | 0.530368 | 0.000330 | 0.786370 |
| 4 | 163076494 | rs62331317 | A | G | 0.108942 | 0.891058 | 0.000113 | 1.821384 |
| 4 | 187239747 | rs7687352 | A | G | 0.486412 | 0.513588 | 0.000288 | 1.144337 |
| 5 | 6471344 | rs507971 | C | T | 0.210730 | 0.789270 | 0.000380 | 0.795710 |
| 5 | 59077872 | rs62370540 | C | T | 0.105859 | 0.894141 | 0.000116 | 0.634414 |
| 5 | 59191612 | rs159616 | C | T | 0.390352 | 0.609648 | 0.000259 | 0.881079 |
| 5 | 106396918 | rs6864971 | C | T | 0.379226 | 0.620774 | 0.000373 | 1.309747 |
| 5 | 122559297 | rs72787582 | T | C | 0.040661 | 0.959339 | 0.000117 | 0.495005 |
| 5 | 122832716 | rs62377777 | C | T | 0.219393 | 0.780607 | 0.000065 | 0.697966 |
| 5 | 122958050 | rs70988587 | A | ATTC | 0.192984 | 0.807016 | 0.000215 | 0.864676 |
| 5 | 123950404 | rs4240376 | A | T | 0.201643 | 0.798357 | 0.000065 | 0.798894 |
| 5 | 124143238 | rs71594388 | T | C | 0.074401 | 0.925599 | 0.000136 | 0.816311 |
| 5 | 135351183 | rs72794907 | A | G | 0.311611 | 0.688389 | 0.000174 | 0.907778 |
| 5 | 135360738 | rs35901765 | T | C | 0.455190 | 0.544810 | 0.000275 | 0.872551 |
| 5 | 135435801 | rs7720483 | T | C | 0.474933 | 0.525067 | 0.000174 | 0.778409 |
| 5 | 142252549 | rs10039856 | T | C | 0.097202 | 0.902798 | 0.000059 | 0.722279 |
| 5 | 159258092 | rs78045322 | C | G | 0.058813 | 0.941187 | 0.000172 | 0.665840 |
| 5 | 161475413 | rs17548653 | T | C | 0.051060 | 0.948940 | 0.000410 | 0.694777 |
| 5 | 173989338 | rs2220543 | A | T | 0.289838 | 0.710162 | 0.000019 | 0.753959 |
| 5 | 176737309 | rs7732626 | G | A | 0.075159 | 0.924841 | 0.000256 | 0.621750 |
| 5 | 180216905 | rs10577599 | C | CAT | 0.060491 | 0.939509 | 0.000025 | 1.117455 |
| 5 | 180237828 | rs113791144 | T | C | 0.066435 | 0.933565 | 0.000144 | 1.437219 |
| 6 | 6925195 | rs6933436 | C | A | 0.283852 | 0.716148 | 0.000098 | 1.259040 |
| 6 | 12216966 | rs10755709 | G | A | 0.300795 | 0.699205 | 0.000030 | 0.798524 |
| 6 | 18015447 | rs140247774 | T | C | 0.066938 | 0.933062 | 0.000047 | 1.795184 |
| 6 | 18271083 | rs10949488 | T | C | 0.058632 | 0.941368 | 0.000355 | 1.420327 |
| 6 | 18739469 | rs2328283 | C | A | 0.439080 | 0.560920 | 0.000333 | 1.340607 |
| 6 | 20013937 | rs13213659 | G | A | 0.356283 | 0.643717 | 0.000233 | 1.432682 |

TABLE 2-continued

Informative polymorphisms of the invention - 306 polymorphism panel.

| Chromsome | Position | SNP ID | Allele 1 | Allele 2 | Frequency Allele 1 | Frequency Allele 2 | p-value for association | OR |
|---|---|---|---|---|---|---|---|---|
| 6 | 20044587 | rs594259 | G | A | 0.405796 | 0.594204 | 0.000375 | 1.066926 |
| 6 | 44184719 | rs2297393 | C | T | 0.428032 | 0.571968 | 0.000409 | 0.802643 |
| 6 | 45704813 | rs16873740 | A | T | 0.118789 | 0.881211 | 0.000030 | 1.293166 |
| 6 | 54128003 | rs12193921 | C | T | 0.055659 | 0.944341 | 0.000184 | 1.567508 |
| 6 | 54353221 | rs76378690 | A | G | 0.133523 | 0.866477 | 0.000206 | 0.703482 |
| 6 | 106326754 | rs9386484 | A | T | 0.236292 | 0.763708 | 0.000006 | 0.700394 |
| 6 | 137545805 | rs11759276 | T | A | 0.066107 | 0.933893 | 0.000183 | 0.633909 |
| 6 | 148522455 | rs117687499 | A | G | 0.080216 | 0.919784 | 0.000262 | 0.638077 |
| 6 | 148557644 | rs9390548 | A | G | 0.172941 | 0.827059 | 0.000149 | 0.785698 |
| 6 | 151433505 | rs6928557 | A | C | 0.177199 | 0.822801 | 0.000121 | 0.662379 |
| 6 | 154813083 | rs6935885 | C | G | 0.146378 | 0.853622 | 0.000306 | 1.227099 |
| 6 | 170445103 | rs9366129 | T | C | 0.377194 | 0.622806 | 0.000133 | 1.169297 |
| 7 | 6687563 | rs55944391 | A | C | 0.287309 | 0.712691 | 0.000395 | 1.259924 |
| 7 | 9397414 | rs13238693 | T | G | 0.426972 | 0.573028 | 0.000286 | 1.212542 |
| 7 | 11301277 | rs7807069 | G | A | 0.485509 | 0.514491 | 0.000271 | 0.780193 |
| 7 | 11362820 | rs76731008 | A | G | 0.141480 | 0.858520 | 0.000277 | 1.500773 |
| 7 | 14862658 | rs2109498 | A | T | 0.153107 | 0.846893 | 0.000419 | 0.865912 |
| 7 | 36662714 | rs58016731 | A | AGTCTT | 0.095719 | 0.904281 | 0.000391 | 0.677730 |
| 7 | 45244259 | rs1294888 | T | C | 0.263570 | 0.736430 | 0.000395 | 0.684875 |
| 7 | 52994281 | rs7804465 | C | T | 0.374660 | 0.625340 | 0.000342 | 1.187107 |
| 7 | 99987236 | rs7798226 | G | T | 0.386582 | 0.613418 | 0.000222 | 1.238744 |
| 7 | 105125204 | rs111283303 | A | G | 0.157476 | 0.842524 | 0.000232 | 0.876698 |
| 7 | 114940068 | rs7800941 | A | G | 0.161413 | 0.838587 | 0.000199 | 1.305293 |
| 7 | 138401542 | rs3778698 | T | C | 0.254384 | 0.745616 | 0.000200 | 0.835206 |
| 7 | 154700565 | rs882469 | A | G | 0.238270 | 0.761730 | 0.000222 | 0.861757 |
| 8 | 12850333 | rs2947375 | A | G | 0.218314 | 0.781686 | 0.000162 | 0.682120 |
| 8 | 16790149 | rs118072448 | C | T | 0.076838 | 0.923162 | 0.000024 | 0.567696 |
| 8 | 32590598 | rs4351382 | A | T | 0.151498 | 0.848502 | 0.000273 | 1.643539 |
| 8 | 38821327 | rs10808999 | A | G | 0.133668 | 0.866332 | 0.000088 | 0.781512 |
| 8 | 38897470 | rs13282163 | C | A | 0.083088 | 0.916912 | 0.000074 | 0.697853 |
| 8 | 40181978 | rs11779911 | A | C | 0.334674 | 0.665326 | 0.000084 | 0.759358 |
| 8 | 55488334 | rs74458553 | T | C | 0.055479 | 0.944521 | 0.000254 | 0.734023 |
| 8 | 61303777 | rs147353244 | GA | G | 0.126562 | 0.873438 | 0.000327 | 0.753803 |
| 8 | 74268198 | rs2010843 | T | C | 0.468438 | 0.531562 | 0.000056 | 0.764239 |
| 8 | 143261211 | rs72685583 | C | T | 0.068522 | 0.931478 | 0.000218 | 1.571550 |
| 9 | 4329170 | rs3895472 | T | C | 0.073518 | 0.926482 | 0.000024 | 0.662754 |
| 9 | 21131627 | rs12236000 | C | G | 0.076624 | 0.923376 | 0.000045 | 0.668847 |
| 9 | 23650820 | rs4584238 | G | C | 0.319618 | 0.680382 | 0.000220 | 1.216505 |
| 9 | 35490636 | rs10814241 | G | C | 0.093586 | 0.906414 | 0.000220 | 1.562150 |
| 9 | 75061917 | rs11143296 | T | C | 0.451371 | 0.548629 | 0.000140 | 0.795898 |
| 9 | 75127404 | rs35460846 | A | AT | 0.481894 | 0.518106 | 0.000082 | 1.428832 |
| 9 | 75136789 | rs7022441 | A | G | 0.473267 | 0.526733 | 0.000343 | 0.709246 |
| 9 | 78174461 | rs13298924 | C | T | 0.237835 | 0.762165 | 0.000210 | 1.184631 |
| 9 | 81158113 | rs7027911 | A | G | 0.428022 | 0.571978 | 0.000091 | 1.184363 |
| 9 | 81158443 | rs3009696 | T | C | 0.260891 | 0.739109 | 0.000130 | 1.413299 |
| 9 | 116468053 | rs75260470 | T | C | 0.062434 | 0.937566 | 0.000402 | 0.657867 |
| 9 | 122045518 | rs487545 | C | T | 0.108712 | 0.891288 | 0.000269 | 0.816792 |
| 9 | 138006474 | rs61018036 | A | G | 0.178813 | 0.821187 | 0.000373 | 1.346902 |
| 9 | 138202418 | rs7032559 | T | C | 0.368961 | 0.631039 | 0.000250 | 1.228692 |
| 9 | 139024232 | rs7021573 | A | G | 0.438519 | 0.561481 | 0.000309 | 0.777563 |
| 9 | 139047766 | rs10858230 | A | G | 0.201935 | 0.798065 | 0.000367 | 1.208077 |
| 9 | 140227646 | rs11523787 | T | C | 0.469081 | 0.530919 | 0.000137 | 1.450898 |
| 10 | 3096047 | rs12241312 | C | A | 0.348689 | 0.651311 | 0.000403 | 0.798146 |
| 10 | 6042472 | rs17322780 | G | A | 0.096814 | 0.903186 | 0.000185 | 0.735578 |
| 10 | 6079344 | rs11256442 | T | C | 0.287927 | 0.712073 | 0.000183 | 0.767768 |
| 10 | 6128547 | rs7078273 | T | G | 0.405064 | 0.594936 | 0.000303 | 1.159191 |
| 10 | 8109274 | rs520236 | G | C | 0.219884 | 0.780116 | 0.000349 | 0.756563 |
| 10 | 9030308 | rs71481792 | A | T | 0.381127 | 0.618873 | 0.000022 | 1.192942 |
| 10 | 27204531 | rs1815323 | C | T | 0.111020 | 0.888980 | 0.000276 | 0.660612 |
| 10 | 27929163 | rs12774308 | A | G | 0.130100 | 0.869900 | 0.000354 | 0.718834 |
| 10 | 31913890 | rs11008551 | T | G | 0.195413 | 0.804587 | 0.000366 | 1.331756 |
| 10 | 37277870 | rs2091431 | A | G | 0.291382 | 0.708618 | 0.000094 | 0.746109 |
| 10 | 37370440 | rs1794410 | A | G | 0.411272 | 0.588728 | 0.000118 | 0.857482 |
| 10 | 37454397 | rs1892429 | G | A | 0.160418 | 0.839582 | 0.000034 | 0.745569 |
| 10 | 43563260 | rs3026716 | G | A | 0.253344 | 0.746656 | 0.000246 | 1.269510 |
| 10 | 43942080 | rs12355127 | A | G | 0.121879 | 0.878121 | 0.000182 | 1.223674 |
| 10 | 44015051 | rs10793436 | T | G | 0.317755 | 0.682245 | 0.000030 | 0.691022 |
| 10 | 50140588 | rs2940708 | G | A | 0.076009 | 0.923991 | 0.000404 | 0.667254 |
| 10 | 54088932 | rs75242872 | G | C | 0.064881 | 0.935119 | 0.000117 | 0.492357 |
| 10 | 54100345 | rs1441121 | A | T | 0.438240 | 0.561760 | 0.000032 | 0.821531 |
| 10 | 57401482 | rs2463950 | T | C | 0.076162 | 0.923838 | 0.000366 | 1.827848 |
| 10 | 63303879 | rs79189092 | G | GA | 0.170880 | 0.829120 | 0.000234 | 1.297045 |
| 10 | 63420128 | rs11595927 | T | C | 0.290509 | 0.709491 | 0.000333 | 1.236769 |
| 10 | 68576077 | rs12218365 | C | T | 0.138063 | 0.861937 | 0.000113 | 0.607017 |
| 10 | 72223789 | rs10740349 | C | G | 0.082859 | 0.917141 | 0.000394 | 1.272646 |

TABLE 2-continued

Informative polymorphisms of the invention - 306 polymorphism panel.

| Chromsome | Position | SNP ID | Allele 1 | Allele 2 | Frequency Allele 1 | Frequency Allele 2 | p-value for association | OR |
|---|---|---|---|---|---|---|---|---|
| 10 | 72532238 | rs2253801 | C | T | 0.423564 | 0.576436 | 0.000387 | 0.810933 |
| 10 | 90464714 | rs303509 | G | T | 0.275512 | 0.724488 | 0.000118 | 0.899337 |
| 10 | 109569850 | rs12570947 | C | T | 0.149219 | 0.850781 | 0.000269 | 1.403835 |
| 10 | 115225859 | rs10430681 | A | T | 0.074066 | 0.925934 | 0.000303 | 0.678792 |
| 11 | 270987 | rs7396066 | C | T | 0.187477 | 0.812523 | 0.000245 | 0.833428 |
| 11 | 2893867 | rs10766439 | A | G | 0.362551 | 0.637449 | 0.000094 | 1.423212 |
| 11 | 2897875 | rs4929952 | T | C | 0.202575 | 0.797425 | 0.000110 | 0.619703 |
| 11 | 2902105 | rs3864883 | T | C | 0.111433 | 0.888567 | 0.000222 | 0.576303 |
| 11 | 10531548 | rs142012992 | C | CTTAG | 0.325845 | 0.674155 | 0.000111 | 0.697824 |
| 11 | 69896252 | rs4980753 | A | G | 0.376448 | 0.623552 | 0.000199 | 1.158722 |
| 11 | 117755082 | rs491292 | T | C | 0.207093 | 0.792907 | 0.000246 | 1.437101 |
| 11 | 119248855 | rs76560104 | C | T | 0.102744 | 0.897256 | 0.000279 | 1.664471 |
| 11 | 120784855 | rs2852238 | G | C | 0.278141 | 0.721859 | 0.000274 | 1.343841 |
| 11 | 126061372 | rs35747384 | T | G | 0.105597 | 0.894403 | 0.000237 | 0.743710 |
| 11 | 130323805 | rs7109513 | T | C | 0.402800 | 0.597200 | 0.000256 | 0.770364 |
| 12 | 2144357 | rs75442877 | C | T | 0.065950 | 0.934050 | 0.000407 | 0.685377 |
| 12 | 7606158 | rs11611785 | C | T | 0.429591 | 0.570409 | 0.000234 | 1.060466 |
| 12 | 8760610 | rs11613792 | G | A | 0.138548 | 0.861452 | 0.000003 | 0.809562 |
| 12 | 25159263 | rs859134 | A | G | 0.496130 | 0.503870 | 0.000368 | 1.187565 |
| 12 | 25427178 | rs140584644 | T | C | 0.253790 | 0.746210 | 0.000107 | 1.424311 |
| 12 | 41970164 | rs970970 | G | A | 0.384510 | 0.615490 | 0.000405 | 1.165447 |
| 12 | 50375477 | rs7979554 | A | G | 0.280549 | 0.719451 | 0.000158 | 1.204227 |
| 12 | 58267346 | rs112976255 | A | C | 0.072297 | 0.927703 | 0.000259 | 0.688523 |
| 12 | 67821215 | rs7955453 | A | C | 0.099287 | 0.900713 | 0.000403 | 1.272926 |
| 12 | 68010614 | rs1904551 | C | T | 0.412363 | 0.587637 | 0.000272 | 0.880242 |
| 12 | 76404693 | rs1433362 | G | T | 0.097993 | 0.902007 | 0.000196 | 0.868310 |
| 12 | 77114964 | rs12827237 | G | A | 0.163516 | 0.836484 | 0.000227 | 0.712866 |
| 12 | 95127606 | rs6538530 | T | C | 0.208557 | 0.791443 | 0.000207 | 1.316565 |
| 12 | 106624953 | rs12823094 | A | T | 0.244075 | 0.755925 | 0.000063 | 1.166247 |
| 12 | 116784113 | rs1732329 | A | G | 0.350353 | 0.649647 | 0.000287 | 1.418587 |
| 12 | 125537439 | rs145578156 | A | AATTTTTT | 0.126772 | 0.873228 | 0.000402 | 1.346757 |
| 12 | 126551205 | rs11058488 | T | C | 0.042023 | 0.957977 | 0.000239 | 1.581584 |
| 12 | 129563020 | rs2002553 | A | G | 0.122964 | 0.877036 | 0.000387 | 0.901839 |
| 12 | 129567952 | rs58003804 | G | A | 0.091258 | 0.908742 | 0.000265 | 0.798624 |
| 12 | 130242016 | rs73436164 | G | A | 0.168624 | 0.831376 | 0.000389 | 0.655603 |
| 12 | 130254478 | rs73160210 | T | G | 0.081785 | 0.918215 | 0.000267 | 1.744820 |
| 13 | 23658838 | rs1984162 | G | A | 0.258794 | 0.741206 | 0.000103 | 1.255399 |
| 13 | 28230642 | rs10712355 | A | AT | 0.211941 | 0.788059 | 0.000415 | 0.841463 |
| 13 | 71296869 | rs2249209 | A | G | 0.409982 | 0.590018 | 0.000385 | 1.243197 |
| 13 | 74558505 | rs12871414 | T | C | 0.265293 | 0.734707 | 0.000094 | 0.752194 |
| 13 | 74804797 | rs2039342 | T | C | 0.110526 | 0.889474 | 0.000345 | 1.761241 |
| 13 | 98753461 | rs545096 | G | C | 0.465548 | 0.534452 | 0.000349 | 1.268761 |
| 13 | 99778655 | rs35784338 | CT | C | 0.199852 | 0.800148 | 0.000199 | 0.777428 |
| 13 | 101425653 | rs9585503 | G | T | 0.079322 | 0.920678 | 0.000250 | 0.503729 |
| 13 | 102622688 | rs7339161 | G | T | 0.306514 | 0.693486 | 0.000203 | 0.859270 |
| 14 | 35857405 | rs61988300 | G | A | 0.189617 | 0.810383 | 0.000315 | 0.790426 |
| 14 | 41523312 | rs11157189 | G | A | 0.498534 | 0.501466 | 0.000314 | 0.893382 |
| 14 | 65225452 | rs58725048 | C | G | 0.056880 | 0.943120 | 0.000269 | 1.285578 |
| 14 | 72891494 | rs2238191 | A | C | 0.428866 | 0.571134 | 0.000196 | 1.256746 |
| 14 | 72908102 | rs2238187 | G | A | 0.352272 | 0.647728 | 0.000008 | 1.442188 |
| 14 | 72934229 | rs12587980 | T | C | 0.374816 | 0.625184 | 0.000093 | 1.277281 |
| 14 | 76011690 | rs2734265 | G | A | 0.480501 | 0.519499 | 0.000178 | 1.168686 |
| 14 | 97526363 | rs75607541 | A | T | 0.050779 | 0.949221 | 0.000337 | 0.566281 |
| 15 | 27274425 | rs149380649 | C | CT | 0.065191 | 0.934809 | 0.000112 | 0.738484 |
| 15 | 33407307 | rs17816808 | G | A | 0.096916 | 0.903084 | 0.000295 | 1.377528 |
| 15 | 33908103 | rs12593288 | T | C | 0.206252 | 0.793748 | 0.000023 | 0.839689 |
| 15 | 33914240 | rs16973353 | A | T | 0.425332 | 0.574668 | 0.000307 | 1.140667 |
| 15 | 33916053 | rs2229117 | C | G | 0.133455 | 0.866545 | 0.000056 | 0.753496 |
| 15 | 46666881 | rs1994195 | C | A | 0.270838 | 0.729162 | 0.000295 | 0.880898 |
| 15 | 53279291 | rs719715 | G | A | 0.181209 | 0.818791 | 0.000321 | 0.711192 |
| 15 | 81412674 | rs2683240 | C | T | 0.237678 | 0.762322 | 0.000184 | 1.164944 |
| 15 | 89162709 | rs112248718 | A | G | 0.105913 | 0.894087 | 0.000406 | 1.241798 |
| 15 | 89165665 | rs73451724 | A | G | 0.038001 | 0.961999 | 0.000235 | 1.633115 |
| 16 | 4065412 | rs12448453 | G | A | 0.079483 | 0.920517 | 0.000148 | 1.385477 |
| 16 | 5898969 | rs11647387 | C | A | 0.250999 | 0.749001 | 0.000406 | 0.804925 |
| 16 | 6081670 | rs8053942 | T | C | 0.473297 | 0.526703 | 0.000304 | 1.121533 |
| 16 | 6653119 | rs12934582 | C | T | 0.096462 | 0.903538 | 0.000264 | 1.562484 |
| 16 | 27040235 | rs2063839 | A | G | 0.077891 | 0.922109 | 0.000272 | 0.703891 |
| 16 | 31392047 | rs11574646 | T | C | 0.219875 | 0.780125 | 0.000358 | 0.816824 |
| 16 | 31404502 | rs2454907 | A | G | 0.149476 | 0.850524 | 0.000304 | 0.758433 |
| 16 | 78624025 | rs72803978 | G | A | 0.065596 | 0.934404 | 0.000061 | 0.651614 |
| 16 | 78865144 | rs68020681 | G | T | 0.093881 | 0.906119 | 0.000404 | 0.750446 |
| 16 | 84006469 | rs2250573 | A | C | 0.112712 | 0.887288 | 0.000148 | 0.614458 |
| 16 | 85992829 | rs11117428 | C | T | 0.233426 | 0.766574 | 0.000318 | 0.861041 |
| 17 | 3110572 | rs34259120 | C | A | 0.446158 | 0.553842 | 0.000320 | 1.312096 |

TABLE 2-continued

Informative polymorphisms of the invention - 306 polymorphism panel.

| Chromsome | Position | SNP ID | Allele 1 | Allele 2 | Frequency Allele 1 | Frequency Allele 2 | p-value for association | OR |
|---|---|---|---|---|---|---|---|---|
| 17 | 9170408 | rs34761447 | T | C | 0.093770 | 0.906230 | 0.000026 | 0.766580 |
| 17 | 15548222 | rs55821658 | T | C | 0.054679 | 0.945321 | 0.000365 | 0.615661 |
| 17 | 18671675 | rs55828488 | A | G | 0.419792 | 0.580208 | 0.000284 | 1.241867 |
| 17 | 29737612 | rs178840 | A | G | 0.245600 | 0.754400 | 0.000075 | 0.704646 |
| 17 | 29740894 | rs35054028 | T | G | 0.087438 | 0.912562 | 0.000250 | 0.638460 |
| 17 | 31676083 | rs59341815 | C | T | 0.290909 | 0.709091 | 0.000294 | 1.271254 |
| 18 | 649311 | rs9966612 | A | G | 0.283148 | 0.716852 | 0.000210 | 0.827402 |
| 18 | 3899729 | rs2667396 | C | T | 0.468088 | 0.531912 | 0.000259 | 1.228547 |
| 18 | 9095227 | rs16954792 | C | T | 0.153181 | 0.846819 | 0.000368 | 0.711941 |
| 18 | 10016417 | rs618909 | A | C | 0.182016 | 0.817984 | 0.000193 | 1.375523 |
| 18 | 59747387 | rs652473 | C | T | 0.491954 | 0.508046 | 0.000338 | 1.348178 |
| 18 | 67208392 | rs12958013 | C | T | 0.135816 | 0.864184 | 0.000032 | 0.755900 |
| 18 | 67209524 | rs34527658 | AT | A | 0.237574 | 0.762426 | 0.000391 | 0.839220 |
| 18 | 76506592 | rs35409638 | T | C | 0.254573 | 0.745427 | 0.000390 | 1.430958 |
| 19 | 3058098 | rs3217064 | CT | C | 0.211726 | 0.788274 | 0.000188 | 0.784584 |
| 19 | 6533402 | rs3097296 | T | C | 0.364959 | 0.635041 | 0.000306 | 0.775131 |
| 19 | 15565046 | rs9646651 | A | G | 0.074145 | 0.925855 | 0.000323 | 0.642400 |
| 19 | 32023957 | rs8105499 | A | C | 0.304119 | 0.695881 | 0.000103 | 0.763075 |
| 19 | 44436733 | rs8100011 | G | A | 0.475911 | 0.524089 | 0.000334 | 0.832135 |
| 19 | 44492164 | rs60744406 | A | G | 0.415555 | 0.584445 | 0.000019 | 0.783341 |
| 19 | 50693096 | rs648691 | C | T | 0.434267 | 0.565733 | 0.000229 | 0.865794 |
| 19 | 53333975 | rs10411226 | G | A | 0.248705 | 0.751295 | 0.000092 | 1.246091 |
| 19 | 55500034 | rs76616660 | C | T | 0.114844 | 0.885156 | 0.000312 | 0.714110 |
| 19 | 57133633 | rs35011777 | T | C | 0.041190 | 0.958810 | 0.000365 | 2.311258 |
| 20 | 20344377 | rs7270923 | C | A | 0.100555 | 0.899445 | 0.000159 | 1.632986 |
| 20 | 38792298 | rs6016275 | T | C | 0.386489 | 0.613511 | 0.000192 | 1.294481 |
| 20 | 45355986 | rs2076293 | G | A | 0.465760 | 0.534240 | 0.000217 | 1.088991 |
| 20 | 52985158 | rs6097944 | G | T | 0.113465 | 0.886535 | 0.000284 | 0.798795 |
| 20 | 53043792 | rs6023232 | T | G | 0.191508 | 0.808492 | 0.000186 | 0.862778 |
| 21 | 20402128 | rs62216866 | G | A | 0.097434 | 0.902566 | 0.000367 | 0.853945 |
| 21 | 35423390 | rs1986076 | C | T | 0.368991 | 0.631009 | 0.000297 | 0.895966 |
| 21 | 39962001 | rs9789875 | T | C | 0.489381 | 0.510619 | 0.000299 | 0.852266 |
| 21 | 39963301 | rs975846 | A | G | 0.323369 | 0.676631 | 0.000268 | 1.326863 |
| 21 | 41321695 | rs11701006 | A | G | 0.233935 | 0.766065 | 0.000196 | 0.842328 |
| 21 | 43080428 | rs2252109 | A | T | 0.481328 | 0.518672 | 0.000043 | 1.207556 |
| 21 | 43086264 | rs2849697 | T | C | 0.458596 | 0.541404 | 0.000144 | 1.228411 |
| 21 | 46991937 | rs76902403 | A | G | 0.100782 | 0.899218 | 0.000155 | 0.578181 |
| 22 | 22564734 | rs5757427 | A | T | 0.351595 | 0.648405 | 0.000002 | 0.764406 |
| 22 | 22724951 | rs7290963 | T | G | 0.448669 | 0.551331 | 0.000072 | 1.306623 |
| 22 | 24407483 | rs11090305 | C | T | 0.186359 | 0.813641 | 0.000038 | 1.155463 |
| 22 | 44323597 | rs139049 | T | C | 0.410270 | 0.589730 | 0.000306 | 1.377674 |
| 22 | 44341300 | rs17494724 | A | G | 0.069631 | 0.930369 | 0.000157 | 1.803635 |
| 22 | 47986266 | rs56813510 | A | C | 0.165988 | 0.834012 | 0.000189 | 0.838987 |
| 22 | 49677464 | rs62220604 | A | G | 0.276036 | 0.723964 | 0.000036 | 0.908008 |

TABLE 3

Informative polymorphisms of the invention - 58 polymorphism panel.

| Chromsome | Position | SNP ID | Allele 1 | Allele 2 | Frequency Allele 1 | Frequency Allele 2 | p-value for association | OR |
|---|---|---|---|---|---|---|---|---|
| 1 | 2998313 | rs12745140 | A | G | 0.088688543 | 0.911311457 | 0.0000317 | 2.2144 |
| 1 | 31624029 | rs12083278 | G | C | 0.295029481 | 0.704970519 | 0.00000243 | 1.8349 |
| 1 | 36374101 | rs2765013 | T | C | 0.086283231 | 0.913716769 | 0.0000039 | 0.4296 |
| 1 | 63766718 | rs112728381 | T | C | 0.310873133 | 0.689126867 | 0.0000252 | 0.6017 |
| 1 | 87628173 | rs10873821 | T | C | 0.247508766 | 0.752491234 | 0.0000228 | 0.5706 |
| 2 | 36905013 | rs6714112 | A | C | 0.138077241 | 0.861922759 | 0.00000781 | 0.457 |
| 2 | 217524986 | rs2270360 | C | A | 0.265435195 | 0.734564805 | 0.0000245 | 0.5804 |
| 3 | 1093795 | rs1504061 | G | C | 0.050105352 | 0.949894648 | 0.0000716 | 2.5193 |
| 3 | 27188298 | rs17317135 | A | G | 0.048132554 | 0.951867446 | 0.0000641 | 0.3776 |
| 3 | 141408691 | rs6440031 | A | G | 0.084557 | 0.915443 | 0.0000714 | 2.188 |
| 4 | 5821877 | rs3774881 | C | T | 0.151610603 | 0.848389397 | 0.0000459 | 0.5358 |
| 4 | 5821922 | rs3774882 | G | C | 0.075889692 | 0.924110308 | 0.0000349 | 0.4206 |
| 4 | 27383278 | rs6810404 | A | C | 0.49098462 | 0.50901538 | 0.0000988 | 0.6344 |
| 4 | 44418592 | rs35540967 | C | T | 0.074930921 | 0.925069079 | 0.0000289 | 2.4621 |
| 4 | 69705994 | rs115162070 | A | G | 0.069850883 | 0.930149117 | 0.0000356 | 0.3716 |
| 4 | 112613026 | rs112641600 | T | C | 0.10467637 | 0.89532363 | 0.000058 | 0.4607 |
| 5 | 122832716 | rs62377777 | C | T | 0.219392587 | 0.780607413 | 0.0000653 | 0.5724 |
| 5 | 123950404 | rs4240376 | T | G | 0.201642654 | 0.798357346 | 0.000065 | 0.5706 |
| 5 | 142252549 | rs10039856 | T | C | 0.097201508 | 0.902798492 | 0.0000585 | 0.4621 |
| 5 | 173989338 | rs2220543 | A | T | 0.28983847 | 0.71016153 | 0.0000187 | 0.5793 |

TABLE 3-continued

Informative polymorphisms of the invention - 58 polymorphism panel.

| Chromsome | Position | SNP ID | Allele 1 | Allele 2 | Frequency Allele 1 | Frequency Allele 2 | p-value for association | OR |
|---|---|---|---|---|---|---|---|---|
| 5 | 180237828 | rs113791144 | T | C | 0.066435175 | 0.933564825 | 0.000144 | 2.2728 |
| 6 | 6925195 | rs6933436 | C | A | 0.283851708 | 0.716148292 | 0.0000983 | 1.6177 |
| 6 | 12216966 | rs10755709 | G | A | 0.300794985 | 0.699205015 | 0.00003 | 0.6017 |
| 6 | 18015447 | rs140247774 | T | C | 0.066938299 | 0.933061701 | 0.000047 | 2.5961 |
| 6 | 45704813 | rs16873740 | A | T | 0.118789191 | 0.881210809 | 0.0000296 | 2.0401 |
| 6 | 106326754 | rs9386484 | A | T | 0.236291943 | 0.763708057 | 0.00000617 | 0.5385 |
| 8 | 16790149 | rs118072448 | C | T | 0.076837933 | 0.923162067 | 0.0000235 | 0.4194 |
| 8 | 38821327 | rs10808999 | A | G | 0.133667804 | 0.866332196 | 0.0000884 | 1.8927 |
| 8 | 38897470 | rs13282163 | C | A | 0.083088415 | 0.916911585 | 0.0000739 | 0.4185 |
| 8 | 40181978 | rs11779911 | A | C | 0.334673592 | 0.665326408 | 0.0000841 | 0.6126 |
| 8 | 74268198 | rs2010843 | T | C | 0.468438061 | 0.531561939 | 0.0000556 | 1.5904 |
| 9 | 4329170 | rs3895472 | T | C | 0.0735178 | 0.9264822 | 0.0000235 | 2.4181 |
| 9 | 21131627 | rs12236000 | C | G | 0.076624262 | 0.923375738 | 0.0000452 | 0.409 |
| 9 | 81158113 | rs7027911 | A | G | 0.428022077 | 0.571977923 | 0.0000905 | 0.6281 |
| 10 | 9030308 | rs71481792 | A | T | 0.38112705 | 0.61887295 | 0.0000223 | 0.5863 |
| 10 | 37277870 | rs2091431 | A | G | 0.29138208 | 0.70861792 | 0.0000935 | 1.6209 |
| 10 | 37454397 | rs1892429 | G | A | 0.160418285 | 0.839581715 | 0.0000335 | 0.5273 |
| 10 | 44015051 | rs10793436 | T | G | 0.317754779 | 0.682245221 | 0.0000302 | 0.5969 |
| 10 | 54100345 | rs1441121 | A | T | 0.438240499 | 0.561759501 | 0.0000322 | 1.5904 |
| 11 | 2893867 | rs10766439 | A | G | 0.362550753 | 0.637449247 | 0.0000937 | 0.6376 |
| 12 | 8760610 | rs11613792 | G | A | 0.138547884 | 0.861452116 | 0.00000256 | 0.4686 |
| 12 | 106624953 | rs12823094 | A | T | 0.244075133 | 0.755924867 | 0.0000633 | 1.7006 |
| 13 | 74558505 | rs12871414 | T | C | 0.265293174 | 0.734706826 | 0.000094 | 0.6108 |
| 14 | 72908102 | rs2238187 | G | A | 0.352271894 | 0.647728106 | 0.00000821 | 1.7023 |
| 14 | 72934229 | rs12587980 | T | C | 0.374815784 | 0.625184216 | 0.0000933 | 1.573 |
| 15 | 33908103 | rs12593288 | T | C | 0.206251661 | 0.793748339 | 0.000023 | 0.5599 |
| 15 | 33916053 | rs2229117 | C | G | 0.133454893 | 0.866545107 | 0.0000561 | 0.5184 |
| 16 | 78624025 | rs72803978 | G | A | 0.065595834 | 0.934404166 | 0.0000612 | 0.3727 |
| 17 | 9170408 | rs34761447 | T | C | 0.093769913 | 0.906230087 | 0.0000262 | 0.4612 |
| 17 | 29737612 | rs178840 | A | G | 0.245600067 | 0.754399933 | 0.0000753 | 0.5886 |
| 18 | 67208392 | rs12958013 | C | T | 0.135815591 | 0.864184409 | 0.0000319 | 0.5148 |
| 19 | 44492164 | rs60744406 | A | G | 0.415555399 | 0.584444601 | 0.000019 | 1.6389 |
| 19 | 53333975 | rs10411226 | G | A | 0.248705364 | 0.751294636 | 0.0000923 | 0.5644 |
| 21 | 43080428 | rs2252109 | A | T | 0.481327711 | 0.518672289 | 0.0000428 | 0.6269 |
| 22 | 22564734 | rs5757427 | A | T | 0.351595363 | 0.648404637 | 0.00000237 | 1.804 |
| 22 | 22724951 | rs7290963 | T | G | 0.448668942 | 0.551331058 | 0.0000716 | 1.5872 |
| 22 | 24407483 | rs11090305 | C | T | 0.18635889 | 0.81364111 | 0.0000377 | 1.8386 |
| 22 | 49677464 | rs62220604 | A | G | 0.276036142 | 0.723963858 | 0.0000355 | 0.5927 |

TABLE 4

Informative polymorphisms used in genetic risk assessment of Example 5 - 64 polymorphism panel. All SNPs are from the COVID-19 Host Genetics Initiative meta-analysis of hospitalisation vs non-hospitalisation except for rs11385942 and rs657152, which are from Ellinghaus et al. (2020).

| Chromosome | ID | Reference allele | Risk allele (A1 allele) | Risk allele odds ratio | Risk allele frequency |
|---|---|---|---|---|---|
| 1 | rs12745140 | G | A | 2.21 | 0.11 |
| 1 | rs12083278 | G | C | 1.83 | 0.70 |
| 1 | rs2765013 | T | C | 2.33 | 0.92 |
| 1 | rs2274122 | G | A | 1.78 | 0.80 |
| 1 | rs10873821 | T | C | 1.75 | 0.77 |
| 2 | rs6714112 | A | C | 2.19 | 0.86 |
| 2 | rs2270360 | C | A | 1.72 | 0.71 |
| 3 | rs1504061 | C | G | 2.52 | 0.06 |
| 3 | rs17317135 | A | G | 2.65 | 0.94 |
| 3 | rs1868132 | C | T | 1.97 | 0.10 |
| 3 | rs6440031 | A | G | 2.19 | 0.89 |
| 4 | rs3774881 | C | T | 1.87 | 0.85 |
| 4 | rs3774882 | G | C | 2.38 | 0.92 |
| 4 | rs6810404 | A | C | 1.58 | 0.51 |
| 4 | rs35540967 | T | C | 2.46 | 0.07 |
| 4 | rs115162070 | A | G | 2.69 | 0.92 |
| 4 | rs11729561 | C | T | 2.25 | 0.92 |
| 4 | rs112641600 | T | C | 2.17 | 0.90 |
| 5 | rs62377777 | C | T | 1.75 | 0.79 |
| 5 | rs4240376 | T | G | 1.75 | 0.80 |
| 5 | rs10039856 | T | C | 2.16 | 0.91 |
| 5 | rs2220543 | A | T | 1.73 | 0.71 |
| 5 | rs113791144 | C | T | 2.27 | 0.06 |
| 6 | rs6933436 | A | C | 1.62 | 0.28 |
| 6 | rs10755709 | G | A | 1.66 | 0.69 |
| 6 | rs140247774 | C | T | 2.60 | 0.06 |
| 6 | rs16873740 | T | A | 2.04 | 0.12 |
| 6 | rs9386484 | A | T | 1.86 | 0.75 |
| 8 | rs118072448 | C | T | 2.38 | 0.91 |
| 8 | rs10808999 | A | G | 1.89 | 0.86 |
| 8 | rs13282163 | C | A | 2.39 | 0.93 |
| 8 | rs11779911 | A | C | 1.63 | 0.66 |
| 8 | rs2010843 | T | C | 1.59 | 0.55 |
| 9 | rs3895472 | T | C | 2.42 | 0.91 |
| 9 | rs12236000 | C | G | 2.44 | 0.93 |
| 9 | rs7027911 | G | A | 1.59 | 0.44 |
| 10 | rs71481792 | T | A | 1.71 | 0.38 |
| 10 | rs2091431 | A | G | 1.62 | 0.71 |
| 10 | rs1892429 | G | A | 1.90 | 0.79 |
| 10 | rs10793436 | T | G | 1.68 | 0.68 |
| 10 | rs1441121 | A | T | 1.59 | 0.56 |
| 11 | rs10766439 | G | A | 1.57 | 0.39 |
| 12 | rs11613792 | G | A | 2.13 | 0.84 |
| 12 | rs12823094 | T | A | 1.70 | 0.26 |

TABLE 4-continued

Informative polymorphisms used in genetic risk assessment of Example 5 - 64 polymorphism panel. All SNPs are from the COVID-19 Host Genetics Initiative meta-analysis of hospitalisation vs non-hospitalisation except for rs11385942 and rs657152, which are from Ellinghaus et al. (2020).

| Chromosome | ID | Reference allele | Risk allele (A1 allele) | Risk allele odds ratio | Risk allele frequency |
|---|---|---|---|---|---|
| 13 | rs1984162 | A | G | 1.65 | 0.26 |
| 13 | rs12871414 | T | C | 1.64 | 0.72 |
| 14 | rs2238187 | A | G | 1.70 | 0.36 |
| 14 | rs12587980 | C | T | 1.54 | 0.39 |
| 15 | rs12593288 | T | C | 1.79 | 0.78 |
| 15 | rs2229117 | C | G | 1.93 | 0.87 |
| 16 | rs72803978 | G | A | 2.68 | 0.94 |
| 17 | rs34761447 | T | C | 2.17 | 0.89 |
| 17 | rs178840 | A | G | 1.70 | 0.75 |
| 18 | rs12958013 | C | T | 1.94 | 0.85 |
| 19 | rs8105499 | A | C | 1.62 | 0.69 |
| 19 | rs60744406 | A | G | 1.64 | 0.61 |
| 19 | rs10411226 | A | G | 1.77 | 0.24 |
| 21 | rs2252109 | T | A | 1.60 | 0.49 |
| 22 | rs5757427 | A | T | 1.80 | 0.63 |
| 22 | rs7290963 | G | T | 1.59 | 0.45 |
| 22 | rs11090305 | T | C | 1.84 | 0.18 |
| 22 | rs62220604 | A | G | 1.69 | 0.71 |
| 3 | rs11385942 | G | GA | 1.77 | 0.09 |
| 9 | rs657152 | C | A | 1.32 | 0.35 |

TABLE 5

New informative polymorphisms used in the development of the models described in Example 6.

| Chromosome | Position | SNP ID | Reference Allele | Effect Allele | Frequency 1 | Frequency 2 | p-value for association | OR | 95% CI |
|---|---|---|---|---|---|---|---|---|---|
| 1 | 46618634 | rs17102023 | A | G | 1 | 0 | 0.5 | 1.33 | 0.63, 2.81 |
| 1 | 150271556 | rs115492982 | G | A | 1 | 0 | 0.01 | 2.46 | 1.23, 4.91 |
| 1 | 152684866 | rs2224986 | C | T | 0.91 | 0.09 | 0.8 | 0.98 | 0.85, 1.14 |
| 1 | 192526317 | rs74508649 | C | T | 1 | 0 | 0.9 | 1.04 | 0.47, 2.32 |
| 1 | 239197542 | rs112317747 | T | C | 0.97 | 0.03 | 0.05 | 1.26 | 1.00, 1.58 |
| 2 | 79895332 | rs183569214 | G | A | 1 | 0 | 0.7 | 0.72 | 0.15, 3.45 |
| 2 | 80029580 | rs77764981 | T | C | 1 | 0 | 0.6 | 1.29 | 0.54, 3.10 |
| 2 | 182353446 | rs2034831 | A | C | 0.94 | 0.06 | 0.02 | 1.22 | 1.03, 1.46 |
| 3 | 3184653 | rs1705826 | C | G | 0.63 | 0.37 | 0.5 | 1.03 | 0.94, 1.12 |
| 3 | 45841938 | rs35896106 | C | T | 0.92 | 0.08 | 0.04 | 1.17 | 1.01, 1.35 |
| 3 | 45900634 | rs76374459 | G | C | 0.94 | 0.06 | 0.03 | 1.2 | 1.02, 1.41 |
| 3 | 45908514 | rs35652899 | C | G | 0.93 | 0.07 | 0.04 | 1.17 | 1.00, 1.36 |
| 3 | 45916222 | rs12639224 | C | T | 0.73 | 0.27 | 0.7 | 1.02 | 0.93, 1.12 |
| 3 | 45916786 | rs34901975 | G | A | 0.89 | 0.11 | 0.09 | 1.12 | 0.98, 1.27 |
| 3 | 46018781 | rs71615437 | A | G | 0.92 | 0.08 | 0.1 | 1.12 | 0.97, 1.29 |
| 3 | 46049765 | rs13433997 | T | C | 0.88 | 0.12 | 0.1 | 1.1 | 0.97, 1.24 |
| 3 | 46180416 | rs10510749 | C | T | 0.91 | 0.09 | 0.9 | 0.99 | 0.85, 1.15 |
| 3 | 46222037 | rs115102354 | A | G | 0.95 | 0.05 | 0.7 | 0.96 | 0.79, 1.16 |
| 3 | 62936766 | rs13062942 | A | G | 0.64 | 0.36 | 0.09 | 0.92 | 0.84, 1.01 |
| 3 | 148718087 | rs76488148 | G | T | 0.96 | 0.04 | 0.03 | 1.25 | 1.02, 1.52 |
| 5 | 169590905 | rs4478338 | T | G | 0.92 | 0.08 | 0.3 | 1.08 | 0.93, 1.25 |
| 5 | 171480160 | rs111265173 | C | T | 1 | 0 | 1 | 0.97 | 0.35, 2.66 |
| 6 | 27604726 | rs61611950 | C | T | 0.99 | 0.01 | 0.8 | 0.92 | 0.56, 1.51 |
| 7 | 152960930 | rs6967210 | T | C | 0.99 | 0.01 | 0.3 | 1.17 | 0.86, 1.59 |
| 8 | 8730488 | rs332040 | G | A | 0.53 | 0.47 | 0.9 | 1 | 0.92, 1.09 |
| 9 | 27121456 | rs71480372 | A | T | 0.66 | 0.34 | 0.7 | 0.98 | 0.90, 1.08 |
| 9 | 29688719 | rs74790577 | A | T | 1 | 0 | 0.9 | 1.05 | 0.27, 4.03 |
| 10 | 123000638 | rs5016035 | T | G | 0.51 | 0.49 | 0.9 | 1 | 0.91, 1.10 |
| 12 | 56084466 | rs7397549 | T | C | 0.59 | 0.41 | 0.9 | 0.99 | 0.90, 1.09 |
| 13 | 63178476 | rs2649134 | C | T | 0.97 | 0.03 | 0.5 | 0.93 | 0.72, 1.19 |
| 14 | 77692036 | rs144114696 | G | A | 1 | 0 | 0.3 | 2.53 | 0.51, 12.44 |
| 15 | 45858905 | rs77055952 | A | G | 0.95 | 0.05 | 0.5 | 1.07 | 0.88, 1.29 |
| 15 | 48984345 | rs74750712 | T | G | 1 | 0 | 0.4 | 1.33 | 0.65, 2.69 |
| 16 | 10579876 | rs72779789 | G | C | 0.95 | 0.05 | 0.7 | 1.04 | 0.85, 1.26 |
| 16 | 49311043 | rs145643452 | G | A | 0.99 | 0.01 | 0.9 | 1.03 | 0.61, 1.74 |
| 17 | 80443309 | rs9890316 | G | A | 0.69 | 0.31 | 0.9 | 1.01 | 0.92, 1.10 |
| 18 | 30006171 | rs142257532 | T | C | 0.97 | 0.03 | 1 | 1.01 | 0.78, 1.30 |
| 20 | 39389409 | rs56259900 | A | G | 1 | 0 | 0.6 | 1.15 | 0.65, 2.04 |
| 20 | 60473717 | rs76253189 | C | G | 0.99 | 0.01 | 1 | 1.01 | 0.72, 1.42 |
| 21 | 44424444 | rs75994231 | C | T | 0.98 | 0.02 | 0.7 | 1.06 | 0.79, 1.43 |

TABLE 6

Surrogate markers for polymorphism provided in Table 3 (Part A) and additional polymorphisms used in Table 4 (Part B).
Part C provides surrogate markers for rs115492982.

| Primary SNP | Proxy SNP | Coordinate (GRCh37/hg19) | Alleles | MAF | Distance | D' | R2 | Correlated_Alleles |
|---|---|---|---|---|---|---|---|---|
| | | | Part A | | | | | |
| rs2765013 | rs581459 | chr1:36375110 | (C/T) | 0.0875 | 1009 | 1 | 1 | C=C,T=T |
| rs2765013 | rs2791961 | chr1:36371419 | (G/C) | 0.0885 | −2682 | 1 | 0.9877 | C=G,T=C |
| rs2765013 | rs2791962 | chr1:36371168 | (T/C) | 0.0885 | −2933 | 1 | 0.9877 | C=T,T=C |
| rs2765013 | rs794222 | chr1:36369024 | (T/C) | 0.0885 | −5077 | 1 | 0.9877 | C=T,T=C |
| rs2765013 | rs661233 | chr1:36364716 | (A/G) | 0.0885 | −9385 | 1 | 0.9877 | C=A,T=G |
| rs2765013 | rs654688 | chr1:36384215 | (T/C) | 0.0885 | 10114 | 1 | 0.9877 | C=T,T=C |
| rs2765013 | rs647690 | chr1:36363982 | (G/C) | 0.0885 | −10119 | 1 | 0.9877 | C=G,T=C |
| rs2765013 | rs636832 | chr1:36363475 | (G/A) | 0.0885 | −10626 | 1 | 0.9877 | C=G,T=A |
| rs2765013 | rs620956 | chr1:36362162 | (T/C) | 0.0885 | −11939 | 1 | 0.9877 | C=T,T=C |
| rs2765013 | rs653417 | chr1:36356842 | (G/T) | 0.0885 | −17259 | 1 | 0.9877 | C=G,T=T |
| rs2765013 | rs2765012 | chr1:36356457 | (A/G) | 0.0885 | −17644 | 1 | 0.9877 | C=A,T=G |
| rs2765013 | rs11263830 | chr1:36345798 | (G/A) | 0.0885 | −28303 | 1 | 0.9877 | C=G,T=A |
| rs2765013 | rs811114 | chr1:36345758 | (G/A) | 0.0885 | −28343 | 1 | 0.9877 | C=G,T=A |
| rs2765013 | rs11263843 | chr1:36405929 | (G/A) | 0.0885 | 31828 | 1 | 0.9877 | C=G,T=A |
| rs2765013 | rs12031138 | chr1:36407806 | (A/G) | 0.0885 | 33705 | 1 | 0.9877 | C=A,T=G |
| rs2765013 | rs6665591 | chr1:36411737 | (A/G) | 0.0885 | 37636 | 1 | 0.9877 | C=A,T=G |
| rs2765013 | rs12041193 | chr1:36412760 | (C/T) | 0.0885 | 38659 | 1 | 0.9877 | C=C,T=T |
| rs2765013 | rs67641270 | chr1:36413329 | (T/C) | 0.0885 | 39228 | 1 | 0.9877 | C=T,T=C |
| rs2765013 | rs142884229 | chr1:36419258 | (—/AGAGAATACAGGTGT) | 0.0885 | 45157 | 1 | 0.9877 | C=—,T=AGAGAATACAGGTGT |
| rs2765013 | rs716926 | chr1:36424476 | (T/C) | 0.0885 | 50375 | 1 | 0.9877 | C=T,T=C |
| rs2765013 | rs716925 | chr1:36424517 | (A/G) | 0.0885 | 50416 | 1 | 0.9877 | C=A,T=G |
| rs2765013 | rs10796876 | chr1:36424985 | (A/G) | 0.0885 | 50884 | 1 | 0.9877 | C=A,T=G |
| rs2765013 | rs60867325 | chr1:36429590 | (—/G) | 0.0885 | 55489 | 1 | 0.9877 | C=—,T=G |
| rs2765013 | rs645864 | chr1:36430941 | (C/A) | 0.0885 | 56840 | 1 | 0.9877 | C=C,T=A |
| rs2765013 | rs649152 | chr1:36438649 | (T/G) | 0.0885 | 64548 | 1 | 0.9877 | C=T,T=G |
| rs2765013 | rs709309 | chr1:36441148 | (G/T) | 0.0885 | 67047 | 1 | 0.9877 | C=G,T=T |
| rs2765013 | rs686650 | chr1:36441613 | (A/G) | 0.0885 | 67512 | 1 | 0.9877 | C=A,T=G |
| rs2765013 | rs682686 | chr1:36443778 | (T/A) | 0.0885 | 69677 | 1 | 0.9877 | C=T,T=A |
| rs2765013 | rs665521 | chr1:36445837 | (T/C) | 0.0885 | 71736 | 1 | 0.9877 | C=T,T=C |
| rs2765013 | rs630364 | chr1:36449304 | (C/T) | 0.0885 | 75203 | 1 | 0.9877 | C=C,T=T |
| rs2765013 | rs625306 | chr1:36454016 | (T/C) | 0.0885 | 79915 | 1 | 0.9877 | C=T,T=C |
| rs2765013 | rs688833 | chr1:36455600 | (C/T) | 0.0885 | 81499 | 1 | 0.9877 | C=C,T=T |
| rs2765013 | rs112607939 | chr1:36460189 | (—/CTAT) | 0.0885 | 86088 | 1 | 0.9877 | C=—,T=CTAT |
| rs2765013 | rs688191 | chr1:36460681 | (G/A) | 0.0885 | 86580 | 1 | 0.9877 | C=G,T=A |
| rs2765013 | rs7542179 | chr1:36461122 | (G/A) | 0.0885 | 87021 | 1 | 0.9877 | C=G,T=A |
| rs2765013 | rs56198971 | chr1:36403174 | (T/C) | 0.0895 | 29073 | 1 | 0.9756 | C=T,T=C |
| rs2765013 | rs644095 | chr1:36363172 | (C/T) | 0.0875 | −10929 | 1 | 0.9752 | C=C,T=T |
| rs2765013 | rs111375913 | chr1:36403173 | (—/C) | 0.0875 | 29072 | 0.9875 | 0.9752 | C=—,TC |
| rs2765013 | rs645383 | chr1:36373823 | (C/G) | 0.0855 | −278 | 1 | 0.9751 | C=C,T=G |
| rs2765013 | rs35467166 | chr1:36410818 | (—/C) | 0.0865 | 36717 | 0.9874 | 0.9628 | C=—,T=C |
| rs2765013 | rs663163 | chr1:36390527 | (A/G) | 0.0915 | 16426 | 1 | 0.9524 | C=A,T=G |
| rs2765013 | rs685370 | chr1:36443214 | (A/G) | 0.0915 | 69113 | 1 | 0.9524 | C=A,T=G |
| rs2765013 | rs614235 | chr1:36450565 | (G/A) | 0.0944 | 76464 | 1 | 0.9193 | C=G,T=A |
| rs2765013 | rs201615643 | chr1:36468742 | (—/T) | 0.0934 | 94641 | 0.9875 | 0.9069 | C=—,T=T |
| rs2765013 | rs683622 | chr1:36443569 | (A/G) | 0.0755 | 69468 | 1 | 0.8525 | C=A,T=G |
| rs2765013 | rs631202 | chr1:36449099 | (G/C) | 0.0755 | 74998 | 1 | 0.8525 | C=G,T=C |
| rs2765013 | rs645123 | chr1:36458075 | (T/C) | 0.0755 | 83974 | 1 | 0.8525 | C=T,T=C |
| rs2765013 | rs72661616 | chr1:36370512 | (G/A) | 0.0746 | −3589 | 1 | 0.8404 | C=G,T=A |
| rs2765013 | rs55762724 | chr1:36382702 | (C/T) | 0.0746 | 8601 | 1 | 0.8404 | C=C,T=T |
| rs2765013 | rs72661613 | chr1:36364781 | (A/G) | 0.0746 | −9320 | 1 | 0.8404 | C=A,T=G |
| rs2765013 | rs199596553 | chr1:36357062 | (T/—) | 0.0746 | −17039 | 1 | 0.8404 | C=T,T=— |
| rs2765013 | rs72661623 | chr1:36398368 | (G/A) | 0.0746 | 24267 | 1 | 0.8404 | C=G,T=A |
| rs2765013 | rs116757422 | chr1:36349560 | (G/A) | 0.0746 | −24541 | 1 | 0.8404 | C=G,T=A |
| rs2765013 | rs72661625 | chr1:36401003 | (T/C) | 0.0746 | 26902 | 1 | 0.8404 | C=T,T=C |
| rs2765013 | rs79303353 | chr1:36402056 | (G/A) | 0.0746 | 27955 | 1 | 0.8404 | C=G,T=A |
| rs2765013 | rs72661628 | chr1:36406547 | (A/G) | 0.0746 | 32446 | 1 | 0.8404 | C=A,T=G |
| rs2765013 | rs74879824 | chr1:36413117 | (T/A) | 0.0746 | 39016 | 1 | 0.8404 | C=T,T=A |
| rs2765013 | rs72661631 | chr1:36417453 | (A/G) | 0.0746 | 43352 | 1 | 0.8404 | C=A,T=G |
| rs2765013 | rs72661632 | chr1:36420715 | (G/A) | 0.0746 | 46614 | 1 | 0.8404 | C=G,T=A |
| rs2765013 | rs72661636 | chr1:36426483 | (T/C) | 0.0746 | 52382 | 1 | 0.8404 | C=T,T=C |
| rs2765013 | rs142370407 | chr1:36430202 | (C/G) | 0.0746 | 56101 | 1 | 0.8404 | C=C,T=G |
| rs2765013 | rs584873 | chr1:36431806 | (C/A) | 0.0746 | 57705 | 1 | 0.8404 | C=C,T=A |
| rs2765013 | rs142324044 | chr1:36433070 | (C/T) | 0.0746 | 58969 | 1 | 0.8404 | C=C,T=T |
| rs2765013 | rs72661640 | chr1:36447232 | (T/G) | 0.0746 | 73131 | 1 | 0.8404 | C=T,T=G |
| rs2765013 | rs72661641 | chr1:36448130 | (A/G) | 0.0746 | 74029 | 1 | 0.8404 | C=A,T=G |
| rs2765013 | rs72661643 | chr1:36451599 | (A/G) | 0.0746 | 77498 | 1 | 0.8404 | C=A,T=G |
| rs2765013 | rs72661644 | chr1:36453894 | (G/A) | 0.0746 | 79793 | 1 | 0.8404 | C=G,T=A |
| rs2765013 | rs72661646 | chr1:36454954 | (A/T) | 0.0746 | 80853 | 1 | 0.8404 | C=A,T=T |
| rs2765013 | rs72661655 | chr1:36475401 | (G/T) | 0.0746 | 101300 | 1 | 0.8404 | C=G,T=T |
| rs2765013 | rs138030683 | chr1:36353261 | (—/T) | 0.0755 | −20840 | 0.9856 | 0.8281 | C=—,T=T |
| rs2765013 | rs148983758 | chr1:36336826 | (T/—) | 0.0755 | −37275 | 0.9856 | 0.8281 | C=T,T=— |

TABLE 6-continued

Surrogate markers for polymorphism provided in Table 3 (Part A) and additional polymorphisms used in Table 4 (Part B).
Part C provides surrogate markers for rs115492982.

| Primary SNP | Proxy SNP | Coordinate (GRCh37/hg19) | Alleles | MAF | Distance | D' | R2 | Correlated_Alleles |
|---|---|---|---|---|---|---|---|---|
| rs2765013 | rs629773 | chr1:36431561 | (A/G) | 0.1064 | 57460 | 1 | 0.8054 | C=A,T=G |
| rs112728381 | rs12732999 | chr1:63766723 | (G/A) | 0.3241 | 5 | 1 | 0.9597 | C=G,T=A |
| rs10873821 | rs7550642 | chr1:87629310 | (G/A) | 0.2227 | 1137 | 1 | 1 | C=G,T=A |
| rs6714112 | rs6716934 | chr2:36912284 | (A/T) | 0.1282 | 7271 | 1 | 0.9646 | C=A,A=T |
| rs1504061 | rs1504061 | chr3:1093795 | (C/G) | 0.0487 | 0 | 1 | 1 | C=C,G=G |
| rs1504061 | rs1312543601 | chr3:1094816 | (—/T) | 0.0567 | 1021 | 1 | 0.8525 | C=—,G=T |
| rs1504061 | rs55975362 | chr3:1103832 | (G/C) | 0.0577 | 10037 | 1 | 0.8369 | C=G,G=C |
| rs1504061 | rs72993835 | chr3:1104218 | (T/C) | 0.0577 | 10423 | 1 | 0.8369 | C=T,G=C |
| rs1504061 | rs111403218 | chr3:1104296 | (C/T) | 0.0577 | 10501 | 1 | 0.8369 | C=C,G=T |
| rs1504061 | rs142136066 | chr3:1104395 | (T/G) | 0.0577 | 10600 | 1 | 0.8369 | C=T,G=G |
| rs1504061 | rs116727350 | chr3:1104957 | (G/A) | 0.0577 | 11162 | 1 | 0.8369 | C=G,G=A |
| rs1504061 | rs72993828 | chr3:1097969 | (T/G) | 0.0586 | 4174 | 1 | 0.8218 | C=T,G=G |
| rs1504061 | rs72993831 | chr3:1099234 | (A/G) | 0.0586 | 5439 | 1 | 0.8218 | C=A,G=G |
| rs1504061 | rs72993838 | chr3:1106164 | (G/A) | 0.0586 | 12369 | 1 | 0.8218 | C=G,G=A |
| rs17317135 | rs9863368 | chr3:27253521 | (T/C) | 0.0567 | 65223 | 1 | 0.947 | G=C,A=T |
| rs3774881 | rs148165034 | chr4:5822073 | (AAC/—) | 0.1412 | 196 | 1 | 0.9838 | T=AAC,C=— |
| rs3774881 | rs6846920 | chr4:5827911 | (A/G) | 0.1471 | 6034 | 0.9104 | 0.8027 | T=A,C=G |
| rs3774881 | rs11318332 | chr4:5827975 | (A/—) | 0.1451 | 6098 | 0.9025 | 0.8015 | T=A,C=— |
| rs6810404 | rs3069341 | chr4:27384266 | (AGC/—) | 0.4791 | 988 | 1 | 0.9921 | C=AGC,A=— |
| rs6810404 | rs7659968 | chr4:27383850 | (G/A) | 0.4831 | 572 | 1 | 0.9764 | C=G,A=A |
| rs6810404 | rs9291496 | chr4:27370190 | (A/G) | 0.4851 | -13088 | 0.9957 | 0.8523 | C=A,A=G |
| rs35540967 | rs17539340 | chr4:44429579 | (A/G) | 0.0765 | 10987 | 1 | 1 | T=A,C=G |
| rs112641600 | rs116432804 | chr4:112626500 | (T/C) | 0.0934 | 13474 | 0.9883 | 0.9767 | C=T,T=C |
| rs112641600 | rs72680134 | chr4:112627204 | (C/T) | 0.0934 | 14178 | 0.9883 | 0.9767 | C=C,T=T |
| rs112641600 | rs72680150 | chr4:112711302 | (A/G) | 0.0934 | 98276 | 0.9765 | 0.9536 | C=A,T=G |
| rs112641600 | rs147521731 | chr4:112680269 | (G/A) | 0.0964 | 67243 | 0.9765 | 0.9209 | C=G,T=A |
| rs62377777 | rs72080072 | chr5:122835924 | (TATAAG/—) | 0.2356 | 3208 | 1 | 0.9891 | T=TATAAG,C=— |
| rs62377777 | rs55893406 | chr5:122837233 | (T/A) | 0.2346 | 4517 | 1 | 0.9836 | T=T,C=A |
| rs62377777 | rs55914925 | chr5:122834333 | (G/A) | 0.2336 | 1617 | 1 | 0.9782 | T=G,C=A |
| rs62377777 | rs2036321 | chr5:122838501 | (C/T) | 0.2336 | 5785 | 1 | 0.9782 | T=C,C=T |
| rs62377777 | rs2173683 | chr5:122841745 | (C/A) | 0.2336 | 9029 | 1 | 0.9782 | T=C,C=A |
| rs62377777 | rs10593358 | chr5:122845970 | (CAAGC/—) | 0.2336 | 13254 | 1 | 0.9782 | T=CAAGC,C=— |
| rs62377777 | rs1392437 | chr5:122821063 | (C/T) | 0.2336 | -11653 | 0.9888 | 0.9564 | T=C,C=T |
| rs62377777 | rs17164879 | chr5:122863961 | (C/T) | 0.2237 | 31245 | 0.9942 | 0.9138 | T=C,C=T |
| rs62377777 | rs12519921 | chr5:122830670 | (G/A) | 0.2078 | -2046 | 1 | 0.8416 | T=G,C=A |
| rs62377777 | rs62377776 | chr5:122814546 | (T/G) | 0.2107 | -18170 | 0.9814 | 0.8254 | T=T,C=G |
| rs62377777 | rs12517980 | chr5:122813888 | (T/C) | 0.2117 | -18828 | 0.9754 | 0.8201 | T=T,C=C |
| rs62377777 | rs6595453 | chr5:122814897 | (T/C) | 0.2117 | -17819 | 0.9692 | 0.8097 | T=T,C=C |
| rs4240376 | rs10066524 | chr5:123950880 | (G/A) | 0.2207 | 476 | 1 | 0.9429 | G=G,T=A |
| rs4240376 | rs10068590 | chr5:123951944 | (C/A) | 0.1998 | 1540 | 1 | 0.9117 | G=C,T=A |
| rs4240376 | rs12520962 | chr5:123953224 | (G/C) | 0.2018 | 2820 | 0.9688 | 0.8886 | G=G,T=C |
| rs4240376 | rs4580771 | chr5:123954814 | (T/C) | 0.2018 | 4410 | 0.9688 | 0.8886 | G=T,T=C |
| rs4240376 | rs6871217 | chr5:123960447 | (G/A) | 0.1988 | 10043 | 0.9747 | 0.8828 | G=G,T=A |
| rs4240376 | rs10428701 | chr5:123960974 | (C/T) | 0.1988 | 10570 | 0.9747 | 0.8828 | G=C,T=T |
| rs4240376 | rs12514836 | chr5:123957328 | (A/G) | 0.2068 | 6924 | 0.933 | 0.8498 | G=A,T=G |
| rs4240376 | rs62372143 | chr5:123957443 | (A/G) | 0.2068 | 7039 | 0.933 | 0.8498 | G=A,T=G |
| rs4240376 | rs62372144 | chr5:123957610 | (A/T) | 0.2068 | 7206 | 0.933 | 0.8498 | G=A,T=T |
| rs4240376 | rs66500836 | chr5:123957985 | (C/G) | 0.2068 | 7581 | 0.933 | 0.8498 | G=C,T=G |
| rs4240376 | rs6899090 | chr5:123958033 | (A/G) | 0.2068 | 7629 | 0.933 | 0.8498 | G=A,T=G |
| rs4240376 | rs6859251 | chr5:123958110 | (G/A) | 0.2068 | 7706 | 0.933 | 0.8498 | G=G,T=A |
| rs4240376 | rs6859613 | chr5:123958332 | (G/C) | 0.2068 | 7928 | 0.933 | 0.8498 | G=G,T=C |
| rs4240376 | rs12513982 | chr5:123959748 | (T/A) | 0.2068 | 9344 | 0.933 | 0.8498 | G=T,T=A |
| rs4240376 | rs373774956 | chr5:123961537 | (TTTGTTTG/—) | 0.2068 | 11133 | 0.933 | 0.8498 | G=TTTGTTTG,T=— |
| rs4240376 | rs6893169 | chr5:123960800 | (T/A) | 0.2058 | 10396 | 0.9327 | 0.844 | G=T,T=A |
| rs4240376 | rs11241757 | chr5:123961500 | (T/C) | 0.2058 | 11096 | 0.9327 | 0.844 | G=T,T=C |
| rs4240376 | rs12516428 | chr5:123959806 | (A/G) | 0.2048 | 9402 | 0.9323 | 0.8383 | G=A,T=G |
| rs4240376 | rs10052511 | chr5:123963652 | (C/T) | 0.1889 | 13248 | 0.98 | 0.8375 | G=C,T=T |
| rs4240376 | rs71574121 | chr5:123964265 | (GA/—) | 0.1849 | 13861 | 0.9796 | 0.8152 | G=GA,T=— |
| rs2220543 | rs7720656 | chr5:173996282 | (A/G) | 0.3012 | 6944 | 0.9952 | 0.9672 | T=G,A=A |
| rs2220543 | rs1387768 | chr5:173993166 | (A/G) | 0.2803 | 3828 | 1 | 0.9254 | T=A,A=G |
| rs2220543 | rs1387769 | chr5:173993252 | (C/A) | 0.2803 | 3914 | 1 | 0.9254 | T=C,A=A |
| rs2220543 | rs4868427 | chr5:173992056 | (A/T) | 0.2813 | 2718 | 0.995 | 0.9206 | T=T,A=A |
| rs113791144 | rs117101214 | chr5:180237845 | (C/T) | 0.0835 | 17 | 1 | 1 | C=C,T=T |
| rs113791144 | rs147634845 | chr5:180237902 | (C/A) | 0.0835 | 74 | 1 | 1 | C=C,T=A |
| rs113791144 | rs78102637 | chr5:180238393 | (G/A) | 0.0835 | 565 | 1 | 1 | C=G,T=A |
| rs113791144 | rs11544558 | chr5:180235737 | (C/A) | 0.0865 | -2091 | 1 | 0.9624 | C=C,T=A |
| rs113791144 | rs75268547 | chr5:180238308 | (G/T) | 0.0845 | 480 | 0.987 | 0.9617 | C=G,T=T |
| rs113791144 | rs112702671 | chr5:180220930 | (C/T) | 0.0885 | -16898 | 0.9869 | 0.9143 | C=C,T=T |
| rs113791144 | rs10577599 | chr5:180216905 | (AT/—) | 0.0845 | -20923 | 0.961 | 0.9116 | C=AT,T=— |
| rs113791144 | rs76809244 | chr5:180216077 | (C/G) | 0.0855 | -21751 | 0.9609 | 0.9 | C=C,T=G |
| rs113791144 | rs145796183 | chr5:180238591 | (T/—) | 0.0686 | 763 | 1 | 0.8083 | C=T,T=— |
| rs113791144 | rs10040542 | chr5:180242178 | (C/T) | 0.0686 | 4350 | 1 | 0.8083 | C=C,T=T |
| rs10755709 | rs7356945 | chr6:12217422 | (C/T) | 0.3022 | 456 | 0.9525 | 0.8988 | A=C,G=T |
| rs16873740 | rs35926878 | chr6:45705862 | (G/A) | 0.1183 | 1049 | 1 | 1 | T=G,A=A |

TABLE 6-continued

Surrogate markers for polymorphism provided in Table 3 (Part A) and additional polymorphisms used in Table 4 (Part B).
Part C provides surrogate markers for rs115492982.

| Primary SNP | Proxy SNP | Coordinate (GRCh37/hg19) | Alleles | MAF | Distance | D' | R2 | Correlated_Alleles |
|---|---|---|---|---|---|---|---|---|
| rs13282163 | rs55750326 | chr8:38949033 | (C/—) | 0.0875 | 51563 | 1 | 0.9877 | A=C,C=— |
| rs12236000 | rs10964856 | chr9:21131785 | (A/G) | 0.0855 | 158 | 1 | 0.9873 | G=A,C=G |
| rs2091431 | rs2505150 | chr10:37278930 | (A/G) | 0.3211 | 1060 | 1 | 1 | A=A,G=G |
| rs2091431 | rs10764117 | chr10:37284272 | (A/G) | 0.325 | 6402 | 1 | 0.982 | A=A,G=G |
| rs2091431 | rs2505172 | chr10:37286042 | (C/A) | 0.325 | 8172 | 1 | 0.982 | A=C,G=A |
| rs2091431 | rs2459442 | chr10:37292750 | (G/A) | 0.3241 | 14880 | 0.9954 | 0.9774 | A=A,G=G |
| rs2091431 | rs2459421 | chr10:37303511 | (C/T) | 0.3231 | 25641 | 0.9863 | 0.9639 | A=T,G=C |
| rs2091431 | rs138295864 | chr10:37302778 | (—/A) | 0.3211 | 24908 | 0.9818 | 0.9639 | A=A,G=— |
| rs2091431 | rs35067257 | chr10:37282717 | (T/—) | 0.336 | 4847 | 1 | 0.9346 | A=T,G=— |
| rs2091431 | rs1914151 | chr10:37304072 | (C/A) | 0.338 | 26202 | 0.9766 | 0.8835 | A=A,G=C |
| rs2091431 | rs1914152 | chr10:37304128 | (A/G) | 0.338 | 26258 | 0.9766 | 0.8835 | A=G,G=A |
| rs2091431 | rs2459426 | chr10:37307089 | (G/A) | 0.337 | 29219 | 0.972 | 0.8791 | A=A,G=G |
| rs2091431 | rs2459429 | chr10:37308202 | (C/T) | 0.337 | 30332 | 0.972 | 0.8791 | A=T,G=C |
| rs2091431 | rs2459433 | chr10:37311324 | (A/G) | 0.337 | 33454 | 0.972 | 0.8791 | A=G,G=A |
| rs2091431 | rs2505166 | chr10:37318114 | (C/T) | 0.337 | 40244 | 0.972 | 0.8791 | A=T,G=C |
| rs2091431 | rs11011000 | chr10:37328362 | (A/G) | 0.337 | 50492 | 0.972 | 0.8791 | A=G,G=A |
| rs2091431 | rs2459440 | chr10:37338386 | (C/T) | 0.337 | 60516 | 0.972 | 0.8791 | A=T,G=C |
| rs2091431 | rs2505174 | chr10:37338614 | (G/A) | 0.337 | 60744 | 0.972 | 0.8791 | A=A,G=G |
| rs2091431 | rs2459441 | chr10:37340271 | (T/C) | 0.337 | 62401 | 0.972 | 0.8791 | A=C,G=T |
| rs2091431 | rs34886927 | chr10:37345130 | (T/—) | 0.337 | 67260 | 0.972 | 0.8791 | A=—,G=T |
| rs2091431 | rs10827752 | chr10:37318895 | (C/T) | 0.338 | 41025 | 0.9719 | 0.8751 | A=T,G=C |
| rs2091431 | rs12221175 | chr10:37327753 | (C/T) | 0.338 | 49883 | 0.9719 | 0.8751 | A=T,G=C |
| rs2091431 | rs2505164 | chr10:37317344 | (C/A) | 0.339 | 39474 | 0.9719 | 0.8711 | A=A,G=C |
| rs2091431 | rs2459434 | chr10:37311831 | (G/T) | 0.337 | 33961 | 0.9626 | 0.8623 | A=T,G=G |
| rs1892429 | rs1200880 | chr10:37450374 | (T/C) | 0.2624 | −4023 | 1 | 0.9 | A=T,G=C |
| rs1892429 | rs1767366 | chr10:37494647 | (G/A) | 0.2624 | 40250 | 1 | 0.9 | A=G,G=A |
| rs1892429 | rs1933748 | chr10:37498227 | (C/T) | 0.2624 | 43830 | 1 | 0.9 | A=C,G=T |
| rs1892429 | rs2490107 | chr10:37484946 | (G/A) | 0.2634 | 30549 | 1 | 0.8954 | A=G,G=A |
| rs1892429 | rs1200876 | chr10:37505141 | (G/A) | 0.2634 | 50744 | 1 | 0.8954 | A=G,G=A |
| rs1892429 | rs1148258 | chr10:37506384 | (G/A) | 0.2634 | 51987 | 1 | 0.8954 | A=G,G=A |
| rs1892429 | rs138860607 | chr10:37515709 | (AGCAGCTATACCATTTTTCATT/—) | 0.2634 | 61312 | 1 | 0.8954 | A=AGCAGCTATACCATTTTTCATT,G=— |
| rs1892429 | rs1200857 | chr10:37521828 | (A/C) | 0.2634 | 67431 | 1 | 0.8954 | A=A,G=C |
| rs1892429 | rs1148264 | chr10:37527168 | (A/T) | 0.2634 | 72771 | 1 | 0.8954 | A=A,G=T |
| rs1892429 | rs1767387 | chr10:37536757 | (C/T) | 0.2634 | 82360 | 1 | 0.8954 | A=C,G=T |
| rs1892429 | rs1200875 | chr10:37505192 | (C/T) | 0.2644 | 50795 | 1 | 0.8908 | A=C,G=T |
| rs1892429 | rs2765819 | chr10:37525622 | (G/T) | 0.2644 | 71225 | 1 | 0.8908 | A=G,G=T |
| rs1892429 | rs1711240 | chr10:37378880 | (C/T) | 0.2604 | −75517 | 0.9446 | 0.8113 | A=C,G=T |
| rs1441121 | rs1441123 | chr10:54101139 | (T/G) | 0.4334 | 794 | 1 | 0.996 | A=T,T=G |
| rs1441121 | rs73331255 | chr10:54105039 | (C/G) | 0.4324 | 4694 | 1 | 0.9919 | A=C,T=G |
| rs1441121 | rs1372107 | chr10:54114458 | (G/C) | 0.4404 | 14113 | 0.9959 | 0.9681 | A=G,T=C |
| rs1441121 | rs1441124 | chr10:54114916 | (G/A) | 0.4404 | 14571 | 0.9959 | 0.9681 | A=G,T=A |
| rs1441121 | rs11001719 | chr10:54108610 | (C/T) | 0.4394 | 8265 | 0.9918 | 0.9641 | A=C,T=T |
| rs1441121 | rs11814479 | chr10:54108930 | (T/G) | 0.4394 | 8585 | 0.9918 | 0.9641 | A=T,T=G |
| rs1441121 | rs11001721 | chr10:54109544 | (A/G) | 0.4394 | 9199 | 0.9918 | 0.9641 | A=A,T=G |
| rs1441121 | rs11001723 | chr10:54110313 | (C/T) | 0.4394 | 9968 | 0.9918 | 0.9641 | A=C,T=T |
| rs1441121 | rs7079513 | chr10:54110965 | (TG) | 0.4394 | 10620 | 0.9918 | 0.9641 | A=T,T=G |
| rs1441121 | rs7075951 | chr10:54111095 | (A/G) | 0.4394 | 10750 | 0.9918 | 0.9641 | A=A,T=G |
| rs1441121 | rs7904997 | chr10:54111864 | (A/T) | 0.4394 | 11519 | 0.9918 | 0.9641 | A=A,T=T |
| rs1441121 | rs10824390 | chr10:54110416 | (A/T) | 0.4404 | 10071 | 0.9918 | 0.9602 | A=A,T=T |
| rs1441121 | rs894104 | chr10:54106670 | (T/C) | 0.4384 | 6325 | 0.9878 | 0.9601 | A=T,T=C |
| rs1441121 | rs10762708 | chr10:54108307 | (C/G) | 0.4384 | 7962 | 0.9878 | 0.9601 | A=C,T=G |
| rs1441121 | rs10762712 | chr10:54112284 | (T/C) | 0.4364 | 11939 | 0.9797 | 0.9521 | A=T,T=C |
| rs1441121 | rs10740457 | chr10:54112762 | (A/G) | 0.4364 | 12417 | 0.9797 | 0.9521 | A=A,T=G |
| rs10766439 | rs2078786 | chr11:2896128 | (A/G) | 0.3678 | 2261 | 1 | 0.9872 | A=A,G=G |
| rs10766439 | rs11024404 | chr11:2894452 | (G/T) | 0.3887 | 585 | 1 | 0.9034 | A=G,G=T |
| rs10766439 | rs148588273 | chr11:2899462 | (—/C) | 0.3986 | 5595 | 0.9955 | 0.8587 | A=—,G=C |
| rs10766439 | rs10766443 | chr11:2899586 | (T/C) | 0.3986 | 5719 | 0.9955 | 0.8587 | A=T,G=C |
| rs10766439 | rs10766442 | chr11:2899538 | (C/T) | 0.3976 | 5671 | 0.991 | 0.8544 | A=C,G=T |
| rs10766439 | rs4929954 | chr11:2900383 | (C/G) | 0.3966 | 6516 | 0.9865 | 0.8502 | A=C,G=G |
| rs12823094 | rs35769445 | chr12:106625862 | (G/C) | 0.2396 | 909 | 0.9945 | 0.9837 | T=G,A=C |
| rs2238187 | rs2283380 | chr14:72909738 | (G/A) | 0.3946 | 1636 | 0.924 | 0.8326 | A=G,G=A |
| rs12587980 | rs917428 | chr14:72935767 | (C/T) | 0.4006 | 1538 | 1 | 0.9959 | C=C,T=T |
| rs2229117 | rs35242916 | chr15:33917374 | (C/T) | 0.1332 | 1321 | 1 | 1 | G=C,C=T |
| rs2229117 | rs34638660 | chr15:33919774 | (C/T) | 0.1332 | 3721 | 1 | 1 | G=C,C=T |
| rs2229117 | rs4780137 | chr15:33922609 | (T/A) | 0.1332 | 6556 | 1 | 1 | G=T,C=A |
| rs2229117 | rs4780138 | chr15:33922983 | (G/A) | 0.1332 | 6930 | 1 | 1 | G=G,C=A |
| rs2229117 | rs71462874 | chr15:33924037 | (G/A) | 0.1332 | 7984 | 1 | 1 | G=G,C=A |
| rs2229117 | rs35203574 | chr15:33928785 | (A/G) | 0.1342 | 12732 | 1 | 0.9915 | G=A,C=G |
| rs2229117 | rs36020093 | chr15:33919750 | (A/G) | 0.1362 | 3697 | 1 | 0.9747 | G=A,C=G |
| rs2229117 | rs2291730 | chr15:33923690 | (C/T) | 0.1362 | 7637 | 1 | 0.9747 | G=C,C=T |
| rs2229117 | rs3816940 | chr15:33925062 | (G/A) | 0.1362 | 9009 | 1 | 0.9747 | G=G,C=A |
| rs2229117 | rs12901506 | chr15:33929755 | (G/C) | 0.1511 | 13702 | 1 | 0.8634 | G=G,C=C |

TABLE 6-continued

Surrogate markers for polymorphism provided in Table 3 (Part A) and additional polymorphisms used in Table 4 (Part B).
Part C provides surrogate markers for rs115492982.

| Primary SNP | Proxy SNP | Coordinate (GRCh37/hg19) | Alleles | MAF | Distance | D' | R2 | Correlated_Alleles |
|---|---|---|---|---|---|---|---|---|
| rs2229117 | rs71462875 | chr15:33931313 | (A/G) | 0.1511 | 15260 | 1 | 0.8634 | G=A,C=G |
| rs72803978 | rs76614455 | chr16:78633493 | (G/A) | 0.0527 | 9468 | 0.98 | 0.873 | A=G,G=A |
| rs72803978 | rs138270756 | chr16:78640700 | (—/AAT) | 0.0626 | 16675 | 0.9448 | 0.8175 | A=—,G=AAT |
| rs34761447 | rs35985527 | chr17:9172769 | (G/A) | 0.1044 | 2361 | 0.9884 | 0.8843 | C=G,T=A |
| rs34761447 | rs12952893 | chr17:9176588 | (G/C) | 0.0994 | 6180 | 0.9306 | 0.8277 | C=G,T=C |
| rs34761447 | rs7215786 | chr17:9172095 | (T/C) | 0.1113 | 1687 | 0.9883 | 0.8224 | C=T,T=C |
| rs34761447 | rs35880517 | chr17:9174045 | (G/A) | 0.1004 | 3637 | 0.9305 | 0.8185 | C=G,T=A |
| rs34761447 | rs35306109 | chr17:9174082 | (A/G) | 0.1004 | 3674 | 0.9305 | 0.8185 | C=A,T=G |
| rs60744406 | rs397964 | chr19:44493969 | (A/T) | 0.4294 | 1805 | 1 | 1 | A=T,G=A |
| rs10411226 | rs1974832 | chr19:53333465 | (G/C) | 0.2247 | −510 | 0.9943 | 0.9886 | G=G,A=C |
| rs5757427 | rs2156880 | chr22:22570271 | (A/G) | 0.3598 | 5537 | 1 | 0.9914 | A=A,T=G |
| rs5757427 | rs11376968 | chr22:22567202 | (—/A) | 0.3549 | 2468 | 1 | 0.9871 | A=—,T=A |
| rs5757427 | rs2330040 | chr22:22567762 | (G/A) | 0.3618 | 3028 | 1 | 0.9829 | A=G,T=A |
| rs5757427 | rs5750729 | chr22:22566976 | (A/G) | 0.3549 | 2242 | 0.9869 | 0.9614 | A=A,T=G |
| rs5757427 | rs1007312 | chr22:22569758 | (A/C) | 0.3539 | 5024 | 0.9869 | 0.9572 | A=A,T=C |
| rs5757427 | rs738876 | chr22:22568531 | (C/T) | 0.3559 | 3797 | 0.9826 | 0.9572 | A=C,T=T |
| rs5757427 | rs5750739 | chr22:22568820 | (T/C) | 0.3559 | 4086 | 0.9826 | 0.9572 | A=T,T=C |
| rs5757427 | rs6001415 | chr22:22569640 | (T/G) | 0.3559 | 4906 | 0.9826 | 0.9572 | A=T,T=G |
| rs5757427 | rs5757477 | chr22:22572904 | (G/A) | 0.3648 | 8170 | 0.9913 | 0.9534 | A=G,T=A |
| rs5757427 | rs111384644 | chr22:22565774 | (—/CAGG) | 0.3569 | 1040 | 0.9783 | 0.953 | A=—,T=CAGG |
| rs5757427 | rs5757443 | chr22:22566563 | (T/G) | 0.3579 | 1829 | 0.974 | 0.9488 | A=T,T=G |
| rs5757427 | rs738874 | chr22:22567948 | (A/G) | 0.3579 | 3214 | 0.974 | 0.9488 | A=A,T=G |
| rs5757427 | rs738875 | chr22:22568014 | (G/T) | 0.3579 | 3280 | 0.974 | 0.9488 | A=G,T=T |
| rs5757427 | rs5750741 | chr22:22569448 | (T/A) | 0.3588 | 4714 | 0.974 | 0.9446 | A=T,T=A |
| rs5757427 | rs762464 | chr22:22574458 | (G/C) | 0.3588 | 9724 | 0.9697 | 0.9362 | A=G,T=C |
| rs5757427 | rs5757469 | chr22:22570658 | (A/G) | 0.3608 | 5924 | 0.9696 | 0.928 | A=A,T=G |
| rs5757427 | rs1029267 | chr22:22571456 | (T/A) | 0.3608 | 6722 | 0.9696 | 0.928 | A=T,T=A |
| rs5757427 | rs1029270 | chr22:22571681 | (G/C) | 0.3608 | 6947 | 0.9696 | 0.928 | A=G,T=C |
| rs5757427 | rs4599223 | chr22:22571981 | (C/T) | 0.3608 | 7247 | 0.9696 | 0.928 | A=C,T=T |
| rs5757427 | rs5757486 | chr22:22574248 | (A/G) | 0.3608 | 9514 | 0.9696 | 0.928 | A=A,T=G |
| rs5757427 | rs35158064 | chr22:22572122 | (T/—) | 0.3618 | 7388 | 0.9695 | 0.9239 | A=T,T=— |
| rs5757427 | rs1023418 | chr22:22572199 | (T/C) | 0.3618 | 7465 | 0.9695 | 0.9239 | A=T,T=C |
| rs5757427 | rs5750745 | chr22:22572812 | (C/T) | 0.3618 | 8078 | 0.9695 | 0.9239 | A=C,T=T |
| rs5757427 | rs5750746 | chr22:22572822 | (G/A) | 0.3618 | 8088 | 0.9695 | 0.9239 | A=G,T=A |
| rs5757427 | rs968897 | chr22:22570821 | (C/T) | 0.3598 | 6087 | 0.9653 | 0.9238 | A=C,T=T |
| rs5757427 | rs5750749 | chr22:22573209 | (T/C) | 0.3628 | 8475 | 0.9695 | 0.9198 | A=T,T=C |
| rs5757427 | rs5750750 | chr22:22573365 | (C/T) | 0.3628 | 8631 | 0.9695 | 0.9198 | A=C,T=T |
| rs5757427 | rs5750751 | chr22:22573414 | (G/A) | 0.3628 | 8680 | 0.9695 | 0.9198 | A=G,T=A |
| rs5757427 | rs5757482 | chr22:22573837 | (C/T) | 0.3628 | 9103 | 0.9695 | 0.9198 | A=C,T=T |
| rs5757427 | rs5757483 | chr22:22573878 | (C/A) | 0.3628 | 9144 | 0.9695 | 0.9198 | A=C,T=A |
| rs5757427 | rs5757484 | chr22:22573973 | (C/G) | 0.3628 | 9239 | 0.9695 | 0.9198 | A=C,T=G |
| rs5757427 | rs5757485 | chr22:22574035 | (T/C) | 0.3628 | 9301 | 0.9695 | 0.9198 | A=T,T=C |
| rs5757427 | rs5750752 | chr22:22574105 | (G/A) | 0.3628 | 9371 | 0.9695 | 0.9198 | A=G,T=A |
| rs5757427 | rs762465 | chr22:22574855 | (C/T) | 0.3618 | 10121 | 0.9652 | 0.9156 | A=C,T=T |
| rs5757427 | rs1029269 | chr22:22571612 | (G/A) | 0.3887 | 6878 | 0.9682 | 0.8217 | A=G,T=A |
| rs7290963 | rs7287541 | chr22:22725057 | (T/G) | 0.4433 | 106 | 1 | 0.992 | G=T,T=G |
| rs11090305 | rs9608231 | chr22:24415817 | (A/T) | 0.2157 | 8334 | 0.9823 | 0.9426 | T=T,C=A |
| rs11090305 | rs6004044 | chr22:24422166 | (A/G) | 0.2157 | 14683 | 0.9823 | 0.9426 | T=G,C=A |
| rs11090305 | rs873833 | chr22:24427878 | (G/A) | 0.2157 | 20395 | 0.9823 | 0.9426 | T=A,C=G |
| rs11090305 | rs5996663 | chr22:24429241 | (C/T) | 0.2157 | 21758 | 0.9823 | 0.9426 | T=T,C=C |
| rs11090305 | rs2282475 | chr22:24438047 | (A/G) | 0.2157 | 30564 | 0.9823 | 0.9426 | T=G,C=A |
| rs11090305 | rs5751798 | chr22:24443473 | (T/C) | 0.2157 | 35990 | 0.9823 | 0.9426 | T=C,C=T |
| rs11090305 | rs2070467 | chr22:24452885 | (A/G) | 0.2157 | 45402 | 0.9823 | 0.9426 | T=G,C=A |
| rs11090305 | rs5760179 | chr22:24411653 | (C/T) | 0.2147 | 4170 | 0.9822 | 0.9369 | T=T,C=C |
| rs11090305 | rs6004042 | chr22:24420722 | (C/T) | 0.2147 | 13239 | 0.9822 | 0.9369 | T=T,C=C |
| rs11090305 | rs2267053 | chr22:24457197 | (C/T) | 0.2147 | 49714 | 0.9822 | 0.9369 | T=T,C=C |
| rs11090305 | rs2051198 | chr22:24465672 | (A/G) | 0.2147 | 58189 | 0.9822 | 0.9369 | T=G,C=A |
| rs11090305 | rs4822469 | chr22:24425114 | (C/G) | 0.2157 | 17631 | 0.9764 | 0.9313 | T=G,C=C |
| rs11090305 | rs2283807 | chr22:24472270 | (A/G) | 0.2157 | 64787 | 0.9764 | 0.9313 | T=G,C=A |
| rs11090305 | rs2000470 | chr22:24488861 | (C/T) | 0.2157 | 81378 | 0.9764 | 0.9313 | T=T,C=C |
| rs11090305 | rs5751803 | chr22:24489649 | (T/C) | 0.2157 | 82166 | 0.9764 | 0.9313 | T=C,C=T |
| rs11090305 | rs5760205 | chr22:24490529 | (C/T) | 0.2157 | 83046 | 0.9764 | 0.9313 | T=T,C=C |
| rs11090305 | rs2236622 | chr22:24492061 | (T/C) | 0.2157 | 84578 | 0.9764 | 0.9313 | T=C,C=T |
| rs11090305 | rs176156 | chr22:24500866 | (G/C) | 0.2157 | 93383 | 0.9764 | 0.9313 | T=G,C=C |
| rs11090305 | rs112272 | chr22:24510620 | (C/T) | 0.2157 | 103137 | 0.9764 | 0.9313 | T=C,C=T |
| rs11090305 | rs2267059 | chr22:24525711 | (T/C) | 0.2157 | 118228 | 0.9764 | 0.9313 | T=T,C=C |
| rs11090305 | rs2003756 | chr22:24527749 | (T/C) | 0.2157 | 120266 | 0.9764 | 0.9313 | T=T,C=C |
| rs11090305 | rs6519499 | chr22:24532468 | (T/C) | 0.2157 | 124985 | 0.9764 | 0.9313 | T=T,C=C |
| rs11090305 | rs2001105 | chr22:24535559 | (T/C) | 0.2157 | 128076 | 0.9764 | 0.9313 | T=T,C=C |
| rs11090305 | rs2267060 | chr22:24535962 | (G/A) | 0.2157 | 128479 | 0.9764 | 0.9313 | T=G,C=A |
| rs11090305 | rs5760218 | chr22:24541432 | (T/C) | 0.2157 | 133949 | 0.9764 | 0.9313 | T=T,C=C |
| rs11090305 | rs5760221 | chr22:24542636 | (T/A) | 0.2157 | 135153 | 0.9764 | 0.9313 | T=T,C=A |
| rs11090305 | rs2267062 | chr22:24544482 | (G/T) | 0.2157 | 136999 | 0.9764 | 0.9313 | T=G,C=T |
| rs11090305 | rs2267063 | chr22:24544607 | (T/C) | 0.2157 | 137124 | 0.9764 | 0.9313 | T=T,C=C |

TABLE 6-continued

Surrogate markers for polymorphism provided in Table 3 (Part A) and additional polymorphisms used in Table 4 (Part B).
Part C provides surrogate markers for rs115492982.

| Primary SNP | Proxy SNP | Coordinate (GRCh37/hg19) | Alleles | MAF | Distance | D' | R2 | Correlated_Alleles |
|---|---|---|---|---|---|---|---|---|
| rs11090305 | rs2267064 | chr22:24544632 | (T/G) | 0.2157 | 137149 | 0.9764 | 0.9313 | T=T,C=G |
| rs11090305 | rs2267068 | chr22:24550303 | (T/C) | 0.2157 | 142820 | 0.9764 | 0.9313 | T=T,C=C |
| rs11090305 | rs915595 | chr22:24551909 | (T/G) | 0.2157 | 144426 | 0.9764 | 0.9313 | T=T,C=G |
| rs11090305 | rs879756 | chr22:24552872 | (C/A) | 0.2157 | 145389 | 0.9764 | 0.9313 | T=C,C=A |
| rs11090305 | rs6519501 | chr22:24556507 | (T/C) | 0.2157 | 149024 | 0.9764 | 0.9313 | T=T,C=C |
| rs11090305 | rs2267070 | chr22:24558318 | (T/C) | 0.2157 | 150835 | 0.9764 | 0.9313 | T=T,C=C |
| rs11090305 | rs5996668 | chr22:24575952 | (T/C) | 0.2157 | 168469 | 0.9764 | 0.9313 | T=T,C=C |
| rs11090305 | rs9624412 | chr22:24585313 | (A/G) | 0.2157 | 177830 | 0.9764 | 0.9313 | T=A,C=G |
| rs11090305 | rs141628202 | chr22:24474904 | (ATC/—) | 0.2167 | 67421 | 0.9706 | 0.9258 | T=—,C=ATC |
| rs11090305 | rs5844585 | chr22:24483878 | (T/—) | 0.2167 | 76395 | 0.9706 | 0.9258 | T=—,C=T |
| rs11090305 | rs8137732 | chr22:24567031 | (A/G) | 0.2167 | 159548 | 0.9706 | 0.9258 | T=A,C=G |
| rs11090305 | rs8137222 | chr22:24576159 | (G/A) | 0.2167 | 168676 | 0.9706 | 0.9258 | T=G,C=A |
| rs11090305 | rs2070470 | chr22:24583879 | (T/C) | 0.2167 | 176396 | 0.9706 | 0.9258 | T=T,C=C |
| rs11090305 | rs5760244 | chr22:24584970 | (G/A) | 0.2167 | 177487 | 0.9706 | 0.9258 | T=G,C=A |
| rs11090305 | rs9624413 | chr22:24585575 | (T/C) | 0.2167 | 178092 | 0.9706 | 0.9258 | T=T,C=C |
| rs11090305 | rs28687166 | chr22:24585835 | (T/C) | 0.2167 | 178352 | 0.9706 | 0.9258 | T=T,C=C |
| rs11090305 | rs5751813 | chr22:24586071 | (T/C) | 0.2167 | 178588 | 0.9706 | 0.9258 | T=T,C=C |
| rs11090305 | rs2267066 | chr22:24546298 | (G/A) | 0.2147 | 138815 | 0.9763 | 0.9256 | T=G,C=A |
| rs11090305 | rs2236623 | chr22:24578659 | (A/G) | 0.2177 | 171176 | 0.9649 | 0.9202 | T=A,C=G |
| rs11090305 | rs67342915 | chr22:24598619 | (G/—) | 0.2127 | 191136 | 0.976 | 0.9143 | T=G,C=— |
| rs11090305 | rs4521150 | chr22:24600438 | (A/G) | 0.2177 | 192955 | 0.959 | 0.9091 | T=A,C=G |
| rs11090305 | rs8138769 | chr22:24591879 | (A/G) | 0.2117 | 184396 | 0.9759 | 0.9087 | T=A,C=G |
| rs11090305 | rs5760254 | chr22:24602382 | (A/C) | 0.2187 | 194899 | 0.9534 | 0.9037 | T=A,C=C |
| rs11090305 |  | chr22:24417287 | (—/G) | 0.2286 | 9804 | 0.9589 | 0.8734 | T=G,C=— |
| rs62220604 | rs6009583 | chr22:49677646 | (C/T) | 0.2465 | 182 | 0.989 | 0.8679 | G=C,A=T |
| rs62220604 | rs11703376 | chr22:49678713 | (C/T) | 0.2485 | 1249 | 0.9781 | 0.858 | G=C,A=T |
| rs62220604 | rs8136272 | chr22:49678782 | (A/T) | 0.2515 | 1318 | 0.9621 | 0.8436 | G=A,A=T |

Part B

| rs2274122 | rs679457 | chr1:36496479 | (A/G) | 0.166 | −53185 | 0.9781 | 0.8679 | G=A,A=G |
| rs2274122 | rs379507 | chr1:36503907 | (A/G) | 0.166 | −45757 | 0.9781 | 0.8679 | G=A,A=G |
| rs2274122 | rs491603 | chr1:36532316 | (T/C) | 0.172 | −17348 | 0.993 | 0.9333 | G=T,A=C |
| rs1984162 | rs1984163 | chr13:23658864 | (A/G) | 0.2704 | 26 | 1 | 0.995 | A=A,G=G |
| rs8105499 | rs8106322 | chr19:32024230 | (A/G) | 0.3519 | 273 | 0.995 | 0.8046 | C=A,A=G |
| rs8105499 | rs8106852 | chr19:32024669 | (A/G) | 0.3211 | 712 | 0.9904 | 0.9153 | C=A,A=G |
| rs8105499 | rs8102936 | chr19:32027330 | (G/A) | 0.336 | 3373 | 0.9853 | 0.8467 | C=G,A=A |
| rs8105499 | rs8103067 | chr19:32027415 | (G/A) | 0.336 | 3458 | 0.9853 | 0.8467 | C=G,A=A |
| rs8105499 | rs139978707 | chr19:32028824 | (—/ACAC) | 0.332 | 4867 | 0.9514 | 0.8036 | C=—,A=ACAC |
| rs11385942 | rs35896106 | chr3:45841938 | (C/T) | 0.0855 | −34521 | 0.9595 | 0.8624 | —=C,A=T |
| rs11385942 | rs13071258 | chr3:45843242 | (G/A) | 0.0805 | −33217 | 0.9866 | 0.9733 | —=G,A=A |
| rs11385942 | rs17763537 | chr3:45843315 | (C/T) | 0.0805 | −33144 | 0.9866 | 0.9733 | —=C,A=T |
| rs11385942 | rs34668658 | chr3:45844198 | (A/C) | 0.0815 | −32261 | 1 | 0.9867 | —=A,A=C |
| rs11385942 | rs17763742 | chr3:45846769 | (A/G) | 0.0805 | −29690 | 0.9866 | 0.9733 | —=A,A=G |
| rs11385942 | rs72893671 | chr3:45850783 | (T/A) | 0.0875 | −25676 | 1 | 0.9135 | —=T,A=A |
| rs11385942 | rs17713054 | chr3:45859651 | (G/A) | 0.0805 | −16808 | 1 | 1 | —=G,A=A |
| rs11385942 | rs13078854 | chr3:45861932 | (G/A) | 0.0805 | −14527 | 1 | 1 | —=G,A=A |
| rs11385942 | rs71325088 | chr3:45862952 | (T/C) | 0.0805 | −13507 | 1 | 1 | —=T,A=C |
| rs11385942 | rs10490770 | chr3:45864732 | (T/C) | 0.0805 | −11727 | 1 | 1 | —=T,A=C |
| rs11385942 | rs35624553 | chr3:45867440 | (A/G) | 0.0805 | −9019 | 1 | 1 | —=A,A=G |
| rs11385942 | rs71619611 | chr3:45871139 | (A/—) | 0.0835 | −5320 | 1 | 0.9612 | —=A,A=— |
| rs11385942 | rs67959919 | chr3:45871908 | (G/A) | 0.0805 | −4551 | 1 | 1 | —=G,A=A |
| rs11385942 | rs35508621 | chr3:45880481 | (T/C) | 0.0805 | 4022 | 1 | 1 | —=T,A=C |
| rs11385942 | rs34288077 | chr3:45888690 | (A/G) | 0.0795 | 12231 | 1 | 0.9866 | —=A,A=G |
| rs11385942 | rs35081325 | chr3:45889921 | (A/T) | 0.0795 | 13462 | 1 | 0.9866 | —=A,A=T |
| rs11385942 | rs35731912 | chr3:45889949 | (C/T) | 0.0795 | 13490 | 1 | 0.9866 | —=C,A=T |
| rs11385942 | rs34326463 | chr3:45899651 | (A/G) | 0.0795 | 23192 | 1 | 0.9866 | —=A,A=G |
| rs11385942 | rs73064425 | chr3:45901089 | (C/T) | 0.0795 | 24630 | 1 | 0.9866 | —=C,A=T |
| rs11385942 | rs13081482 | chr3:45908116 | (A/T) | 0.0795 | 31657 | 1 | 0.9866 | —=A,A=T |
| rs11385942 | rs35652899 | chr3:45908514 | (C/G) | 0.0775 | 32055 | 1 | 0.9598 | —=C,A=G |
| rs11385942 | rs35044562 | chr3:45909024 | (A/G) | 0.0795 | 32565 | 1 | 0.9866 | —=A,A=G |
| rs11385942 | rs73064431 | chr3:45909528 | (C/T) | 0.0885 | 33069 | 0.9865 | 0.878 | —=C,A=T |
| rs11385942 | rs13092887 | chr3:45909644 | (C/A) | 0.0865 | 33185 | 0.9595 | 0.8515 | —=C,A=A |
| rs11729561 | rs11729561 | chr4:106943200 | (T/C) | 0.0736 | 0 | 1 | 1 | T=T,C=C |
| rs11729561 | rs143299240 | chr4:106952273 | (—/T) | 0.0736 | 9073 | 1 | 1 | T=—,C=T |
| rs11729561 | rs28472461 | chr4:106956065 | (C/T) | 0.0736 | 12865 | 1 | 1 | T=C,C=T |
| rs11729561 | rs28709953 | chr4:106958075 | (C/A) | 0.0736 | 14875 | 1 | 1 | T=C,C=A |
| rs11729561 | rs28663259 | chr4:106958076 | (C/T) | 0.0736 | 14876 | 1 | 1 | T=C,C=T |
| rs11729561 | rs10023586 | chr4:106973602 | (A/G) | 0.0746 | 30402 | 1 | 0.9856 | T=A,C=G |
| rs11729561 | rs79449940 | chr4:106979613 | (G/T) | 0.0746 | 36413 | 1 | 0.9856 | T=G,C=T |
| rs11729561 | rs75853787 | chr4:106981645 | (C/T) | 0.0736 | 38445 | 0.9854 | 0.971 | T=C,C=T |
| rs11729561 | rs7679603 | chr4:106987746 | (C/A) | 0.0746 | 44546 | 1 | 0.9856 | T=C,C=A |
| rs11729561 | rs28783132 | chr4:106994627 | (T/C) | 0.0746 | 51427 | 1 | 0.9856 | T=T,C=C |
| rs11729561 | rs11736679 | chr4:106995182 | (T/G) | 0.0746 | 51982 | 1 | 0.9856 | T=T,C=G |
| rs11729561 | rs74725815 | chr4:106998315 | (G/A) | 0.0746 | 55115 | 1 | 0.9856 | T=G,C=A |

TABLE 6-continued

Surrogate markers for polymorphism provided in Table 3 (Part A) and additional polymorphisms used in Table 4 (Part B).
Part C provides surrogate markers for rs115492982.

| Primary SNP | Proxy SNP | Coordinate (GRCh37/hg19) | Alleles | MAF | Distance | D' | R2 | Correlated_Alleles |
|---|---|---|---|---|---|---|---|---|
| rs11729561 | rs28857517 | chr4:107009841 | (T/C) | 0.0746 | 66641 | 1 | 0.9856 | T=T,C=C |
| rs11729561 | rs78336797 | chr4:107010481 | (G/A) | 0.0746 | 67281 | 1 | 0.9856 | T=G,C=A |
| rs11729561 | rs77454815 | chr4:107018793 | (A/C) | 0.0736 | 75593 | 0.9854 | 0.971 | T=A,C=C |
| rs11729561 | rs28597815 | chr4:107020234 | (T/C) | 0.0736 | 77034 | 0.9854 | 0.971 | T=T,C=C |
| rs11729561 | rs28823294 | chr4:107026693 | (C/T) | 0.0746 | 83493 | 1 | 0.9856 | T=C,C=T |
| rs11729561 | rs28786397 | chr4:107032979 | (T/G) | 0.0746 | 89779 | 1 | 0.9856 | T=T,C=G |
| rs11729561 | rs28648796 | chr4:107037155 | (G/C) | 0.0746 | 93955 | 1 | 0.9856 | T=G,C=C |
| rs11729561 | rs140517213 | chr4:107038130 | (C/—) | 0.0765 | 94930 | 1 | 0.9579 | T=C,C=— |
| rs11729561 | rs28786712 | chr4:107041195 | (A/G) | 0.0746 | 97995 | 1 | 0.9856 | T=A,C=G |
| rs11729561 | rs185825831 | chr4:107041846 | (C/A) | 0.0746 | 98646 | 1 | 0.9856 | T=C,C=A |
| rs11729561 | rs28890246 | chr4:107046012 | (C/G) | 0.0746 | 102812 | 1 | 0.9856 | T=C,C=G |
| rs11729561 | rs116513184 | chr4:107052399 | (A/G) | 0.0785 | 109199 | 1 | 0.9317 | T=A,C=G |
| rs11729561 | rs10010622 | chr4:107064347 | (A/G) | 0.0785 | 121147 | 1 | 0.9317 | T=A,C=G |
| rs11729561 | rs28843476 | chr4:107074493 | (G/A) | 0.0785 | 131293 | 1 | 0.9317 | T=G,C=A |
| rs11729561 | rs28848568 | chr4:107083274 | (C/A) | 0.0785 | 140074 | 1 | 0.9317 | T=C,C=A |
| rs11729561 | rs10010712 | chr4:107087041 | (G/A) | 0.0785 | 143841 | 1 | 0.9317 | T=G,C=A |
| rs11729561 | rs28852980 | chr4:107108590 | (T/C) | 0.0785 | 165390 | 1 | 0.9317 | T=T,C=C |
| rs11729561 | rs577231943 | chr4:107118572 | (A/G) | 0.0785 | 175372 | 1 | 0.9317 | T=A,C=G |
| rs11729561 | rs74349962 | chr4:107121289 | (T/A) | 0.0785 | 178089 | 1 | 0.9317 | T=T,C=A |
| rs11729561 | rs10026011 | chr4:107125358 | (A/C) | 0.0785 | 182158 | 1 | 0.9317 | T=A,C=C |
| rs11729561 | rs28668834 | chr4:107131465 | (G/A) | 0.0785 | 188265 | 1 | 0.9317 | T=G,C=A |
| rs11729561 | rs13258128 | chr4:107136176 | (G/A) | 0.0785 | 192976 | 1 | 0.9317 | T=G,C=A |
| rs11729561 | rs191250332 | chr4:107138855 | (A/T) | 0.0785 | 195655 | 1 | 0.9317 | T=A,C=T |
| rs11729561 | rs11729801 | chr4:107158823 | (C/T) | 0.0785 | 215623 | 1 | 0.9317 | T=C,C=T |
| rs11729561 | rs76805843 | chr4:107159508 | (A/G) | 0.0785 | 216308 | 1 | 0.9317 | T=A,C=G |
| rs11729561 | rs9996386 | chr4:107163773 | (T/C) | 0.0785 | 220573 | 1 | 0.9317 | T=T,C=C |
| rs11729561 | rs10033060 | chr4:107175191 | (C/T) | 0.0785 | 231991 | 1 | 0.9317 | T=C,C=T |
| rs11729561 | rs78279936 | chr4:107179034 | (T/A) | 0.0785 | 235834 | 1 | 0.9317 | T=T,C=A |
| rs11729561 | rs10213435 | chr4:107185588 | (A/C) | 0.0785 | 242388 | 1 | 0.9317 | T=A,C=C |
| rs11729561 | rs28432701 | chr4:107206834 | (G/A) | 0.0785 | 263634 | 1 | 0.9317 | T=G,C=A |
| rs11729561 | rs28600674 | chr4:107207836 | (T/G) | 0.0785 | 264636 | 1 | 0.9317 | T=T,C=G |
| rs11729561 | rs10009873 | chr4:107222264 | (C/T) | 0.0785 | 279064 | 1 | 0.9317 | T=C,C=T |
| rs11729561 | rs7356173 | chr4:107223219 | (T/C) | 0.0785 | 280019 | 1 | 0.9317 | T=T,C=C |
| rs11729561 | rs28408532 | chr4:107228745 | (G/A) | 0.0775 | 285545 | 0.9854 | 0.9172 | T=G,C=A |
| rs11729561 | rs28722963 | chr4:107232881 | (T/C) | 0.0785 | 289681 | 1 | 0.9317 | T=T,C=C |
| rs11729561 | rs11544776 | chr4:107236833 | (C/T) | 0.0795 | 293633 | 1 | 0.919 | T=C,C=T |
| rs11729561 | rs143098221 | chr4:107242218 | (A/G) | 0.0785 | 299018 | 0.9853 | 0.9046 | T=A,C=G |
| rs11729561 | rs9995260 | chr4:107242748 | (C/G) | 0.0785 | 299548 | 0.9853 | 0.9046 | T=C,C=G |
| rs11729561 | rs114592099 | chr4:107243136 | (G/A) | 0.0785 | 299936 | 0.9853 | 0.9046 | T=G,C=A |
| rs11729561 | rs28615207 | chr4:107248029 | (G/A) | 0.0785 | 304829 | 0.9853 | 0.9046 | T=G,C=A |
| rs11729561 | rs6820647 | chr4:107268203 | (G/A) | 0.0785 | 325003 | 0.9853 | 0.9046 | T=G,C=A |
| rs11729561 | rs76860372 | chr4:107271232 | (T/C) | 0.0785 | 328032 | 0.9853 | 0.9046 | T=T,C=C |
| rs11729561 | rs148911649 | chr4:107275349 | (ATC/—) | 0.0785 | 332149 | 0.9853 | 0.9046 | T=ATC,C=— |
| rs11729561 | rs7682001 | chr4:107276380 | (G/A) | 0.0785 | 333180 | 0.9853 | 0.9046 | T=G,C=A |
| rs11729561 | rs75431821 | chr4:107279518 | (T/C) | 0.0785 | 336318 | 0.9853 | 0.9046 | T=T,C=C |
| rs11729561 | rs146578076 | chr4:107288993 | (—/AAGT) | 0.0775 | 345793 | 0.9707 | 0.8901 | T=—,C=AAGT |
| rs657152 | rs8176719 | chr9:136132908 | (—/C) | 0.3946 | −6357 | 0.9958 | 0.9713 | C=—,A=C |
| rs657152 | rs687621 | chr9:136137065 | (A/G) | 0.3708 | −2200 | 0.9955 | 0.8775 | C=A,A=G |
| rs657152 | rs687289 | chr9:136137106 | (G/A) | 0.3718 | −2159 | 0.9955 | 0.8812 | C=G,A=A |
| rs657152 | rs576123 | chr9:136144308 | (T/C) | 0.3698 | 5043 | 0.9955 | 0.8737 | C=T,A=C |
| rs657152 | rs61457395 | chr9:136145907 | (—/A) | 0.3708 | 6642 | 1 | 0.8854 | C=—,A=A |
| rs657152 | rs367689313 | chr9:136145993 | (AGAAGGGAAATTAATAAATATT/—) | 0.3698 | 6728 | 1 | 0.8816 | C=AGAAGGGAAATTAATAAATATT,A= |
| rs657152 | rs8176645 | chr9:136149098 | (T/A) | 0.3966 | 9833 | | 0.9876 | C=T,A=A |
| Part C |
| rs115492982 | rs7543314 | chr1:150271247 | (G/A) | 0.002 | −309 | 1 | 1 | G=G,A=A |
| rs115492982 | rs3738322 | chr1:150272038 | (G/A) | 0.002 | 482 | 1 | 1 | G=G,A=A |
| rs115492982 | rs16835865 | chr1:150270667 | (C/T) | 0.002 | −889 | 1 | 1 | G=C,A=T |
| rs115492982 | rs73013119 | chr1:150272447 | (A/G) | 0.002 | 891 | 1 | 1 | G=A,A=G |
| rs115492982 | rs112587175 | chr1:150273621 | (C/A) | 0.002 | 2065 | 1 | 1 | G=C,A=A |
| rs115492982 | rs56965166 | chr1:150269187 | (A/T) | 0.002 | −2369 | 1 | 1 | G=A,A=T |
| rs115492982 | rs16830437 | chr1:150266903 | (T/C) | 0.002 | −4653 | 1 | 1 | G=T,A=C |
| rs115492982 | rs16835791 | chr1:150265839 | (A/C) | 0.002 | −5717 | 1 | 1 | G=A,A=C |
| rs115492982 | rs143549387 | chr1:150277642 | (A/—) | 0.002 | 6086 | 1 | 1 | G=A,A=— |
| rs115492982 | rs16835782 | chr1:150265360 | (A/G) | 0.002 | −6196 | 1 | 1 | G=A,A=G |
| rs115492982 | rs369956581 | chr1:150264667 | (T/—) | 0.002 | −6889 | 1 | 1 | G=T,A=— |
| rs115492982 | rs73011400 | chr1:150264215 | (A/G) | 0.002 | −7341 | 1 | 1 | G=A,A=G |
| rs115492982 | rs16835911 | chr1:150279333 | (A/C) | 0.002 | 7777 | 1 | 1 | G=A,A=C |
| rs115492982 | rs57361164 | chr1:150261893 | (A/G) | 0.002 | −9663 | 1 | 1 | G=A,A=G |
| rs115492982 | rs73013129 | chr1:150281404 | (T/C) | 0.002 | 9848 | 1 | 1 | G=T,A=C |
| rs115492982 | rs112097040 | chr1:150283854 | (C/T) | 0.002 | 12298 | 1 | 1 | G=C,A=T |
| rs115492982 | rs146795912 | chr1:150285359 | (G/A) | 0.002 | 13803 | 1 | 1 | G=G,A=A |

TABLE 6-continued

Surrogate markers for polymorphism provided in Table 3 (Part A) and additional polymorphisms used in Table 4 (Part B).
Part C provides surrogate markers for rs115492982.

| Primary SNP | Proxy SNP | Coordinate (GRCh37/hg19) | Alleles | MAF | Distance | D' | R2 | Correlated_Alleles |
|---|---|---|---|---|---|---|---|---|
| rs115492982 | rs113720135 | chr1:150285600 | (G/A) | 0.002 | 14044 | 1 | 1 | G=G,A=A |
| rs115492982 | rs60531845 | chr1:150285818 | (C/T) | 0.002 | 14262 | 1 | 1 | G=C,A=T |
| rs115492982 | rs3054393 | chr1:150256412 | (—/TTTATT) | 0.002 | −15144 | 1 | 1 | G=—,A=TTTATT |
| rs115492982 | rs16835708 | chr1:150253872 | (C/G) | 0.002 | −17684 | 1 | 1 | G=C,A=G |
| rs115492982 | rs112511224 | chr1:150289455 | (C/A) | 0.002 | 17899 | 1 | 1 | G=C,A=A |
| rs115492982 | rs142046449 | chr1:150290133 | (C/T) | 0.002 | 18577 | 1 | 1 | G=C,A=T |
| rs115492982 | rs16835699 | chr1:150252247 | (T/C) | 0.002 | −19309 | 1 | 1 | G=T,A=C |
| rs115492982 | rs58516261 | chr1:150290969 | (C/T) | 0.002 | 19413 | 1 | 1 | G=C,A=T |
| rs115492982 | rs74953512 | chr1:150251816 | (T/A) | 0.002 | −19740 | 1 | 1 | G=T,A=A |
| rs115492982 | rs79484682 | chr1:150292342 | (C/T) | 0.002 | 20786 | 1 | 1 | G=C,A=T |
| rs115492982 | rs73015063 | chr1:150293416 | (A/G) | 0.002 | 21860 | 1 | 1 | G=A,A=G |
| rs115492982 | rs113579391 | chr1:150247103 | (C/T) | 0.002 | −24453 | 1 | 1 | G=C,A=T |
| rs115492982 | rs73011384 | chr1:150246411 | (C/T) | 0.002 | −25145 | 1 | 1 | G=C,A=T |
| rs115492982 | rs60758881 | chr1:150297241 | (T/C) | 0.002 | 25685 | 1 | 1 | G=T,A=C |
| rs115492982 | rs114657335 | chr1:150298649 | (C/G) | 0.002 | 27093 | 1 | 1 | G=C,A=G |
| rs115492982 | rs587687867 | chr1:150244075 | (G/A) | 0.002 | −27481 | 1 | 1 | G=G,A=A |
| rs115492982 | rs111644778 | chr1:150243179 | (C/T) | 0.002 | −28377 | 1 | 1 | G=C,A=T |
| rs115492982 | rs2275779 | chr1:150300507 | (A/G) | 0.002 | 28951 | 1 | 1 | G=A,A=G |
| rs115492982 | rs4926420 | chr1:150303244 | (T/C) | 0.002 | 31688 | 1 | 1 | G=T,A=C |
| rs115492982 | rs112431552 | chr1:150303670 | (A/G) | 0.002 | 32114 | 1 | 1 | G=A,A=G |
| rs115492982 | rs112265199 | chr1:150303734 | (C/G) | 0.002 | 32178 | 1 | 1 | G=C,A=G |
| rs115492982 | rs6700607 | chr1:150304107 | (T/G) | 0.002 | 32551 | 1 | 1 | G=T,A=G |
| rs115492982 | rs587595457 | chr1:150237837 | (T/C) | 0.002 | −33719 | 1 | 1 | G=T,A=C |
| rs115492982 | rs80215841 | chr1:150306471 | (A/G) | 0.002 | 34915 | 1 | 1 | G=A,A=G |
| rs115492982 | rs60456922 | chr1:150236472 | (C/T) | 0.002 | −35084 | 1 | 1 | G=C,A=T |
| rs115492982 | rs6679726 | chr1:150308908 | (G/A) | 0.002 | 37352 | 1 | 1 | G=G,A=A |
| rs115492982 | rs58373639 | chr1:150309640 | (A/T) | 0.002 | 38084 | 1 | 1 | G=A,A=T |
| rs115492982 | rs6700009 | chr1:150310159 | (A/C) | 0.002 | 38603 | 1 | 1 | G=A,A=C |
| rs115492982 | rs73015081 | chr1:150313761 | (T/C) | 0.002 | 42205 | 1 | 1 | G=T,A=C |
| rs115492982 | rs373322282 | chr1:150227390 | (ATGGA/—) | 0.002 | −44166 | 1 | 1 | G=ATGGA,A=— |
| rs115492982 | rs16836130 | chr1:150316265 | (A/C) | 0.002 | 44709 | 1 | 1 | G=A,A=C |
| rs115492982 | rs16836139 | chr1:150318369 | (G/A) | 0.002 | 46813 | 1 | 1 | G=G,A=A |
| rs115492982 | rs111863435 | chr1:150223285 | (C/T) | 0.002 | −48271 | 1 | 1 | G=C,A=T |
| rs115492982 | rs57163995 | chr1:150320622 | (G/A) | 0.002 | 49066 | 1 | 1 | G=G,A=A |
| rs115492982 | rs3737319 | chr1:150321798 | (T/G) | 0.002 | 50242 | 1 | 1 | G=T,A=G |
| rs115492982 | rs111334066 | chr1:150219183 | (C/A) | 0.002 | −52373 | 1 | 1 | G=C,A=A |
| rs115492982 | rs116262820 | chr1:150218023 | (C/T) | 0.002 | −53533 | 1 | 1 | G=C,A=T |
| rs115492982 | rs587674887 | chr1:150215634 | (A/C) | 0.002 | −55922 | 1 | 1 | G=A,A=C |
| rs115492982 | rs2015955 | chr1:150327788 | (C/T) | 0.002 | 56232 | 1 | 1 | G=C,A=T |
| rs115492982 | rs2015966 | chr1:150327847 | (G/A) | 0.002 | 56291 | 1 | 1 | G=G,A=A |
| rs115492982 | rs111275178 | chr1:150213525 | (G/A) | 0.002 | −58031 | 1 | 1 | G=G,A=A |
| rs115492982 | rs73015095 | chr1:150329821 | (G/T) | 0.002 | 58265 | 1 | 1 | G=G,A=T |
| rs115492982 | rs200378817 | chr1:150329986 | (—/TT) | 0.002 | 58430 | 1 | 1 | G=—,A=TT |
| rs115492982 | rs73015096 | chr1:150331437 | (G/A) | 0.002 | 59881 | 1 | 1 | G=G,A=A |
| rs115492982 | rs112896715 | chr1:150333692 | (G/A) | 0.002 | 62136 | 1 | 1 | G=G,A=A |
| rs115492982 | rs16836442 | chr1:150338613 | (T/C) | 0.002 | 67057 | 1 | 1 | G=T,A=C |
| rs115492982 | rs149553874 | chr1:150341202 | (A/G) | 0.002 | 69646 | 1 | 1 | G=A,A=G |
| rs115492982 | rs73017006 | chr1:150341765 | (G/A) | 0.002 | 70209 | 1 | 1 | G=G,A=A |
| rs115492982 | rs3850843 | chr1:150348335 | (A/G) | 0.002 | 76779 | 1 | 1 | G=A,A=G |
| rs115492982 | rs148424403 | chr1:150349418 | (G/A) | 0.002 | 77862 | 1 | 1 | G=G,A=A |
| rs115492982 | rs16836576 | chr1:150351001 | (T/C) | 0.002 | 79445 | 1 | 1 | G=T,A=C |
| rs115492982 | rs73017073 | chr1:150353003 | (T/C) | 0.002 | 81447 | 1 | 1 | G=T,A=C |
| rs115492982 | rs16836594 | chr1:150354584 | (T/C) | 0.002 | 83028 | 1 | 1 | G=T,A=C |
| rs115492982 | rs16836601 | chr1:150356343 | (T/C) | 0.002 | 84787 | 1 | 1 | G=T,A=C |
| rs115492982 | rs60459288 | chr1:150356425 | (A/G) | 0.002 | 84869 | 1 | 1 | G=A,A=G |
| rs115492982 | rs145792768 | chr1:150356925 | (C/—) | 0.002 | 85369 | 1 | 1 | G=C,A=— |
| rs115492982 | rs200485038 | chr1:150360844 | (TATACACA/—) | 0.002 | 89288 | 1 | 1 | G=TATACACA,A=— |
| rs115492982 | rs145326563 | chr1:150176573 | (G/A) | 0.002 | −94983 | 1 | 1 | G=G,A=A |
| rs115492982 | rs59367061 | chr1:150368788 | (C/T) | 0.002 | 97232 | 1 | 1 | G=C,A=T |
| rs115492982 | rs75909586 | chr1:150174286 | (T/C) | 0.002 | −97270 | 1 | 1 | G=T,A=C |
| rs115492982 | rs56909494 | chr1:150368879 | (G/T) | 0.002 | 97323 | 1 | 1 | G=G,A=T |
| rs115492982 | rs56882505 | chr1:150371505 | (G/T) | 0.002 | 99949 | 1 | 1 | G=G,A=T |
| rs115492982 | rs76711752 | chr1:150371599 | (T/C) | 0.002 | 100043 | 1 | 1 | G=T,A=C |
| rs115492982 | rs112294023 | chr1:150374142 | (C/T) | 0.002 | 102586 | 1 | 1 | G=C,A=T |
| rs115492982 | rs59639798 | chr1:150374712 | (G/A) | 0.002 | 103156 | 1 | 1 | G=G,A=A |
| rs115492982 | rs146199040 | chr1:150167946 | (C/T) | 0.002 | −103610 | 1 | 1 | G=C,A=T |
| rs115492982 | rs73017086 | chr1:150376628 | (T/C) | 0.002 | 105072 | 1 | 1 | G=T,A=C |
| rs115492982 | rs587746671 | chr1:150166093 | (G/A) | 0.002 | −105463 | 1 | 1 | G=G,A=A |
| rs115492982 | rs76176241 | chr1:150379851 | (G/T) | 0.002 | 108295 | 1 | 1 | G=G,A=T |
| rs115492982 | rs16836786 | chr1:150380364 | (C/G) | 0.002 | 108808 | 1 | 1 | G=C,A=G |
| rs115492982 | rs111982037 | chr1:150380739 | (C/G) | 0.002 | 109183 | 1 | 1 | G=C,A=G |
| rs115492982 | rs80029546 | chr1:150160082 | (A/G) | 0.002 | −111474 | 1 | 1 | G=A,A=G |
| rs115492982 | rs145119256 | chr1:150383919 | (A/G) | 0.002 | 112363 | 1 | 1 | G=A,A=G |
| rs115492982 | rs73017092 | chr1:150384576 | (G/T) | 0.002 | 113020 | 1 | 1 | G=G,A=T |

TABLE 6-continued

Surrogate markers for polymorphism provided in Table 3 (Part A) and additional polymorphisms used in Table 4 (Part B).
Part C provides surrogate markers for rs115492982.

| Primary SNP | Proxy SNP | Coordinate (GRCh37/hg19) | Alleles | MAF | Distance | D' | R2 | Correlated_Alleles |
|---|---|---|---|---|---|---|---|---|
| rs115492982 | rs4926430 | chr1:150385500 | (G/A) | 0.002 | 113944 | 1 | 1 | G=G,A=A |
| rs115492982 | rs144073030 | chr1:150385864 | (G/A) | 0.002 | 114308 | 1 | 1 | G=G,A=A |
| rs115492982 | rs6688983 | chr1:150157150 | (C/T) | 0.002 | −114406 | 1 | 1 | G=C,A=T |
| rs115492982 | rs111802234 | chr1:150386950 | (G/—) | 0.002 | 115394 | 1 | 1 | G=G,A=— |
| rs115492982 | rs115006285 | chr1:150155187 | (C/T) | 0.002 | −116369 | 1 | 1 | G=C,A=T |
| rs115492982 | rs370281030 | chr1:150388745 | (TGA/—) | 0.002 | 117189 | 1 | 1 | G=TGA,A=— |
| rs115492982 | rs59378360 | chr1:150391946 | (A/G) | 0.002 | 120390 | 1 | 1 | G=A,A=G |
| rs115492982 | rs112490454 | chr1:150392392 | (A/G) | 0.002 | 120836 | 1 | 1 | G=A,A=G |
| rs115492982 | rs80012313 | chr1:150147374 | (T/A) | 0.002 | −124182 | 1 | 1 | G=T,A=A |
| rs115492982 | rs113371939 | chr1:150396417 | (C/G) | 0.002 | 124861 | 1 | 1 | G=C,A=G |
| rs115492982 | rs147729724 | chr1:150397877 | (T/C) | 0.002 | 126321 | 1 | 1 | G=T,A=C |
| rs115492982 | rs59662772 | chr1:150398202 | (G/A) | 0.002 | 126646 | 1 | 1 | G=G,A=A |
| rs115492982 | rs7550339 | chr1:150140661 | (C/T) | 0.002 | −130895 | 1 | 1 | G=T,A=C |
| rs115492982 | rs77778882 | chr1:150140581 | (A/G) | 0.002 | −130975 | 1 | 1 | G=A,A=G |
| rs115492982 | rs10788870 | chr1:150140540 | (A/C) | 0.002 | −131016 | 1 | 1 | G=C,A=A |
| rs115492982 | rs1382572 | chr1:150139471 | (T/C) | 0.002 | −132085 | 1 | 1 | G=C,A=T |
| rs115492982 | rs73017102 | chr1:150403756 | (G/A) | 0.002 | 132200 | 1 | 1 | G=G,A=A |
| rs115492982 | rs112235324 | chr1:150404205 | (T/C) | 0.002 | 132649 | 1 | 1 | G=T,A=C |
| rs115492982 | rs73020860 | chr1:150134895 | (G/A) | 0.002 | −136661 | 1 | 1 | G=G,A=A |
| rs115492982 | rs6685607 | chr1:150134341 | (G/A) | 0.002 | −137215 | 1 | 1 | G=G,A=A |
| rs115492982 | rs111400442 | chr1:150410258 | (G/A) | 0.002 | 138702 | 1 | 1 | G=G,A=A |
| rs115492982 | rs113274217 | chr1:150410365 | (C/T) | 0.002 | 138809 | 1 | 1 | G=C,A=T |
| rs115492982 | rs60527237 | chr1:150131893 | (C/T) | 0.002 | −139663 | 1 | 1 | G=C,A=T |
| rs115492982 | rs57971032 | chr1:150411292 | (G/A) | 0.002 | 139736 | 1 | 1 | G=G,A=A |
| rs115492982 | rs113408614 | chr1:150411507 | (C/T) | 0.002 | 139951 | 1 | 1 | G=C,A=T |
| rs115492982 | rs6681679 | chr1:150130526 | (C/T) | 0.002 | −141030 | 1 | 1 | G=C,A=T |
| rs115492982 | rs149608182 | chr1:150416426 | (G/A) | 0.002 | 144870 | 1 | 1 | G=G,A=A |
| rs115492982 | rs149443445 | chr1:150126326 | (—/CT) | 0.002 | −145230 | 1 | 1 | G=—,A=CT |
| rs115492982 | rs16836943 | chr1:150418796 | (C/T) | 0.002 | 147240 | 1 | 1 | G=C,A=T |
| rs115492982 | rs112272272 | chr1:150419395 | (T/C) | 0.002 | 147839 | 1 | 1 | G=T,A=C |
| rs115492982 | rs73019017 | chr1:150421654 | (T/C) | 0.002 | 150098 | 1 | 1 | G=T,A=C |
| rs115492982 | rs73019018 | chr1:150421965 | (T/C) | 0.002 | 150409 | 1 | 1 | G=T,A=C |
| rs115492982 | rs73019020 | chr1:150422271 | (G/A) | 0.002 | 150715 | 1 | 1 | G=G,A=A |
| rs115492982 | rs73019021 | chr1:150422548 | (T/A) | 0.002 | 150992 | 1 | 1 | G=T,A=A |
| rs115492982 | rs6680391 | chr1:150424182 | (A/G) | 0.002 | 152626 | 1 | 1 | G=A,A=G |
| rs115492982 | rs7532297 | chr1:150117691 | (A/G) | 0.002 | −153865 | 1 | 1 | G=A,A=G |
| rs115492982 | rs77553465 | chr1:150427507 | (G/A) | 0.002 | 155951 | 1 | 1 | G=G,A=A |
| rs115492982 | rs7517537 | chr1:150114083 | (C/T) | 0.002 | −157473 | 1 | 1 | G=C,A=T |
| rs115492982 | rs371028395 | chr1:150430107 | (A/—) | 0.002 | 158551 | 1 | 1 | G=A,A=— |
| rs115492982 | rs73019027 | chr1:150430552 | (C/T) | 0.002 | 158996 | 1 | 1 | G=C,A=T |
| rs115492982 | rs113104968 | chr1:150109281 | (C/T) | 0.002 | −162275 | 1 | 1 | G=C,A=T |
| rs115492982 | rs12090508 | chr1:150107793 | (A/G) | 0.002 | −163763 | 1 | 1 | G=A,A=G |
| rs115492982 | rs57272513 | chr1:150436496 | (A/G) | 0.002 | 164940 | 1 | 1 | G=A,A=G |
| rs115492982 | rs73019028 | chr1:150437283 | (G/C) | 0.002 | 165727 | 1 | 1 | G=G,A=C |
| rs115492982 | rs111536367 | chr1:150438467 | (C/A) | 0.002 | 166911 | 1 | 1 | G=C,A=A |
| rs115492982 | rs35766167 | chr1:150103818 | (1/—) | 0.002 | −167738 | 1 | 1 | G=—,A=T |
| rs115492982 | rs112640811 | chr1:150097784 | (G/A) | 0.002 | −173772 | 1 | 1 | G=G,A=A |
| rs115492982 | rs12082615 | chr1:150097384 | (A/C) | 0.002 | −174172 | 1 | 1 | G=A,A=C |
| rs115492982 | rs7530672 | chr1:150096444 | (G/A) | 0.002 | −175112 | 1 | 1 | G=G,A=A |
| rs115492982 | rs13057 | chr1:150448688 | (G/T) | 0.002 | 177132 | 1 | 1 | G=G,A=T |
| rs115492982 | rs6677707 | chr1:150092918 | (A/G) | 0.002 | −178638 | 1 | 1 | G=A,A=G |
| rs115492982 | rs7533714 | chr1:150092086 | (T/C) | 0.002 | −179470 | 1 | 1 | G=C,A=T |
| rs115492982 | rs9727702 | chr1:150090669 | (G/A) | 0.002 | −180887 | 1 | 1 | G=G,A=A |
| rs115492982 | rs11205328 | chr1:150087865 | (T/C) | 0.002 | −183691 | 1 | 1 | G=T,A=C |
| rs115492982 | rs113887124 | chr1:150456665 | (G/A) | 0.002 | 185109 | 1 | 1 | G=G,A=A |
| rs115492982 | rs3840448 | chr1:150459893 | (TGTT/—) | 0.002 | 188337 | 1 | 1 | G=TGIT,A=— |
| rs115492982 | rs2275245 | chr1:150460348 | (C/T) | 0.002 | 188792 | 1 | 1 | G=C,A=T |
| rs115492982 | rs3839012 | chr1:150461761 | (C/—) | 0.002 | 190205 | 1 | 1 | G=C,A=— |
| rs115492982 | rs871527 | chr1:150462088 | (C/G) | 0.002 | 190532 | 1 | 1 | G=C,A=G |
| rs115492982 | rs10624875 | chr1:150463530 | (—/AA) | 0.002 | 191974 | 1 | 1 | G=—,A=AA |
| rs115492982 | rs142587704 | chr1:150078791 | (CTC/—) | 0.002 | −192765 | 1 | 1 | G=CTC,A=— |
| rs115492982 | rs111842933 | chr1:150465271 | (G/A) | 0.002 | 193715 | 1 | 1 | G=G,A=A |
| rs115492982 | rs143706301 | chr1:150467213 | (—/A) | 0.002 | 195657 | 1 | 1 | G=—,A=A |
| rs115492982 | rs953127 | chr1:150469256 | (G/T) | 0.002 | 197700 | 1 | 1 | G=G,A=T |
| rs115492982 | rs112071489 | chr1:150471548 | (C/T) | 0.002 | −200067 | 1 | 1 | G=C,A=T |
| rs115492982 | rs587637589 | chr1:150476115 | (TA/—) | 0.002 | 204559 | 1 | 1 | G=TA,A=— |
| rs115492982 | rs28541919 | chr1:150476117 | (A/G) | 0.002 | 204561 | 1 | 1 | G=A,A=G |
| rs115492982 | rs12058524 | chr1:150066384 | (C/T) | 0.002 | −205172 | 1 | 1 | G=C,A=T |
| rs115492982 | rs3834087 | chr1:150478538 | (GAG/—) | 0.002 | 206982 | 1 | 1 | G=GAG,A=— |
| rs115492982 | rs111414303 | chr1:150063936 | (G/A) | 0.002 | −207620 | 1 | 1 | G=G,A=A |
| rs115492982 | rs73019054 | chr1:150485599 | (G/A) | 0.002 | 214043 | 1 | 1 | G=G,A=A |
| rs115492982 | rs79595845 | chr1:150055388 | (T/A) | 0.002 | −216168 | 1 | 1 | G=T,A=A |
| rs115492982 | rs78312541 | chr1:150487797 | (C/A) | 0.002 | 216241 | 1 | 1 | G=C,A=A |
| rs115492982 | rs58419446 | chr1:150490370 | (C/T) | 0.002 | 218814 | 1 | 1 | G=C,A=T |

TABLE 6-continued

Surrogate markers for polymorphism provided in Table 3 (Part A) and additional polymorphisms used in Table 4 (Part B).
Part C provides surrogate markers for rs115492982.

| Primary SNP | Proxy SNP | Coordinate (GRCh37/hg19) | Alleles | MAF | Distance | D' | R2 | Correlated_Alleles |
|---|---|---|---|---|---|---|---|---|
| rs115492982 | rs113872537 | chr1:150493557 | (G/A) | 0.002 | 222001 | 1 | 1 | G=G,A=A |
| rs115492982 | rs79524321 | chr1:150495269 | (T/C) | 0.002 | 223713 | 1 | 1 | G=T,A=C |
| rs115492982 | rs11205325 | chr1:150044324 | (G/A) | 0.002 | −227232 | 1 | 1 | G=G,A=A |
| rs115492982 | rs11205324 | chr1:150041872 | (G/T) | 0.002 | −229684 | 1 | 1 | G=T,A=G |
| rs115492982 | rs11205323 | chr1:150041871 | (C/A) | 0.002 | −229685 | 1 | 1 | G=A,A=C |
| rs115492982 | rs147106269 | chr1:150502105 | (G/A) | 0.002 | 230549 | 1 | 1 | G=G,A=A |
| rs115492982 | rs9887866 | chr1:150039267 | (T/C) | 0.002 | −232289 | 1 | 1 | G=C,A=T |
| rs115492982 | rs77173601 | chr1:150505070 | (G/A) | 0.002 | 233514 | 1 | 1 | G=G,A=A |
| rs115492982 | rs6657478 | chr1:150507567 | (A/G) | 0.002 | 236011 | 1 | 1 | G=A,A=G |
| rs115492982 | rs78006356 | chr1:150032621 | (C/T) | 0.002 | −238935 | 1 | 1 | G=C,A=T |
| rs115492982 | rs113085079 | chr1:150512512 | (G/T) | 0.002 | 240956 | 1 | 1 | G=G,A=T |
| rs115492982 | rs6687257 | chr1:150029702 | (T/C) | 0.002 | −241854 | 1 | 1 | G=T,A=C |
| rs115492982 | rs139447592 | chr1:150513837 | (G/T) | 0.002 | 242281 | 1 | 1 | G=G,A=T |
| rs115492982 | rs145793287 | chr1:150514145 | (C/T) | 0.002 | 242589 | 1 | 1 | G=C,A=T |
| rs115492982 | rs7514515 | chr1:150517312 | (G/C) | 0.002 | 245756 | 1 | 1 | G=G,A=C |
| rs115492982 | rs75513680 | chr1:150021709 | (G/A) | 0.002 | −249847 | 1 | 1 | G=G,A=A |
| rs115492982 | rs57507911 | chr1:150523982 | (AG/—) | 0.002 | 252426 | 1 | 1 | G=AG,A=— |
| rs115492982 | rs61684558 | chr1:150524277 | (G/A) | 0.002 | 252721 | 1 | 1 | G=G,A=A |
| rs115492982 | rs144832337 | chr1:150531320 | (G/A) | 0.002 | 259764 | 1 | 1 | G=G,A=A |
| rs115492982 | rs140930998 | chr1:150011383 | (G/A) | 0.002 | −260173 | 1 | 1 | G=G,A=A |
| rs115492982 | rs147310031 | chr1:150011375 | (G/A) | 0.002 | −260181 | 1 | 1 | G=G,A=A |
| rs115492982 | rs116614291 | chr1:150531959 | (G/A) | 0.002 | 260403 | 1 | 1 | G=G,A=A |
| rs115492982 | rs79568347 | chr1:150006818 | (T/C) | 0.002 | −264738 | 1 | 1 | G=T,A=C |
| rs115492982 | rs145686348 | chr1:150558152 | (G/T) | 0.002 | 286596 | 1 | 1 | G=G,A=T |
| rs115492982 | rs142892208 | chr1:150560164 | (A/—) | 0.002 | 288608 | 1 | 1 | G=A,A=— |
| rs115492982 | rs6691535 | chr1:150568894 | (A/G) | 0.002 | 297338 | 1 | 1 | G=A,A=G |
| rs115492982 | rs143004068 | chr1:150582871 | (G/A) | 0.002 | 311315 | 1 | 1 | G=G,A=A |
| rs115492982 | rs74124941 | chr1:150588009 | (G/A) | 0.002 | 316453 | 1 | 1 | G=G,A=A |
| rs115492982 | rs587647594 | chr1:150601298 | (G/T) | 0.002 | 329742 | 1 | 1 | G=G,A=T |
| rs115492982 | rs74124944 | chr1:150603752 | (T/A) | 0.002 | 332196 | 1 | 1 | G=T,A=A |
| rs115492982 | rs75508758 | chr1:150604410 | (A/G) | 0.002 | 332854 | 1 | 1 | G=A,A=G |
| rs115492982 | rs145393663 | chr1:150605772 | (C/T) | 0.002 | 334216 | 1 | 1 | G=C,A=T |
| rs115492982 | rs57025631 | chr1:150607284 | (G/T) | 0.002 | 335728 | 1 | 1 | G=G,A=T |
| rs115492982 | rs74124966 | chr1:150609082 | (G/A) | 0.002 | 337526 | 1 | 1 | G=G,A=A |
| rs115492982 | rs139726900 | chr1:150612476 | (G/A) | 0.002 | 340920 | 1 | 1 | G=G,A=A |
| rs115492982 | rs1877469 | chr1:150619602 | (T/C) | 0.002 | 348046 | 1 | 1 | G=C,A=T |
| rs115492982 | rs1151917 | chr1:150622696 | (T/A) | 0.002 | 351140 | 1 | 1 | G=T,A=A |
| rs115492982 | rs1241578 | chr1:150628365 | (A/C) | 0.002 | 356809 | 1 | 1 | G=A,A=C |
| rs115492982 | rs1241579 | chr1:150630869 | (T/C) | 0.002 | 359313 | 1 | 1 | G=T,A=C |
| rs115492982 | rs1707158 | chr1:150633833 | (A/G) | 0.002 | 362277 | 1 | 1 | G=A,A=G |
| rs115492982 | rs2458393 | chr1:150634596 | (G/A) | 0.002 | 363040 | 1 | 1 | G=G,A=A |
| rs115492982 | rs1241575 | chr1:150646372 | (A/T) | 0.002 | 374816 | 1 | 1 | G=A,A=T |
| rs115492982 | rs73008805 | chr1:150676968 | (T/C) | 0.002 | 405412 | 1 | 1 | G=T,A=C |
| rs115492982 | rs57127659 | chr1:150684117 | (C/T) | 0.002 | 412561 | 1 | 1 | G=C,A=T |
| rs115492982 | rs73008807 | chr1:150687686 | (G/T) | 0.002 | 416130 | 1 | 1 | G=G,A=T |
| rs115492982 | rs587594230 | chr1:150700505 | (G/A) | 0.002 | 428949 | 1 | 1 | G=G,A=A |
| rs115492982 | rs192267029 | chr1:150702269 | (G/C) | 0.002 | 430713 | 1 | 1 | G=G,A=C |
| rs115492982 | rs113739463 | chr1:150714363 | (G/C) | 0.002 | 442807 | 1 | 1 | G=G,A=C |
| rs115492982 | rs73008818 | chr1:150718179 | (G/A) | 0.002 | 446623 | 1 | 1 | G=G,A=A |
| rs115492982 | rs112325265 | chr1:150727987 | (G/A) | 0.002 | 456431 | 1 | 1 | G=G,A=A |
| rs115492982 | rs113422136 | chr1:150733416 | (G/A) | 0.002 | 461860 | 1 | 1 | G=G,A=A |
| rs115492982 | rs28675769 | chr1:150736807 | (C/T) | 0.002 | 465251 | 1 | 1 | G=C,A=T |
| rs115492982 | rs112049924 | chr1:150748342 | (T/C) | 0.002 | 476786 | 1 | 1 | G=T,A=C |
| rs115492982 | rs112037529 | chr1:150757290 | (G/C) | 0.002 | 485734 | 1 | 1 | G=G,A=C |

In an embodiment, the at least three, at least four, at least five, at least six, at least seven, at least eight, at least nine, at least ten, at least 20, at least 30, at least 40, at least 50, at least 60, at least 70, at least 80, at least 100, at least 120, at least 140, at least 160, at least 180, at least 200, at least 250, at least 300 or at least 306 polymorphisms associated with a severe response to a Coronavirus infection are selected from the polymorphisms provided Table 1 and Table 6a or a polymorphism in linkage disequilibrium with one or more thereof.

In an embodiment, the at least three, at least four, at least five, at least six, at least seven, at least eight, at least nine, at least ten, at least 20, at least 30, at least 40, at least 50, at least 60, at least 70, at least 80, at least 100, at least 120, at least 140, at least 160, at least 180, at least 200, at least 250, at least 300 or at least 306 polymorphisms associated with a severe response to a Coronavirus infection are selected from the polymorphisms provided Table 1 or a polymorphism in linkage disequilibrium with one or more thereof.

In an embodiment, the at least three, at least four, at least five, at least six, at least seven, at least eight, at least nine, at least ten, at least 20, at least 30, at least 40, at least 50, at least 60, at least 70, at least 80, at least 100, at least 120, at least 140, at least 160, at least 180, at least 200, at least 250, at least 300 or at least 306 polymorphisms associated with a severe response to a Coronavirus infection are selected from the polymorphisms provided Table 2 and Table 6a or a polymorphism in linkage disequilibrium with one or more thereof.

In an embodiment, the at least three, at least four, at least five, at least six, at least seven, at least eight, at least nine, at least ten, at least 20, at least 30, at least 40 or at least 50 polymorphisms associated with a severe response to a Coronavirus infection are selected from polymorphisms provided in Table 2 or Table 6a or a polymorphism in linkage disequilibrium with one or more thereof.

In an embodiment, the at least three, at least four, at least five, at least six, at least seven, at least eight, at least nine, at least ten, at least 20, at least 30, at least 40 or at least 50 polymorphisms associated with a severe response to a Coronavirus infection are selected from polymorphisms provided in Table 2 or a polymorphism in linkage disequilibrium with one or more thereof.

In an embodiment, the at least three, at least four, at least five, at least six, at least seven, at least eight, at least nine, at least ten, at least 20, at least 30, at least 40 or at least 50 polymorphisms associated with a severe response to a Coronavirus infection are selected from polymorphisms provided in Table 3 or a polymorphism in linkage disequilibrium with one or more thereof.

In an embodiment, the at least three, at least four, at least five, at least six, at least seven, at least eight, at least nine, at least ten, at least 20, at least 30, at least 40, at least 50 or at least 60 polymorphisms associated with a severe response to a Coronavirus infection are selected from polymorphisms provided in Table 4 or a polymorphism in linkage disequilibrium with one or more thereof.

In embodiment, the method of the invention involves detecting the presence of each of the polymorphisms provided in Table 2 or a polymorphism in linkage disequilibrium with one or more thereof.

In an embodiment, the method of the invention involves detecting the presence of each of the polymorphisms provided in Table 3 or a polymorphism in linkage disequilibrium with one or more thereof.

In an embodiment, the method of the invention involves detecting the presence of each of the polymorphisms provided in Table 4 or a polymorphism in linkage disequilibrium with one or more thereof.

In an embodiment, the method of the invention involves detecting the presence of each of the polymorphisms provided in Table 19 or a polymorphism in linkage disequilibrium with one or more thereof.

In an embodiment, the method of the invention involves detecting the presence of each of the polymorphisms provided in Table 22 or a polymorphism in linkage disequilibrium with one or more thereof.

Polymorphisms in linkage disequilibrium with those specifically mentioned herein are easily identified by those of skill in the art. Table 6a provides examples of linked loci for the polymorphisms listed in Table 3. Table 6b provides examples of linked loci for the polymorphisms listed in Table 4 which are not provided in Table 6a. Such linked polymorphisms for the other polymorphisms listed in Table 1 can very easily be identified by the skilled person using the HAPMAP database.

Where relevant in each Table, the A1 or Allele 1 is the risk (minor allele) associated allele. The risk allele may be associated with a decreased or increased risk as described herein. As used herein, the terms "A1" and "Allele 1" are used interchangeably. As used herein, the terms "A2" and "Allele 2" are used interchangeably.

In an embodiment, if the method includes the analysis of rs11385942 and/or rs657152 the method further comprises detecting at least one other polymorphism provided in any one of Tables 1 to 6, 8, 19 or 22, or a polymorphism in linkage disequilibrium therewith.

Calculating Composite Relative Risk "Genetic Risk"

An individual's "genetic risk" can be defined as the product of genotype relative risk values for each polymorphism assessed. A log-additive risk model can then be used to define three genotypes AA, AB and BB for a polymorphism having relative risk values of 1, OR, and $OR^2$, under a rare disease model, where OR is the previously reported disease odds ratio for the high-risk allele, B, vs the low-risk allele, A. If the B allele has frequency (p), then these genotypes have population frequencies of $(1-p)^2$, $2p(1-p)$, and $p^2$, assuming Hardy-Weinberg equilibrium. The genotype relative risk values for each polymorphism can then be scaled so that based on these frequencies the average relative risk in the population is 1. Specifically, given the unsealed population average relative risk for each SNP:

$$(\mu)=(1-p)^2+2p(1-p)OR+p^2OR^2$$

Adjusted risk values $1/p$, $OR/p$, and $OR^2/p$ are used for AA, AB, and BB genotypes for each SNP. Missing genotypes are assigned a relative risk of 1. The following formula can be used to define the genetic risk:

$$SNP_1 \times SNP_2 \times SNP_3 \times SNP_4 \times SNP_5 \times SNP_6 \times SNP_7 \times SNP_8, \text{etc.}$$

Similar calculations can be performed for non-SNP polymorphisms or a combination thereof.

An alternate method for calculating the composite risk is described in Mavaddat et al. (2015). In this example, the following formula is used;

$$PRS=\beta_1 x_1+\beta_2 x_2+ \ldots \beta_k x_k+\beta_n x_n$$

where $\beta_K$ is the per-allele log odds ratio (OR) for the minor allele for SNP κ, and $x_K$ the number of alleles for the same SNP (0, 1 or 2), n is the total number of SNPs and PRS is the polygenic risk score (which can also be referred to as composite SNP risk). Similar calculations can be performed for non-SNP polymorphisms or a combination thereof.

In an alternate embodiment, the magnitude of effect of each risk allele is not used when calculating the genetic risk score. More specifically, allele counting as generally described in WO 2005/086770 is used. For example, in one embodiment if the subject was homozygous for the risk allele they were scored as 2, if they were heterozygous for the risk allele they were scored as 1, and if they were homozygous for the risk allele they were scored as 0. As the skilled person would appreciate, alternate values such as 1, 0.5 and 0 respectively, could be used.

In an embodiment, the percent of risk alleles present out of the total possible number of loci analysed is used to produce the genetic risk score. For example, in the 64 allele panel described in Example 5 the subject may have at most 128 risk alleles. If a subject had 64 out of these 128 alleles, they would have 50% of the total possible alleles which can be expressed as 0.5.

The genetic risk score can be expressed as:

ln_risk=−8.4953 (i.e. the model intercept)+0.1496× SNP %. Then, risk=exp(ln_risk).

In this example, the risk is the relative risk for severe disease (e.g. a person with risk=3.5 is at 3.5 times increased risk compared with a person with the average number of risk alleles). exp(β) is the odds ratio for an increase of 1% in risk alleles. So, exp(0.1496)=1.16, which means that risk increases by 16% for a 1% increase in SNP %. In an embodiment, the β coefficient (model intercept) is between −10.06391 to −6.926615, or −9.5 to −7.5, or −9 to −8. In an embodiment of the above formula, the adjustment of the starting ln(risk) for the percentage of risk alleles is 0.1237336 to 0.1755347, or 0.16 to 0.14.

In an embodiment, the genetic risk is the SNP Risk Factor (SNF). In one embodiment, SNF=Σ(No of Risk Alleles× SNP β coefficient).

The "risk" of a human subject developing a severe response to a Coronavirus infection can be provided as a relative risk (or risk ratio).

In an embodiment, the genetic risk assessment obtains the "relative risk" of a human subject developing a severe response to a Coronavirus infection. Relative risk (or risk ratio), measured as the incidence of a disease in individuals with a particular characteristic (or exposure) divided by the incidence of the disease in individuals without the characteristic, indicates whether that particular exposure increases or decreases risk. Relative risk is helpful to identify characteristics that are associated with a disease, but by itself is not particularly helpful in guiding screening decisions because the frequency of the risk (incidence) is cancelled out.

In an embodiment, a threshold value(s) is set for determining a particular action such as the need for routine diagnostic testing, the need for prophylactic anti-Coronavirus therapy, selection of a person for a vaccine or the need to administer an anti-Coronavirus therapy. For example, a score determined using a method of the invention is compared to a pre-determined threshold, and if the score is higher than the threshold a recommendation is made to take the pre-determined action. Methods of setting such thresholds have now become widely used in the art and are described in, for example, US 20140018258.

Clinical Risk Assessment

In an embodiment, the method further comprises performing a clinical risk assessment of the human subject; and combining the clinical risk assessment and the genetic risk assessment to obtain the risk of a human subject developing a severe response to a Coronavirus infection. The clinical risk assessment procedure can include obtaining clinical information from a human subject. In other embodiments, these details have already been determined (such as in the subject's medical records).

Examples of factors which can be used to produce the clinical risk assessment include, but are not limited to, obtaining information from the human on one or more of the following: age, family history of a severe response to a Coronavirus infection, race/ethnicity, gender, body mass index, total cholesterol level, systolic and/or diastolic blood pressure, smoking status, does the human have diabetes, does the human have a cardiovascular disease, is the subject on hypertension medication, loss of taste, loss of smell and white blood cell count.

In an embodiment, the clinical risk assessment is based only one or more or all of age, body mass index, loss of taste, loss of smell and smoking status.

In another embodiment, the clinical risk assessment is based only one or more or all of age, loss of taste, loss of smell and smoking status.

In an embodiment, the clinical risk assessment includes obtaining information from the subject on one or more or all of age, gender, race/ethnicity, blood type, does the human have or has had an autoimmune disease, does the human have or has had an haematological cancer, does the human have or has had an non-haematological cancer, does the human have or has had diabetes, does the human have or has had hypertension and does the human have or has had a respiratory disease (other than asthma).

In an embodiment, the clinical risk assessment at least includes age and gender.

The present inventors have also found that a severe response to a Coronavirus infection risk model that relies solely on clinical factors provides useful risk discrimination for assessing a subject's risk of developing a severe response to a Coronavirus infection such as a SARS-CoV-2 infection. Such a test may be particularly useful in circumstances where a rapid decision needs to be made and/or when genetic testing is not readily available. Thus, in another aspect the present invention provides a method for assessing the risk of a human subject developing a severe response to a Coronavirus infection, the method comprising performing a clinical risk assessment of the human subject, wherein the clinical risk assessment comprises obtaining information from the subject on two, three, four, five or more or all of age, gender, race/ethnicity, height, weight, blood type, does the human have or has had an cerebrovascular disease, does the human have or has had a chronic kidney disease, does the human have or has had an autoimmune disease, does the human have or has had an haematological cancer, does the human have or has had an immunocompromised disease, does the human have or has had an non-haematological cancer, does the human have or has had diabetes, does the human have or has had liver disease, does the human have or has had hypertension and does the human have or has had a respiratory disease (other than asthma).

In an embodiment, the method comprises obtaining information from the subject on age and gender.

In an embodiment, the method comprises obtaining information from the subject on age, gender, race/ethnicity, height, weight, does the human have or has had an cerebrovascular disease, does the human have or has had a chronic kidney disease, does the human have or has had diabetes, does the human have or has had an haematological cancer, does the human have or has had hypertension, does the human have or has had an non-haematological cancer, and does the human have or has had a respiratory disease (other than asthma).

In an embodiment, the method comprises obtaining information from the subject on age, gender, race/ethnicity, blood type, height, weight, does the human have or has had an cerebrovascular disease, does the human have or has had a chronic kidney disease, does the human have or has had diabetes, does the human have or has had an haematological cancer, does the human have or has had hypertension, does the human have or has had an immunocompromised disease, does the human have or has had an haematological cancer, does the human have or has had liver disease, does the human have or has had an non-haematological cancer, and does the human have or has had a respiratory disease (other than asthma).

Examples of respiratory diseases which are included in the test are chronic obstructive pulmonary disease, chronic bronchitis and emphysema.

The diabetes can be any type of diabetes.

In an embodiment, the clinical risk assessment is conducted using the following formula:

$$\begin{aligned}
\ln(\text{risk}) = &\text{ Model Intercept} \\
&+ \text{OR if clinical factor one applies} \\
&+ \text{OR if clinical factor two applies} \\
&+ \text{OR if clinical factor three applies} \\
&\ldots \\
&+ \text{OR if clinical factor } n \text{ applies}.
\end{aligned}$$

In an embodiment, the clinical risk assessment is conducted using the following formula:

ln(risk) = Model Intercept
+ OR if age group = 18-29 years or
+ OR if age group = 30-39 years or
+ OR if age group = 40-49 years or
+ OR if age group = 60-69 years or
+ OR if age group = 70+ years
+ OR if gender = male
+ OR if ethnicity = non-Caucasian
+ OR if ABO blood type = A or
+ OR if ABO blood type = B or
+ OR if ABO blood type = AB
+ OR if has/had autoimmune disease (namely, rheumatoid arthritis, lupus or psoriasis) = yes
+ OR if has/had cancer, haematological = yes
+ OR if has/had cancer, non-haematological = yes
+ OR if has/had diabetes = yes
+ OR if has/had hypertension = yes
+ OR if has/had respiratory disease (other than asthma) = yes Where OR=Odds Ratio.

Using the above formulae the relative risk of a human subject developing a severe response to a Coronavirus infection is: risk=$e^{ln(risk)}$.

In one example, the clinical risk assessment is conducted using the following formula:

| | | | |
|---|---|---|---|
| ln(risk) | = | −0.2645 | |
| | + | −1.3111 | if age group = 18-29 years |
| | + | −0.8348 | if age group = 30-39 years |
| | + | −0.4038 | if age group = 40-49 years |
| | + | −0.0973 | if age group = 60-69 years |
| | + | 0.4419 | if age group = 70+ years |
| | + | 0.0855 | if gender = male |
| | + | 0.0404 | if ethnicity = non-Caucasian |
| | + | −0.0614 | if ABO blood type = A |
| | + | 0.2039 | if ABO blood type = B |
| | + | −0.5541 | if ABO blood type = AB |
| | + | 0.5424 | if has/had autoimmune disease (namely, rheumatoid arthritis, lupus or psoriasis) = yes |
| | + | 1.0104 | if has/had cancer, haematological = yes |
| | + | 0.2436 | if has/had cancer, non-haematological = yes |
| | + | 0.3863 | if has/had diabetes = yes |
| | + | 0.3064 | if has/had hypertension = yes |
| | + | 1.2642 | if has/had respiratory disease (other than asthma) = yes |

In an embodiment of the above formula, the starting ln(risk) (model intercept) is −0.5284 to 1.5509, or −0.16 to −0.36.

In an embodiment of the above formula, the adjustment of the starting ln(risk) for ages 18 to 29 is −1.5 to −1, or −1.4 to −1.2.

In an embodiment of the above formula, the adjustment of the starting ln(risk) for ages 30 to 39 is −1 to −0.7, or −0.9 to −0.8.

In an embodiment of the above formula, the adjustment of the starting ln(risk) for ages 40 to 49 is −0.6 to −0.2, or −0.45 to −0.35.

In an embodiment of the above formula, the adjustment of the starting ln(risk) for ages 60 to 69 is −0.4021263 to 0.2075385, or −0.19 to 0.09.

In an embodiment of the above formula, the adjustment of the starting ln(risk) for ages 70+ is 0.1504677 to 0.73339, or 0.34 to 0.54.

In an embodiment of the above formula, the adjustment of the starting ln(risk) for males is −0.140599 to 0.3115929, or −0.3 to 0.19.

In an embodiment of the above formula, the adjustment of the starting ln(risk) for non-Caucasians is −0.3029713 to 0.3837958, or −0.06 to 0.14.

In an embodiment of the above formula, the adjustment of the starting ln(risk) for A blood type is −0.3018427 to 0.1791056, or −0.16 to 0.04.

In an embodiment of the above formula, the adjustment of the starting ln(risk) for B blood type is −0.1817567 to 0.5895909, or 0.1 to 0.3.

In an embodiment of the above formula, the adjustment of the starting ln(risk) for AB blood type is −1.172319 to 0.0641862, or −0.45 to −0.65.

In an embodiment of the above formula, the adjustment of the starting ln(risk) for a human who has, or has had, rheumatoid arthritis, lupus or psoriasis is −0.0309265 to 1.115784, or 0.44 to 0.64.

In an embodiment of the above formula, the adjustment of the starting ln(risk) for a human who has, or has had, a haematological cancer is 0.1211918 to 1.899663, or 0.9 to 1.1.

In an embodiment of the above formula, the adjustment of the starting ln(risk) for a human who has, or has had, a non-haematological cancer is −0.0625866 to 0.5498824, or 0.14 to 0.34.

In an embodiment of the above formula, the adjustment of the starting ln(risk) for a human who has, or has had, diabetes is 0.0624018 to 0.7101834, or 0.28 to 0.48.

In an embodiment of the above formula, the adjustment of the starting ln(risk) for a human who has, or has had, hypertension is 0.0504567 to 0.5623362, or 0.1 to 0.3.

In an embodiment of the above formula, the adjustment of the starting ln(risk) for a human who has, or has had, a respiratory disease (excluding asthma) is 0.9775684 to 1.550944, or 1.16 to 1.36.

The present invention provides a method for assessing the risk of a human subject developing a severe response to a Coronavirus infection, the method comprising performing a clinical risk assessment of the human subject, wherein the clinical risk assessment involves determining at least the age and sex of the subject and producing a score. In an embodiment, the method further comprises comparing the score to a predetermined threshold, wherein if the score is at, or above, the threshold the subject is assessed at being at risk of developing a severe response to a Coronavirus infection.

In one embodiment, the subject is between 50 and 84 years of age and is asked their age and their sex.

In an embodiment, the method comprises determining the Log odds (LO). For example, the LO can be calculated using the formula:

$$LO=X+\Sigma \text{ Clinical } \beta \text{ coefficients}$$

In an embodiment, X is −2.25 to −1.25 or −2 or −1.5. In an embodiment, X is −1.749562.

In an embodiment, the relative risk is determined. In an embodiment, the relative risk is determined using the formula:

$$\text{relative risk}=e^{LO}$$

In an embodiment, the probability is determined. In an embodiment, the probability is determined using the formula:

$$\text{probability}=e^{LO}/(1+e^{LO})$$

"e" is the mathematical constant that is the base of the natural logarithm.

In an embodiment, the probability obtained by the above formula is multiplied by 100 to obtain a percent chance of a severe response to a Coronavirus infection such as hospitalisation being required.

In an embodiment, if the subject is between 50 and 64 years of age they are assigned a β coefficient of −0.5 to 0.5, or −0.25 to 0.25 or 0.

In an embodiment, if the subject is between 65 and 69 years of age they are assigned a β coefficient of 0 to 1, or 0.25 to 0.75 or 0.4694892.

In an embodiment, if the subject is between 70 and 74 years of age they are assigned a β coefficient of 0.5 to 1.5, or 0.75 to 1.25 or 1.006561.

In an embodiment, if the subject is between 75 and 79 years of age they are assigned a β coefficient of 0.9 to 1.9, or 1.15 to 1.65 or 1.435318.

In an embodiment, if the subject is between 80 and 84 years of age they are assigned a β coefficient of 1.1 to 2.1, or 1.35 to 1.85 or 1.599188.

In an embodiment, if the subject is female they are assigned a β coefficient of −0.5 to 0.5, or −0.25 to 0.25 or 0.

In an embodiment, if the subject is male they are assigned a β coefficient of −0.1 to 0.9, or 0.15 to 0.65 or 0.3911169.

In an embodiment, the last value provided above in each criteria is used.

In an embodiment, the clinical risk assessment includes obtaining information from the subject on one or more or all of age, gender, race/ethnicity, height, weight, does the human have or has had an cerebrovascular disease, does the human have or has had a chronic kidney disease, does the human have or has had diabetes, does the human have or has had an haematological cancer, does the human have or has had hypertension, does the human have or has had an non-haematological cancer, and does the human have or has had a respiratory disease (other than asthma).

In an embodiment, each of the above factors are assessed and

LO=X+Σ Clinical β coefficients, where X is −1.8 to −0.8 or −1.6 or −1.15 or −1.36523;

if the subject is between 50 and 69 years of age they are assigned a β coefficient of −0.5 to 0.5, or −0.25 to 0.25 or 0;

if the subject is between 70 and 74 years of age they are assigned a β coefficient of 0.1 to 1.1, or 0.35 to 0.85 or 0.5747727;

if the subject is between 75 and 79 years of age they are assigned a β coefficient of 0.3 to 1.3, or −0.55 to 1.05 or 0.8243711;

if the subject is between 18 and 29 years of age they are assigned a β coefficient of −2.3 to −0.3, or −0.18 to −0.8 or −1.3111;

if the subject is between 30 and 39 years of age they are assigned a β coefficient of −1.8 to 0.2, or −1.23 to −0.3 or −0.8348;

if the subject is between 40 and 49 years of age they are assigned a β coefficient of −1.4 to 0.6, or −0.9 to −0.1 or −0.4038;

if the subject is between 80 and 84 years of age they are assigned a β coefficient of 0.5 to 1.5, or 0.25 to 1.25 or 1.013973;

if the subject is female they are assigned a β coefficient of −0.5 to 0.5, or −0.25 to 0.25 or 0;

if the subject is male they are assigned a β coefficient of −0.25 to 0.75, or 0 to 0.5 or 0.2444891;

if the subject is Caucasian they are assigned a β coefficient of −0.5 to 0.5, or −0.25 to 0.25 or 0;

if the subject is an ethnicity other than Caucasian they are assigned a β coefficient of −0.2 to 0.8, or 0.05 to 1.55 or 0.29311;

the subjects height (in metres (m)) and weight (in kilograms (kg)) is applied to the formula: (10 times m$^2$) divided by kg, which is multiplied by −1.1 to 2.1, or −1.35 to −1.85, or −1.602056 to provide the β coefficient to be assigned;

if the subject has ever been diagnosed as having a cerebrovascular disease they are assigned a β coefficient of −0.1 to 0.9, or 0.15 to 0.65 or 0.4041337;

if the subject has not ever been diagnosed as having a cerebrovascular disease they are assigned a β coefficient of −0.5 to 0.5, or −0.25 to 0.25 or 0;

if the subject has ever been diagnosed as having a chronic kidney disease they are assigned a β coefficient of 0.2 to 1.2, or 0.55 to 0.95 or 0.6938494;

if the subject has not ever been diagnosed as having a chronic kidney disease they are assigned a β coefficient of −0.5 to 0.5, or −0.25 to 0.25 or 0;

if the subject has ever been diagnosed as having diabetes they are assigned a β coefficient of −0.1 to 0.9, or 0.15 to 0.65 or 0.4297612;

if the subject has not ever been diagnosed as having diabetes they are assigned a β coefficient of −0.5 to 0.5, or −0.25 to 0.25 or 0;

if the subject has ever been diagnosed as having haematological cancer they are assigned a β coefficient of 0.5 to 1.5, or 0.75 to 1.25 or 1.003877;

if the subject has not ever been diagnosed as having haematological cancer they are assigned a β coefficient of −0.5 to 0.5, or −0.25 to 0.25 or 0;

if the subject has ever been diagnosed as having hypertension they are assigned a β coefficient of −0.2 to 0.8, or 0.05 to 1.55 or 0.2922307;

if the subject has not ever been diagnosed as having hypertension they are assigned a β coefficient of −0.5 to 0.5, or −0.25 to 0.25 or 0;

if the subject has ever been diagnosed as having a non-haematological cancer they are assigned a β coefficient of −0.25 to 1, or 0 to 0.5 or 0.2558464;

if the subject has not ever been diagnosed as having a non-haematological cancer they are assigned a β coefficient of −0.5 to 0.5, or −0.25 to 0.25 or 0;

if the subject has ever been diagnosed as having a respiratory disease (other than asthma) they are assigned a β coefficient of 0.7 to 1.7, or 0.95 to 1.45 or 1.173753; and if the subject has ever been diagnosed as having a respiratory disease (other than asthma) they are assigned a β coefficient of −0.5 to 0.5, or −0.25 to 0.25 or 0.

In an embodiment, the last value provided above in each criteria is used.

In an embodiment, the clinical risk assessment includes obtaining information from the subject on one or more or all of age, gender, race/ethnicity, blood type, height, weight, does the human have or has had an cerebrovascular disease, does the human have or has had a chronic kidney disease, does the human have or has had diabetes, does the human have or has had an haematological cancer, does the human have or has had hypertension, does the human have or has had an immunocompromised disease, does the human have or has had an haematological cancer, does the human have or has had liver disease, does the human have or has had an non-haematological cancer, and does the human have or has had a respiratory disease (other than asthma).

In an embodiment, each of the above factors are assessed and

LO=X+Σ Clinical β coefficients, where X is −2 to −1.5 or −1.75 or −1.25 or −1.469939;

if the subject is between 50 and 64 years of age they are assigned a β coefficient of −0.5 to 0.5, or −0.25 to 0.25 or 0;
if the subject is between 65 and 69 years of age they are assigned a β coefficient of −0.3 to 0.7, or −0.05 to 0.45 or 0.1677566;
if the subject is between 70 and 74 years of age they are assigned a β coefficient of 0.1 to 1.1, or 0.35 to 1.85 or 0.6352682;
if the subject is between 75 and 79 years of age they are assigned a β coefficient of 0.4 to 1.4, or 0.65 to 1.15 or 0.8940548;
if the subject is between 80 and 84 years of age they are assigned a β coefficient of 0.5 to 1.5, or 0.25 to 1.25 or 1.082477;
if the subject is female they are assigned a β coefficient of −0.5 to 0.5, or −0.25 to 0.25 or 0;
if the subject is male they are assigned a β coefficient of −0.25 to 0.75, or 0 to 0.5 or 0.2418454;
if the subject is Caucasian they are assigned a β coefficient of −0.5 to 0.5, or −0.25 to 0.25 or 0;
if the subject is an ethnicity other than Caucasian they are assigned a β coefficient of −0.2 to 0.8, or 0.05 to 1.55 or 0.2967777;
if the subject has a blood type other than ABO they are assigned a β coefficient of −0.5 to 0.5, or −0.25 to 0.25 or 0;
if the subject has an ABO blood type they are assigned a β coefficient of −0.25 to 0.75, or 0 to 0.5 or −0.229737;
the subjects height (in metres (m)) and weight (in kilograms (kg)) is applied to the formula: (10 times $m^2$) divided by kg, which is multiplied by −1.1 to 2.1, or −1.35 to −1.85, or −1.560943 to provide the β coefficient to be assigned;
if the subject has ever been diagnosed as having a cerebrovascular disease they are assigned a β coefficient of −0.1 to 0.9, or 0.15 to 0.65 or 0.3950113;
if the subject has not ever been diagnosed as having a cerebrovascular disease they are assigned a β coefficient of −0.5 to 0.5, or −0.25 to 0.25 or 0;
if the subject has ever been diagnosed as having a chronic kidney disease they are assigned a β coefficient of 0.2 to 1.2, or 0.55 to 0.95 or 0.6650257;
if the subject has not ever been diagnosed as having a chronic kidney disease they are assigned a β coefficient of −0.5 to 0.5, or −0.25 to 0.25 or 0;
if the subject has ever been diagnosed as having diabetes they are assigned a β coefficient of −0.1 to 0.9, or 0.15 to 0.65 or 0.4126633;
if the subject has not ever been diagnosed as having diabetes they are assigned a β coefficient of −0.5 to 0.5, or −0.25 to 0.25 or 0;
if the subject has ever been diagnosed as having haematological cancer they are assigned a β coefficient of 0.5 to 1.5, or 0.75 to 1.25 or 1.001079;
if the subject has not ever been diagnosed as having haematological cancer they are assigned a β coefficient of −0.5 to 0.5, or −0.25 to 0.25 or 0;
if the subject has ever been diagnosed as having hypertension they are assigned a β coefficient of −0.2 to 0.8, or 0.05 to 1.55 or 0.2640989;
if the subject has not ever been diagnosed as having hypertension they are assigned a β coefficient of −0.5 to 0.5, or −0.25 to 0.25 or 0;
if the subject has ever been diagnosed as having an immunocompromised disease they are assigned a β coefficient of 0.1 to 1.1, or 0.35 to 0.85 or 0.6033541;
if the subject has not ever been diagnosed as having an immunocompromised disease they are assigned a β coefficient of −0.5 to 0.5, or −0.25 to 0.25 or 0;
if the subject has ever been diagnosed as having liver disease they are assigned a β coefficient of −0.2 to 0.8, or 0.05 to 1.55 or 0.2301902;
if the subject has not ever been diagnosed as having liver disease they are assigned a β coefficient of −0.5 to 0.5, or −0.25 to 0.25 or 0;
if the subject has ever been diagnosed as having a non-haematological cancer they are assigned a β coefficient of −0.25 to 1, or 0 to 0.5 or 0.2381579;
if the subject has not ever been diagnosed as having a non-haematological cancer they are assigned a β coefficient of −0.5 to 0.5, or −0.25 to 0.25 or 0;
if the subject has ever been diagnosed as having a respiratory disease (other than asthma) they are assigned a β coefficient of 0.7 to 1.7, or 0.95 to 1.45 or 1.148496; and
if the subject has ever been diagnosed as having a respiratory disease (other than asthma) they are assigned a β coefficient of −0.5 to 0.5, or −0.25 to 0.25 or 0.

In an embodiment, the last value provided above in each criteria is used.

In an embodiment, the subject's body mass index is determined using their height and weight.

In an embodiment, if any of the clinical factors are unknown, or the subject is unwilling to supply the relevant details, that factor(s) is assigned a β coefficient of 0.

In an embodiment, one or more or all of the clinical factors are self-assessed (self-reported). In an embodiment, the race/ethnicity is self-assessed (self-reported). In an embodiment, one or more or all of current or previous disease status, such as an autoimmune disease, an haematological cancer, an non-haematological cancer, diabetes, hypertension or a respiratory disease, is self-assessed (self-reported).

In an embodiment, the clinical assessment comprises determining the blood type of the subject. This will typically comprise obtaining a sample comprising blood from the subject. The detection method used can any be any suitable method known in the art. In embodiment, a genetic test as described in the Examples is used, preferably concurrently with a genetic analysis for assessing the risk of a human subject developing a severe response to a coronavirus infection.

For instance, ABO blood type can be imputed using three SNPs, namely rs505922, rs8176719 and rs8176746) in the ABO gene on chromosome 9q34.2. An rs8176719 deletion (or for those with no result for rs8176719, a T allele at rs505922) indicates haplotype O. At rs8176746, haplotype A is indicated by the presence of the G allele and haplotype B is indicated by the presence of the T allele (see Table 7).

TABLE 7

SNPS and ABO Imputation.

| rs8176719 | rs505922 | rs8176746 | Genotype | Phenotype |
|---|---|---|---|---|
| T/T | | | OO | O |
| TC/T | | C/C (G/G) | AO | A |
| TC/T | | C/A (G/T) | BO | B |
| TC/T | | A/A (T/T) | BO | B |
| TC/TC | | C/C (G/G) | AA | A |
| TC/TC | | A/A (T/T) | BB | B |
| TC/TC | | C/A (G/T) | AB | AB |

TABLE 7-continued

SNPS and ABO Imputation.

| rs8176719 | rs505922 | rs8176746 | Genotype | Phenotype |
|---|---|---|---|---|
| missing | T/T | | OO | O |
| missing | C/T | C/C (G/G) | AO | A |
| missing | C/T | C/A (G/T) | BO | B |
| missing | C/T | A/A (T/T) | BO | B |
| missing | C/C | C/C (G/G) | AA | A |
| missing | C/C | A/A (T/T) | BB | B |
| missing | C/C | C/A (G/T) | AB | AB |

In an embodiment, whether a subject has or has had (also referred to herein as "has ever been diagnosed") with a particular disease state, the disease is classified using the international Classification of Disease (ICD) system. Thus,
asthma is as per ICD9 (493*) and ICD10 (J45* and J46),
an autoimmune (rheumatoid/lupus/psoriasis) is as per ICD9 (954, 696*, 7100, 714, 7140* and 7142* and ICD10 (J990, L40*, L41*, M05*-M07* and M32*),
a haematological cancer is as per ICD9 (200*-208*) and ICD10 (C81*-C86*, C88* and C90*-C96*),
a non-haematological cancer is as per ICD9 (140*-165*, 169*-175*, 179*-195* and 196*-199*) and ICD10 (C00*-C26*, C30*-C34*, C37*-C58*, C60*-C80*, C97*),
a cerebrovascular disease is as per ICD9 (430*-438*) and ICD10 (G46* and I60*-I69*),
diabetes is as per ICD9 (250*) and ICD10 (E10*-E14*),
heart disease is as per ICD9 (413*-416*, V422, V432-V434) and ICD10 (120*-125*, 148*, Z95*),
hypertension is as per ICD9 (401*, 405*, 6420-6422) and ICD10 (110*, 115*, 010*),
an immunocompromised disease is as per ICD9 (V420, V421, V426, V427, V429, 042, 043, 044, 279, 2790*) and ICD10 (B20*-B24, D80*-D84*, Z940-Z944, Z949),
a kidney disease is as per ICD9 (585*) and ICD10 (N18*),
liver disease is as per ICD9 (571*) and ICD10 (K70*-K77*), and
a respiratory disease (excluding asthma) is as per ICD9 (494*-496*, 500*, 501*-508*, 491*, 492*, 496*) and ICD10 (J60*-J70*, J80*-J82, J84*-J86*, J90-J96*, J98*, J41*-J44*).

Combined Clinical Assessment and Genetic Assessment

In an embodiment, to obtain the "risk" of a human subject developing a severe response to a Coronavirus infection, the following formula can be used:

ln(risk) = Model Intercept
+ OR x percentage of the number of risk alleles
+ OR if clinical factor one applies
+ OR if clinical factor two applies
+ OR if clinical factor three applies
. . .
+ OR if clinical factor n applies.

Where OR=Odds Ratio.

In an embodiment, to obtain the "risk" of a human subject developing a severe response to a Coronavirus infection, the following formula can be used:

ln(risk) = Model Intercept
+ OR x percentage of the number of risk alleles
+ OR if age group = 18-29 years or
+ OR if age group = 30-39 years or
+ OR if age group = 40-49 years or
+ OR if age group = 60-69 years or
+ OR if age group = 70+ years
+ OR if gender = male
+ OR if ethnicity = non-Caucasian
+ OR if ABO blood type = A or
+ OR if ABO blood type = B or
+ OR if ABO blood type = AB
+ OR if has/had autoimmune disease (namely, rheumatoid arthritis, lupus or psoriasis) = yes
+ OR if has/had cancer, haematological = yes
+ OR if has/had cancer, non-haematological = yes
+ OR if has/had diabetes = yes
+ OR if has/had hypertension = yes
+ OR if has/had respiratory disease (other than asthma) = yes Where OR=Odds Ratio Using the above formulae the relative risk of a human subject developing a severe response to a Coronavirus infection is: risk=.

In one example, to obtain the "risk" of a human subject developing a severe response to a Coronavirus infection, the following formula can be used:

| ln(risk) | = | −10.7657 | |
|---|---|---|---|
| | + | 0.1717 x percentage of the number of risk alleles | |
| | + | −1.3111 | if age group = 18-29 years |
| | + | −0.8348 | if age group = 30-39 years |
| | + | −0.4038 | if age group = 40-49 years |
| | + | −0.0600 | if age group = 60-69 years |
| | + | 0.5325 | if age group = 70+years |
| | + | 0.1387 | if gender = male |
| | + | 0.3542 | if ethnicity = non-Caucasian |
| | + | −0.2164 | if ABO blood type = A |
| | + | −0.1712 | if ABO blood type = B |
| | + | −0.8746 | if ABO blood type = AB |
| | + | 0.7876 | if has/had autoimmune disease (namely, rheumatoid arthritis, lupus or psoriasis) = yes |
| | + | 1.0375 | if has/had cancer, haematological = yes |
| | + | 0.3667 | if has/had cancer, non-haematological = yes |
| | + | 0.4890 | if has/had diabetes = yes |
| | + | 0.3034 | if has/had hypertension = yes |
| | + | 1.2331 | if has/had respiratory disease (other than asthma) = yes |

Using this formula the relative risk of a human subject developing a severe response to a Coronavirus infection is: risk=$e^{ln(risk)}$.

In an embodiment of the above formula, the starting ln(risk) (model intercept) is −12.5559 to −8.9755, or −12 to −8, or −11 to −10.5.

In an embodiment of the above formula, the adjustment of the starting ln(risk) for the percentage of risk alleles is 0.142 to 0.2006, or 0.16 to 0.18.

In an embodiment of the above formula, the adjustment of the starting ln(risk) for ages 18 to 29 is −1.5 to −1, or −1.4 to −1.2.

In an embodiment of the above formula, the adjustment of the starting ln(risk) for ages 30 to 39 is −1 to −0.7, or −0.9 to −0.8.

In an embodiment of the above formula, the adjustment of the starting ln(risk) for ages 40 to 49 is −0.6 to −0.2, or −0.45 to −0.35.

In an embodiment of the above formula, the adjustment of the starting ln(risk) for ages 60 to 69 is −0.3819 to 0.2619, or −0.1 to 0.1.

In an embodiment of the above formula, the adjustment of the starting ln(risk) for ages 70+ is 0.2213 to 0.8438, or 0.43 to 0.63.

In an embodiment of the above formula, the adjustment of the starting ln(risk) for males is −0.1005 to 0.3779, or 0.03 to 0.23.

In an embodiment of the above formula, the adjustment of the starting ln(risk) for non-Caucasians is −0.0084 to 0.7167, or 0.25 to 0.45.

In an embodiment of the above formula, the adjustment of the starting ln(risk) for A blood type is −0.4726 to 0.0397, or −0.11 to −0.31.

In an embodiment of the above formula, the adjustment of the starting ln(risk) for B blood type is −0.2348 to 0.5773, or 0.07 to 0.27.

In an embodiment of the above formula, the adjustment of the starting ln(risk) for AB blood type is −1.5087 to −0.2404, or −0.77 to −0.97.

In an embodiment of the above formula, the adjustment of the starting ln(risk) for a human who has, or has had, rheumatoid arthritis, lupus or psoriasis is 0.1832 to 1.3920, or 0.68 to 0.88.

In an embodiment of the above formula, the adjustment of the starting ln(risk) for a human who has, or has had, a haematological cancer is 0.0994 to 1.9756, or 0.93 to 1.13.

In an embodiment of the above formula, the adjustment of the starting ln(risk) for a human who has, or has had, a non-haematological cancer is 0.0401 to 0.6933, or 0.26 to 0.46.

In an embodiment of the above formula, the adjustment of the starting ln(risk) for a human who has, or has had, diabetes is 0.1450 to 0.8330, or 0.39 to 0.59.

In an embodiment of the above formula, the adjustment of the starting ln(risk) for a human who has, or has had, hypertension is 0.0313 to 0.5756, or 0.2 to 0.4.

In an embodiment of the above formula, the adjustment of the starting ln(risk) for a human who has, or has had, a respiratory disease (excluding asthma) is 0.9317 to 0.1535, or 1.13 to 1.33.

In an alternate embodiment, and as outlined above, the method comprises determining the Log odds (LO). For example, the LO can be calculated using the formula:

$$LO = X + SRF + \Sigma \text{ Clinical } \beta \text{ coefficients}$$

In an embodiment, the SRF is the SNP Risk Factor which is: $\Sigma$(No of Risk Alleles×SNP $\beta$ coefficient).

In an embodiment, the relative risk is determined. In an embodiment, the relative risk is determined using the formula:

$$\text{relative risk} = e^{LO}$$

In an embodiment, the probability is determined. In an embodiment, the probability is determined using the formula:

$$\text{probability} = e^{LO}/(1 + e^{LO})$$

"e" is the mathematical constant that is the base of the natural logarithm.

In an embodiment, the probability obtained by the above formula is multiplied by 100 to obtain a percent chance of a severe response to a Coronavirus infection such as hospitalisation being required.

In an embodiment, the genetic risk assessment involves the analysis of rs10755709, rs112317747, rs112641600, rs118072448, rs2034831, rs7027911 and rs71481792. In an embodiment, X is −1.8 to −0.8 or −1.6 or −1.15. In an embodiment, X is −1.36523. In an embodiment, the subject is assigned a $\beta$ coefficient of −0.08 to 0.32, or 0.02 to 0.22 or 0.124239 for each G (risk) allele present at rs10755709. Thus, for example, if the subject is homozygous for the risk allele they can be assigned a $\beta$ coefficient of 0.248478, if they are heterozygous can be assigned a $\beta$ coefficient of 0.124239, and if they is homozygous for the non-risk allele (C at rs10755709) they can be assigned a $\beta$ coefficient of 0.248478. In an embodiment, the subject is assigned a $\beta$ coefficient of 0.07 to 0.47, or 0.17 to 0.37 or 0.2737487 for each C (risk) allele present at rs112317747. In an embodiment, the subject is assigned a $\beta$ coefficient of −0.43 to −0.03, or −0.33 to −0.13 or −0.2362513 for each T (risk) allele present at rs112641600. In an embodiment, the subject is assigned a $\beta$ coefficient of −0.4 to 0, or −0.3 to −0.1 or −0.1995879 for each C (risk) allele present at rs118072448. In an embodiment, the subject is assigned a $\beta$ coefficient of 0.04 to 0.44, or 0.14 to 0.34 or 0.2371955 for each C (risk) allele present at rs2034831. In an embodiment, the subject is assigned a $\beta$ coefficient of −0.1 to 0.3, or 0 to 0.2 or 0.1019074 for each A (risk) allele present at rs7027911. In an embodiment, the subject is assigned a $\beta$ coefficient of −0.3 to 0.1, or −0.2 to 0 or −0.1058025 for each T (risk) allele present at rs71481792. In an embodiment, the $\Sigma$ Clinical $\beta$ coefficients is determined as above such as factoring in p coefficients for each of age, gender, race/ethnicity, height, weight, does the human have or has had an cerebrovascular disease, does the human have or has had a chronic kidney disease, does the human have or has had diabetes, does the human have or has had an haematological cancer, does the human have or has had hypertension, does the human have or has had an non-haematological cancer, and does the human have or has had a respiratory disease (other than asthma).

In an embodiment, the genetic risk assessment involves the analysis of rs10755709, rs112317747, rs112641600, rs118072448, rs2034831, rs7027911, rs71481792, rs115492982 and rs1984162. In an embodiment, X is −2 to −1.5 or −1.75 or −1.25. In an embodiment, X is −1.469939. In an embodiment, the subject is assigned a $\beta$ coefficient of −0.08 to 0.32, or 0.02 to 0.22 or 0.1231766 for each G (risk) allele present at rs10755709. Thus, for example, if the subject is homozygous for the risk allele they can be assigned a $\beta$ coefficient of 0.2463532, if they are heterozygous can be assigned a $\beta$ coefficient of 0.1231766, and if they is homozygous for the non-risk allele (C at rs10755709) they can be assigned a $\beta$ coefficient of 0.248478. In an embodiment, the subject is assigned a $\beta$ coefficient of 0.06 to 0.46, or 0.16 to 0.36 or 0.2576692 for each C (risk) allele present at rs112317747. In an embodiment, the subject is assigned a $\beta$ coefficient of −0.43 to −0.03, or −0.33 to −0.13 or −0.2384001 for each T (risk) allele present at rs112641600. In an embodiment, the subject is assigned a $\beta$ coefficient of −0.4 to 0, or −0.3 to −0.1 or −0.1965609 for each C (risk) allele present at rs118072448. In an embodiment, the subject is assigned a $\beta$ coefficient of 0.04 to 0.44, or 0.14 to 0.34 or 0.2414792 for each C (risk) allele present at rs2034831. In an embodiment, the subject is assigned a $\beta$ coefficient of −0.1 to 0.3, or 0 to 0.2 or 0.0998459 for each A (risk) allele present at rs7027911. In an embodiment, the subject is assigned a $\beta$ coefficient of −0.3 to 0.1, or −0.2 to 0 or −0.1032044 for each T (risk) allele present at rs71481792. In an embodiment the subject is assigned a $\beta$ coefficient of 0.21 to 0.61, or 0.31 to 0.51 or 0.4163575 for each A (risk) allele present at rs115492982. In an embodiment the subject is assigned a $\beta$ coefficient of −0.1 to 0.3, or 0 to 0.2 or 0.1034362 for each A (risk) allele present at rs1984162. In an embodiment, the $\Sigma$ Clinical $\beta$ coefficients is determined as above such as factoring in p coefficients for each of age, gender, race/ethnicity, blood type, height, weight, does the human have or has had an cerebrovascular disease, does the human have or has had a chronic kidney disease, does the human have or has had diabetes, does the human have or has had an haematological cancer, does the human have or has had hypertension, does the human have or has had an haematological cancer, does the human have or has had an immunocompromised disease, does the human have or has had an haematological cancer, does the human have or has had liver disease, does the human have or has had an non-haematological cancer, and does the human have or has had a respiratory disease (other than asthma).

Any of the above calculations can be performed for non-SNP polymorphisms or a combination thereof.

In another embodiment, when combining the clinical risk assessment with the genetic risk assessment to obtain the "risk" of a human subject developing a severe response to a Coronavirus infection, the following formula can be used:

$$[\text{Risk (i.e. Clinical Evaluation} \times \text{SNP risk)}] = [\text{Clinical Evaluation risk}] \times SNP_1 \times SNP_2 \times SNP_3 \times SNP_4 \times SNP_5 \times SNP_6 \times SNP_7 \times SNP_8, \ldots \times SNP_N \text{ etc.}$$

Where Clinical Evaluation is the risk provided by the clinical evaluation, and $SNP_1$ to $SNP_N$ are the relative risk for the individual SNPs, each scaled to have a population average of 1 as outlined above. Because the SNP risk values have been "centred" to have a population average risk of 1, if one assumes independence among the SNPs, then the population average risk across all genotypes for the combined value is consistent with the underlying Clinical Evaluation risk estimate.

In an embodiment, the genetic risk assessment is combined with the clinical risk assessment to obtain the "relative risk" of a human subject developing a severe response to a Coronavirus infection.

A threshold(s) can be set as described above when genetic risk is assessed alone. In one example, the threshold could be set to be at least 5, at least 6, at least 7, at least 8, at least 9 or at least 10, when using the embodiment of the test described in Example 5. If set at 5 in this example, about 10% of the UK biobank population have a risk score over 5.0 resulting in the following performance characteristics for the test:

Sensitivity 38.41%
Specificity 93.79%
Positive predictive value 91.78%
Negative predictive value 45.76%

As the skilled person would understand, various different thresholds could be set altering performance depending on the level of risk the entity conducting the test is willing accept.

Depending upon the end-usage of the test, a threshold may be altered to the most appropriate values.

Marker Detection Strategies

Amplification primers for amplifying markers (e.g., marker loci) and suitable probes to detect such markers or to genotype a sample with respect to multiple marker alleles, can be used in the disclosure. For example, primer selection for long-range PCR is described in U.S. Ser. No. 10/042,406 and U.S. Ser. No. 10/236,480; for short-range PCR, U.S. Ser. No. 10/341,832 provides guidance with respect to primer selection. Also, there are publicly available programs such as "Oligo" available for primer design. With such available primer selection and design software, the publicly available human genome sequence and the polymorphism locations, one of skill can construct primers to amplify the polymorphisms to practice the disclosure. Further, it will be appreciated that the precise probe to be used for detection of a nucleic acid comprising a polymorphism (e.g., an amplicon comprising the polymorphism) can vary, e.g., any probe that can identify the region of a marker amplicon to be detected can be used in conjunction with the present disclosure. Further, the configuration of the detection probes can, of course, vary. Thus, the disclosure is not limited to the sequences recited herein.

Examples of primer pairs for detecting some of the SNP's disclosed herein include:

```
rs11549298 (ACCTGGTATCAGTGAAGAGGATCAG (SEQ ID NO: 1)
and
TCTTGATACAACTGTAAGAAGTGGT (SEQ ID NO: 2)), rs112317747 (TATTTCTTTGTTGCCCTCTATCTCT (SEQ ID NO: 3)
and
GAAAGAGATGGGTTGGCATTATTAT (SEQ ID NO: 4)),
and
rs2034831 (TAAAATTAGAACTGGAGGGCTGGGT (SEQ ID NO: 5)

TGGCATTATAAACACTCACTGAAGT (SEQ ID NO: 6)), rs112641600 (AATGCCATCTGATGAGAGAAGTTTT (SEQ ID NO: 7)
and
TACAGTTTTAAAAATGGGCGTTTCT (SEQ ID NO: 8)), rs10755709 (TATAATAACACGTGGAAGTGAAAAT (SEQ ID NO: 9)
and
TTGTTTGTATGTGTGAAATGATTCT (SEQ ID NO: 10)), rs118072448 (AAGCAAACTATTCTTCAGGAATCCA (SEQ ID NO: 11)
and
ATTTCTGCATTTCACTTTGTGTGGT (SEQ ID NO: 12)), rs7027911 (GTAAATGCTGCTAACAGAGCTCTTT (SEQ ID NO: 13)
and
GAAGAGAGTTTATTAGCAAGGCCTC (SEQ ID NO: 14)), rs71481792 (CATTTGGGAAAAGCCACTGAATGGA (SEQ ID NO: 15)
and
AGATTGACTAGCCGTTGAGAGTAGA (SEQ ID NO: 16)),
and
```

```
-continued
rs1984162 (ACTGACTCCTGACACTCTTGAAGCG (SEQ ID NO: 17)
and
GACTCTTCTCTGGCATCTTCTCATG (SEQ ID NO: 18)).
```

Indeed, it will be appreciated that amplification is not a requirement for marker detection, for example one can directly detect unamplified genomic DNA simply by performing a Southern blot on a sample of genomic DNA.

Typically, molecular markers are detected by any established method available in the art, including, without limitation, allele specific hybridization (ASH), detection of extension, array hybridization (optionally including ASH), or other methods for detecting polymorphisms, amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, and single-strand conformation polymorphisms (SSCP) detection.

Some techniques for detecting genetic markers utilize hybridization of a probe nucleic acid to nucleic acids corresponding to the genetic marker (e.g., amplified nucleic acids produced using genomic DNA as a template). Hybridization formats, including, but not limited to: solution phase, solid phase, mixed phase, or in situ hybridization assays are useful for allele detection. An extensive guide to the hybridization of nucleic acids is found in Tijssen (1993) Laboratory Techniques in Biochemistry and Molecular Biology-Hybridization with Nucleic Acid Probes Elsevier, New York, as well as in Sambrook et al. (supra).

PCR detection using dual-labelled fluorogenic oligonucleotide probes, commonly referred to as "TaqMan™" probes, can also be performed according to the present disclosure. These probes are composed of short (e.g., 20-25 base) oligodeoxynucleotides that are labelled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes). Further details regarding dual-label probe strategies can be found, e.g., in WO 92/02638.

Other similar methods include e.g. fluorescence resonance energy transfer between two adjacently hybridized probes, e.g., using the "LightCycler®" format described in U.S. Pat. No. 6,174,670.

Array-based detection can be performed using commercially available arrays, e.g., from Affymetrix (Santa Clara, Calif.) or other manufacturers. Reviews regarding the operation of nucleic acid arrays include Sapolsky et al. (1999); Lockhart (1998); Fodor (1997a); Fodor (1997b) and Chee et al. (1996). Array based detection is one preferred method for identification markers of the disclosure in samples, due to the inherently high-throughput nature of array based detection.

The nucleic acid sample to be analysed is isolated, amplified and, typically, labelled with biotin and/or a fluorescent reporter group. The labelled nucleic acid sample is then incubated with the array using a fluidics station and hybridization oven. The array can be washed and or stained or counter-stained, as appropriate to the detection method. After hybridization, washing and staining, the array is inserted into a scanner, where patterns of hybridization are detected. The hybridization data are collected as light emitted from the fluorescent reporter groups already incorporated into the labelled nucleic acid, which is now bound to the probe array. Probes that most clearly match the labelled nucleic acid produce stronger signals than those that have mismatches. Since the sequence and position of each probe on the array are known, by complementarity, the identity of the nucleic acid sample applied to the probe array can be identified.

Markers and polymorphisms can also be detected using DNA sequencing. DNA sequencing methods are well known in the art and can be found for example in Ausubel et al, eds., Short Protocols in Molecular Biology, 3rd ed., Wiley, (1995) and Sambrook et al, Molecular Cloning, 2nd ed., Chap. 13, Cold Spring Harbor Laboratory Press, (1989). Sequencing can be carried out by any suitable method, for example, dideoxy sequencing, chemical sequencing, or variations thereof.

Suitable sequencing methods also include Second Generation, Third Generation, or Fourth Generation sequencing technologies, all referred to herein as "next generation sequencing", including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. A review of some such technologies can be found in (Morozova and Marra, 2008), herein incorporated by reference. Accordingly, in some embodiments, performing a genetic risk assessment as described herein involves detecting the at least two polymorphisms by DNA sequencing. In an embodiment, the at least two polymorphisms are detected by next generation sequencing.

Next generation sequencing (NGS) methods share the common feature of massively parallel, high-throughput strategies, with the goal of lower costs in comparison to older sequencing methods (see, Voelkerding et al., 2009; MacLean et al., 2009).

A number of such DNA sequencing techniques are known in the art, including fluorescence-based sequencing methodologies. In some embodiments, automated sequencing techniques are used. In some embodiments, parallel sequencing of partitioned amplicons is used (WO2006084132). In some embodiments, DNA sequencing is achieved by parallel oligonucleotide extension (See, e.g., U.S. Pat. Nos. 5,750,341 and 6,306,597). Additional examples of sequencing techniques include the Church polony technology (Mitra et al., 2003; Shendure et al., 2005;

U.S. Pat. Nos. 6,432,36; 6,485,944; 6,511,803), the 454 picotiter pyrosequencing technology (Margulies et al., 2005; US 20050130173), the Solexa single base addition technology (Bennett et al., 2005; U.S. Pat. Nos. 6,787,308; 6,833,246), the Lynx massively parallel signature sequencing technology (Brenner et al., 2000; U.S. Pat. Nos. 5,695,934; 5,714,330), and the Adessi PCR colony technology (Adessi et al., 2000).

Correlating Markers to Phenotypes

These correlations can be performed by any method that can identify a relationship between an allele and a phenotype, or a combination of alleles and a combination of phenotypes. For example, alleles defined herein can be correlated with a severe response to Coronavirus infection phenotypes. The methods can involve referencing a look up table that comprises correlations between alleles of the polymorphism and the phenotype. The table can include data for multiple allele-phenotype relationships and can take account of additive or other higher order effects of multiple allele-phenotype relationships, e.g., through the use of statistical tools such as principle component analysis, heuristic algorithms, etc.

Correlation of a marker to a phenotype optionally includes performing one or more statistical tests for correlation. Many statistical tests are known, and most are computer-implemented for ease of analysis. A variety of statistical methods of determining associations/correlations between phenotypic traits and biological markers are known and can be applied to the present disclosure (Hartl et al., 1981). A variety of appropriate statistical models are described in Lynch and Walsh (1998). These models can, for example, provide for correlations between genotypic and phenotypic values, characterize the influence of a locus on a phenotype, sort out the relationship between environment and genotype, determine dominance or penetrance of genes, determine maternal and other epigenetic effects, determine principle components in an analysis (via principle component analysis, or "PCA"), and the like. The references cited in these texts provides considerable further detail on statistical models for correlating markers and phenotype.

In addition to standard statistical methods for determining correlation, other methods that determine correlations by pattern recognition and training, such as the use of genetic algorithms, can be used to determine correlations between markers and phenotypes. This is particularly useful when identifying higher order correlations between multiple alleles and multiple phenotypes. To illustrate, neural network approaches can be coupled to genetic algorithm-type programming for heuristic development of a structure-function data space model that determines correlations between genetic information and phenotypic outcomes.

In any case, essentially any statistical test can be applied in a computer implemented model, by standard programming methods, or using any of a variety of "off the shelf" software packages that perform such statistical analyses, including, for example, those noted above and those that are commercially available, e.g., from Partek Incorporated (St. Peters, Mo.; world wide web address partek.com), e.g., that provide software for pattern recognition (e.g., which provide Partek Pro 2000 Pattern Recognition Software).

Systems for performing the above correlations are also a feature of the disclosure. Typically, the system will include system instructions that correlate the presence or absence of an allele (whether detected directly or, e.g., through expression levels) with a predicted phenotype.

Optionally, the system instructions can also include software that accepts diagnostic information associated with any detected allele information, e.g., a diagnosis that a subject with the relevant allele has a particular phenotype. This software can be heuristic in nature, using such inputted associations to improve the accuracy of the look up tables and/or interpretation of the look up tables by the system. A variety of such approaches, including neural networks, Markov modelling, and other statistical analysis are described above.

Polymorphic Profiling

The disclosure provides methods of determining the polymorphic profile of an individual at the polymorphisms outlined in the present disclosure (e.g. Tables 1 to 3, 5a or 6, or Tables 1 to 6, 8, 19 or 22) or polymorphisms in linkage disequilibrium with one or more thereof.

The polymorphic profile constitutes the polymorphic forms occupying the various polymorphic sites in an individual. In a diploid genome, two polymorphic forms, the same or different from each other, usually occupy each polymorphic site. Thus, the polymorphic profile at sites X and Y can be represented in the form X (x1, x1), and Y (y1, y2), wherein x1, x1 represents two copies of allele x1 occupying site X and y1, y2 represent heterozygous alleles occupying site Y.

The polymorphic profile of an individual can be scored by comparison with the polymorphic forms associated with resistance or susceptibility to a severe response to a Coronavirus infection occurring at each site. The comparison can be performed on at least, e.g., 1, 2, 5, 10, 25, 50, or all of the polymorphic sites, and optionally, others in linkage disequilibrium with them. The polymorphic sites can be analysed in combination with other polymorphic sites.

Polymorphic profiling is useful, for example, in selecting agents to affect treatment or prophylaxis of a severe response to a Coronavirus infection in a given individual. Individuals having similar polymorphic profiles are likely to respond to agents in a similar way.

Polymorphic profiling is also useful for stratifying individuals in clinical trials of agents being tested for capacity to treat a severe response to a Coronavirus infection or related conditions. Such trials are performed on treated or control populations having similar or identical polymorphic profiles (see EP 99965095.5), for example, a polymorphic profile indicating an individual has an increased risk of developing a severe response to a Coronavirus infection. Use of genetically matched populations eliminates or reduces variation in treatment outcome due to genetic factors, leading to a more accurate assessment of the efficacy of a potential drug.

Polymorphic profiling is also useful for excluding individuals with no predisposition to a severe response to a Coronavirus infection from clinical trials. Including such individuals in the trial increases the size of the population needed to achieve a statistically significant result. Individuals with no predisposition to a severe response to a Coronavirus infection can be identified by determining the numbers of resistances and susceptibility alleles in a polymorphic profile as described above. For example, if a subject is genotyped at ten sites of the disclosure associated with a severe response to a Coronavirus infection, twenty alleles are determined in total. If over 50% and alternatively over 60% or 75% percent of these are resistance genes, the individual is unlikely to develop a severe response to a Coronavirus infection and can be excluded from the trial.

Computer Implemented Method

The methods of the present disclosure may be implemented by a system such as a computer implemented method. For example, the system may be a computer system comprising one or a plurality of processors which may operate together (referred to for convenience as "processor") connected to a memory. The memory may be a non-transitory computer readable medium, such as a hard drive, a solid state disk or CD-ROM. Software, that is executable instructions or program code, such as program code grouped into code modules, may be stored on the memory, and may, when executed by the processor, cause the computer system to perform functions such as determining that a task is to be performed to assist a user to determine the risk of a human subject developing a severe response to a Coronavirus infection; receiving data indicating the clinical risk assessment and the genetic risk assessment of the human subject developing a severe response to a Coronavirus infection, wherein the genetic risk was derived by detecting at least two polymorphisms known to be associated with a severe response to a Coronavirus infection; processing the data to combine the clinical risk assessment and the genetic risk assessment to obtain the risk of a human subject developing a severe response to a Coronavirus infection; outputting the risk of a human subject developing a severe response to a Coronavirus infection.

For example, the memory may comprise program code which when executed by the processor causes the system to determine at least two polymorphisms known to be associated with a severe response to a Coronavirus infection; process the data to combine the clinical risk assessment and the genetic risk assessment to obtain the risk of a human subject developing a severe response to a Coronavirus infection; report the risk of a human subject developing a severe response to a Coronavirus infection.

In another embodiment, the system may be coupled to a user interface to enable the system to receive information from a user and/or to output or display information. For example, the user interface may comprise a graphical user interface, a voice user interface or a touchscreen.

In an embodiment, the program code may causes the system to determine the "Polymorphism risk".

In an embodiment, the program code may causes the system to determine CombinedClinical Risk×Genetic Risk (for example Polymorphism risk).

In an embodiment, the system may be configured to communicate with at least one remote device or server across a communications network such as a wireless communications network. For example, the system may be configured to receive information from the device or server across the communications network and to transmit information to the same or a different device or server across the communications network. In other embodiments, the system may be isolated from direct user interaction.

In another embodiment, performing the methods of the present disclosure to assess the risk of a human subject developing a severe response to a Coronavirus infection, enables establishment of a diagnostic or prognostic rule based on the the clinical risk assessment and the genetic risk assessment of the human subject developing a severe response to a Coronavirus infection. For example, the diagnostic or prognostic rule can be based on the Combined Clinical Risk×Genetic Risk score relative to a control, standard or threshold level of risk.

In another embodiment, the diagnostic or prognostic rule is based on the application of a statistical and machine learning algorithm. Such an algorithm uses relationships between a population of polymorphisms and disease status observed in training data (with known disease status) to infer relationships which are then used to determine the risk of a human subject developing a severe response to a Coronavirus infection in subjects with an unknown risk. An algorithm is employed which provides an risk of a human subject developing a severe response to a Coronavirus infection. The algorithm performs a multivariate or univariate analysis function.

Kits and Products

In an embodiment, the present disclosure provides a kit comprising at least two sets of primers for amplifying two or more nucleic acids, wherein the two or more nucleic acids comprise a polymorphism selected from any one of Tables 1 to 3, 5a or 6, or Tables 1 to 6, 8, 19 or 22, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40, at least 50, at least 60, at least 70, at least 80, at least 100, at least 120, at least 140, at least 160, at least 180, at least 200, at least 250, at least 300 or at least 306 sets of the primers for amplifying nucleic acids comprising a polymorphism selected from any one of Tables 1 to 3, 5a or 6, or Tables 1 to 6, 8, 19 or 22, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40, at least 50, at least 60, at least 70, at least 80, at least 100, at least 120, at least 140, at least 160, at least 180, at least 200, at least 250, at least 300 or at least 306 sets sets of the primers for amplifying nucleic acids comprising a polymorphism selected from Table 2 and Table 3, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40, at least 50, or at least 60 sets of the primers for amplifying nucleic acids comprising a polymorphism selected from Table 4 or Table 6, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40, at least 50, or at least 60 sets of the primers for amplifying nucleic acids comprising a polymorphism selected from Table 4, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40 or at least 50, sets of the primers for amplifying nucleic acids comprising a polymorphism selected from Table 3 or Table 6a, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40 or at least 50, sets of the primers for amplifying nucleic acids comprising a polymorphism selected from Table 3, or a single nucleotide polymorphism in linkage disequilibrium with one or more thereof.

In an embodiment, the kit comprises sets of primers for amplifying nucleic acids comprising one or more or all of the polymorphisms provided in Table 19, or a single nucleotide polymorphism in linkage disequilibrium with one or more thereof.

In an embodiment, the kit comprises sets of primers for amplifying nucleic acids comprising one or more or all of the polymorphisms provided in Table 22, or a single nucleotide polymorphism in linkage disequilibrium with one or more thereof.

As would be appreciated by those of skill in the art, once a polymorphism is identified, primers can be designed to amplify the polymorphism as a matter of routine. Various software programs are freely available that can suggest suitable primers for amplifying polymorphisms of interest.

Again, it would be known to those of skill in the art that PCR primers of a PCR primer pair can be designed to specifically amplify a region of interest from human DNA. Each PCR primer of a PCR primer pair can be placed adjacent to a particular single-base variation on opposing sites of the DNA sequence variation. Furthermore, PCR primers can be designed to avoid any known DNA sequence variation and repetitive DNA sequences in their PCR primer binding sites.

The kit may further comprise other reagents required to perform an amplification reaction such as a buffer, nucleotides and/or a polymerase, as well as reagents for extracting nucleic acids from a sample.

Array based detection is one preferred method for assessing the polymorphisms of the disclosure in samples, due to the inherently high-throughput nature of array based detection. A variety of probe arrays have been described in the literature and can be used in the context of the present disclosure for detection of polymorphisms that can be correlated to a severe response to a Coronavirus infection. For example, DNA probe array chips are used in one embodiment of the disclosure. The recognition of sample DNA by the set of DNA probes takes place through DNA hybridization. When a DNA sample hybridizes with an array of DNA probes, the sample binds to those probes that are complementary to the sample DNA sequence. By evaluating to which probes the sample DNA for an individual hybridizes more strongly, it is possible to determine whether a known sequence of nucleic acid is present or not in the sample, thereby determining whether a marker found in the nucleic acid is present.

Thus, in another embodiment, the present disclosure provides a genetic array comprising at least two sets of probes for hybridising to two or more nucleic acids, wherein the two or more nucleic acids comprise a polymorphism selected from any one of Tables 1 to 3, 5a or 6, or Tables 1 to 6, 8, 19 or 22, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40, at least 50, at least 60, at least 70, at least 80, at least 100, at least 120, at least 140, at least 160, at least 180, at least 200, at least 250, at least 300 or at least 306 sets of probes for hybridising a polymorphism selected from any one of Tables 1 to 3, 5a or 6, or Tables 1 to 6, 8, 19 or 22, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40, at least 50, at least 60, at least 70, at least 80, at least 100, at least 120, at least 140, at least 160, at least 180, at least 200, at least 250, at least 300 or at least 306 sets of probes for hybridising a polymorphism selected from Table 2 and Table 3, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40, at least 50, or at least 60 sets of probes for hybridising a polymorphism selected from Table 4 or Table 5, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40, at least 50, or at least 60 sets of probes for hybridising a polymorphism selected from Table 4, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40 or at least 50, sets of probes for hybridising a polymorphism selected from Table 3 or Table 6a, or a single nucleotide polymorphism in linkage disequilibrium with one or more thereof.

In an embodiment, the kit comprises at least three, at least four, at least five, at least six, at least seven, at least eight, at least nine, at least ten, at least 20, at least 30, at least 40 or at least 50, sets of probes for hybridising a polymorphism selected from Table 3, or a single nucleotide polymorphism in linkage disequilibrium with one or more thereof.

In an embodiment, the kit comprises a probe(s) for hybridising one or more or all of the polymorphisms provided in Table 19, or a single nucleotide polymorphism in linkage disequilibrium with one or more thereof.

In an embodiment, the kit comprising a probe(s) for hybridising one or more or all of the polymorphisms provided in in Table 22, or a single nucleotide polymorphism in linkage disequilibrium with one or more thereof.

Primers and probes for other polymorphisms can be included with the above exemplified kits. For example, primers and/or probes may be included for detecting a Coronavirus, such as a SARS-CoV-2 viral, infection.

EXAMPLES

Example 1—Polymorphisms Associated with Disease Severity in Covid-19 Infected Patients Approximately 11 million SNP results were analysed. These were sorted by p-value, from lowest to highest and the top one million of these were utilised for further pruning. This equated to all variants p<0.0969. A p-value threshold of p≤0.001 was then applied, as was a beta value window between −1 to 1 and an average pooled allele frequency of 0.01-0.99.

These were then further pruned for linkage disequilibrium using the online tool LDLink, snpclip (ldlink.nci.nih.gov) using the EUR populations as reference, set to threshold at R2 of <0.5. Non-single nucleotide variants were excluded if no linked surrogate/proxy SNP was available.

Informative polymorphisms derived from publicly available pooled genome-wide association study (GWAS) results from 716 cases (confirmed COVID-19 (severe acute respiratory syndrome coronavirus 2 (SARS-CoV-2)) diagnosis and hospitalised) and 616 controls (confirmed COVID-19 diagnosis and non-hospitalised are provided in Table 2.

Informative polymorphisms derived from 2,863 patients within the UK Biobank Study, of which 825 were hospitalized for severe response to the infection. GWAS results were sorted by p-value. A p-value threshold of p<0.00001 was applied, as was an allele frequency threshold set at a minor allele frequency >0.01. The identified polymorphisms are provided in Table 8.

TABLE 8

Informative polymorphisms derived from 2,863 patients within the UK Biobank Study.

| Chromosome | Position | SNP ID | Allele 1 | Allele 2 | Frequency Allele 1 | Frequency Allele 2 | p-value for association | OR |
|---|---|---|---|---|---|---|---|---|
| 1 | 3680362 | rs146866117 | T | C | 0.00042 | 0.99958 | 3.21516E-05 | 11.3818 |
| 1 | 10993680 | rs75721992 | C | T | 0.00091 | 0.99909 | 8.03153E-09 | 18.9971 |
| 1 | 15698556 | rs12562412 | G | C | 0.18020 | 0.81980 | 7.34872E-05 | 1.43641 |
| 1 | 15758944 | rs117338853 | A | G | 0.00125 | 0.99875 | 9.31685E-05 | 9.83042 |
| 1 | 16109212 | rs72647169 | G | C | 0.03574 | 0.96426 | 1.72286E-05 | 4.49562 |
| 1 | 17295659 | rs199765517 | T | C | 0.00045 | 0.99955 | 6.47434E-05 | 10.3168 |
| 1 | 20072025 | rs199727655 | A | G | 0.00003 | 0.99997 | 3.41489E-05 | 11.3655 |
| 1 | 22538788 | rs78360109 | A | G | 0.00727 | 0.99273 | 1.32276E-06 | 3.74574 |
| 1 | 34829829 | rs79955780 | G | A | 0.03884 | 0.96116 | 8.74145E-05 | 1.8346 |
| 1 | 38661814 | rs61778695 | C | A | 0.03148 | 0.96852 | 4.43093E-05 | 1.93677 |
| 1 | 67804320 | rs578200723 | GTTA | G | 0.00168 | 0.99832 | 0.000020482 | 5.75441 |
| 1 | 72488455 | rs116544454 | T | G | 0.01396 | 0.98604 | 1.85829E-05 | 2.48638 |
| 1 | 109823418 | rs144022094 | T | C | 0.00064 | 0.99936 | 3.57493E-05 | 6.50582 |
| 1 | 109933450 | rs56072034 | A | G | 0.02556 | 0.97444 | 4.12342E-05 | 2.10457 |
| 1 | 168696733 | rs76129265 | T | G | 0.05740 | 0.94260 | 7.51539E-05 | 1.68733 |
| 1 | 204092087 | rs201772428 | A | G | 0.00036 | 0.99964 | 4.3011E-06 | 14.8225 |
| 1 | 206776460 | rs35252702 | A | G | 0.00679 | 0.99321 | 1.56671E-07 | 8.81138 |
| 1 | 207610967 | rs61821114 | T | C | 0.01504 | 0.98496 | 3.00757E-05 | 2.42913 |
| 1 | 210901242 | rs1934624 | A | T | 0.02193 | 0.97807 | 5.48665E-05 | 2.16618 |
| 1 | 218938774 | rs76354174 | A | G | 0.02281 | 0.97719 | 7.54499E-05 | 2.10557 |
| 1 | 230907829 | rs143186556 | A | G | 0.00089 | 0.99911 | 5.46536E-05 | 7.7448 |
| 1 | 231133014 | rs200114138 | A | G | 0.00101 | 0.99899 | 3.96515E-06 | 8.13897 |
| 2 | 22958939 | rs59447738 | G | T | 0.10234 | 0.89766 | 8.21388E-05 | 1.5646 |
| 2 | 23005876 | rs73918088 | A | C | 0.05530 | 0.94470 | 7.50922E-05 | 1.7204 |
| 2 | 25861939 | rs189303418 | T | C | 0.00156 | 0.99844 | 0.000040202 | 5.43754 |
| 2 | 34108876 | rs1718746 | C | G | 0.15379 | 0.84621 | 8.52475E-05 | 0.678928 |
| 2 | 34119632 | rs1705143 | A | G | 0.15212 | 0.84788 | 8.08594E-05 | 0.676255 |
| 2 | 64630299 | rs872241 | G | A | 0.35970 | 0.64030 | 7.17367E-05 | 1.37043 |
| 2 | 64641736 | rs11676644 | C | T | 0.30746 | 0.69254 | 0.000032141 | 1.39753 |
| 2 | 115258481 | rs56735442 | A | G | 0.02150 | 0.97850 | 3.59163E-05 | 2.25221 |
| 2 | 122952399 | rs75945051 | G | A | 0.01208 | 0.98792 | 4.38486E-05 | 2.48027 |
| 2 | 126726522 | rs76187206 | C | G | 0.00948 | 0.99052 | 5.74668E-05 | 2.79499 |
| 2 | 160721407 | chr2_160721407 | A | AC | 0.00001 | 0.99999 | 4.45501E-05 | 10.9923 |
| 2 | 179428061 | rs11896637 | T | C | 0.00304 | 0.99696 | 1.81846E-06 | 11.2684 |
| 2 | 179441917 | rs72646881 | C | T | 0.00324 | 0.99676 | 1.59099E-05 | 8.89845 |
| 2 | 179612315 | rs145581345 | C | T | 0.00135 | 0.99865 | 8.45307E-05 | 5.91193 |
| 2 | 181910717 | rs78593095 | A | G | 0.01388 | 0.98612 | 2.26398E-05 | 2.66342 |
| 2 | 191278341 | rs6725814 | G | A | 0.37811 | 0.62189 | 1.88302E-05 | 0.714396 |
| 3 | 2748191 | rs80225140 | G | A | 0.03080 | 0.96920 | 8.74289E-06 | 2.11655 |
| 3 | 34944013 | rs17032477 | G | A | 0.01700 | 0.98300 | 3.63638E-05 | 2.54994 |
| 3 | 65100060 | rs2128405 | C | A | 0.07271 | 0.92729 | 1.71219E-05 | 1.69956 |
| 3 | 70783491 | rs6766000 | T | C | 0.13852 | 0.86148 | 2.00031E-05 | 1.53315 |
| 3 | 81810551 | rs35196441 | T | G | 0.00100 | 0.99900 | 3.53506E-05 | 11.2502 |
| 3 | 154812638 | rs2196521 | G | A | 0.12811 | 0.87189 | 3.73634E-05 | 0.662498 |
| 3 | 160379672 | rs4679910 | G | A | 0.38677 | 0.61323 | 1.90222E-05 | 1.4334 |
| 3 | 171853417 | rs73167212 | G | A | 0.11289 | 0.88711 | 0.00002702 | 1.5595 |
| 3 | 177796194 | rs74911757 | T | C | 0.01229 | 0.98771 | 1.43291E-05 | 2.6372 |
| 4 | 39943691 | rs115509062 | G | C | 0.03178 | 0.96822 | 6.54964E-05 | 1.90376 |
| 4 | 45517625 | rs75072424 | A | G | 0.11765 | 0.88235 | 2.80438E-05 | 1.54719 |
| 4 | 69795670 | rs144454074 | A | G | 0.00307 | 0.99693 | 4.19779E-05 | 4.35549 |
| 4 | 73555556 | rs28616128 | G | A | 0.06206 | 0.93794 | 3.02015E-06 | 1.78187 |
| 4 | 75191300 | rs115044024 | C | T | 0.01950 | 0.98050 | 4.15557E-05 | 2.18747 |
| 4 | 84216649 | rs144185023 | A | G | 0.00166 | 0.99834 | 3.72469E-05 | 5.50931 |
| 4 | 87939942 | rs76456240 | C | T | 0.02364 | 0.97636 | 9.48747E-05 | 2.09846 |
| 4 | 121958473 | rs202221151 | C | T | 0.00031 | 0.99969 | 1.61977E-06 | 16.7318 |
| 4 | 142326546 | rs76589765 | G | A | 0.01836 | 0.98164 | 4.20983E-06 | 2.39938 |
| 4 | 151724769 | rs116015734 | T | C | 0.01283 | 0.98717 | 9.26679E-05 | 2.44853 |
| 4 | 153821201 | rs62319956 | C | A | 0.00963 | 0.99037 | 2.01266E-06 | 3.02949 |
| 4 | 170238293 | rs76519323 | A | C | 0.03375 | 0.96625 | 2.30315E-05 | 1.98212 |
| 4 | 170498270 | rs74557505 | C | T | 0.03048 | 0.96952 | 6.57926E-05 | 2.01122 |
| 4 | 181162752 | rs17069033 | T | G | 0.00223 | 0.99777 | 1.35337E-05 | 9.07875 |
| 4 | 185567903 | rs4647611 | C | G | 0.00897 | 0.99103 | 2.72675E-05 | 6.07186 |
| 5 | 6826973 | rs275444 | C | G | 0.12706 | 0.87294 | 3.53004E-05 | 0.530803 |
| 5 | 19993490 | rs4466171 | A | T | 0.02086 | 0.97914 | 3.08251E-06 | 5.43862 |
| 5 | 43280480 | rs55770078 | A | G | 0.00266 | 0.99734 | 1.16965E-05 | 4.82309 |
| 5 | 99815379 | rs115319054 | A | C | 0.01396 | 0.98604 | 8.88589E-05 | 2.37898 |
| 5 | 133519273 | rs79601653 | G | A | 0.05445 | 0.94555 | 9.89897E-05 | 1.68817 |
| 5 | 155405405 | rs958444 | T | C | 0.04320 | 0.95680 | 2.01272E-05 | 0.540169 |
| 5 | 160448591 | rs11749317 | C | T | 0.01465 | 0.98535 | 0.000080983 | 2.31323 |
| 6 | 2885791 | rs318470 | C | A | 0.03985 | 0.96015 | 9.76222E-05 | 0.534104 |
| 6 | 16217762 | rs149442766 | A | G | 0.00598 | 0.99402 | 3.42524E-05 | 3.20428 |
| 6 | 26408145 | rs144114619 | A | T | 0.00298 | 0.99702 | 4.57681E-05 | 4.32309 |
| 6 | 33156845 | rs41268014 | G | C | 0.00111 | 0.99889 | 1.61406E-05 | 7.06085 |
| 6 | 36976747 | rs140572234 | C | G | 0.00360 | 0.99640 | 6.20165E-08 | 4.94704 |
| 6 | 36999980 | rs114925152 | G | C | 0.01045 | 0.98955 | 0.000019845 | 2.8117 |

TABLE 8-continued

Informative polymorphisms derived from 2,863 patients within the UK Biobank Study.

| Chromosome | Position | SNP ID | Allele 1 | Allele 2 | Frequency Allele 1 | Frequency Allele 2 | p-value for association | OR |
|---|---|---|---|---|---|---|---|---|
| 6 | 37139030 | rs35760989 | C | G | 0.00316 | 0.99684 | 2.15792E−05 | 4.19015 |
| 6 | 101279459 | rs9485415 | T | C | 0.05955 | 0.94045 | 2.95345E−05 | 1.79563 |
| 6 | 147885588 | rs140643252 | A | G | 0.00080 | 0.99920 | 0.000080315 | 7.36219 |
| 7 | 21730647 | rs7790948 | G | T | 0.14286 | 0.85714 | 3.13489E−05 | 1.51436 |
| 7 | 35720134 | rs79496619 | T | G | 0.01734 | 0.98266 | 3.21712E−05 | 4.65324 |
| 7 | 38677134 | rs78966608 | A | C | 0.06041 | 0.93959 | 7.06676E−05 | 1.69619 |
| 7 | 100483400 | rs200675508 | A | G | 0.00165 | 0.99835 | 7.25535E−05 | 5.06219 |
| 7 | 104782689 | rs55743527 | G | T | 0.00060 | 0.99940 | 1.36022E−06 | 11.6143 |
| 7 | 122122078 | rs73431600 | A | G | 0.01909 | 0.98091 | 5.15467E−05 | 2.32846 |
| 7 | 122196872 | rs73433754 | A | C | 0.01639 | 0.98361 | 3.48011E−05 | 2.47199 |
| 7 | 154926067 | rs117164958 | C | G | 0.01908 | 0.98092 | 7.61301E−06 | 4.84386 |
| 7 | 158928541 | rs13225056 | A | G | 0.02825 | 0.97175 | 1.53596E−05 | 2.04944 |
| 8 | 2044114 | rs147776183 | T | C | 0.00025 | 0.99975 | 8.64871E−06 | 13.5674 |
| 8 | 9478274 | rs78876374 | T | C | 0.05327 | 0.94673 | 8.85355E−05 | 1.69943 |
| 8 | 19218826 | rs145746072 | A | G | 0.00063 | 0.99937 | 1.91735E−05 | 5.15347 |
| 8 | 20354600 | rs13249119 | G | A | 0.12835 | 0.87165 | 1.33633E−05 | 1.57795 |
| 8 | 20447019 | rs73626732 | A | G | 0.08816 | 0.91184 | 1.40229E−05 | 1.65522 |
| 8 | 20460661 | rs35258926 | G | T | 0.08444 | 0.91556 | 9.04111E−06 | 1.68733 |
| 8 | 39799765 | rs7845003 | T | C | 0.38763 | 0.61237 | 9.39614E−05 | 1.37383 |
| 8 | 125839433 | rs118040942 | T | C | 0.02098 | 0.97902 | 0.000059504 | 2.11631 |
| 8 | 130677813 | rs57557483 | A | G | 0.03911 | 0.96089 | 8.17573E−06 | 1.95465 |
| 8 | 130694201 | rs75572486 | A | G | 0.03949 | 0.96051 | 2.53314E−05 | 1.8823 |
| 9 | 10276812 | rs10959000 | A | G | 0.06996 | 0.93004 | 7.85152E−05 | 1.65945 |
| 9 | 22080363 | rs16905613 | G | A | 0.00861 | 0.99139 | 5.78633E−06 | 3.06828 |
| 9 | 38669062 | rs2993177 | A | G | 0.02733 | 0.97267 | 7.37838E−05 | 0.512648 |
| 9 | 79453107 | rs7853555 | T | C | 0.39843 | 0.60157 | 5.25711E−05 | 0.726342 |
| 9 | 83032179 | rs72744937 | G | A | 0.01117 | 0.98883 | 6.92799E−05 | 2.60258 |
| 9 | 100137855 | rs200908751 | A | G | 0.00074 | 0.99926 | 6.57652E−05 | 7.53882 |
| 9 | 101874496 | rs76094400 | A | G | 0.01217 | 0.98783 | 3.95481E−08 | 3.22873 |
| 9 | 125704675 | rs76670825 | A | G | 0.01316 | 0.98684 | 5.01185E−05 | 2.47436 |
| 9 | 125903047 | rs77089732 | A | G | 0.01284 | 0.98716 | 0.00005145 | 2.45902 |
| 9 | 128794405 | rs62570501 | T | C | 0.05704 | 0.94296 | 7.35517E−05 | 1.70643 |
| 9 | 131771551 | rs17455482 | A | G | 0.00240 | 0.99760 | 5.2118E−06 | 5.14273 |
| 10 | 67680203 | rs41313840 | G | A | 0.00029 | 0.99971 | 7.19977E−08 | 11.5573 |
| 10 | 127258691 | rs7084502 | A | G | 0.41534 | 0.58466 | 7.81329E−05 | 0.720431 |
| 10 | 131456440 | rs79858702 | T | C | 0.00885 | 0.99115 | 0.000070971 | 2.83622 |
| 11 | 1795214 | rs79194907 | G | A | 0.08673 | 0.91327 | 6.83674E−05 | 0.457071 |
| 11 | 5146083 | rs12365149 | T | C | 0.08312 | 0.91688 | 3.11673E−05 | 0.427618 |
| 11 | 44547746 | rs12275504 | G | T | 0.02803 | 0.97197 | 1.40655E−05 | 2.13659 |
| 11 | 46727333 | rs149066130 | A | G | 0.00042 | 0.99958 | 7.98651E−05 | 10.0401 |
| 11 | 57982229 | rs1966836 | A | G | 0.29483 | 0.70517 | 6.87681E−05 | 0.720184 |
| 11 | 65414949 | rs199717374 | T | C | 0.00021 | 0.99979 | 1.05822E−05 | 9.34606 |
| 11 | 78904266 | rs75970706 | T | C | 0.03718 | 0.96282 | 0.000040305 | 1.8614 |
| 11 | 94665002 | rs76360689 | A | G | 0.00749 | 0.99251 | 1.05432E−06 | 3.44965 |
| 11 | 133713033 | rs75786498 | A | G | 0.01903 | 0.98097 | 3.13102E−05 | 2.20737 |
| 12 | 2174748 | rs117821007 | C | T | 0.01160 | 0.98840 | 4.86991E−05 | 2.65265 |
| 12 | 25681286 | rs58907459 | T | C | 0.12688 | 0.87312 | 6.07118E−05 | 1.50994 |
| 12 | 57589676 | rs143285614 | A | G | 0.00041 | 0.99959 | 2.69071E−05 | 11.6706 |
| 12 | 125302200 | rs143093152 | G | A | 0.00050 | 0.99950 | 6.62377E−06 | 14.0613 |
| 13 | 39433574 | rs138539682 | A | G | 0.00073 | 0.99927 | 3.32149E−05 | 8.17464 |
| 13 | 68302925 | rs75022796 | T | C | 0.00560 | 0.99440 | 7.24669E−05 | 3.17997 |
| 14 | 52276643 | rs117852779 | C | T | 0.02739 | 0.97261 | 2.89233E−06 | 2.17106 |
| 14 | 80405359 | rs11159425 | T | G | 0.11363 | 0.88637 | 4.36025E−07 | 0.583 |
| 14 | 80570671 | rs114463019 | G | T | 0.01076 | 0.98924 | 3.85403E−05 | 2.71426 |
| 14 | 87813714 | rs28450466 | A | G | 0.37204 | 0.62796 | 9.45754E−05 | 1.35996 |
| 14 | 93016441 | rs57851052 | C | T | 0.32996 | 0.67004 | 5.53318E−05 | 1.37778 |
| 14 | 104863663 | rs80083325 | A | G | 0.05367 | 0.94633 | 0.000073746 | 1.71423 |
| 15 | 22845849 | rs150408740 | G | A | 0.00068 | 0.99932 | 1.76793E−05 | 8.79206 |
| 15 | 34498314 | rs75915717 | T | C | 0.08459 | 0.91541 | 1.0293E−06 | 1.74564 |
| 15 | 41047777 | rs35673728 | C | T | 0.06056 | 0.93944 | 6.67895E−05 | 1.67388 |
| 15 | 41254865 | rs12915860 | C | A | 0.06743 | 0.93257 | 1.01336E−05 | 1.72191 |
| 15 | 41712936 | rs62001419 | A | C | 0.05640 | 0.94360 | 9.84979E−05 | 1.68361 |
| 15 | 52689631 | rs1724577 | T | G | 0.00955 | 0.99045 | 2.42041E−05 | 0.197849 |
| 15 | 58047086 | rs77910305 | G | C | 0.00656 | 0.99344 | 1.30369E−05 | 3.14637 |
| 15 | 65851028 | rs200531541 | A | G | 0.00017 | 0.99983 | 3.83063E−06 | 13.9416 |
| 15 | 78471034 | rs34921279 | T | C | 0.00117 | 0.99883 | 2.40367E−05 | 8.48175 |
| 15 | 84063245 | rs12591031 | G | A | 0.21734 | 0.78266 | 1.16687E−05 | 1.46192 |
| 15 | 91452594 | rs142925505 | T | C | 0.00205 | 0.99795 | 6.04339E−07 | 5.95363 |
| 16 | 49391921 | rs62029091 | A | G | 0.11884 | 0.88116 | 7.11949E−05 | 1.52258 |
| 16 | 49394276 | rs8057939 | C | T | 0.12559 | 0.87441 | 1.12522E−05 | 1.57483 |
| 16 | 60671279 | rs118097562 | T | A | 0.00770 | 0.99230 | 1.90641E−05 | 6.63236 |
| 16 | 61851413 | rs151208133 | T | C | 0.00057 | 0.99943 | 6.3915E−06 | 9.86885 |
| 16 | 81194912 | rs11642802 | C | A | 0.26295 | 0.73705 | 4.32104E−06 | 1.45947 |
| 16 | 90075827 | rs201800670 | T | C | 0.00044 | 0.99956 | 1.60067E−05 | 12.5559 |
| 17 | 1462712 | rs73298816 | G | A | 0.29300 | 0.70700 | 5.44207E−05 | 0.682825 |

TABLE 8-continued

Informative polymorphisms derived from 2,863 patients within the UK Biobank Study.

| Chromo-some | Position | SNP ID | Allele 1 | Allele 2 | Frequency Allele 1 | Frequency Allele 2 | p-value for association | OR |
|---|---|---|---|---|---|---|---|---|
| 17 | 3844344 | rs144535413 | T | C | 0.00487 | 0.99513 | 1.11488E−05 | 3.62812 |
| 17 | 36485146 | rs147966258 | A | G | 0.00198 | 0.99802 | 1.64933E−05 | 5.06987 |
| 17 | 39240563 | rs193005959 | A | C | 0.00837 | 0.99163 | 3.72836E−05 | 2.98372 |
| 17 | 55803083 | rs72841559 | C | G | 0.01897 | 0.98103 | 2.26086E−05 | 2.2379 |
| 17 | 56329775 | rs368901060 | ACCAT | A | 0.00219 | 0.99781 | 4.70507E−06 | 5.18629 |
| 17 | 63919929 | rs7220318 | G | A | 0.00461 | 0.99539 | 2.39945E−05 | 10.9127 |
| 17 | 72890474 | rs689992 | T | A | 0.26539 | 0.73461 | 8.97907E−05 | 1.39123 |
| 17 | 78215658 | rs117140258 | A | G | 0.02691 | 0.97309 | 4.15567E−05 | 2.08397 |
| 18 | 4610215 | rs76902871 | G | T | 0.01267 | 0.98733 | 2.95635E−05 | 2.56921 |
| 18 | 13501162 | rs2298530 | C | T | 0.03718 | 0.96282 | 6.48889E−05 | 1.85512 |
| 18 | 14310187 | rs117505121 | G | A | 0.01057 | 0.98943 | 3.59448E−05 | 2.71447 |
| 18 | 49288587 | rs117781678 | A | C | 0.01002 | 0.98998 | 4.32852E−05 | 2.66495 |
| 18 | 76650871 | rs7240086 | G | A | 0.43336 | 0.56664 | 6.95487E−06 | 1.42281 |
| 19 | 36018109 | rs74726174 | C | T | 0.00069 | 0.99931 | 1.82372E−05 | 12.2885 |
| 19 | 38867031 | rs200403794 | A | G | 0.00019 | 0.99981 | 8.36021E−05 | 10.0252 |
| 20 | 8782776 | rs138434221 | A | C | 0.00031 | 0.99969 | 4.80296E−06 | 14.6291 |
| 20 | 15632993 | rs6110707 | C | T | 0.17779 | 0.82221 | 1.31264E−05 | 1.50802 |
| 20 | 55021575 | rs6069749 | T | C | 0.07845 | 0.92155 | 2.92257E−05 | 1.64645 |
| 20 | 55111747 | rs6014757 | A | G | 0.15160 | 0.84840 | 6.44584E−05 | 1.47163 |
| 21 | 19045795 | rs73200561 | A | T | 0.00879 | 0.99121 | 9.40896E−05 | 2.714 |
| 21 | 37444937 | rs2230191 | A | G | 0.00079 | 0.99921 | 3.4537E−07 | 13.3335 |
| 22 | 28016883 | rs1885362 | A | C | 0.15733 | 0.84267 | 4.65803E−05 | 1.70351 |
| 22 | 40056937 | rs113038998 | T | C | 0.06752 | 0.93248 | 1.37758E−05 | 1.73209 |
| 22 | 44285118 | rs117421847 | A | G | 0.01292 | 0.98708 | 6.60782E−05 | 2.4314 |

Example 2—Genetic Risk Assessment—108 Polymorphism Panel

SNP-based (relative) risk score was calculated using estimates of the odds ratio (OR) per allele and risk allele frequency (p) assuming independent and additive risks on the log OR scale. For each SNP, the unsealed population average risk was calculated as $\mu=(1-p)2+2p(1-p)OR+p2OR2$. Adjusted risk values (with a population average risk equal to 1 were calculated as $1/\mu$, $OR/\mu$ and $OR2/\mu$ for the three genotypes defined by number of risk alleles (0, 1, or 2). The overall SNP-based risk score was then calculated by multiplying the adjusted risk values for each of the 108 SNPs (Tables 9 and 10).

Thus, a polygenic risk score can discriminate between patients with a confirmed Covid-19 infection who developed a severe response to that infection, requiring hospitalization, and those who did not require hospitalization.

Example 3—Genetic Risk Assessment—58 Polymorphism Panel

The present inventors have found that a polygenic risk score can discriminate between patients with a confirmed Covid-19 infection who developed a severe response to that infection, requiring hospitalization, and those who did not require hospitalization.

The model has been developed using 2,863 patients within the UK Biobank Study, of which 825 were hospitalized for severe response to the infection.

SNP-based (relative) risk score was calculated using estimates of the odds ratio (OR) per allele and risk allele frequency (p) assuming independent and additive risks on the log OR scale. For each SNP, the unsealed population average risk was calculated as $p=(1-p)2+2p(1-p)OR+p2OR2$. Adjusted risk values (with a population average risk equal to 1 were calculated as $1/p$, $OR/p$ and $OR2/p$ for the three genotypes defined by number of risk alleles (0, 1, or 2). The overall SNP-based risk score was then calculated by multiplying the adjusted risk values for each of the 58 SNPs (Table 11). The 58 SNPs analysed are provided in Table 3.

Thus, a polygenic risk score can discriminate between patients with a confirmed Covid-19 infection who developed a severe response to that infection, requiring hospitalization, and those who did not require hospitalization. Due to the higher OR, this panel performed better than the 108 SNP panel described in Example 2.

TABLE 9

Informative polymorphisms used in genetic risk assessment of Example 2.

| Chromo-some | Position | SNP ID | Allele 1 | Allele 2 | Frequency Allele 1 | Frequency Allele 2 | p-value for association | OR |
|---|---|---|---|---|---|---|---|---|
| 1 | 15698556 | rs12562412 | G | C | 0.180202869 | 0.819797131 | 7.34872E−05 | 1.43641 |
| 1 | 16109212 | rs72647169 | G | C | 0.035742611 | 0.964257389 | 1.72286E−05 | 4.49562 |
| 1 | 34829829 | rs79955780 | G | A | 0.038842122 | 0.961157878 | 8.74145E−05 | 1.8346 |
| 1 | 38661814 | rs61778695 | C | A | 0.031483826 | 0.968516174 | 4.43093E−05 | 1.93677 |
| 1 | 72488455 | rs116544454 | T | G | 0.013959529 | 0.986040471 | 1.85829E−05 | 2.48638 |
| 1 | 109933450 | rs56072034 | A | G | 0.02556272 | 0.97443728 | 4.12342E−05 | 2.10457 |
| 1 | 168696733 | rs76129265 | T | G | 0.05740251 | 0.94259749 | 7.51539E−05 | 1.68733 |
| 1 | 207610967 | rs61821114 | T | C | 0.015043834 | 0.984956166 | 3.00757E−05 | 2.42913 |
| 1 | 210901242 | rs1934624 | A | T | 0.021933325 | 0.978066675 | 5.48665E−05 | 2.16618 |
| 1 | 218938774 | rs76354174 | A | G | 0.022811438 | 0.977188562 | 7.54499E−05 | 2.10557 |

TABLE 9-continued

Informative polymorphisms used in genetic risk assessment of Example 2.

| Chromosome | Position | SNP ID | Allele 1 | Allele 2 | Frequency Allele 1 | Frequency Allele 2 | p-value for association | OR |
|---|---|---|---|---|---|---|---|---|
| 2 | 22958939 | rs59447738 | G | T | 0.102337052 | 0.897662948 | 8.21388E−05 | 1.5646 |
| 2 | 23005876 | rs73918088 | A | C | 0.055296476 | 0.944703524 | 7.50922E−05 | 1.7204 |
| 2 | 34108876 | rs1718746 | C | G | 0.153787681 | 0.846212319 | 8.52475E−05 | 0.678928 |
| 2 | 34119632 | rs1705143 | A | G | 0.152124807 | 0.847875193 | 8.08594E−05 | 0.676255 |
| 2 | 64630299 | rs872241 | G | A | 0.359695861 | 0.640304139 | 7.17367E−05 | 1.37043 |
| 2 | 64641736 | rs11676644 | C | T | 0.30746047 | 0.69253953 | 0.000032141 | 1.39753 |
| 2 | 115258481 | rs56735442 | A | G | 0.021502475 | 0.978497525 | 3.59163E−05 | 2.25221 |
| 2 | 122952399 | rs75945051 | G | A | 0.012078152 | 0.987921848 | 4.38486E−05 | 2.48027 |
| 2 | 181910717 | rs78593095 | A | G | 0.013875458 | 0.986124542 | 2.26398E−05 | 2.66342 |
| 2 | 191278341 | rs6725814 | G | A | 0.378106477 | 0.621893523 | 1.88302E−05 | 0.714396 |
| 3 | 2748191 | rs80225140 | G | A | 0.030803699 | 0.969196301 | 8.74289E−06 | 2.11655 |
| 3 | 34944013 | rs17032477 | G | A | 0.017000358 | 0.982999642 | 3.63638E−05 | 2.54994 |
| 3 | 65100060 | rs2128405 | C | A | 0.072712034 | 0.927287966 | 1.71219E−05 | 1.69956 |
| 3 | 70783491 | rs6766000 | T | C | 0.138522268 | 0.861477732 | 2.00031E−05 | 1.53315 |
| 3 | 81810551 | rs2196521 | G | A | 0.128112119 | 0.871887881 | 3.73634E−05 | 0.662498 |
| 3 | 160379672 | rs4679910 | G | A | 0.386771125 | 0.613228875 | 1.90222E−05 | 1.4334 |
| 3 | 171853417 | rs73167212 | G | A | 0.112891842 | 0.887108158 | 0.00002702 | 1.5595 |
| 3 | 177796194 | rs74911757 | T | C | 0.012287422 | 0.987712578 | 1.43291E−05 | 2.6372 |
| 4 | 39943691 | rs115509062 | G | C | 0.031782343 | 0.968217657 | 6.54964E−05 | 1.90376 |
| 4 | 45117625 | rs75072424 | A | G | 0.117654783 | 0.882345217 | 2.80438E−05 | 1.54717 |
| 4 | 73555556 | rs28616128 | G | A | 0.06205979 | 0.93794021 | 3.02015E−06 | 1.78187 |
| 4 | 75191300 | rs115044024 | C | T | 0.019501076 | 0.980498924 | 4.15557E−05 | 2.18747 |
| 4 | 87939942 | rs76456240 | C | T | 0.02364031 | 0.97635969 | 9.48747E−05 | 2.09846 |
| 4 | 142326546 | rs76589765 | G | A | 0.018356247 | 0.981643753 | 4.20983E−06 | 2.39938 |
| 4 | 151724769 | rs116015734 | T | C | 0.012831113 | 0.987168887 | 9.26679E−05 | 2.44853 |
| 4 | 170238293 | rs76519323 | A | C | 0.033750916 | 0.966249084 | 2.30315E−05 | 1.98212 |
| 4 | 170498270 | rs74557505 | C | T | 0.030475432 | 0.969524568 | 6.57926E−05 | 2.01122 |
| 5 | 6826973 | rs275444 | C | G | 0.127064744 | 0.872935256 | 3.53004E−05 | 0.530803 |
| 5 | 19993490 | rs4466171 | A | T | 0.020864374 | 0.979135626 | 3.08251E−06 | 5.43862 |
| 5 | 99815379 | rs115319054 | A | C | 0.013956451 | 0.986043549 | 8.88589E−05 | 2.37898 |
| 5 | 133519273 | rs79601653 | G | A | 0.054445035 | 0.945554965 | 9.89897E−05 | 1.68817 |
| 5 | 155405405 | rs958444 | T | C | 0.043203962 | 0.956796038 | 2.01272E−05 | 0.540169 |
| 5 | 160448591 | rs11749317 | C | T | 0.014652992 | 0.985347008 | 0.000080983 | 2.31323 |
| 6 | 2885791 | rs318470 | C | A | 0.039851542 | 0.960148458 | 9.76222E−05 | 0.534104 |
| 6 | 36999980 | rs114925152 | G | C | 0.010452207 | 0.989547793 | 0.000019845 | 2.8117 |
| 6 | 101279459 | rs9485415 | T | C | 0.059550603 | 0.940449397 | 2.95345E−05 | 1.79563 |
| 7 | 21730647 | rs7790948 | G | T | 0.142864617 | 0.857135383 | 3.13489E−05 | 1.51436 |
| 7 | 35720134 | rs79496619 | T | G | 0.01734375 | 0.98265625 | 3.21712E−05 | 4.65324 |
| 7 | 38677134 | rs78966608 | A | C | 0.060412303 | 0.939587697 | 7.06676E−05 | 1.69619 |
| 7 | 122122078 | rs73431600 | A | G | 0.019090743 | 0.980909257 | 5.15467E−05 | 2.32846 |
| 7 | 122196872 | rs73433754 | A | C | 0.016394855 | 0.983605145 | 3.48011E−05 | 2.47199 |
| 7 | 154926067 | rs117164958 | C | G | 0.019077785 | 0.980922215 | 7.61301E−06 | 4.84386 |
| 7 | 158928541 | rs13225056 | A | G | 0.028246298 | 0.971753702 | 1.53596E−05 | 2.04944 |
| 8 | 9478274 | rs78876374 | T | C | 0.053269431 | 0.946730569 | 8.85355E−05 | 1.69943 |
| 8 | 20354600 | rs13249119 | G | A | 0.12835319 | 0.87164681 | 1.33633E−05 | 1.57795 |
| 8 | 20447019 | rs73626732 | A | G | 0.088162098 | 0.911837902 | 1.40229E−05 | 1.65522 |
| 8 | 20460661 | rs35258926 | G | T | 0.084440378 | 0.915559622 | 9.04111E−06 | 1.68733 |
| 8 | 39799765 | rs7845003 | T | C | 0.387630529 | 0.612369471 | 9.39614E−05 | 1.37383 |
| 8 | 125839433 | rs118040942 | T | C | 0.020977249 | 0.979022751 | 0.000059504 | 2.11631 |
| 8 | 130677813 | rs57557483 | A | G | 0.039111916 | 0.960888084 | 8.17573E−06 | 1.95465 |
| 8 | 130694201 | rs75572486 | A | G | 0.039487371 | 0.960512629 | 2.53314E−05 | 1.8823 |
| 9 | 10276812 | rs10959000 | A | G | 0.069955622 | 0.930044378 | 7.85152E−05 | 1.65945 |
| 9 | 38669062 | rs2993177 | A | G | 0.027325082 | 0.972674918 | 7.37838E−05 | 0.512648 |
| 9 | 79453107 | rs7853555 | T | C | 0.398429245 | 0.601570755 | 5.25711E−05 | 0.726342 |
| 9 | 83032179 | rs72744937 | G | A | 0.011167213 | 0.988832787 | 6.92799E−05 | 2.60258 |
| 9 | 101874496 | rs76094400 | A | G | 0.012165395 | 0.987834605 | 3.95481E−08 | 3.22873 |
| 9 | 125704675 | rs76670825 | A | G | 0.013160405 | 0.986839595 | 5.01185E−05 | 2.47436 |
| 9 | 125903047 | rs77089732 | A | G | 0.012843423 | 0.987156577 | 0.00005145 | 2.45902 |
| 9 | 128794405 | rs62570501 | A | T | 0.057035262 | 0.942964738 | 7.35517E−05 | 1.70643 |
| 10 | 127258691 | rs7084502 | A | G | 0.415343172 | 0.584656828 | 7.81329E−05 | 0.720431 |
| 11 | 1795214 | rs79194907 | G | A | 0.086733113 | 0.913266887 | 6.83674E−05 | 0.457071 |
| 11 | 5146083 | rs12365149 | T | C | 0.083117054 | 0.916882946 | 3.11673E−05 | 0.427618 |
| 11 | 44547746 | rs12275504 | G | T | 0.028028822 | 0.971971178 | 1.40655E−05 | 2.13659 |
| 11 | 57982229 | rs1966836 | A | G | 0.294826316 | 0.705173684 | 6.87681E−05 | 0.720184 |
| 11 | 78904266 | rs75970706 | T | C | 0.037184377 | 0.962815623 | 0.000040305 | 1.8614 |
| 11 | 133713033 | rs75786498 | A | G | 0.019027141 | 0.980972859 | 3.13102E−05 | 2.20737 |
| 12 | 2174748 | rs117821007 | C | T | 0.011596011 | 0.988403989 | 4.86991E−05 | 2.65265 |
| 12 | 25681286 | rs58907459 | T | C | 0.126878043 | 0.873121957 | 6.07118E−05 | 1.50994 |
| 14 | 52276643 | rs117852779 | C | T | 0.027392806 | 0.972607194 | 2.89233E−06 | 2.17106 |
| 14 | 80405359 | rs11159425 | T | G | 0.113626338 | 0.886373662 | 4.36025E−07 | 0.583 |
| 14 | 80570671 | rs114463019 | G | T | 0.010759957 | 0.989240043 | 3.85403E−05 | 2.71426 |
| 14 | 87813714 | rs28450466 | A | G | 0.372042781 | 0.627957219 | 9.45754E−05 | 1.35996 |
| 14 | 93016441 | rs57851052 | C | T | 0.329959028 | 0.670040972 | 5.53318E−05 | 1.37778 |
| 14 | 104863663 | rs80083325 | A | G | 0.053669505 | 0.946330495 | 0.000073746 | 1.71423 |
| 15 | 34498314 | rs75915717 | T | C | 0.084593227 | 0.915406773 | 1.0293E−06 | 1.74564 |

TABLE 9-continued

Informative polymorphisms used in genetic risk assessment of Example 2.

| Chromo-some | Position | SNP ID | Allele 1 | Allele 2 | Frequency Allele 1 | Frequency Allele 2 | p-value for association | OR |
|---|---|---|---|---|---|---|---|---|
| 15 | 41047777 | rs35673728 | C | T | 0.060558997 | 0.939441003 | 6.67895E−05 | 1.67388 |
| 15 | 41254865 | rs12915860 | C | A | 0.06742592 | 0.93257408 | 1.01336E−05 | 1.72191 |
| 15 | 41712936 | rs62001419 | A | C | 0.056399246 | 0.943600754 | 9.84979E−05 | 1.68361 |
| 15 | 84063245 | rs12591031 | G | A | 0.217339031 | 0.782660969 | 1.16687E−05 | 1.46192 |
| 16 | 49391921 | rs62029091 | A | G | 0.118836542 | 0.881163458 | 7.11949E−05 | 1.52258 |
| 16 | 49394276 | rs8057939 | C | T | 0.125591649 | 0.874408351 | 1.12522E−05 | 1.57483 |
| 16 | 81194912 | rs11642802 | C | A | 0.262949597 | 0.737050403 | 4.32104E−06 | 1.45947 |
| 17 | 1462712 | rs73298816 | G | A | 0.292998283 | 0.707001717 | 5.44207E−05 | 0.682825 |
| 17 | 55803083 | rs72841559 | C | G | 0.018970721 | 0.981029279 | 2.26086E−05 | 2.2379 |
| 17 | 72890474 | rs689992 | T | A | 0.265385949 | 0.734614051 | 8.97907E−05 | 1.39123 |
| 17 | 78215658 | rs117140258 | A | G | 0.026907587 | 0.973092413 | 4.15567E−05 | 2.08397 |
| 18 | 4610215 | rs76902871 | G | T | 0.012668006 | 0.987331994 | 2.95635E−05 | 2.56921 |
| 18 | 13501162 | rs2298530 | C | T | 0.03717617 | 0.96282383 | 6.48889E−05 | 1.85512 |
| 18 | 14310187 | rs117505121 | G | A | 0.010569152 | 0.989430848 | 3.59448E−05 | 2.71447 |
| 18 | 49288587 | rs117781678 | A | C | 0.010023409 | 0.989976591 | 4.32852E−05 | 2.66495 |
| 18 | 76650871 | rs7240086 | G | A | 0.433358842 | 0.566641158 | 6.95487E−06 | 1.42281 |
| 20 | 15632993 | rs6110707 | C | T | 0.177787033 | 0.822212967 | 1.31264E−05 | 1.50802 |
| 20 | 55021575 | rs6069749 | T | C | 0.078451567 | 0.921548433 | 2.92257E−05 | 1.64645 |
| 20 | 55111747 | rs6014757 | A | G | 0.15160471 | 0.84839529 | 6.44584E−05 | 1.47163 |
| 22 | 28016883 | rs1885362 | A | C | 0.157331933 | 0.842668067 | 4.65803E−05 | 1.70351 |
| 22 | 40056937 | rs113038998 | T | C | 0.067518225 | 0.932481775 | 1.37758E−05 | 1.73209 |
| 22 | 44285118 | rs117421847 | A | G | 0.012916257 | 0.987083743 | 6.60782E−05 | 2.4314 |

Example 4—Combining Genetic and Clinical Risk Assessment

The present specification provides methods for a Covid-19 risk model which combines a clinical risk assessment and a genetic risk assessment which can be used discriminate between cases with a severe response to Covid-19 infection, versus controls without a severe response.

The clinical risk factors incorporated into a combined model are assigned a relative risk, which indicates the magnitude of association with the severity of a Covid-19 infection, the clinical factors are combined with the polygenic risk score by multiplication. For example clinical risk factor A is assigned the relative risk RRa and clinical risk factor B is assigned the relative risk RRb. The full risk score is then calculated as Polygenic Risk Score×RRa×RRb=Combined Risk.

TABLE 10

Performance characteristics of a 108 SNP polygenic risk score to discriminate between cases with a severe response to Covid-19 infection, versus controls without a severe response.

| Number of SNPs in the polygenic risk score | Odds Ratio | Standard Error | Z-statistic | P > z | 95% Conf. interval | Area of ROC |
|---|---|---|---|---|---|---|
| 108 | 1.57 | 0.109307 | 6.51 | 0.00 | 1.371796-1.801599 | 0.66 |

TABLE 11

Performance characteristics of a 58 SNP polygenic risk score to discriminate between cases with a severe response to Covid-19 infection, versus controls without a severe response.

| Number of SNPs in the polygenic risk score | Odds Ratio | Standard Error | Z-statistic | P > z | 95% Conf. interval | Area of ROC |
|---|---|---|---|---|---|---|
| 58 | 5.49 | 0.6401827 | 14.61 | 0.00 | 4.369035-6.900403 | 0.87 |

Example 5—Combined Genetic and Clinical Risk Assessment—64 Polymorphism Panel

Data and Eligibility

The inventors extracted COVID-19 testing and hospital records from the UK Biobank COVID-19 data portal on 15 Sep. 2020. At the time of data extraction, primary care data was only available for just over half of the identified participants and was therefore not used in these analyses.

Eligible participants were those who had tested positive for COVID-19 and for whom SNP genotyping data and linked hospital records were available. Of the 18,221 participants with COVID-19 test results, 1,713 had tested positive and 1,582 of those had both SNP and hospital data available.

COVID-19 Severity

The inventors used source of test result as a proxy for severity of disease: outpatient representing non-severe disease and inpatient representing severe disease. For participants with multiple test results, the disease was considered to be severe if at least one result came from an inpatient setting.

Selection of SNPs for Risk of Severe COVID-19

The inventors identified 62 SNPs from the publicly available (release 2) results of the meta-analysis of non-hospitalised versus hospitalised cases of COVID-19 conducted by the COVID-19 Host Genetics Initiative consortium (COVID-19 Host Genetics Initiative (2020) and COVID-19 Host Genetics Initiative: results. 2020 accessed May 13, 2020, at world wide web address covid19hg.org/results). ( ). P<0.0001 was used as the threshold for loci selection and variants that were associated with hospitalisation in only one of the five studies included in the meta-analysis were removed. Variants that had a minor allele frequency of <0.01 and beta coefficients from −1 to 1 were then discarded (Dayem et al., 2018). Linkage disequilibrium pruning was performed using an $r^2$ threshold of 0.5 against the 1000 Genomes European populations (CEU, TSI, FIN, GBR, IBS) representing the ethnicities of the submitted populations (Machiela et al., 2015). Where possible, SNP variants were chosen over insertion-deletion variants to facilitate laboratory validation testing.

The two lead SNPs from the loci found by Ellinghaus et al. (2020) that reached genome-wide significance were also included. Therefore, a panel of 64 SNPs for severe COVID-19 was used.

Genetic Risk Score

For the SNPs identified from the COVID-19 Host Genetics Initiative, the odds ratios for severe disease ranged from 1.5 to 2.7 (Table 4). While the inventors would normally construct a SNP relative risk score by using published odds ratios and allele frequencies to calculate adjusted risk values (with a population average of 1) for each SNP and then multiplying the risks for each SNP (Mealiffe et al., 2020), the size of the odds ratios for each SNP meant that this approach could result in relative risk SNP scores of several orders of magnitude. Therefore, to construct the SNP score for this study, the inventors calculated the percentage of risk alleles present in the genotyped SNPs for each participant as generally described in WO 2005/086770. More specifically, for each of the 64 SNPs, if the subject was homozygous for the risk allele they were scored as 2, if they were heterozygous for the risk allele they were scored as 1, and if they we homozygous for the risk allele they were scored as 0. The total number was then converted to a percentage for use in determining risk.

Percentage rather than a count was used because some of the eligible participants had missing data for some SNPs (9% had all SNPs genotyped, 82% were missing 1-5 SNPs and 9% were missing 6-15 SNPs).

Imputation of ABO Genotype

Blood type was imputed for genotyped UK Biobank participants using three SNPs (rs505922, rs8176719 and rs8176746) in the ABO gene on chromosome 9q34.2. A rs8176719 deletion (or for those with no result for rs8176719, a T allele at rs505922) was considered to indicate haplotype O. At rs8176746, haplotype A was indicated by the presence of the G allele and haplotype B was indicated by the presence of the T allele (Melzer et al., 2008; Wolpin et al., 2010).

Clinical Risk Factors

Risk factors for severe COVID-19 were identified from large epidemiological studies of electronic health records (Williamson et al., 2020; Petrilli et al., 2020) and advice posted on the Centers for Disease Control and Prevention website. Rare monogenic diseases (thalassemia, cystic fibrosis and sickle cell disease) were not considered in these analyses.

Age was classified as 50-59 years, 60-69 year and 70+ years. This was based on the participants' approximate age at the peak of the first wave of infections (April 2020) and was calculated using the participants' month and year of birth. Self-reported ethnicity was classified as white and other (including unknown). The Townsend deprivation score at baseline was classified into quintiles defined by the distribution of the score in the UK Biobank as a whole. Body mass index and smoking status were also obtained from the baseline assessment data. Body mass index was inverse transformed and then rescaled by multiplying by 10. Smoking status was defined as current versus past, never or unknown. The other clinical risk factors were extracted from hospital records by selecting records with ICD9 or ICD10 codes for the disease of interest.

Statistical Methods

Logistic regression was used to examine the association of risk factors with severity of COVID-19 disease. To develop the final model, the inventors began with a base model that included SNP score, age group and gender. They then included all of the candidate variables and used stepwise backwards selection to remove variables with p-values of >0.05. The final model was refined by considering the addition of the removed candidate variables one at a time. Model selection was informed by examination of the Akaike information criterion and the Bayesian information criterion, with a decrease of >2 indicating a statistically significant improvement.

Model calibration was assessed using the Pearson-Windmeijer goodness-of-fit test and model discrimination was measured using the area under the receiver operating characteristic curve (AUC). To compare the effect sizes of the variables in the final model, the inventors used the odds per adjusted standard deviation (Hopper, 2015) using dummy variables for age group and ABO blood type. The intercept and beta coefficients from the final model were used to calculate the COVID-19 risk score for all UK Biobank participants.

Stata (version 16.1) (StataCorp LLC: College Station, Tex., USA) was used for analyses; all statistical tests were two-sided, and p-values of less than 0.05 were considered nominally statistically significant.

Results

Of the 1,582 UK Biobank participants with a positive SARS-CoV-2 test result and hospital and SNP data available, 564 (35.7%) were from an outpatient setting and considered not to have severe disease (controls), while 1,018 (64.4%) were from an inpatient setting and considered to have severe disease (cases). Cases ranged in age from 51 to 82 years with a mean of 69.1 (standard deviation [SD]=8.8) years. Controls ranged in age from 50 to 82 years with a mean of 65.0 (SD=9.0) years. Mean body mass index was 29.0 kg/m2 (SD=5.4) for cases and 28.5 (SD=5.4) for controls. Body mass index was transformed to the inverse multiplied by 10 for all analyses and ranged from 0.2 to 0.6 for both cases and controls. The percentage of risk alleles in the SNP score ranged from 47.6 to 73.8 for cases and from 43.7 to 72.5 for controls. The distributions of the variables of interest for cases and controls and the unadjusted odd ratios and 95% confidence intervals (CI) are shown in Table 12.

The model selected included SNP score, age group, gender, ethnicity, ABO blood type, and a history of autoimmune disease (rheumatoid arthritis, lupus or psoriasis), haematological cancer, non-haematological cancer, diabetes, hypertension or respiratory disease (excluding asthma) and was a good fit to the data (Windmeijer's H=0.02, p=0.9) (Table 13). The SNP score was strongly associated with severity of disease, increasing risk by 19% per percentage increase in risk alleles. A negative impact of age was only evident in the group aged 70 years and over, and while gender was not statistically significant (p=0.3), it was retained because it was one of the three variables considered the base model to which other variables were added. Ethnicity showed a 43% increase in risk for non-whites but was only marginally statistically significant (p=0.06). The AB blood type was protective (p=0.007), but the protective effect of blood type A and the increased risk for blood type B were not statistically significant (p=0.1 and p=0.4, respectively).

The SNP score was, by far, the strongest predictor followed by respiratory disease and age 70 years or older.

The receiver operating characteristic curves for the final model and for alternative models with clinical factors only; SNP score only; and age and gender are shown in FIG. 1. The SNP score alone had an AUC of 0.680 (95% CI=0.652, 0.708). The model with age and gender had an AUC of 0.635 (95% CI=0.607, 0.662), while the model with clinical factors only had an AUC of 0.723 (95% CI=0.698, 0.749). Given that the minimum possible value for an AUC is 0.5, the model with clinical factors only was a 65% improvement over the model with age and gender ($\chi2$=57.97, df=1, p<0.001). The combined model had an AUC of 0.786 (95% CI=0.763, 0.808) and was an 28% improvement over the model with clinical factors only ($\chi2$=39.54, df=1, p<0.001) and a 111% improvement over the model with age and sex ($\chi2$=113.67, df=1, p<0.001).

TABLE 12

Characteristics of cases and controls and unadjusted odds ratios for risk of severe COVID-19.

| Variable | | Cases | Controls | Unadjusted odds ratio | 95% confidence interval | p-value |
|---|---|---|---|---|---|---|
| Continuous variables | | Mean (SD) | Mean (SD) | | | |
| SNP score | % risk alleles | 62.1 (4.1) | 59.3 (4.7) | 1.16 | 1.13, 1.19 | <0.001 |
| Inverse of body mass index (kg/m$^2$) | 10/BMI | 0.36 (0.06) | 0.36 (0.06) | 0.15 | 0.03, 0.79 | 0.03 |
| Categorical variables | | N (%) | N (%) | | | |
| Age group (years) | 50-59 | 218 (21.4) | 210 (37.2) | — | | |
| | 60-60 | 210 (20.6) | 157 (27.8) | 1.29 | 0.97, 1.71 | 0.08 |
| | 70+ | 590 (58.0) | 197 (34.9) | 2.89 | 2.25, 3.70 | <0.001 |
| Gender | Female | 443 (43.5) | 298 (52.8) | — | | |
| | Male | 575 (56.5) | 266 (47.2) | 1.45 | 1.18, 1.79 | <0.001 |
| Ethnicity | White | 888 (87.2) | 489 (86.7) | — | | |
| | Other | 123 (12.1) | 73 (12.9) | 0.93 | 0.68, 1.26 | 0.6 |
| | Missing | 7 (0.7) | 2 (0.4) | | | |
| Quintile of Townsend deprivation index at baseline | 1 | 134 (13.2) | 84 (14.9) | — | | |
| | 2 | 165 (16.2) | 95 (16.8) | 1.09 | 0.75, 1.58 | 0.7 |
| | 3 | 179 (17.6) | 98 (17.4) | 1.14 | 0.79, 1.65 | 0.5 |
| | 4 | 215 (21.1) | 124 (22.0) | 1.09 | 0.77, 1.54 | 0.6 |
| | 5 | 325 (31.9) | 162 (28.7) | 1.26 | 0.90, 1.75 | 0.2 |
| | Missing | 0 (0.0) | 1 (0.2) | | | |
| ABO blood type | O | 425 (41.8) | 235 (41.7) | — | | |
| | A | 450 (44.2) | 249 (44.2) | 1.00 | 0.80, 1.25 | 1.0 |
| | B | 113 (11.1) | 55 (9.8) | 1.14 | 0.79, 1.63 | 0.5 |
| | AB | 30 (3.0) | 25 (4.4) | 0.66 | 0.38, 1.15 | 0.1 |
| Smoking status at baseline | Never/previous | 882 (86.6) | 499 (88.5) | — | | |
| | Current | 124 (12.2) | 60 (10.6) | 1.17 | 0.84, 1.62 | 0.3 |
| | Missing | 12 (1.2) | 5 (0.9) | | | |
| Asthma | No | 852 (83.7) | 487 (86.4) | — | | |
| | Yes | 166 (16.3) | 77 (13.7) | 1.23 | 0.92, 1.65 | 0.2 |
| Autoimmune (rheumatoid/lupus/psoriasis) | No | 947 (93.0) | 547 (97.0) | — | | |
| | Yes | 71 (7.0) | 17 (3.0) | 2.41 | 1.41, 4.14 | 0.001 |
| Cancer - haematological | No | 972 (95.5) | 558 (98.9) | — | | |
| | Yes | 46 (4.5) | 6 (1.1) | 4.40 | 1.87, 10.37 | 0.001 |
| Cancer - non-haematological | No | 799 (78.5) | 486 (86.2) | — | | |
| | Yes | 219 (21.5) | 78 (13.8) | 1.71 | 1.29, 2.26 | <0.001 |
| Cerebrovascular disease | No | 847 (83.2) | 503 (89.2) | — | | |
| | Yes | 171 (16.8) | 61 (10.8) | 1.66 | 1.22, 2.28 | 0.001 |
| Diabetes | No | 765 (75.2) | 493 (87.4) | — | | |
| | Yes | 253 (24.9) | 71 (12.6) | 2.30 | 1.72, 3.06 | <0.001 |
| Heart disease | No | 633 (62.2) | 437 (77.5) | — | | |
| | Yes | 385 (37.8) | 127 (22.5) | 2.09 | 1.66, 2.65 | <0.001 |
| Hypertension | No | 419 (41.2) | 354 (62.8) | — | | |
| | Yes | 599 (58.8) | 210 (37.2) | 2.41 | 1.95, 2.98 | <0.001 |
| Immunocompromised | No | 1,001 (98.3) | 560 (99.3) | — | | |
| | Yes | 17 (1.7) | 4 (0.7) | 2.38 | 0.80, 7.10 | 0.1 |
| Kidney disease | No | 859 (84.4) | 521 (92.4) | — | | |
| | Yes | 159 (15.6) | 43 (7.6) | 2.24 | 1.57, 3.19 | <0.001 |
| Liver disease | No | 937 (92.0) | 541 (95.9) | — | | |
| | Yes | 81 (8.0) | 23 (4.1) | 2.03 | 1.26, 3.27 | 0.003 |
| Respiratory disease (excluding | No | 571 (56.1) | 486 (86.2) | — | | |
| | Yes | 447 (43.9) | 78 (13.8) | 4.88 | 3.73, 6.38 | <0.001 |

TABLE 13

Final model for risk of severe COVID-19 given a positive test.

| Variable | | β coefficient | 95% confidence interval | p-value |
|---|---|---|---|---|
| Model intercept | | -10.7657 | -12.5559, -8.9755 | <0.001 |
| SNP score | % risk alleles | 0.1717 | 0.1429, 0.2006 | <0.001 |
| Age group (years)* | 18-29 | -1.3111 | | |
| | 30-39 | -0.8348 | | |
| | 40-49 | -0.4038 | | |
| | 50-59 | — | | |
| | 60-69 | -0.0600 | -0.3819, 0.2619 | 0.7 |
| | 70+ | 0.5325 | 0.2213, 0.8438 | 0.001 |
| Gender | Female | — | | |
| | Male | 0.1387 | -0.1005, 0.3779 | 0.3 |
| Ethnicity | White | — | | |
| | Other | 0.3542 | -0.0084, 0.7167 | 0.06 |
| ABO blood type | O | — | | |
| | A | -0.2164 | -0.4726, 0.0397 | 0.1 |
| | B | 0.1712 | -0.2348, 0.5773 | 0.4 |
| | AB | -0.8746 | -1.5087, -0.2404 | 0.007 |

TABLE 13-continued

Final model for risk of severe COVID-19 given a positive test.

| Variable | | β coefficient | 95% confidence interval | p-value |
|---|---|---|---|---|
| Autoimmune disease (rheumatoid arthritis/lupus/psoriasis) | No | — | | |
| | Yes | 0.7876 | 0.1832, 1.3920 | 0.01 |
| Cancer - haematological | No | — | | |
| | Yes | 1.0375 | 0.0994, 1.9756 | 0.03 |
| Cancer - non-haematological | No | — | | |
| | Yes | 0.3667 | 0.0401, 0.6933 | 0.03 |
| Diabetes | No | — | | |
| | Yes | 0.4890 | 0.1450, 0.8330 | 0.005 |
| Hypertension | No | — | | |
| | Yes | 0.3034 | 0.0313, 0.5756 | 0.03 |
| Respiratory disease (excluding asthma) | No | — | | |
| | Yes | 1.2331 | 0.9317, 0.1535 | <0.001 |

\* Note: The β coefficient is the natural log of the odds ratio; estimates for the 18-29, 30-39 and 40-49 age groups are based on information on page 9 of the Centers for Disease Control COVIDView report for 1 Aug. 2020.

FIG. 2 illustrates the difference in the distributions of the COVID-19 risk scores in cases and controls. The median score was 3.35 for cases and 0.90 for controls. Fifteen percent of cases and 53% of controls had COVID-19 risk scores of less than 1, and 18% of cases and 25% of controls had scores ≥1 and <2. COVID-19 risk scores ≥2 were more common in cases than in controls, with 13% of cases and 9% of controls having scores ≥2 and <3, 8% of cases and 4% of controls having scores ≥3 and <4, and 38% of cases and 6% of controls having scores ≥4.

FIG. 3 shows that the distribution of the COVID-19 risk score in the whole UK Biobank is similar to that for the controls in FIG. 2b. The median risk score in the whole UK Biobank was 1.32. Thirty-eight percent of the UK Biobank have COVID-19 risk scores of less than 1, while 29% have scores ≥1 and <2, 13% have scores ≥2 and <3, 6% have scores ≥3 and <2, and 14% have scores of 4 or over.

Example 6—Combined Genetic and Clinical Risk Assessment—7 and 10 Polymorphism Panels To further improve the method of the invention the inventors downloaded an updated results file on 8 Jan. 2021 from the UK Biobank. Eligible participants were active UK Biobank participants with a positive SARS-CoV-2 test result and who had SNP and hospital data available. Of the 47,990 UK Biobank participants with a SARS-CoV-2 test result available, 8,672 (18.1%) had a positive test result, and of these, 7,621 met the eligibility criteria.

The inventors used source of test result as a proxy for severity of disease, where inpatient results were considered severe disease (cases) and outpatient results were considered non-severe disease (controls). If a participant had more than one test result, they were classified as having severe disease if at least one of their results was from an inpatient setting. Of the 7,621 eligible participants, 2,205 were cases and 5,416 were controls.

The inventors identified a further 40 SNPs from the publicly available (release 4) results of the meta-analysis of non-hospitalised versus hospitalised cases of COVID-19 conducted by the COVID-19 Host Genetics Initiative consortium (COVID-19 Host Genetics Initiative (2020) and COVID-19 Host Genetics Initiative: results. 2020 accessed Jan. 7, 2020, at world wide web address covid19hg.org/results). P<0.0001 was used as the threshold for loci selection and variants that were associated with hospitalisation in only one of the five studies included in the meta-analysis were removed. Variants that had a minor allele frequency of <0.01 and beta coefficients from −1 to 1 were then discarded (Dayem et al., 2018). Linkage disequilibrium pruning was performed using an r2 threshold of 0.5 against the 1000 Genomes European populations (CEU, TSI, FIN, GBR, IBS) representing the ethnicities of the submitted populations (Machiela et al., 2015). Where possible, SNP variants were chosen over insertion-deletion variants to facilitate laboratory validation testing. A further 12 SNPs were identified from publicly available meta-analysis of Covid-19 data (Pairo-Castineira et al., 2020).

The above identified SNPs were combined with the 64 identified in our original study to provide a test SNP panel of 116 SNPs.

To develop a new model to predict risk of severe COVID-19, the inventors used all of the available data and randomly divided it into a 70% training dataset and a 30% validation dataset (ensuring that it was balanced for origin of test result). Because the missing data is assumed to be missing at random (if not missing completely at random), a multiple imputation with 20 imputations was used to address the missing data for body mass index (linear regression) and the SNP data (predictive mean matching) for the development of the new model in the training dataset. To more closely reflect the availability of data in the real world, the inventors did not use imputed data in the validation dataset.

The clinical variables considered for inclusion in the new model were age, sex, BMI, ethnicity, ABO blood type and the following chronic health conditions: asthma, autoimmune disease (rheumatoid arthritis, lupus or psoriasis), haematological cancer, non-haematological cancer, cerebrovascular disease, diabetes, heart disease, hypertension, immunocompromised, kidney disease, liver disease and respiratory disease (excluding asthma). Dummy variables were used for the categorical classifications of age and ABO blood type.

The SNPs selected for the development of the new model came from three sources: (i) from Tables 2 to 4, (ii) the 40 SNPs newly selected from the (release 4) results of the COVID-19 Host Genetics Initiative meta-analysis of non-hospitalised versus hospitalised cases of COVID-19 1 2 and (iii) the 12 SNPs from the paper by Pairo-Castineira et al. (2020). The inventors used unadjusted logistic regression in the testing dataset to identify SNPS that were associated with risk of severe COVID-19 with P<0.05 (see Table 14).

Stata (version 16.1) was used for analyses; all statistical tests were two-sided and P<0.05 was considered nominally statistically significant.

TABLE 14

Informative polymorphisms assessed in Example 6.

| Chr | SNP | Position (GRCh37) | Reference Allele | Frequency | Effect Allele | Frequency | OR | 95% Cl | P |
|---|---|---|---|---|---|---|---|---|---|
| 1 | rs10873821 | 87628173 | C | 0.75 | T | 0.25 | 0.92 | 0.84, 1.02 | 0.10 |
| 1 | rs112317747 | 239197542 | T | 0.97 | C | 0.03 | 1.26 | 1.00, 1.58 | 0.05 |
| 1 | rs115492982 | 150271556 | G | 1.00 | A | 0.00 | 2.46 | 1.23, 4.91 | 0.01 |
| 1 | rs12083278 | 31624029 | G | 0.29 | C | 0.71 | 1.04 | 0.95, 1.15 | 0.40 |
| 1 | rs12745140 | 2998313 | G | 0.91 | A | 0.09 | 0.90 | 0.77, 1.06 | 0.20 |
| 1 | rs17102023 | 46618634 | A | 1.00 | G | 0.00 | 1.33 | 0.63, 2.81 | 0.50 |
| 1 | rs2224986 | 152684866 | C | 0.91 | T | 0.09 | 0.98 | 0.85, 1.14 | 0.80 |
| 1 | rs2274122 | 36549664 | G | 0.20 | A | 0.80 | 0.97 | 0.88, 1.07 | 0.50 |
| 1 | rs2765013 | 36374101 | C | 0.91 | T | 0.09 | 1.01 | 0.96, 1.26 | 0.20 |
| 1 | rs74508649 | 192526317 | C | 1.00 | T | 0.00 | 1.04 | 0.47, 2.32 | 0.90 |
| 2 | rs183569214 | 79895332 | G | 1.00 | A | 0.00 | 0.72 | 0.15, 3.45 | 0.70 |
| 2 | rs2034831 | 182353446 | A | 0.94 | C | 0.06 | 1.22 | 1.03, 1.46 | 0.02 |
| 2 | rs2270360 | 217524986 | A | 0.74 | C | 0.26 | 0.94 | 0.85, 1.04 | 0.20 |
| 2 | rs6714112 | 36905013 | C | 0.86 | A | 0.14 | 1.02 | 0.90, 1.16 | 0.70 |
| 2 | rs77764981 | 80029580 | T | 1.00 | C | 0.00 | 1.29 | 0.54, 3.10 | 0.60 |
| 3 | rs10510749 | 46180416 | C | 0.91 | T | 0.09 | 0.99 | 0.85, 1.15 | 0.90 |
| 3 | rs11385942 | 45876459 | G | 0.92 | GA | 0.08 | 1.16 | 1.00, 1.34 | 0.05 |
| 3 | rs115102354 | 46222037 | A | 0.95 | G | 0.05 | 0.96 | 0.79, 1.16 | 0.70 |
| 3 | rs12639224 | 45916222 | C | 0.73 | T | 0.27 | 1.02 | 0.93, 1.12 | 0.70 |
| 3 | rs13062942 | 62936766 | A | 0.64 | G | 0.36 | 0.92 | 0.84, 1.01 | 0.09 |
| 3 | rs13433997 | 46049765 | T | 0.88 | C | 0.12 | 1.10 | 0.97, 1.24 | 0.10 |
| 3 | rs1504061 | 1093795 | C | 0.95 | G | 0.05 | 1.13 | 0.94, 1.36 | 0.20 |
| 3 | rs1705826 | 3184653 | C | 0.63 | G | 0.37 | 1.03 | 0.94, 1.12 | 0.50 |
| 3 | rs17317135 | 27188298 | G | 0.95 | A | 0.05 | 0.89 | 0.73, 1.09 | 0.30 |
| 3 | rs1868132 | 125837737 | C | 0.90 | T | 0.10 | 1.02 | 0.89, 1.17 | 0.80 |
| 3 | rs34901975 | 45916786 | G | 0.89 | A | 0.11 | 1.12 | 0.98, 1.27 | 0.09 |
| 3 | rs35652899 | 45908514 | C | 0.93 | G | 0.07 | 1.17 | 1.00, 1.36 | 0.04 |
| 3 | rs35896106 | 45841938 | C | 0.92 | T | 0.08 | 1.17 | 1.01, 1.35 | 0.04 |
| 3 | rs6440031 | 141408691 | A | 0.08 | G | 0.92 | 0.94 | 0.80, 1.11 | 0.50 |
| 3 | rs71325088 | 45862952 | T | 0.92 | C | 0.08 | 1.15 | 0.99, 1.33 | 0.07 |
| 3 | rs71615437 | 46018781 | A | 0.92 | G | 0.08 | 1.12 | 0.97, 1.29 | 0.10 |
| 3 | rs73064425 | 45901089 | C | 0.92 | T | 0.08 | 1.15 | 0.99, 1.33 | 0.07 |
| 3 | rs76374459 | 45900634 | G | 0.94 | C | 0.06 | 1.20 | 1.02, 1.41 | 0.03 |
| 3 | rs76488148 | 148718087 | G | 0.96 | T | 0.04 | 1.25 | 1.02, 1.52 | 0.03 |
| 4 | rs112641600 | 112613026 | C | 0.89 | T | 0.11 | 0.83 | 0.72, 0.96 | 0.01 |
| 4 | rs115162070 | 69705994 | G | 0.93 | A | 0.07 | 0.90 | 0.75, 1.07 | 0.20 |
| 4 | rs11729561 | 106943200 | T | 0.92 | C | 0.08 | 0.96 | 0.82, 1.12 | 0.60 |
| 4 | rs35540967 | 44418592 | T | 0.93 | C | 0.07 | 1.02 | 0.87, 1.19 | 0.80 |
| 4 | rs3774881 | 5821877 | T | 0.84 | C | 0.16 | 0.91 | 0.81, 1.02 | 0.10 |
| 4 | rs3774882 | 5821922 | C | 0.92 | G | 0.08 | 0.90 | 0.77, 1.06 | 0.20 |
| 4 | rs6810404 | 27383278 | G | 0.51 | A | 0.49 | 0.97 | 0.89, 1.05 | 0.50 |
| 5 | rs10039856 | 142252549 | C | 0.90 | T | 0.10 | 1.10 | 0.96, 1.26 | 0.20 |
| 5 | rs111265173 | 171480160 | C | 1.00 | T | 0.00 | 0.97 | 0.35, 2.66 | 1.00 |
| 5 | rs113791144 | 180237828 | C | 0.93 | T | 0.07 | 0.97 | 0.82, 1.15 | 0.70 |
| 5 | rs2220543 | 173989338 | T | 0.71 | A | 0.29 | 1.04 | 0.94, 1.14 | 0.50 |
| 5 | rs4240376 | 123950404 | G | 0.80 | T | 0.20 | 0.99 | 0.89, 1.10 | 0.80 |
| 5 | rs4478338 | 169590905 | T | 0.92 | G | 0.08 | 1.08 | 0.93, 1.25 | 0.30 |
| 5 | rs62377777 | 122832716 | T | 0.79 | C | 0.21 | 0.96 | 0.87, 1.07 | 0.50 |
| 6 | rs10755709 | 12216966 | A | 0.70 | G | 0.30 | 1.11 | 1.01, 1.21 | 0.03 |
| 6 | rs140247774 | 18015447 | C | 0.93 | T | 0.07 | 0.93 | 0.78, 1.10 | 0.40 |
| 6 | rs143334143 | 31121426 | G | 0.93 | A | 0.07 | 1.00 | 0.85, 1.18 | 1.00 |
| 6 | rs16873740 | 45704813 | T | 0.88 | A | 0.12 | 1.16 | 1.03, 1.32 | 0.02 |
| 6 | rs3131294 | 32180146 | A | 0.13 | G | 0.87 | 1.00 | 0.88, 1.13 | 1.00 |
| 6 | rs61611950 | 27604726 | C | 0.99 | T | 0.01 | 0.92 | 0.56, 1.51 | 0.80 |
| 6 | rs6933436 | 6925195 | A | 0.71 | C | 0.29 | 1.01 | 0.92, 1.11 | 0.90 |
| 6 | rs9380142 | 29798794 | G | 0.30 | A | 0.70 | 1.08 | 0.99, 1.19 | 0.09 |
| 6 | rs9386484 | 106326754 | T | 0.76 | A | 0.24 | 0.95 | 0.85, 1.05 | 0.30 |
| 7 | rs6967210 | 152960930 | T | 0.99 | C | 0.01 | 1.17 | 0.86, 1.59 | 0.30 |
| 8 | rs10808999 | 38821327 | A | 0.13 | G | 0.87 | 1.01 | 0.89, 1.14 | 0.90 |
| 8 | rs11779911 | 40181978 | C | 0.67 | A | 0.33 | 0.99 | 0.90, 1.09 | 0.90 |
| 8 | rs118072448 | 16790149 | T | 0.92 | C | 0.08 | 0.82 | 0.70, 0.97 | 0.02 |
| 8 | rs13282163 | 38897470 | A | 0.92 | C | 0.08 | 0.93 | 0.80, 1.09 | 0.40 |
| 8 | rs2010843 | 74268198 | T | 0.47 | C | 0.53 | 1.04 | 0.96, 1.13 | 0.40 |
| 8 | rs332040 | 8730488 | G | 0.53 | A | 0.47 | 1.00 | 0.92, 1.09 | 0.90 |
| 9 | rs12236000 | 21131627 | G | 0.92 | C | 0.08 | 0.95 | 0.81, 1.11 | 0.50 |
| 9 | rs3895472 | 4329170 | T | 0.08 | C | 0.92 | 1.04 | 0.88, 1.22 | 0.70 |
| 9 | rs657152 | 136139265 | C | 0.63 | A | 0.37 | 0.95 | 0.87, 1.03 | 0.20 |
| 9 | rs7027911 | 81158113 | G | 0.57 | A | 0.43 | 1.11 | 1.01, 1.21 | 0.02 |
| 9 | rs71480372 | 27121456 | A | 0.66 | T | 0.34 | 0.98 | 0.90, 1.08 | 0.70 |
| 9 | rs74790577 | 29688719 | A | 1.00 | T | 0.00 | 1.05 | 0.27, 4.03 | 0.90 |
| 10 | rs10793436 | 44015051 | G | 0.68 | T | 0.32 | 0.95 | 0.86, 1.04 | 0.20 |
| 10 | rs1441121 | 54100345 | T | 0.57 | A | 0.43 | 0.95 | 0.87, 1.03 | 0.20 |
| 10 | rs1892429 | 37454397 | A | 0.84 | G | 0.16 | 0.99 | 0.88, 1.11 | 0.80 |
| 10 | rs2091431 | 37277870 | A | 0.28 | G | 0.72 | 1.03 | 0.94, 1.14 | 0.50 |
| 10 | rs5016035 | 123000638 | T | 0.51 | G | 0.49 | 1.00 | 0.91, 1.10 | 0.90 |

TABLE 14-continued

Informative polymorphisms assessed in Example 6.

| Chr | SNP | Position (GRCh37) | Reference Allele | Frequency | Effect Allele | Frequency | OR | 95% CI | P |
|---|---|---|---|---|---|---|---|---|---|
| 10 | rs71481792 | 9030308 | A | 0.38 | T | 0.62 | 0.89 | 0.82, 0.97 | 0.01 |
| 11 | rs10766439 | 2893867 | A | 0.37 | G | 0.63 | 0.97 | 0.89, 1.05 | 0.40 |
| 12 | rs10735079 | 113380008 | G | 0.36 | A | 0.64 | 0.98 | 0.90, 1.07 | 0.60 |
| 12 | rs11613792 | 8760610 | A | 0.85 | G | 0.15 | 1.01 | 0.88, 1.14 | 0.90 |
| 12 | rs12823094 | 106624953 | T | 0.76 | A | 0.24 | 1.08 | 0.98, 1.19 | 0.10 |
| 12 | rs6489867 | 113363550 | C | 0.36 | T | 0.64 | 0.98 | 0.90, 1.07 | 0.70 |
| 12 | rs7397549 | 56084466 | T | 0.59 | C | 0.41 | 0.99 | 0.90, 1.09 | 0.90 |
| 13 | rs12871414 | 74558505 | C | 0.74 | T | 0.26 | 0.95 | 0.86, 1.05 | 0.30 |
| 13 | rs1984162 | 23658838 | A | 0.75 | G | 0.25 | 1.10 | 1.00, 1.21 | 0.05 |
| 13 | rs2649134 | 63178476 | C | 0.97 | T | 0.03 | 0.93 | 0.72, 1.19 | 0.50 |
| 14 | rs12587980 | 72934229 | C | 0.63 | T | 0.37 | 1.03 | 0.95, 1.13 | 0.40 |
| 14 | rs144114696 | 77692036 | G | 1.00 | A | 0.00 | 2.53 | 0.51, 12.44 | 0.30 |
| 14 | rs2238187 | 72908102 | A | 0.65 | G | 0.35 | 1.07 | 0.97, 1.17 | 0.20 |
| 15 | rs12593288 | 33908103 | C | 0.80 | T | 0.20 | 0.91 | 0.82, 1.01 | 0.08 |
| 15 | rs2229117 | 33916053 | G | 0.86 | C | 0.14 | 0.90 | 0.80, 1.02 | 0.10 |
| 15 | rs74750712 | 48984345 | T | 1.00 | G | 0.00 | 1.33 | 0.65, 2.69 | 0.40 |
| 15 | rs77055952 | 45858905 | A | 0.95 | G | 0.05 | 1.07 | 0.88, 1.29 | 0.50 |
| 16 | rs145643452 | 49311043 | G | 0.99 | A | 0.01 | 1.03 | 0.61, 1.74 | 0.90 |
| 16 | rs72779789 | 10579876 | G | 0.95 | C | 0.05 | 1.04 | 0.85, 1.26 | 0.70 |
| 16 | rs72803978 | 78624025 | A | 0.94 | G | 0.06 | 0.88 | 0.74, 1.05 | 0.20 |
| 17 | rs178840 | 29737612 | G | 0.75 | A | 0.25 | 0.93 | 0.84, 1.03 | 0.20 |
| 17 | rs34761447 | 9170408 | C | 0.90 | T | 0.10 | 1.02 | 0.89, 1.18 | 0.80 |
| 17 | rs9890316 | 80443309 | G | 0.69 | A | 0.31 | 1.01 | 0.92, 1.10 | 0.90 |
| 18 | rs12958013 | 67208392 | T | 0.86 | C | 0.14 | 1.08 | 0.96, 1.22 | 0.20 |
| 18 | rs142257532 | 30006171 | T | 0.97 | C | 0.03 | 1.01 | 0.78, 1.30 | 1.00 |
| 19 | rs10411226 | 53333975 | G | 0.25 | A | 0.75 | 1.04 | 0.94, 1.16 | 0.40 |
| 19 | rs11085727 | 10466123 | C | 0.72 | T | 0.28 | 1.06 | 0.96, 1.16 | 0.20 |
| 19 | rs2109069 | 4719443 | G | 0.68 | A | 0.32 | 1.01 | 0.92, 1.10 | 0.80 |
| 19 | rs60744406 | 44492164 | A | 0.41 | G | 0.59 | 1.02 | 0.94, 1.11 | 0.60 |
| 19 | rs74956615 | 10427721 | T | 0.95 | A | 0.05 | 1.05 | 0.87, 1.27 | 0.60 |
| 19 | rs8105499 | 32023957 | C | 0.70 | A | 0.30 | 0.98 | 0.90, 1.08 | 0.70 |
| 20 | rs56259900 | 39389409 | A | 1.00 | G | 0.00 | 1.15 | 0.65, 2.04 | 0.60 |
| 20 | rs76253189 | 60473717 | C | 0.99 | G | 0.01 | 1.01 | 0.72, 1.42 | 1.00 |
| 21 | rs13050728 | 34615210 | C | 0.68 | T | 0.32 | 1.08 | 0.99, 1.18 | 0.10 |
| 21 | rs2236757 | 34624917 | G | 0.70 | A | 0.30 | 1.06 | 0.97, 1.16 | 0.20 |
| 21 | rs2252109 | 43080428 | A | 0.48 | T | 0.52 | 0.98 | 0.90, 1.07 | 0.70 |
| 21 | rs75994231 | 44424444 | C | 0.98 | T | 0.02 | 1.06 | 0.79, 1.43 | 0.70 |
| 22 | rs11090305 | 24407483 | T | 0.80 | C | 0.20 | 1.06 | 0.96, 1.18 | 0.20 |
| 22 | rs5757427 | 22564734 | T | 0.65 | A | 0.35 | 0.96 | 0.88, 1.05 | 0.40 |
| 22 | rs62220604 | 49677464 | G | 0.73 | A | 0.27 | 0.97 | 0.88, 1.07 | 0.50 |
| 22 | rs7290963 | 22724951 | G | 0.55 | T | 0.45 | 1.00 | 0.92, 1.09 | 1.00 |

Development of New Model

The inventors used multivariable logistic regression in the multiple imputation training dataset to develop the new model to predict risk of severe COVID-19. The inventors began with a model that included all the clinical variables and the SNPs with unadjusted associations with severe COVID-19 and used backwards stepwise selection to develop the most parsimonious model. For the removed variables a final determination was made on their inclusion or exclusion by adding them one at a time to the parsimonious model. To directly compare the effect sizes of the variables in the final model, regardless of the scale on which they were measured, the odds per adjusted standard deviation was used. The intercept and beta coefficients from the new model to calculate the COVID-19 risk score was used for all eligible UK Biobank participants.

Model Performance

The inventors assessed the performance of the new model in the imputed development dataset and in the non-imputed validation dataset. The association between the risk score and severe COVID-19 was assessed using logistic regression to estimate the odds ratio per quintile of risk score. It was assessed model discrimination using the area under the receiver operating characteristic curve (AUC). For models that showed good discrimination, calibration was assessed using logistic regression of the log of the risk score to estimate the intercept and the slope (beta coefficient). An intercept close to 0 indicated good calibration, while an intercept less than 0 indicated overall overestimation of risk and an intercept greater than 0 indicated overall underestimation of risk. A slope of close to 1 indicated good dispersion with a slope of less than 1 indicating over-dispersion and slope of greater than 1 indicating under-dispersion.

The best performing tests are detailed below.

Risk Models

Three models were developed for assessing the risk of a human subject developing a severe response to a Coronavirus infection. In particular, the methods can be used to determine the probability the subject would require hospitalisation if infected with a Coronavirus. The first model is based solely on sex and age (referred to herein as the "age and sex model"), the second model (referred to herein as the "full model") includes numerous clinical factors and genetic factors, whereas the third model (referred to herein as the "expanded model") includes additional clinical factors and genetic factors to those in the full model.

Age and Sex Model

Inputs of the age and sex model are provided in Table 15 and the β-coefficients provided in Table 16.

TABLE 15

Age and Sex Model Product Inputs

| Clinical Risk Factor | Input | Acceptance | TRF Question |
|---|---|---|---|
| Age (years) | Value | 50-84 | What is your age? |
| Gender | Male | Male | What is your gender? |
|  | Female | Female |  |

TABLE 16

Age and Sex Model Risk Factors

| Variable | Value | β coefficient |
|---|---|---|
| Age group (years) | 50-64 | 0 |
|  | 65-69 | 0.4694892 |
|  | 70-74 | 1.006561 |
|  | 75-79 | 1.435318 |
|  | 80-84 | 1.599188 |
| Gender | Female | 0 |
|  | Male | 0.3911169 |

The log odds is calculated using: Log odds (LO)=−1.749562+Σ Clinical β coefficients.

The age and sex relative risk=$e^{LO}$.

Age and sex probability=$e^{LO}/(1+e^{LO})$.

If any of the clinical factors are unknown, or the subject is unwilling to supply the relevant details, that factor(s) is assigned a β coefficient of 0.

Full Model

Inputs of the full model are provided in Table 17 and the β-coefficients provided in Tables 18 and 19.

TABLE 17

Full Model Product Inputs

| Clinical Risk Factor | Input | Acceptance | TRF Question |
|---|---|---|---|
| Age (years) | Value | 50-84 | What is your age? |
| Gender | Male | Male | What is your gender? |
|  | Female | Female |  |
| Ethnicity | Caucasian | All | What is your ethnicity? |
|  | Non-Caucasian |  |  |
|  | Unknown |  |  |
| Height (m) | (m) | All | What is your height? |
|  | Unknown |  |  |
| Weight (kg) | (kg) | All | What is your weight? |
|  | Unknown |  |  |
| Cerebrovascular disease | No | All | Have you ever been diagnosed with cerebrovascular disease? |
|  | Yes |  |  |
|  | Unknown |  |  |
| Chronic kidney disease | No | All | Have you ever been diagnosed with chronic kidney disease? |
|  | Yes |  |  |
|  | Unknown |  |  |
| Diabetes | No | All | Have you ever been diagnosed with any type of diabetes? |
|  | Yes |  |  |
|  | Unknown |  |  |
| Haematological cancer | No | All | Have you ever been diagnosed with haematological cancer? |
|  | Yes |  |  |
|  | Unknown |  |  |
| Hypertension | No | All | Have you ever been diagnosed with hypertension? |
|  | Yes |  |  |
|  | Unknown |  |  |
| Non-haematological cancer | No | All | Have you ever been diagnosed with another type of cancer? |
|  | Yes |  |  |
|  | Unknown |  |  |
| Respiratory disease (excluding asthma) | No | All | Have you ever been diagnosed with a respiratory disease (excluding asthma)? |
|  | Yes |  |  |
|  | Unknown |  |  |

TABLE 18

Full Model Clinical Risk Factors

| Variable | Value | β coefficient |
|---|---|---|
| Age group (years) | 50-69 | 0 |
|  | 70-74 | 0.5747727 |
|  | 75-79 | 0.8243711 |
|  | 80-84 | 1.013973 |
| Gender | Female | 0 |
|  | Male | 0.2444891 |
| Ethnicity | Caucasian | 0 |
|  | Other/Unknown | 0.29311 |
| Height (m) |  |  |
| Weight (kg) |  |  |
| $10 \times \text{inverse BMI} = \dfrac{10 \times m^2}{kg}$ | $\dfrac{10 \times m^2}{kg}$ | −1.602056 |
| Cerebrovascular disease | No | 0 |
|  | Yes | 0.4041337 |
| Chronic kidney disease | No | 0 |
|  | Yes | 0.6938494 |
| Diabetes | No | 0 |
|  | Yes | 0.4297612 |
| Haematological cancer | No | 0 |
|  | Yes | 1.003877 |
| Hypertension | No | 0 |
|  | Yes | 0.2922307 |
| Non-haematological cancer | No | 0 |
|  | Yes | 0.2558464 |
| Respiratory disease (excluding asthma) | No | 0 |
|  | Yes | 1.173753 |

TABLE 19

Full Model SNP Risk Alleles

| SNPs | Risk Allele | No of Risk Alleles | β coefficient |
|---|---|---|---|
| rs10755709 | G | 0, 1, or 2 | 0.124239 |
| rs112317747 | C | 0, 1, or 2 | 0.2737487 |
| rs112641600 | T | 0, 1, or 2 | −0.2362513 |
| rs118072448 | C | 0, 1, or 2 | −0.1995879 |
| rs2034831 | C | 0, 1, or 2 | 0.2371955 |
| rs7027911 | A | 0, 1, or 2 | 0.1019074 |
| rs71481792 | T | 0, 1, or 2 | −0.1058025 |

The SNP risk factor (SRF) is determined using: (SRF)=Σ (No of Risk Alleles×SNP β coefficient).

The log odds is calculated using: Log odds (LO)=−1.36523+SRF+Σ Clinical β coefficients.

The age and sex relative risk=$e^{LO}$.

Age and sex probability=$e^{LO}/(1+e^{LO})$.

If any of the clinical factors are unknown, or the subject is unwilling to supply the relevant details, that factor(s) is assigned a β coefficient of 0.

Expanded Model

Inputs of the expanded model are provided in Table 20 and the β-coefficients provided in Tables 21 and 22.

TABLE 20

Expanded Model Product Inputs

| Clinical Risk Factor | Input | Acceptance | TRF Question |
|---|---|---|---|
| Age (years) | Value | 50-84 | What is your age? |
| Gender | Male | Male | What is your gender? |
|  | Female | Female |  |

TABLE 20-continued

Expanded Model Product Inputs

| Clinical Risk Factor | Input | Acceptance | TRF Question |
|---|---|---|---|
| Ethnicity | Caucasian<br>Non-Caucasian<br>Unknown | All | What is your ethnicity? |
| Blood Type | O<br>A<br>B<br>AB<br>Unknown | All | What is your blood type? |
| Height (m) | (m)<br>Unknown | All | What is your height? |
| Weight (kg) | (kg)<br>Unknown | All | What is your weight? |
| Cerebrovascular disease | No<br>Yes<br>Unknown | All | Have you ever been diagnosed with cerebrovascular disease? |
| Chronic kidney disease | No<br>Yes<br>Unknown | All | Have you ever been diagnosed with chronic kidney disease? |
| Diabetes | No<br>Yes<br>Unknown | All | Have you ever been diagnosed with any type of diabetes? |
| Haematological cancer | No<br>Yes<br>Unknown | All | Have you ever been diagnosed with haematological cancer? |
| Hypertension | No<br>Yes<br>Unknown | All | Have you ever been diagnosed with hypertension? |
| Immuno-compromised disease | No<br>Yes<br>Unknown | All | Have you ever been diagnosed with an immuno compromised disease? |
| Liver disease | No<br>Yes<br>Unknown | All | Have you ever been diagnosed with a liver disease? |
| Non-haematological cancer | No<br>Yes<br>Unknown | All | Have you ever been diagnosed with another type of cancer? |
| Respiratory disease (excluding asthma) | No<br>Yes<br>Unknown | All | Have you ever been diagnosed with a respiratory disease (excluding asthma)? |

TABLE 21

Expanded Model Clinical and SNP Risk Factors

| Variable | Value | β coefficient |
|---|---|---|
| Age group (years) | 50-64 | 0 |
|  | 65-69 | 0.1677566 |
|  | 70-74 | 0.6352682 |
|  | 75-79 | 0.8940548 |
|  | 80-84 | 1.082477 |
| Gender | Female | 0 |
|  | Male | 0.2418454 |
| Ethnicity | Caucasian | 0 |
|  | Other/Unknown | 0.2967777 |
| Blood Type | O | 0 |
|  | A | 0 |
|  | B | 0 |
|  | AB | −0.229737 |
| Height (m)<br>Weight (kg)<br>$10 \times \text{inverse BMI} = \dfrac{10 \times m^2}{kg}$ | $\dfrac{10 \times m^2}{kg}$ | −1.560943 |
| Cerebrovascular disease | No | 0 |
|  | Yes | 0.3950113 |
| Chronic kidney disease | No | 0 |
|  | Yes | 0.6650257 |
| Diabetes | No | 0 |
|  | Yes | 0.4126633 |
| Haematological cancer | No | 0 |
|  | Yes | 1.001079 |
| Hypertension | No | 0 |
|  | Yes | 0.2640989 |
| Immunocompromised disease | No | 0 |
|  | Yes | 0.6033541 |
| Liver disease | No | 0 |
|  | Yes | 0.2301902 |
| Non-haematological cancer | No | 0 |
|  | Yes | 0.2381579 |
| Respiratory disease (excluding asthma) | No | 0 |
|  | Yes | 1.148496 |

TABLE 22

Expanded Model SNP Risk Alleles

| SNPs | Risk Allele | No of Risk Alleles | β coefficient |
|---|---|---|---|
| rs10755709 | G | 0, 1, or 2 | 0.1231766 |
| rs112317747 | C | 0, 1, or 2 | 0.2576692 |
| rs112641600 | T | 0, 1, or 2 | −0.2384001 |
| rs115492982 | A | 0, 1, or 2 | 0.4163575 |
| rs118072448 | C | 0, 1, or 2 | −0.1965609 |
| rs1984162 | A | 0, 1, or 2 | 0.1034362 |
| rs2034831 | C | 0, 1, or 2 | 0.2414792 |
| rs7027911 | A | 0, 1, or 2 | 0.0998459 |
| rs71481792 | T | 0, 1, or 2 | −0.1032044 |

The SNP risk factor (SRF) is determined using: (SRF)=Σ (No of Risk Alleles×SNP β coefficient).

The log odds is calculated using: Log odds (LO)=−1.469939+SRF+Σ Clinical β coefficients.

The age and sex relative risk=$e^{LO}$.

Age and sex probability=$e^{LO}/(1+e^{LO})$.

If any of the clinical factors are unknown, or the subject is unwilling to supply the relevant details, that factor(s) is assigned a β coefficient of 0.

Summary

In terms of discrimination between cases and controls, the age and sex model had an AUC of 0.671 (95% CI=0.646, 0.696) but the full model with an AUC of 0.732 (95% CI=0.708, 0.756) was a substantial improvement ($\chi2$=41.23, df=1, P<0.001). The receiver operating characteristic curves for both models are shown in FIG. 4.

The models were well calibrated with no evidence of overall overestimation or underestimation for the age and sex model ($\alpha$=−0.02; 95% CI=−0.18, 0.13; P=0.7) or the full model ($\alpha$=−0.08; 95% CI=−0.21, 0.05; P=0.3). There was also no evidence of under or over dispersion for the age and sex model (β=0.96, 95% 0=0.81, 1.10, P=0.6) and for the full model (β=0.90, 95% 0=0.80, 1.00, P=0.06). Calibration plots for both models are shown in FIG. 5.

The inventors calculated the probability of severe COVID-19 for all UK Biobank participants who met our eligibility criteria for this study; the distributions are shown in FIG. 6. Using the age and sex model, the mean probability was 0.32 (SD=0.13) and ranged from a minimum of 0.15 to a maximum of 0.56. Using the full model, the mean probability was 0.27 (SD=0.16) and the range was from 0.04 to 0.98, a much wider range than for the age and sex model.

The expanded model provided a slight improvement in discrimination in this dataset (Table 23).

TABLE 23

| Model | AUC | 95% Confidence interval |
| --- | --- | --- |
| Age and Sex | 0.6755 | 0.65948-0.69160 |
| Full Model | 0.7512 | 0.73653-0.76673 |
| Expanded Model | 0.7524 | 0.73730-0.76749 |

Example 7—Combined Genetic and Clinical Risk Assessment—Under 50 Years of Age

The algorithm to calculate the risk of developing severe Covid-19 has been modified to enable a risk calculation to be provided for patients aged 18-85 years (previously 50-85 years). More specifically, the look-up tables providing the age-related risk values have been modified to include three additional values for the following age ranges: 18-29, 30-39, 40-49 (Tables 24).

For people aged under 50 years, the probability of severe disease is adjusted using data on risk of hospitalization due to Covid-19 which were obtained from the United States Centers for Disease Control and Prevention (world wide web address cdc.gov).

The SNPs analysed, and the methods used for analysis, are the same as used in Example 6.

TABLE 24

| Variable | Value | β coefficient |
| --- | --- | --- |
| Age group (years) | 18-29 | −1.3111 |
| | 30-39 | −0.8348 |
| | 40-49 | −0.4038 |
| | 50-69 | 0 |
| | 70-74 | 0.5747727 |
| | 75-79 | 0.8243711 |
| | 80-84 | 1.013973 |
| Gender | Female | 0 |
| | Male | 0.2444891 |
| Ethnicity | Caucasian | 0 |
| | Other/Unknown | 0.29311 |
| Height (m) | Value | Used in in BMI calculation |
| Weight (kg) | Value | Used in in BMI calculation |
| $10 \times \text{inverse BMI} = \dfrac{10 \times m^2}{kg}$ | $\dfrac{10 \times m^2}{kg}$ | −1.602056 |
| Cerebrovascular disease | No | 0 |
| | Yes | 0.4041337 |
| Chronic kidney disease | No | 0 |
| | Yes | 0.6938494 |
| Diabetes | No | 0 |
| | Yes | 0.4297612 |
| Haematological cancer | No | 0 |
| | Yes | 1.003877 |
| Hypertension | No | 0 |
| | Yes | 0.2922307 |
| Non-haematological cancer | No | 0 |
| | Yes | 0.2558464 |
| Respiratory disease (excluding asthma) | No | 0 |
| | Yes | 1.173753 |

The present application claims priority from AU 2020901739 filed 27 May 2020, AU 2020902052 filed 19 Jun. 2020, AU 2020903536 filed 30 Sep. 2020, and AU 2021900392 filed 17 Feb. 2021, the entire contents of each of which are incorporated herein by reference.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Adessi et al. (2000) Nucl. Acids Res. 28, E87.
Bennett et al. (2005) Pharmacogenomics 6: 373-382.
Brenner et al. (2000) Nat. Biotechnol. 18:630-634.
Centres for Disease Control and Prevention. (2020) COVID-View: a weekly surveillance summary of U.S. COVID-19 activity. Available from world wide web address cdc.gov (accessed 14 Aug. 2020).
Chee et al. (1996) Science 274:610-614.
COVID-19 Host Genetics Initiative. (2020) Eur J Hum Genet 28:715-718.
Dayem et al. (2018) Nucl. Acids Res. 46:W109-W113.
Devlin and Risch (1995) Genomics. 29: 311-322.
Ellinghaus et al. (2020) N. Engl. J. Med. doi: 10.1056/NEJMoa2020283.
Fodor (1997a) FASEB Journal 11:A879.
Fodor (1997b) Science 277: 393-395.
Hartl et al. (1981) A Primer of Population Genetics Washington University, Saint Louis.
Hopper (2015) J. Epidemiol. 182:863-867.
Katella (2021) Yale Medicine, 13 May 2021 (world wide web address yalemedicine.org/news/covid-19-vaccine-comparison).
Lockhart (1998) Nature Medicine 4:1235-1236.
Lynch and Walsh (1998) Genetics and Analysis of Quantitative Traits, Sinauer Associates, Inc. Sunderland Mass. ISBN 0-87893-481-2.
Machiela et al. (2015) Bioinformatics 31:3555-3557.
MacLean et al. (2009) Nature Rev. Microbiol, 7:287-296.
Margulies et al. (2005) Nature 437: 376-380.
Mealiffe et al. (2010) J. Natl. Cancer Inst. 102:1618-1627.
Melzer et al. (2008) PLoS Genect. 4:e1000072.
Mitra et al. (2003) Analytical Biochemistry 320:55-65.
Morozova & Marra (2008) Genomics 92:255.
Pairo-Castineira et al. (2020) Nature doi.org/10.1038/s41586-020-03065-y.
Petrilli et al. (2020) BMJ 369:m1966. doi: 10.1136/bmj.m1966.
Sapolsky et al. (1999) Genet Anal: Biomolec Engin 14:187-192.
Shendure et al. (2005) Science 309:1728-1732.
Slatkin and Excoffier (1996) Heredity 76: 377-383.
Voelkerding et al. (2009) Clinical Chem. 55: 641-658.
Williamson et al. (2020) Nature 584:430436.
Wolpin et al. (2010) Cancer Res. 70:1015-1023.

The invention claimed is:

1. A method for determining the probability a human subject will develop a severe response to a severe acute respiratory syndrome coronavirus 2 (SARS-CoV-2) infection, the method comprising:
   i) performing a genetic risk assessment of the human subject, wherein the genetic risk assessment comprises:
      (a) detecting, in a biological sample derived from the human subject, polymorphisms at rs10755709, rs112317747, rs112641600, rs118072448, rs2034831, rs7027911 and rs71481792;
      (b) determining the number of risk alleles at each of rs10755709, rs112317747, rs112641600, rs118072448, rs2034831, rs7027911 and rs71481792, wherein;
         i) G is the risk allele at rs10755709;
         ii) C is the risk allele at rs112317747;
         iii) T is the risk allele at rs112641600;
         iv) C is the risk allele at rs118072448;
         v) C is the risk allele at rs2034831;
         vi) A is the risk allele at rs7027911; and
         vii) T is the risk allele at rs71481792;
      (c) multiplying the number of risk alleles at each of rs10755709, rs112317747, rs112641600, rs118072448, rs2034831, rs7027911 and rs71481792 by their respective SNP β coefficients; and
      (d) adding together the numbers produced in step (i) (c) to produce a SNP Risk Factor (SRF);
   ii) performing a clinical risk assessment of the human subject, wherein the clinical risk assessment comprises:

(a) obtaining information from the subject on age, gender, race/ethnicity, height, weight, does the human have or has had a cerebrovascular disease, does the human have or has had a chronic kidney disease, does the human have or has had diabetes, does the human have or has had a haematological cancer, does the human have or has had hypertension, does the human have or has had a non-haematological cancer, and does the human have or has had a respiratory disease (other than asthma);

(b) assigning a clinical β coefficient based on each piece of information obtained from the subject in step (ii) (a);

iii) combining the genetic risk assessment with the clinical risk assessment using the following formula, Long Log Odds (LO)=−1.36523+SRF+Σ Clinical β coefficients iv) determining the probability the subject will develop a severe response to a SARS-CoV-2 infection using the following formula:

$e^{LO}/(1+e^{LO})$, which is then multiplied by 100.

2. The method of claim 1, wherein in the genetic risk assessment:
   i) the β coefficient for the risk allele at rs10755709 is 0.124239;
   ii) the β coefficient for the risk allele at rs112317747 is 0.2737487;
   iii) the β coefficient for the risk allele at rs112641600 is −0.2362513;
   iv) the β coefficient for the risk allele at rs118072448 is −0.1995879;
   v) the β coefficient for the risk allele at rs2034831 is 0.2371955;
   vi) the β coefficient for the risk allele at rs7027911 is 0.1019074; and
   vii) the β coefficient for the risk allele at rs71481792 is −0.1058025.

3. The method of claim 1, wherein the subject is between 18 and 84 years of age and in the clinical risk assessment
   a) a β coefficient of −1.3111 is assigned if the subject is between 18 and 29 years of age;
   b) a β coefficient of −0.8348 is assigned if the subject is between 30 and 39 years of age;
   c) a β coefficient of −0.4038 is assigned if the subject is between 40 and 49 years of age;
   d) a β coefficient of 0.5747727 is assigned if the subject is between 70 and 74 years of age;
   e) a β coefficient of 0.8243711 is assigned if the subject is between 75 and 79 years of age;
   f) a β coefficient of 1.013973 is assigned if the subject is between 80 and 84 years of age;
   g) a β coefficient of 0.2444891 is assigned if the subject is male;
   h) a β coefficient of 0.29311 is assigned if the subject is an ethnicity other than Caucasian;
   i) the subjects height (in metres (m)) and weight (in kilograms (kg)) is applied to the formula: (10 times m2) divided by kg, which is multiplied by −1.602056 to provide the β coefficient to be assigned;
   j) a β coefficient of 0.4041337 is assigned if the subject has ever been diagnosed as having a cerebrovascular disease;
   k) a β coefficient of 0.6938494 is assigned if the subject has ever been diagnosed as having a chronic kidney disease;
   l) a β coefficient of 0.4297612 is assigned if the subject has ever been diagnosed as having diabetes;
   m) a β coefficient of 1.003877 is assigned if the subject has ever been diagnosed as having haematological cancer;
   n) a β coefficient of 0.2922307 is assigned if the subject has ever been diagnosed as having hypertension;
   o) a β coefficient of 0.2558464 is assigned if the subject has ever been diagnosed as having a non-haematological cancer; and
   p) a β coefficient of 1.173753 is assigned if the subject has ever been diagnosed as having a respiratory disease (other than asthma).

4. The method of claim 1, further comprising comparing the probability to a predetermined threshold, wherein if the probability is at, or above, the threshold the subject is assessed as being at risk of developing a severe response to a SARS-CoV-2 infection.

5. A method for determining the probability a human subject will develop a severe response to a severe acute respiratory syndrome coronavirus 2 (SARS-CoV-2) infection, the method comprising:
   i) performing a genetic risk assessment of the human subject, wherein the genetic risk assessment comprises:
      (a) detecting, in a biological sample derived from the human subject, polymorphisms at rs10755709, rs112317747, rs112641600, rs118072448, rs2034831, rs7027911 and rs71481792;
      (b) determining the number of risk alleles at each of rs10755709, rs112317747, rs112641600, rs118072448, rs2034831, rs7027911 and rs71481792, wherein;
         i) G is the risk allele at rs10755709;
         ii) C is the risk allele at rs112317747;
         iii) T is the risk allele at rs112641600;
         iv) C is the risk allele at rs118072448;
         v) C is the risk allele at rs2034831;
         vi) A is the risk allele at rs7027911; and
         vii) T is the risk allele at rs71481792;
      (c) multiplying the number of risk alleles at each of rs10755709, rs112317747, rs112641600, rs118072448, rs2034831, rs7027911 and rs71481792 by their respective SNP β coefficient, wherein
         i) the β coefficient for the risk allele at rs10755709 is 0.124239;
         ii) the β coefficient for the risk allele at rs112317747 is 0.2737487;
         iii) the β coefficient for the risk allele at rs112641600 is −0.2362513;
         iv) the β coefficient for the risk allele at rs118072448 is −0.1995879;
         v) the β coefficient for the risk allele at rs2034831 is 0.2371955;
         vi) the β coefficient for the risk allele at rs7027911 is 0.1019074; and
         vii) the β coefficient for the risk allele at rs71481792 is −0.1058025; and
      (d) adding together the numbers produced in step (i) (c) to produce a SNP Risk Factor (SRF);
   ii) performing a clinical risk assessment of the human subject wherein the clinical risk assessment comprises:
      (a) obtaining information from the subject on age, gender, race/ethnicity, height, weight, does the human have or has had a cerebrovascular disease, does the human have or has had a chronic kidney disease, does the human have or has had diabetes, does the human have or has had a haematological cancer, does the human have or has had hypertension, does the human have or has had a non-haematological cancer, and does the human have or has had a respiratory disease (other than asthma); and (b) assigning a clinical β coefficient based on each piece of information obtained from the subject in step (ii)(a), wherein:
  i) a β coefficient of −1.3111 is assigned if the subject is between 18 and 29 years of age;
  ii) a β coefficient of −0.8348 is assigned if the subject is between 30 and 39 years of age;
  iii) a β coefficient of −0.4038 is assigned if the subject is between 40 and 49 years of age;
  iv) a β coefficient of 0.5747727 is assigned if the subject is between 70 and 74 years of age;
  v) a β coefficient of 0.8243711 is assigned if the subject is between 75 and 79 years of age;
  vii) a β coefficient of 1.013973 is assigned if the subject is between 80 and 84 years of age;
  viii) a β coefficient of 0.2444891 is assigned if the subject is male;
  ix) a β coefficient of 0.29311 is assigned if the subject is an ethnicity other than Caucasian;
  x) the subjects height (in metres (m)) and weight (in kilograms (kg)) is applied to the formula: (10 times m2) divided by kg, which is multiplied by −1.602056 to provide the β coefficient to be assigned;
  xi) a β coefficient of 0.4041337 is assigned if the subject has ever been diagnosed as having a cerebrovascular disease;
  xii) a β coefficient of 0.6938494 is assigned if the subject has ever been diagnosed as having a chronic kidney disease;
  xiii) a β coefficient of 0.4297612 is assigned if the subject has ever been diagnosed as having diabetes;
  xiv) a β coefficient of 1.003877 is assigned if the subject has ever been diagnosed as having haematological cancer;
  xv) a β coefficient of 0.2922307 is assigned if the subject has ever been diagnosed as having hypertension;
  xvi) a β coefficient of 0.2558464 is assigned if the subject has ever been diagnosed as having a non-haematological cancer; and
  xvii) a β coefficient of 1.173753 is assigned if the subject has ever been diagnosed as having a respiratory disease (other than asthma);
iii) combining the genetic risk assessment with the clinical risk assessment using the following formula:

Log Odds (LO)=−1.36523+SRF+Σ Clinical β coefficients; and iv) determining the probability the subject will develop a severe response to a SARS-CoV-2 infection using the following formula:

$e^{LO}/(1+e^{LO})$, which is then multiplied by 100.

6. The method of claim 5, further comprising comparing the probability to a predetermined threshold, wherein if the probability is at, or above, the threshold the subject is assessed as being at risk of developing a severe response to a SARS-CoV-2 infection.

* * * * *